United States Patent
Franco-Obregon et al.

(10) Patent No.: US 10,898,708 B2
(45) Date of Patent: Jan. 26, 2021

(54) SYSTEM AND METHOD FOR APPLYING PULSED ELECTROMAGNETIC FIELDS

(71) Applicants: National University of Singapore, Singapore (SG); ETH Zurich, Zurich (CH)

(72) Inventors: Alfredo Franco-Obregon, Singapore (SG); Chuen Neng Lee, Singapore (SG); Wee Chuan Melvin Loh, Singapore (SG); Jürg Hans Fröhlich, Zurich (CH); Christian Beyer, Olten (CH); Tien Min David Lai, Singapore (SG)

(73) Assignees: National University of Singapore, Singapore (SG); ETH Zurich, Zurich (CH)

( * ) Notice: Subject to any disclaimer, the term of this patent is extended or adjusted under 35 U.S.C. 154(b) by 307 days.

(21) Appl. No.: 15/571,687

(22) PCT Filed: May 5, 2016

(86) PCT No.: PCT/SG2016/050208
§ 371 (c)(1),
(2) Date: Nov. 3, 2017

(87) PCT Pub. No.: WO2016/178631
PCT Pub. Date: Nov. 10, 2016

(65) Prior Publication Data
US 2019/0126036 A1      May 2, 2019

Related U.S. Application Data

(60) Provisional application No. 62/263,042, filed on Dec. 4, 2015.

(30) Foreign Application Priority Data

May 5, 2015   (SG) .......................... 10201503520V

(51) Int. Cl.
*A61N 1/32*      (2006.01)
*A61N 2/02*      (2006.01)
*A61N 1/40*      (2006.01)

(52) U.S. Cl.
CPC ............... *A61N 1/326* (2013.01); *A61N 2/02* (2013.01); *A61N 1/40* (2013.01)

(58) Field of Classification Search
CPC ............. A61N 1/326; A61N 1/40; A61N 2/02
(Continued)

(56) References Cited

U.S. PATENT DOCUMENTS 6,353,763 B1   3/2002   George et al.
7,160,241 B1 *   1/2007   Herbst ..................... A61N 2/00
                                                  600/13
(Continued)

FOREIGN PATENT DOCUMENTS

WO   2001/015774 A2   3/2001
WO   2010/007614 A2   1/2010
(Continued)

OTHER PUBLICATIONS

International Search Report issued in PCT/SG2016/050208 dated Aug. 9, 2016 (8 pages).
(Continued)

*Primary Examiner* — Mallika D Fairchild
*Assistant Examiner* — Minh Duc G Pham
(74) *Attorney, Agent, or Firm* — Osha Bergman Watanabe & Burton

(57) ABSTRACT

Systems and methods for applying a pulsed electromagnetic fields. A system for applying a pulsed electromagnetic field (PEMF) to a cell, comprising: a sensor for obtaining a characteristic of the cell; a memory module having stored therein a plurality of characteristics and PEMF efficacy window data, each characteristic having its corresponding
(Continued)

PEMF efficacy window data; a pulse generator coupled to a set of PEMF coils and configured to generate an output of electrical pulses to drive the set of PEMF coils; and a controller in communication with the sensor, the memory module and the pulse generator, wherein the controller is configured to: retrieve, from the memory module, the PEMF efficacy window data that corresponds to the characteristic of the cell obtained by the sensor; and control the output of the pulse generator based on the retrieved PEMF efficacy window data such that the set of PEMF coils apply a PEMF in accordance with the PEMF efficacy window data.

13 Claims, 84 Drawing Sheets

(58) Field of Classification Search
USPC .......................................................... 607/50
See application file for complete search history.

(56) References Cited

U.S. PATENT DOCUMENTS

2012/0116149 A1* 5/2012 Pilla ....................... A61N 2/006
                                                              600/14
2014/0024882 A1    1/2014 Chornenky et al.

FOREIGN PATENT DOCUMENTS

WO    2010/095147 A2    8/2010
WO    2014/145239 A1    9/2014

OTHER PUBLICATIONS

Written Opinion of the International Searching Authority issued in PCT/SG2016/050208 dated Aug. 9, 2016 (9 pages).

* cited by examiner

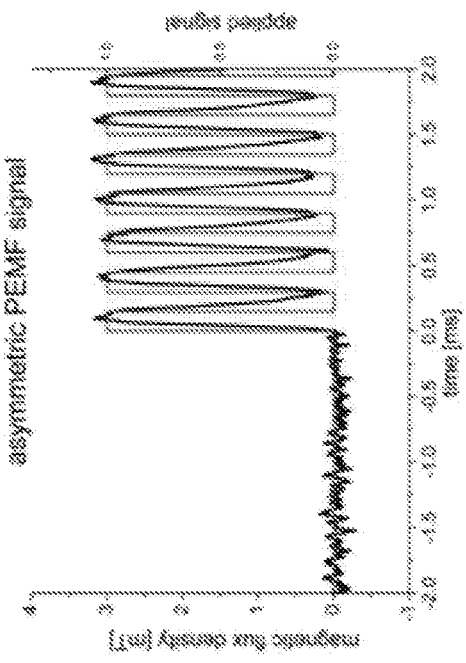

FIG. 1D

Measured Magnetic Flux Density vs. Time Characteristics of a Representative Asymmetric PEMF Burst Sequence

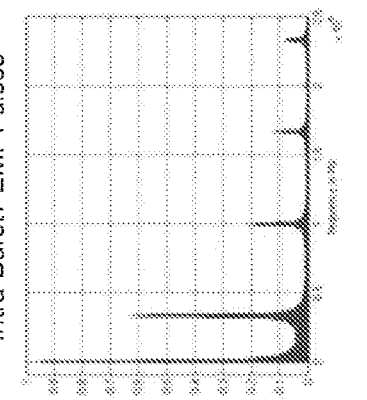

FIG. 1C

Representative Frequency Spectrum of Intra-Burst PEMF Pulses

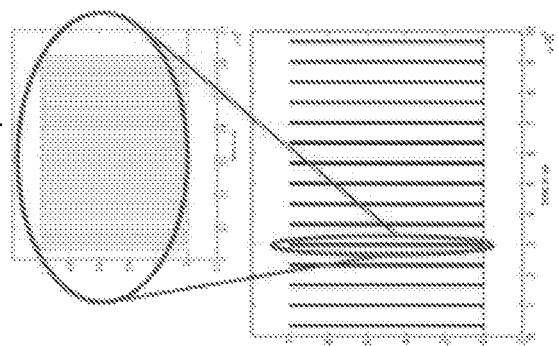

FIG. 1B

Representative Intra-Burst PEMF Pulse Sequence:

Representative PEMF Burst Sequence:

signal shape | spectrum | measured characteristics

Representative Example Parameters of PEMF Signals to which Target Tissues such as Muscle Tissues are Exposable / Exposed During one or more PEMF Exposure Sessions:

- Maximum peak field strength up to 5mT
- 15 bursts per second (15Hz repetition frequency)
- 1 burst: 20 pulses at 150 µs
- main frequency components: 0.015, 3.3, 10, 16.6 kHz

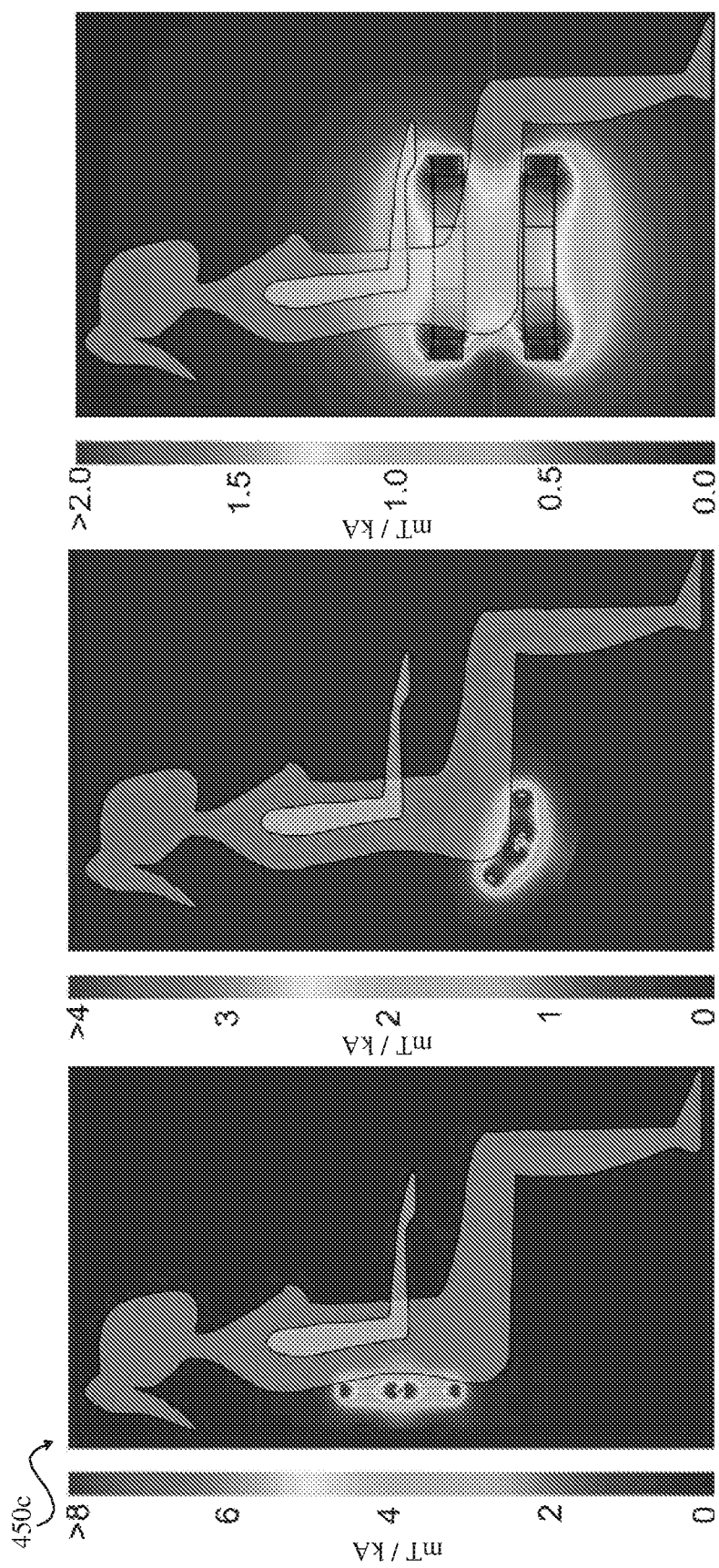

Subject ID: ##########
Subject Name: John Smith
Today's Date: ##/##/####

☒ Generate PEMF Signals

PEMF Exposure Regimen: 3 Times / Week, M-W-F

PEMF Exposure Session: 1 mT, 10 min.

[ Start PEMF Exposure Session ]

*View Subject Details / History*

*Edit Regimen Details*

*Edit Exposure Session Details*

☐ Perform MR Scan

| | PEMF Efficacy Window (EEW) Lookup Table | | | | |
|---|---|---|---|---|---|
| | | PEMF parameters (i.e. efficacy window data) | | | |
| Cell of Tissue Type | Amplitude (mT) | Duration (min) | Frequency (Hz) | Directionality | Exposures/week |
| Skeletal Muscle | 1.5 | 10 | 15 | Orthogonal | 1 |
| Cardiac Muscle | 3 | 10 | 15 | Orthogonal | 1 |
| Lymphocytes | 2 | 10 | 15 | Orthogonal | 1 |
| MSCs | 3 | 10 | 15 | Orthogonal | 1 |
| Chondrocytes | 2 | 10 | 15 | Orthogonal | 1 |
| Browning Adipocytes | 1 | 10 | 15 | Orthogonal | 1 |
| Smooth Muscle | 3 | 10 | 15 | Orthogonal | 1 |

FIG. 4B

| Protein | 3 mT/0 mT | Protein | 3mT/0 mT |
|---|---|---|---|
| GAPDH | 6,244 | Protein disulfide-isomerase A6 | 4,068 |
| Neuroblast differentiation-associated protein | 5,984 | Plasminogen | 3,557 |
| Cofilin-2 | 4,770 | Epididymal secretory protein E1 | 2,913 |
| Pyruvate kinase | 4,718 | Protein canopy homolog 2 | 2,831 |
| Annexin A1 | 4,592 | Major prion protein (PrP) | 2,801 |
| Triosephosphate isomerase | 4,511 | Perilipin-3 | 2,774 |
| Filamin-B | 4,319 | Thymosin beta-10 | 2,710 |
| Vasorin | 3,759 | ATP synthase subunit beta | 2,587 |
| Protein disulfide-isomerase A4 | 3,453 | Bone morphogenetic protein 1 | 2,586 |
| Follistatin-related protein | 3,446 | Thymosin beta-4 | 2,467 |
| Heterogeneous nuclear ribonucleoprotein A1-like 2 | 3,303 | Calmodulin | 2,145 |
| Moesin | 3,301 | ATP-citrate synthase | 2,069 |
| Peptidyl-prolyl cis-trans isomerase A | 3,185 | Reticulocalbin-3 | 2,083 |
| Myosin-9 | 3,159 | Macrophage colony-stimulating factor 1 | 1,998 |
| Protein S100-A6 | 3,043 | Transitional endoplasmic reticulum ATPase | 1,882 |
| Insulin-like growth factor-binding protein 2 | 2,990 | Peroxiredoxin-2 | 1,879 |
| Heat shock cognate 71 kDa protein | 2,866 | Phosphatidylethanolamine-binding protein 1 | 1,870 |
| Transitional endoplasmic reticulum ATPase | 2,724 | Cysteine and glycine-rich protein 1 | 1,852 |
| Transgelin-2 | 2,678 | Complement C3 | 1,811 |
| Macrophage migration inhibitory factor | 2,522 | Annexin A1 | 1,808 |
| Thymosin beta-10 | 2,474 | Nucleoside diphosphate kinase B | 1,791 |
| Extracellular matrix protein 1 | 2,242 | Testican-1 | 1,764 |
| Heterogeneous nuclear ribonucleoproteins A2/B1 | 2,235 | Collagen alpha-1(I) chain | 1,749 |
| Thymosin beta-4 | 2,133 | Glutathione S-transferase P | 1,749 |
| Thioredoxin domain-containing protein 17 | 2,030 | Vitamin D-binding protein | 1,746 |
| Filamin-A | 2,001 | Thioredoxin domain-containing protein 5 | 1,669 |
| Alpha-enolase | 1,989 | Collagen alpha-2(V) chain | 1,663 |
| Beta-enolase | 1,986 | Biglycan | 1,556 |
| 45 kDa calcium-binding protein | 1,970 | Lactotransferrin | 1,653 |
| Spectrin beta chain, non-erythrocytic 1 | 1,947 | Fibulin-1 | 1,553 |
| Protein deglycase DJ-1 | 1,936 | Collagen alpha-2(VI) chain | 1,617 |
| Phosphoglycerate kinase 1 | 1,923 | Latent-transforming growth factor beta-binding protein 1 | 1,581 |
| Tenascin | 1,910 | Beta-enolase | 1,578 |
| A disintegrin and metalloproteinase with thrombospondin motifs 1 | 1,891 | Insulin-like growth factor-binding protein 2 | 1,577 |
| Alpha-2-macroglobulin | 1,867 | Decorin | 1,565 |
| Heat shock protein beta-1 | 1,839 | Transforming growth factor-beta-induced protein ig-h3 | 1,521 |
| Semaphorin-7A | 1,809 | | |
| Parathymosin | 1,781 | | |
| Insulin-like growth factor-binding protein 4 | 1,757 | | |
| Translationally-controlled tumor protein | 1,728 | | |
| Prothymosin alpha | 1,677 | | |
| Annexin A2 | 1,656 | | |
| Galectin-1 | 1,628 | | |
| Vinculin | 1,611 | | |
| L-lactate dehydrogenase B chain | 1,600 | | |
| Histone H2A type 1-B/E | 1,598 | | |
| Nucleolin | 1,583 | | |
| Caldesmon | 1,566 | | |
| Nucleobindin-1 | 1,526 | | |
| 14-3-3 protein gamma | 1,525 | | |
| Heat shock protein HSP 90-alpha | 1,525 | | |

FIG. 59B

SYSTEM AND METHOD FOR APPLYING PULSED ELECTROMAGNETIC FIELDS

TECHNICAL FIELD

The present disclosure relate to systems and methods for applying pulsed electromagnetic fields (PEMFs) to cells.

BACKGROUND

Pulsed Electromagnetic Fields (PEMFs) have been shown to promote the healing of skeletal bone non-unions and fractures that are otherwise resistant to conventional means of therapy. Typically, a PEMF generator is used to create a high magnetic flux penetration into hard and soft tissues for treatment of a variety of conditions, including fractures and osteoporosis, to achieve an anticipated shorter healing and rehabilitation time. PEMF waveforms typically consist of time-variant magnetic pulses of irregular and non-uniform signal parameters in the Hz range. However, waveforms of this type do not effectively activate cells or tissues.

Current systems and techniques for applying PEMFs to subject tissues fail to recognize, understand, or contemplate the actual manner(s) in which target tissues respond to applied PEMF signals, and/or the time and amplitude regimes within which target tissues remain responsive or become progressively more unresponsive or are substantially nonresponsive to applied PEMF signals. For example, bone and cartilage tissues are typically exposed to PEMFs for hours per day, on multiple consecutive days, which is unnecessarily long, undesirably frequent, less than optimal and/or possibly counterproductive.

A need therefore exists to provide systems and methods for applying pulsed electromagnetic fields (PEMFs) to cells that seek to address the above problem.

SUMMARY

According to a first aspect, there is provided a system for applying a pulsed electromagnetic field (PEMF) to a cell, comprising: a sensor for obtaining a characteristic of the cell; a memory module having stored therein a plurality of characteristics and EMF efficacy window data, each characteristic having its corresponding EMF efficacy window data; a pulse generator coupled to a set of PEMF coils and configured to generate an output of electrical pulses to drive the set of PEMF coils; and a controller in communication with the sensor, the memory module and the pulse generator, wherein the controller is configured to: retrieve, from the memory module, the EMF efficacy window data that corresponds to the characteristic of the cell obtained by the sensor; and control the output of the pulse generator based on the retrieved EMF efficacy window data such that the set of PEMF coils apply a PEMF in accordance with the EMF efficacy window data.

The EMF efficacy window data may comprise PEMF signal parameters. The PEMF signal parameters may comprise one of more of: amplitude, frequency, symmetry, field gradient, uniformity, direction and duration of the PEMF that is emitted by the set of PEMF coils.

The plurality of characteristics may comprise a type of the cell, and the cell may be part of a tissue. In such a case, the sensor may be a tissue sensor capable of detecting a type of the tissue.

The system may further comprise an amplifier that is in communication with the pulse generator. The amplifier may be configured to support the frequency range of the PEMF signal.

The memory module may further have stored therein data relating to a plurality of PEMF regimens, each characteristic having its corresponding PEMF regimen, wherein the data relating to the plurality of PEMF regimens may comprise a minimum time period between successive PEMF application sessions and/or a maximum number of PEMF application sessions within a certain amount of time.

The system may further comprise an identification module for obtaining an identity of the cell, the memory module further having stored therein a PEMF application history of an identified cell/tissue/subject relating to at least one previous application of PEMF to the identified cell/tissue/subject. The controller may be further configured to control the output of the pulse generator based on the PEMF exposure history of the identified cell/tissue/subject for a subsequent application of PEMF to the identified cell.

The system may further comprise a detector for detecting the response from the cell after a first application of PEMF. The controller may be further configured to control the output of the pulse generator based on the detected response from the cell/tissue/subject for a second subsequent application of PEMF to the cell.

According to a second aspect, there is provided a method of modulating a pre-selected target cell type using a directional pulsed electromagnetic field (PEMF) comprising: applying a directional PEMF in a specific direction to the cell for a predetermined duration at a predetermined field strength to modulate the target cell type. The pre-selected target cell type may be one or more cell types.

The modulation of a target cell may be selected from the group consisting of one or more behavior of cell proliferation, cell growth inhibition, cell cycle arrest, cell differentiation, cell death, cell force generation, activation or quenching of cellular metabolism and regulation of gene and/or protein expression.

The pre-selected target cell may be a cell selected from the group consisting of a stem cell, a muscle cell, a bone cell, a skin cell, hematopoietic cell, a fat cell and a cartilage cell. The stem cell may be selected from the group consisting of a satellite cell or myoblast, a mesenchymal stem cell (MSC), a chondrocyte and an osteoblast.

The modulation of the cell may be mediated by transient receptor potential channel 1 (TRPC1) and/or in combination with TRPV channels.

According to a third aspect, there is provided a method of accelerating myogenesis, comprising: applying a directional PEMF to a myoblast, wherein the PEMF is applied for 10 minutes, at a field strength of 1.5 mT, and wherein the directional PEMF is applied orthogonal to the long axis of the myoblast.

According to a fourth aspect, there is provided a method of regenerating muscle in a subject, the method comprising: applying a directional PEMF to a muscle cell of the subject, wherein the PEMF is applied for about 10 minutes, at a field strength of about 1.5 mT to 3 mT and wherein the directional PEMF is applied orthogonal to the long axis of the muscle cell. The subject may be immobile and may suffer from muscle disuse, and/or may be undergoing rehabilitation subsequent to a period of injury, exercise, disease, surgery, immobilization, hospitalization, depression, is aged, or suffering from a degenerative muscle condition or combinations thereof. The method may increase muscle regeneration after exercise in a healthy subject.

According to a fifth aspect, there is provided a method of modulating a pre-selected target cell type using a directional pulsed electromagnetic field (PEMF) comprising: applying a directional PEMF to the cell using the system according to the first aspect, wherein said target cell type is modulated by the directional PEMF and wherein a cell type other than the target cell type is not modulated by the directional PEMF at that PEMF amplitude outside of its EMF efficacy window.

According to another aspect, there is provided a method of modulating skeletal muscle in a subject, the method comprising: applying a directional PEMF to a skeletal muscle cell of the subject, wherein the PEMF is applied for about 10 minutes, at a field strength of about 1.5 mT and wherein the direction of the PEMF is orthogonal to the longest axis of the skeletal muscle cell. The method may regenerate skeletal muscle in a subject.

According to another aspect, there is provided a method of modulating cardiac muscle in a subject, the method comprising: applying a directional PEMF to a cardiac muscle cell of the subject, wherein the PEMF is applied for about 10 minutes, at a field strength of about 3 mT and wherein the direction of the PEMF is orthogonal to the longest axis of the cardiac muscle cell. The method may promote metabolic stabilization and oxidative stress resistance in a subject.

According to another aspect, there is provided a method of modulating lymphocytes in a subject, the method comprising: applying a directional PEMF to a lymphocyte of the subject, wherein the PEMF is applied for about 10 minutes, at a field strength of about 2 mT. The method may regenerate or activate cytokine production by lymphocytes in a subject.

According to another aspect, there is provided a method of modulating mesenchymal stem cells (MSC) in a subject, the method comprising: applying a directional PEMF to a MSC of the subject, wherein the PEMF is applied for about 10 minutes, at a field strength of about 3 mT and wherein the direction of the PEMF is orthogonal to the long axis of the MSC. The method may regenerate MSC in a subject.

According to another aspect, there is provided a method of modulating chondrocytes in a subject, the method comprising: applying a directional PEMF to a chondrocyte of the subject, wherein the PEMF is applied for about 10 minutes, at a field strength of about 2 mT and wherein the direction of the PEMF is orthogonal to the long axis of the chondrocyte. The method may regenerate chondrocytes in a subject.

According to another aspect, there is provided a method of modulating browning adipocytes in a subject, the method comprising: applying a directional PEMF to a browning adipocyte of the subject, wherein the PEMF is applied for about 10 minutes, at a field strength of about 1 mT and wherein the direction of the PEMF is orthogonal to the long axis of the browning adipocyte. The method may regenerate browning adipocytes in a subject.

According to another aspect, there is provided a method of modulating smooth muscle cells of a subject, the method comprising: applying a directional PEMF to a smooth muscle cell of the subject, wherein the PEMF is applied for about 10 minutes, at a field strength of about 3 mT and wherein the direction of the PEMF is orthogonal to the long axis of the smooth muscle cell. The method may induce quiescence or cell cycle withdrawal in smooth muscle cells in a subject.

According to another aspect, there is provided a method of producing conditioned media from a cell, the method comprising: applying a directional PEMF to a cell cultured in a cell culture media.

BRIEF DESCRIPTION OF THE DRAWINGS

Embodiments of the disclosure will be better understood and readily apparent to one of ordinary skill in the art from the following written description, by way of example only, and in conjunction with the drawings, in which:

FIGS. 1B-1D illustrate representative PEMF signal characteristics, including PEMF burst and PEMF pulse characteristics, and corresponding PEMF signal parameters, in accordance with an embodiment of the present disclosure.

FIGS. 2A-2E illustrate aspects of representative PEMF application coil configurations in accordance with particular embodiments of the present disclosure.

FIG. 2G shows a representative user interface in accordance with an embodiment of the present disclosure.

FIG. 4B is an exemplary PEMF signal parameter database which can be utilized as a look-up table in accordance with an embodiment of the present disclosure.

FIG. 59B shows regenerative trophic factors released by MSCs in response to PEMF stimulation.

DETAILED DESCRIPTION

Figure 1A:
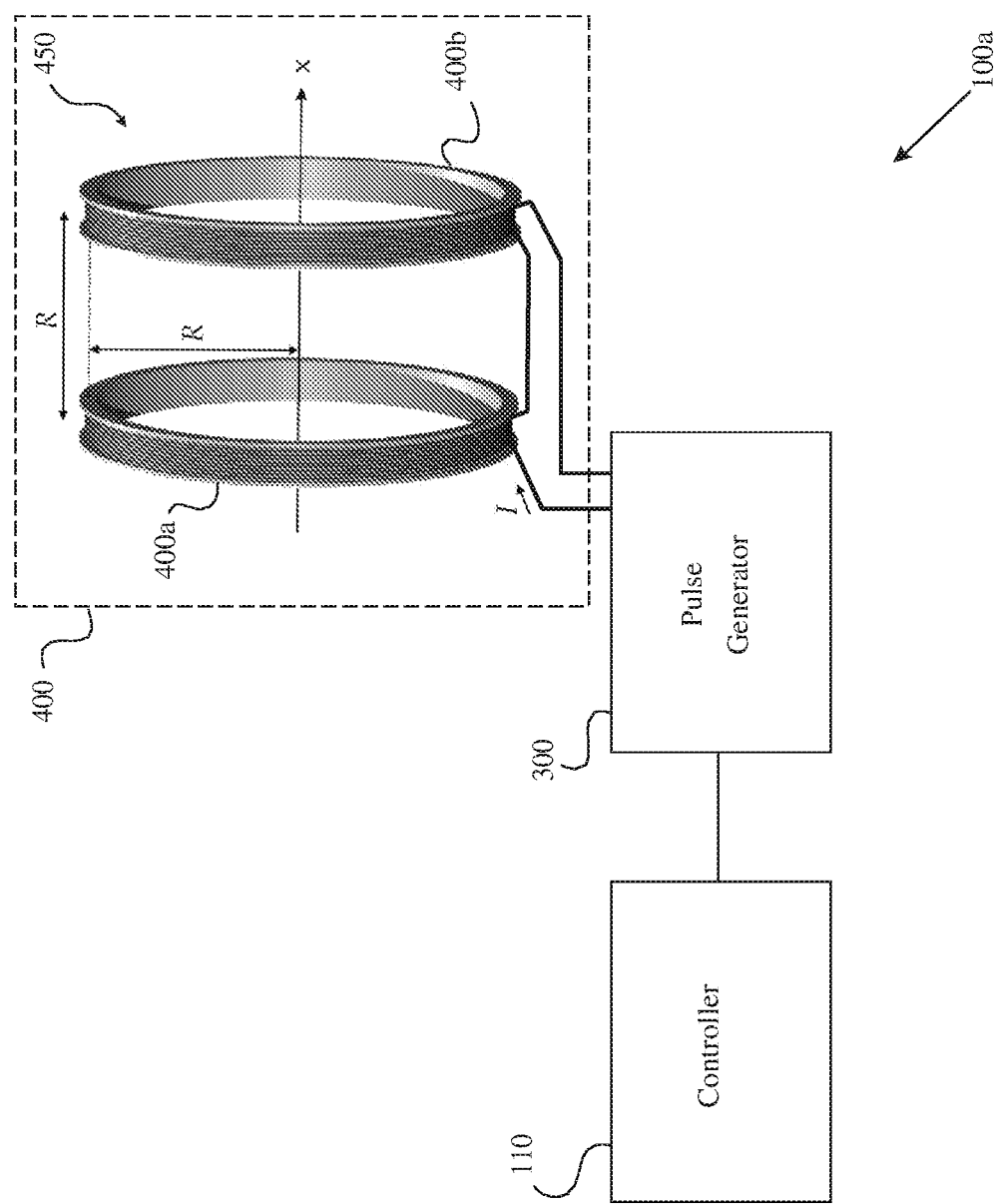
FIG. 1A is a schematic illustration showing portions of a pulsed electromagnetic field (PEMF) application system in accordance with an embodiment of the present disclosure.

In the present disclosure, depiction of a given element or consideration or use of a particular element number in a particular FIG. or a reference thereto in corresponding descriptive material can encompass the same, an equivalent, or an analogous element or element number identified in another FIG. or descriptive material associated therewith.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The use of "/" in a FIG. or associated text is understood to mean "and/or" unless otherwise indicated. The recitation of a particular numerical value or value range herein is understood to include or be a recitation of an approximate numerical value or value range, for instance, within +/−20%, +/−15%, +/−10%, +/−5%, or +/−0%. With respect to recitations herein directed to dimensional or numerical comparisons or equivalence, reference to the terms "generally," "approximately," or "substantially" is understood as falling within +/−20%, +/−15%, +/−10%, +/−5%, or +/−0% of a representative/example comparison, or a specified or target value or value range; and reference to the term "essentially" is understood as falling within +/−10%, +/−5%, +/−2%, +/−1%, or +/−0% of a representative/example comparison, or a specified or target value or value range.

As used herein, the term "about", in the context of PEMF field strength, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions (for instance, in a manner corresponding to that described in An Introduction to Mathematical Reasoning: Numbers, Sets, and Functions, "Chapter 11: Properties of Finite Sets" (e.g., as indicated on p. 140), by Peter J. Eccles. Cambridge University Press (1998)). In general, an element of a set can include or be a system, an apparatus, a device, a structure, an object, a process, a physical parameter, or a value depending upon the type of set under consideration.

In one aspect, there is provided a method of modulating a pre-selected target cell type using a directional pulsed electromagnetic field (PEMF) comprising: applying a directional PEMF in a specific direction to the cell for a predetermined duration at a predetermined field strength. Application of the PEMF may be restricted to a predetermined period of time between each application and/or to a predetermined number of applications within a certain amount of time. A predetermined period of time between each PEMF exposure or application session may be 1 day, 2 days, 3 days, 4 days, 5 days, 6 days, 7 days, 8 days, 9 days, 10 days, 11 days, 12 days, 13 days or 14 days. In one example, a directional PEMF in a specific direction is applied to a cell for a predetermined duration at a predetermined field strength, wherein the PEMF application is restricted to a predetermined period of time of between 3 to 4 days imposed between exposure sessions to modulate the target cell type.

As used herein, the terms "modulating" or "modulation" with respect to a cell or cell type, refer to the alteration of one or more characteristics of a cell. Characteristics of a cell that may be modulated include physiological and/or biochemical characteristics such as cell proliferation, cell growth inhibition/quiescence, cell cycle arrest, cell differentiation, cell death, regulation of gene and/or protein expression and production of factors, such as extracellular matrix (ECM) components, trophic, anti-inflammatory and inflammatory factors, exosomes and microvesicles.

In other words, the modulation of a cell or cell type by PEMF may have regenerative and/or degenerative effects. Regenerative effects include but are not limited to accelerated cell cycle, increased protein synthesis, decreased apoptosis whilst degenerative effects include but are not limited to cell cycle withdrawal, decreased protein synthesis, pro-apoptosis.

PEMF may also modulate a cell or cell type by activating cellular pathways such as pathways that stimulate mitochondrial respiration, for example, production of reactive oxygen species (ROS), increased fatty acid oxidation, enhanced caloric expenditure, as well as pathways involved in cytokine/myokine release, for example, reduced inflammation in response to stress and disease that potentiates systemic regeneration.

In one example, a muscle cell may be modulated to stimulate proliferation. In another example, a muscle progenitor cell such as a myoblast may be modulated to stimulate myogenic differentiation. In yet another example, a cell may be modulated to alter the expression of one or more epigenetic factors. The alteration of the expression of one or more epigenetic factors may in turn regulate the expression of one or more genes and/or proteins. It will generally be understood that modulation of a cell or cell type may involve the alteration of one or more of the above mentioned characteristics.

In one example, a stem cell may be modulated to direct differentiation of the stem cell towards a particular lineage by applying a directional PEMF for a pre-determined duration and at a pre-determined field strength to the stem cell that is specific for the lineage. In another example, a stem cell may be modulated to direct differentiation of the stem cell towards a particular lineage by applying a directional PEMF for a pre-determined duration and at a pre-determined field strength wherein the directional PEMF, pre-determined duration and pre-determined field strength mimics a mechanical environment specific for the lineage.

In another example, a stem cell such as a mesenchymal stem cell (MSC) may be modulated to proliferate. In another example, a MSC may be modulated to condition the media in which it is cultured in. It will generally be understood to one of skill in the art that a cell may "condition" the media in which it is cultured in by secreting factors into the media. It will also be generally understood that the conditioned media can be collected and used for subsequent applications such as analysis, protein extraction and cell culture.

In one example, a MSC may be modulated by PEMF to secrete extracellular matrix (ECM) components and/or down regulate levels of ECM-degradation enzymes. In another example, a MSC may be modulated by PEMF to secrete trophic factors, or anti-inflammatory factors or inflammatory factors or a combination thereof. In yet another example, a MSC may be modulated by PEMF to secrete exosomes and/or microvesicles. It will be generally understood that a MSC may be modulated by PEMF to secrete one or more of the above mentioned factors either alone or in combination.

As used herein, the term "pre-selected target cell type" refers to one or more cells, cell types or tissues to be modulated. Suitable examples of a pre-selected target cell type include a stem cell, a muscle cell, a bone cell, a skin cell and a cartilage cell.

"Stem cell" refers to a totipotent, pluripotent or multipotent progenitor cell. A stem cell may be selected from embryonic stem cells (ESC), induced pluripotent stem cells (iPSC), mesenchymal stem cells (MSC) and progenitor cells of a tissue, such as myoblasts, osteoblasts and chondroblasts. In a preferred embodiment, the stem cell is a myoblast or satellite cell.

The term "muscle cell" and "myocyte" may be used interchangeably to refer to any type of muscle cell, including a skeletal muscle cell, a cardiac muscle cell or a smooth muscle cell. It will be generally understood that a muscle cell is derived from myoblasts, or satellite cells, through the process of myogenesis.

The term "bone cell" refers to any type of bone cell including osteoclasts, osteoblasts, osteocytes and bone lining cells. It will be generally understood that osteocytes are derived from osteoblasts.

The term "cartilage cell" refers to any cell of the cartilage including chondroblasts, chondrocytes or chondrogenically-directed cells derived from stem cells.

A pre-selected target cell type may be one or more cells of the same lineage, one or more cell types within a given tissue, one or more cell types in different tissues. For example, a pre-selected target cell type may be one or more myoblasts. In another example, a pre-selected target cell type may be one or more myoblasts and one or more osteoblasts. In yet another example, a pre-selected target cell type may be one or more myoblasts and one or more myocytes.

A suitable pre-selected target cell type that may be modulated is one that is situated in vivo in a subject or in vitro as a primary cell culture or a continuous/immortalized cell line. Examples of a subject include but are not limited to a primate, a mouse, a rat, a guinea pig, a rabbit, a dog or livestock. In a preferred embodiment, the subject is a human or livestock. The cell culture may be an adherent cell culture or a suspension cell culture. The cell may be from a human, a bovine, a canine, a murine, a rat, a fish, a rabbit or monkey cell culture line. In a preferred embodiment, the cell is a C2C12 or primary mammalian myoblast.

In one aspect, the present invention provides a method of regenerating muscle in a subject, the muscle comprising applying a directional PEMF to muscle cell, wherein the PEMF is applied for between 5 to 15 minutes, at a field strength of about 1 mT to about 3 mT. It will be generally understood to one of skill in the art that longer exposure durations may be employed if the directionality of the applied field is not optimal for the alignment of the tissue in question. In this manner the empirically determined electromagnetic efficacy window (EMF efficacy window or here, EEW) will be changed in accordance with the direction of the applied PEMF and orientation of the tissue or cell being targeted. In the following description, "direction"/"directionality" refers to a direction of a PEMF, while "orientation" refers to an orientation of a cell/tissue/organ/subject, etc. In a preferred embodiment, the PEMF is applied for 10 minutes, at a field strength of about 1.5 mT and the PEMF is applied in a direction that is orthogonal to the long axis of the muscle cell.

The method of muscle regeneration as disclosed herein may be used in a subject that is immobile and suffers from muscle disuse, and/or is undergoing rehabilitation subsequent to a period of injury, disease, surgery, immobilization, hospitalization, depression, is aged, or suffering from a degenerative muscle condition, or combinations thereof. The subject may be completely immobile, for example, the subject may be bedridden, or suffering from paralysis, or partially immobile, for example, the subject may be unable to move one or more parts of the body. In one example, the subject may be suffering from muscular dystrophy or from disease or damage of the peripheral nervous system controlling the muscle.

The method of muscle regeneration as disclosed herein may also be used to increase muscle regeneration after exercise in a healthy subject.

The skilled person would be able to envisage that the method of the present invention may be used in any situation where muscle regeneration is desired.

As used herein, the term "accelerating myogenesis" refers to enhancing the formation of muscle cells. Acceleration of myogenesis includes an increase in the rate of differentiation of myocytes from myoblasts, an increase in the rate of muscle cell proliferation, and a decrease in the rate of cell death.

Embodiments in accordance with the present disclosure are directed to systems, apparatuses, devices, processes, and procedures for selectively applying or delivering low amplitude, extremely low frequency (ELF) pulsed electromagnetic fields (PEMFs) to (a) target tissues of human or animal subjects; (b) in vitro or ex vivo target tissues (e.g., target tissues grown in vitro); and/or (c) target tissues or cells that can be incorporated or implanted into human or animal subjects. The amplitude of the PEMFs is sufficiently low that the PEMFs are sub-threshold with respect to triggering neuronal action potentials, cause contraction of skeletal, smooth or cardiac muscle or any cellular contraction on an acute timescale, e.g. 20 minutes to a few hours.

For purpose of simplicity and brevity, in the context of the present disclosure the application of PEMFs to target tissues encompasses the application of PEMFs to a single tissue or cell type or multiple tissue or cell types at one or more locations, for instance, at least one anatomical region or location corresponding to, forming, or within a specific subject body part (e.g., an appendage) and/or within a given organ being exposed to the fields. The PEMFs are applied to such target tissues in accordance with particular types of PEMF signal characteristics or parameters and exposure period/electromagnetic energy dosing conditions, paradigms, or protocols, using particular types of PEMF coil configurations, as further detailed below.

The application PEMFs to target tissues in accordance with embodiments of the present disclosure can give rise to biological effects in (a) the target tissues; (b) tissues sharing direct biological communication pathways (e.g., paracrine diffusible gaseous, protein (including extracellular matrix components), exosomal or other biochemical factors and/or bioelectrical communication pathways) with the target tissues; and/or (c) other tissues wherein biological processes occur that are mediated/modulatable/modulated by biological processes within the target tissues. Such biological effects can effectively or substantially match, mimic, simulate, initiate, or give rise to biological mechanotransductive processes because of PEMFs generated in accordance with embodiments of the present invention can preferentially, selectively, or specifically affect, target, recruit, activate, or modulate certain transient receptor potential (TRP) channels in the target tissues to which the PEMFs are applied, and in particular, TRP-C or TRP-V (TRPC1 and TRPV2, in particular) cation channels, either alone, in synergistic combination, or any TRP channel cross-modulating the activity of another TRP channel responsive to the fields, which are mechanosensitive/mechano-gated cation channels. This preferential, selective, or specific recruitment or activation of TRPC1/V2 channels in the target tissues can facilitate the activation of cellular processes downstream of/external to the target tissues, which are mediated, activated, or modulated as a result of processes associated with mechanotransduction that occur in the target tissues.

Without being bound by theory, it is believed that the sensitivity of a cell or tissue to PEMF and sensitivity of a cell or tissue to modulation by PEMF, is mediated by transient receptor potential C1 channels (TRPC1) and/or in combination with TRPV channels, which contributes to the inherent mechanosensitivity of the cell or tissue.

Figure 20A:
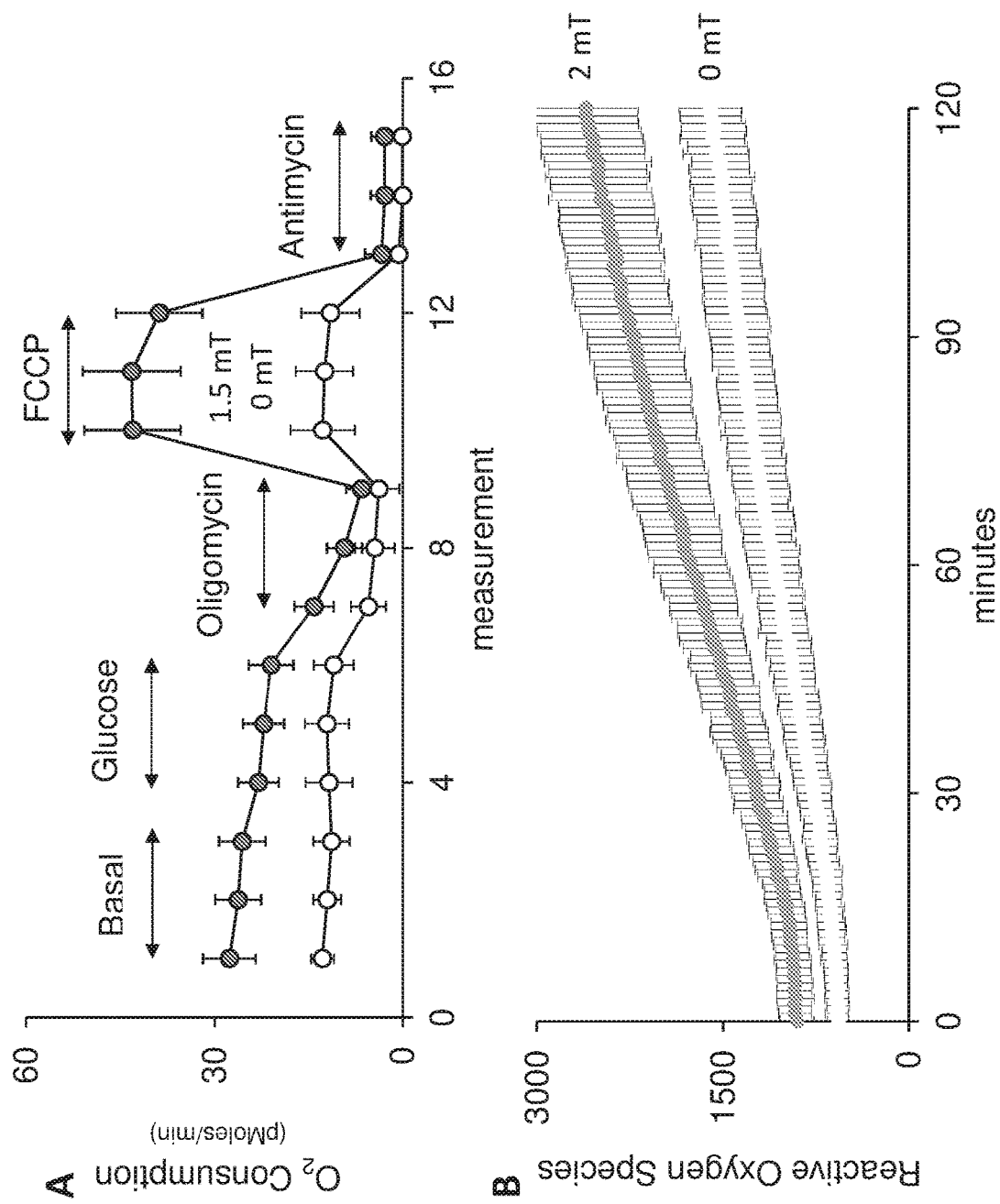
FIG. 20A shows that PEMF-induced TRPC1-mediated calcium entry in myoblasts increases oxygen consumption rate (OCR) and reactive oxygen species (ROS) production.
Figure 20B:
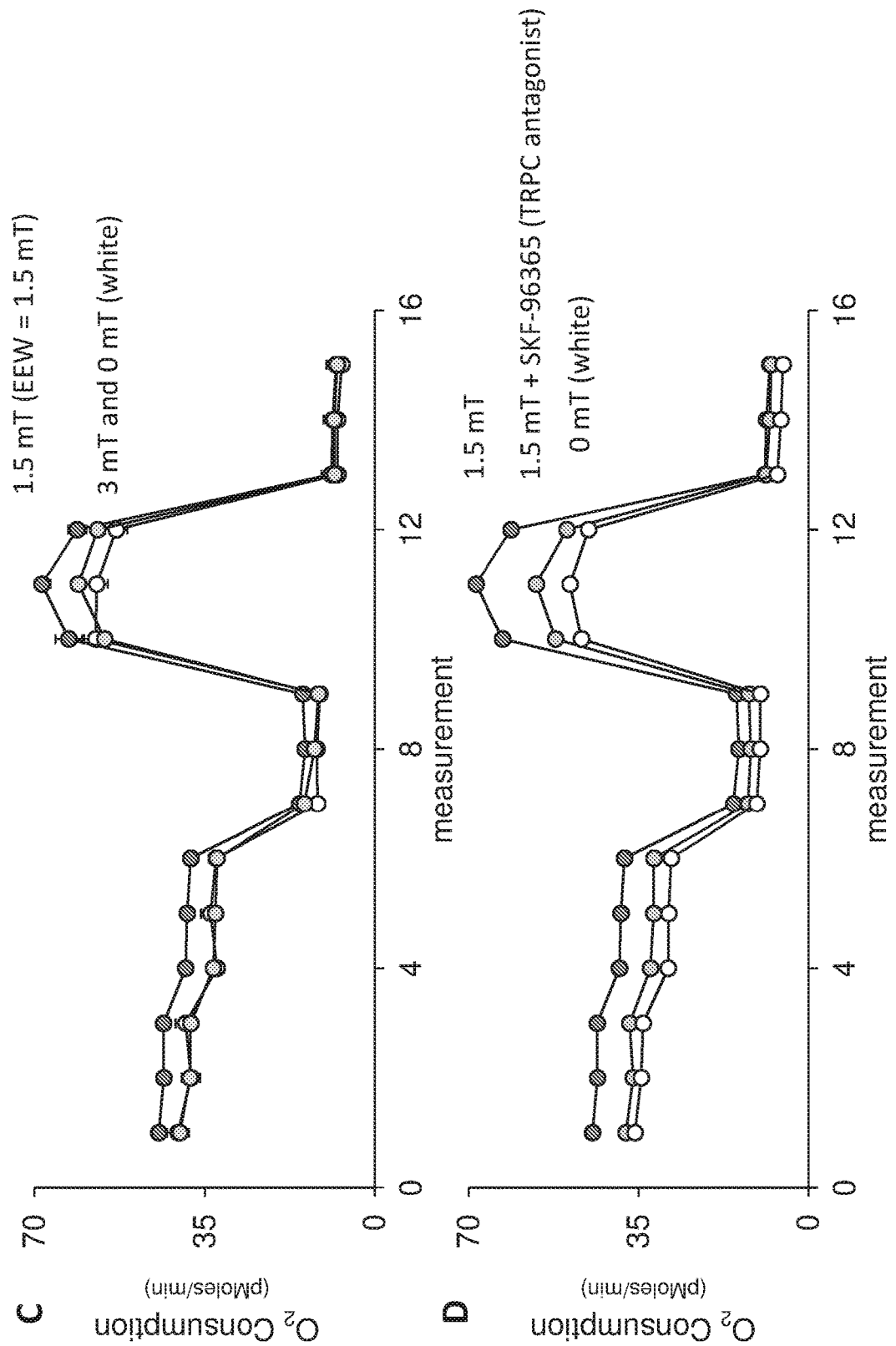
FIG. 20B shows that PEMF-induced TRPC1-mediated calcium entry in myoblasts increases oxygen consumption rate (OCR) and reactive oxygen species (ROS) production.
Figure 23:
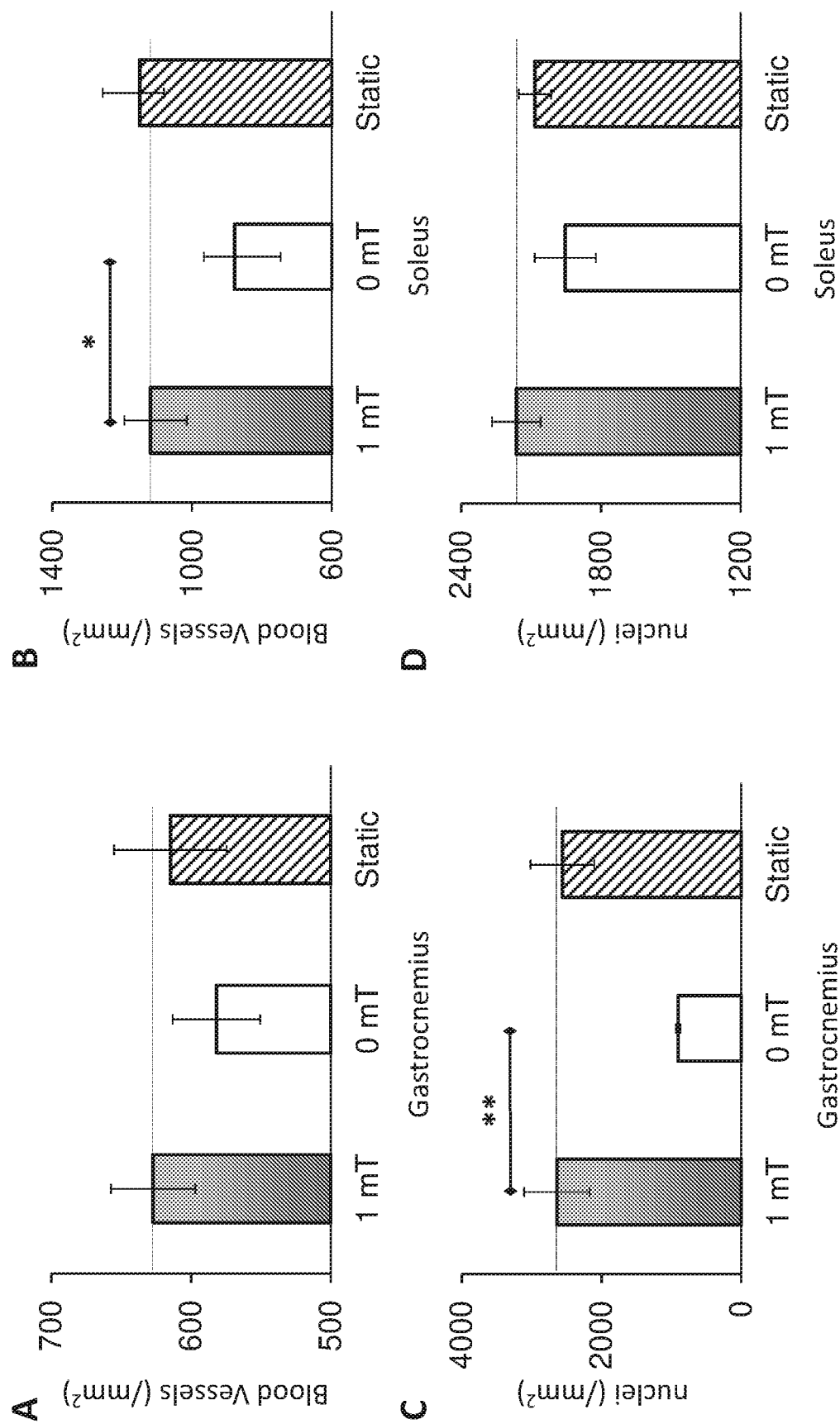
FIG. 23 shows that PEMF exposure induces angiogenesis principally in oxidative muscle when applied near the EMF efficacy window of skeletal muscle.
Figure 33:
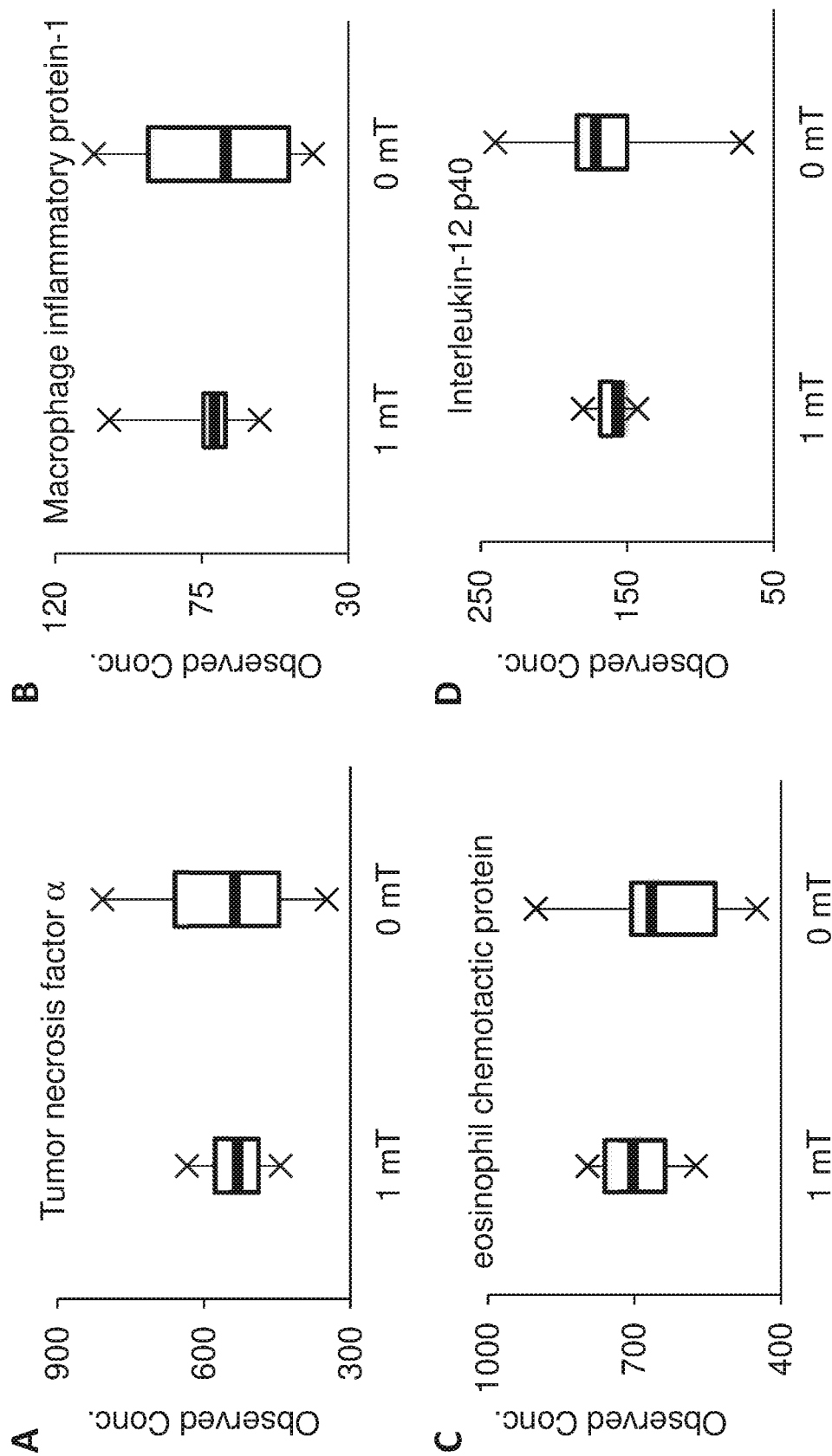
FIG. 33 shows that PEMFs protect against systemic inflammation.
Figure 37:
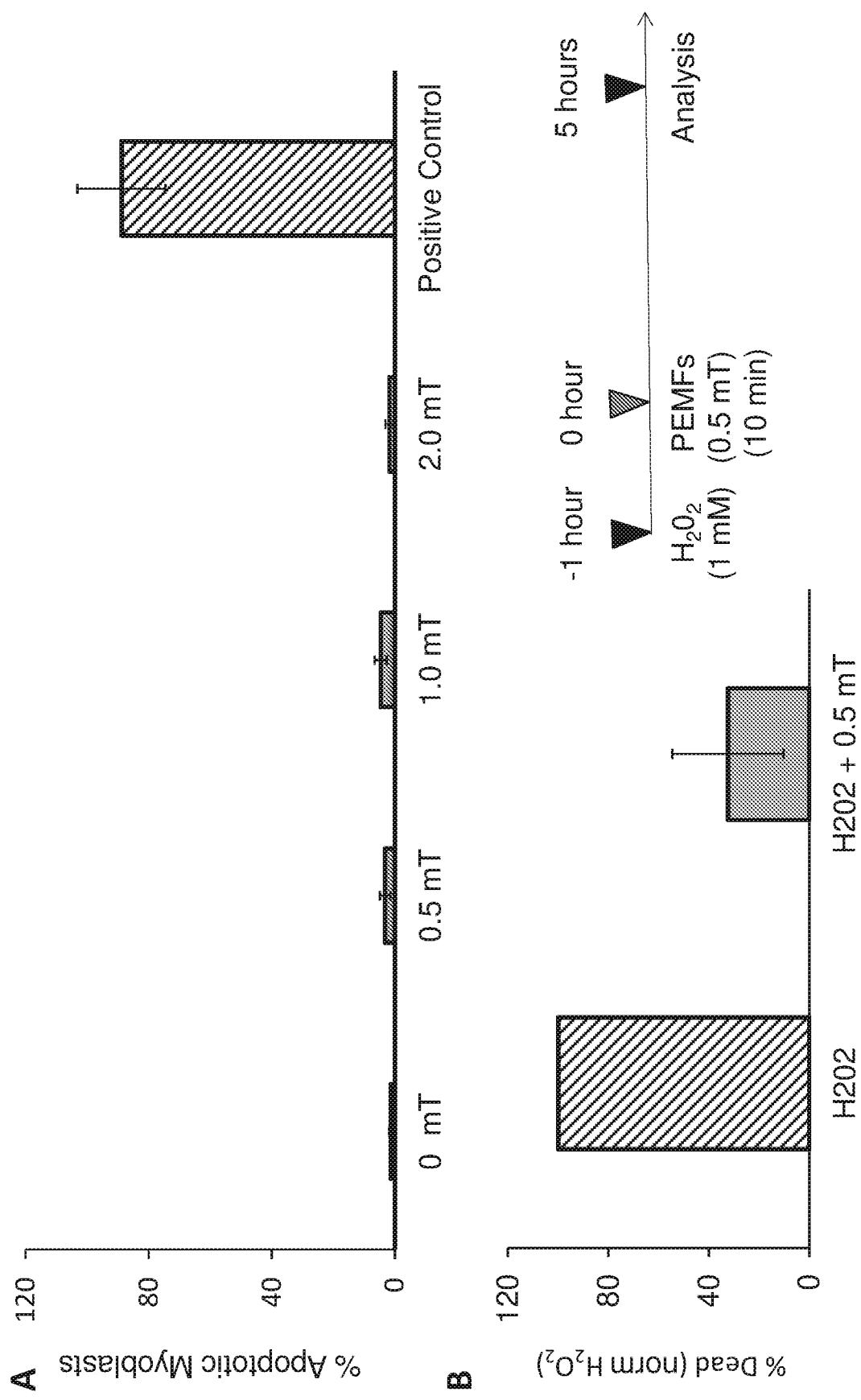
FIG. 37 shows that PEMF exposure does not increase resting apoptosis (top) and is able to protect against apoptosis in response to apoptotic stimuli (below).
Figure 38:
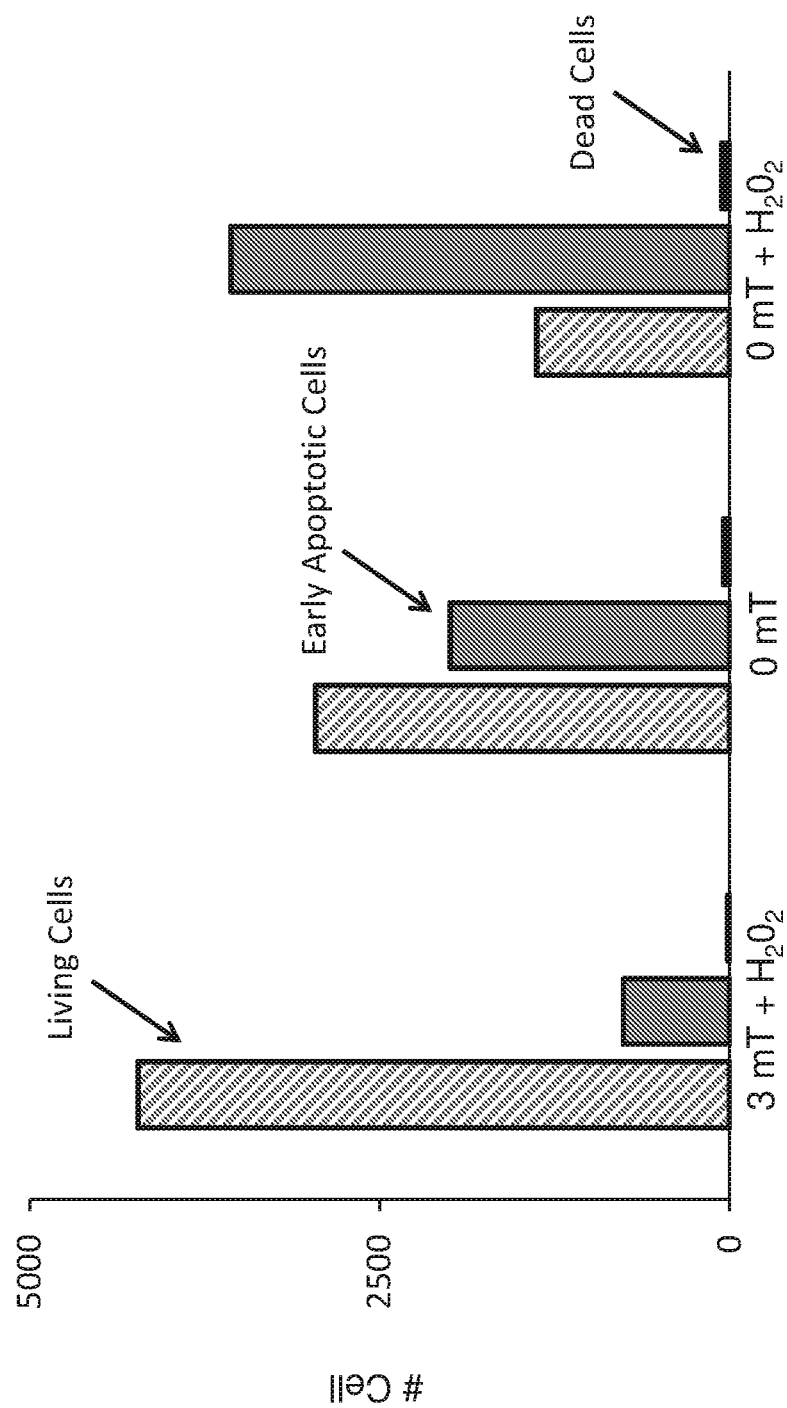
FIG. 38 shows that pre-Exposure of cardiac myocytes to their EMF Efficacy Window (3 mT for 10 minutes) protects against oxidative damage.
Figure 42:
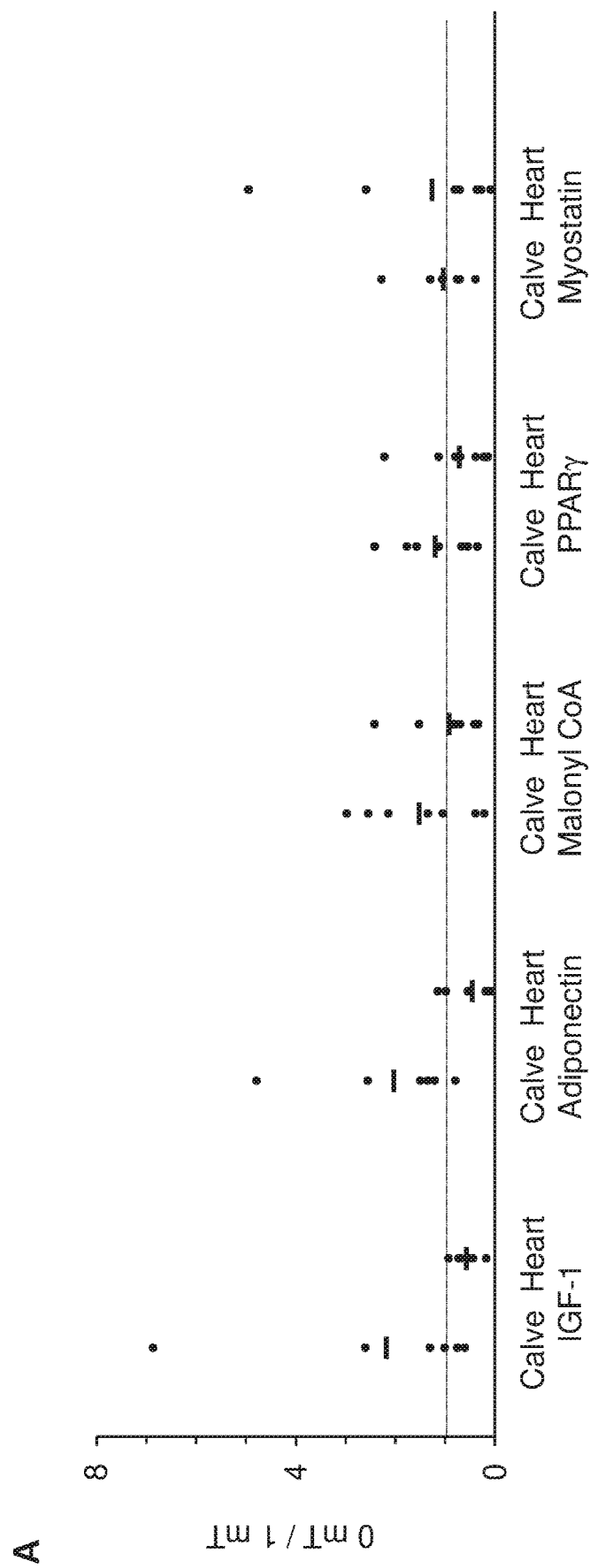
FIG. 42 shows that PEMFs at the EMF Efficacy window of muscle has a cardioprotective effect as indicated by the upregulation of the indicated genes.
Figure 54:
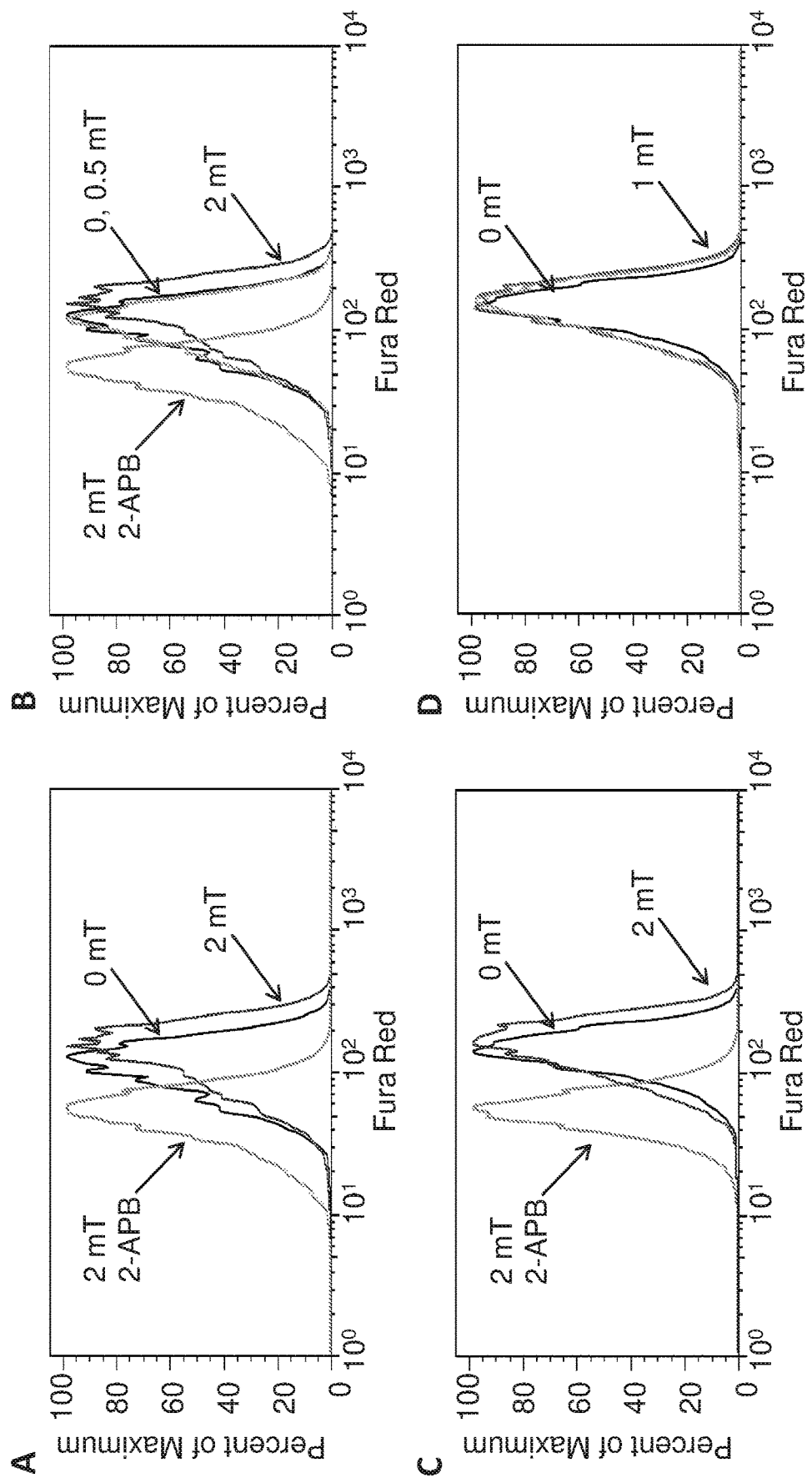
FIG. 54 shows that PEMFs stimulate calcium entry in Jurkat T Cells and follows their EMF efficacy window of 2 mT for 10 minutes.
Figure 56:
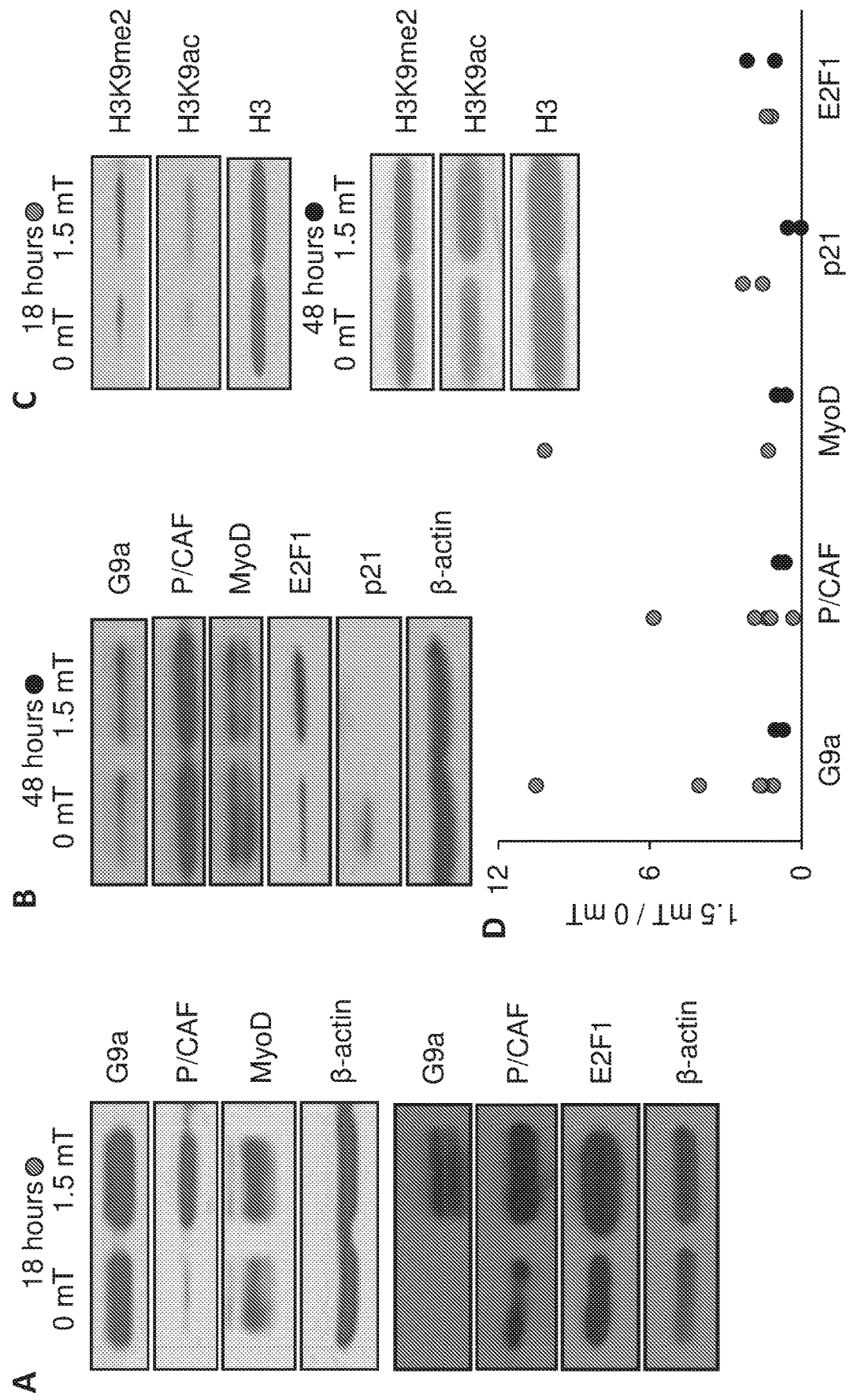
FIG. 56 shows that PEMF exposure at the EMF efficacy window of skeletal muscle progenitor cells produces epigenetic changes that reflect overall acceleration of myogenesis.
Figure 67:
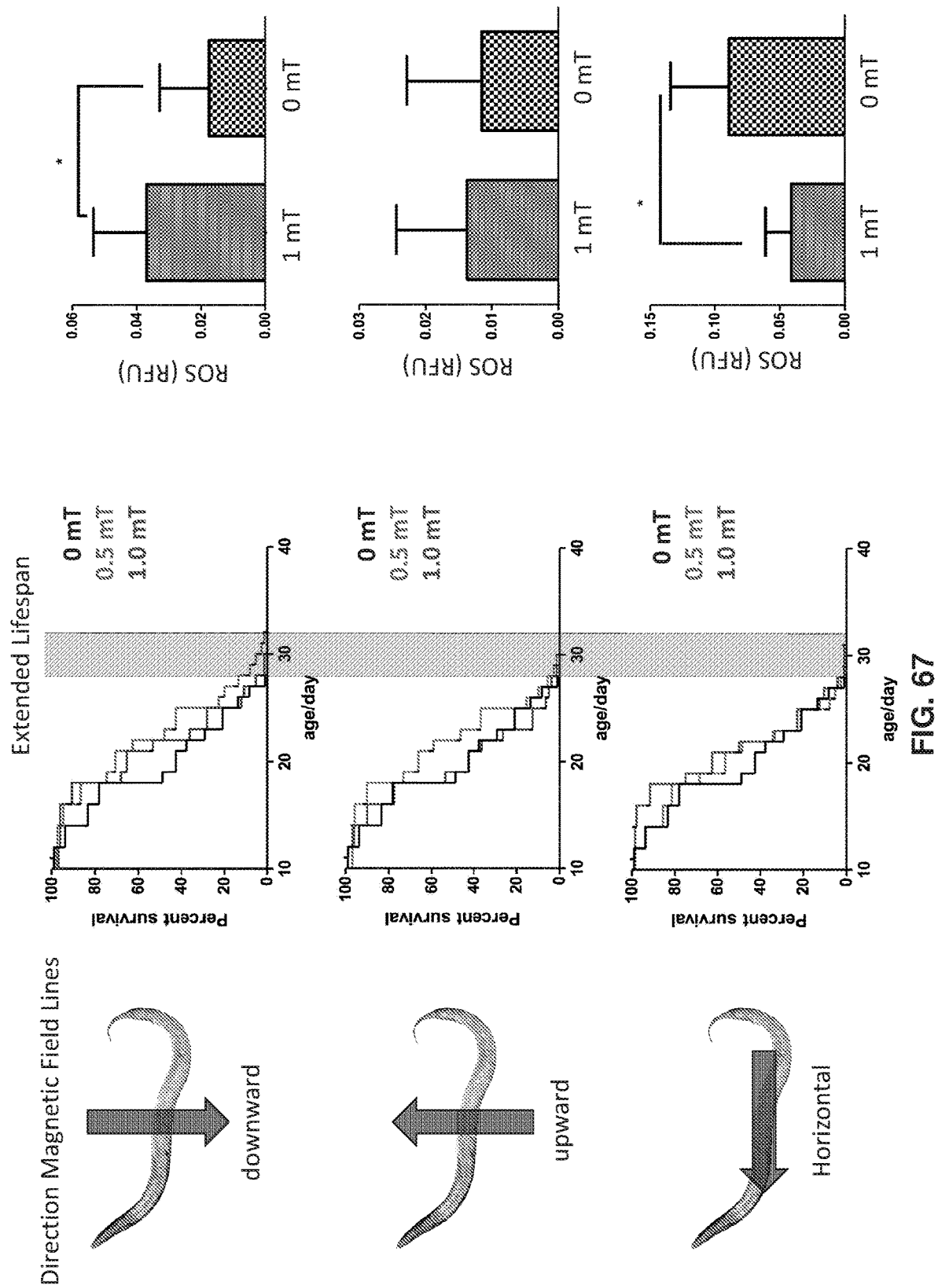
FIG. 67 shows lifespan extension in C. elegans correlated field orientation and ROS production.

Direct or indirect biological effects that can arise as a result of exposing target tissues to PEMFs in accordance with embodiments of the present disclosure include at least some of the following:

(a) the synthesis, development, structural maintenance, and/or regeneration of mechanosensitive tissues or constituents/components thereof (e.g., by way of myogenesis in skeletal as well as other types of muscle tissues, such as cardiac and vascular tissues; osteogenesis; or chondrogenesis) and in such capacity provide a manner to offset the age- or disease-related degenerative effects of sarcopenia, osteopenia, osteoporosis, osteoarthritis, degenerative joint disease or forestall frailty observed with advanced aging;

(b) mitochondrial biogenesis and respiratory capacity (FIGS. 19, 20A, 20B, and 21);

(c) enhanced oxidation of fatty acids (FIGS. 16, 19, 25-27, 31 and 32);

(d) induction angiogenesis in health and disease (FIG. 23);

(e) anti-cachexia effects (FIGS. 15 to 18);

(f) immunogenic effects (e.g., immunoregulatory/immunomodulatory/immunostimulatory effects) (FIG. 54);

(g) anti-inflammatory effects (FIG. 33);

(h) homeostasis regulation effects (FIG. 38);

(i) cellular antioxidant defense expression effects (FIGS. 37-38);

(j) hormesis-related reactive oxygen species (ROS) expression effects (e.g., as a result of PEMF-mediated calcium entry that activates the production of ROS which have a hormesis-like effect, in that such ROS upregulate cellular antioxidant defenses to thereby increase cellular or organism resistance to free radical attack) (FIGS. 20A-20B);

(k) cardioprotective effects (FIG. 42);

(l) neuroprotective and/or neurogenic effects (FIGS. 38-41);

(m) adipogenic browning effect (brite/beige transition) via the production of FND-C5 (precursor to Irisin), and the regulation of the production of adiponectin (FIGS. 19, 25, 26, 27, 42);

(n) upregulation or downregulation of specific biochemical metabolites (e.g., kynurenine downregulation);

(o) stem cell differentiation effects (FIGS. 34-40, 45, 46, 56);

(p) lifespan extension (FIG. 67);

(q) tissue-specific anti-proliferative effects (FIG. 48-51, 62A-D, 63);

(r) tissue-specific apoptosis (FIG. 48-51);

(s) epigenetic effects/alterations observed as with exercise (FIG. 56);

(t) improve immune response by stimulating the systemic production of certain interleukins via their capacity to produce a slight inflammatory response (IL-6) similar to the effects of exercise and possibly other effects (FIG. 33, 41) and by activating calcium entry via immune cells (FIG. 54). Such effects can be referred to as PEMF signal exposure effects;

(u) mitigate systemic response to stress (FIG. 33).

In view of the above biological or PEMF exposure effects, depending upon the type of target tissues to which PEMFs generated in accordance with embodiments of the present disclosure are applied, and the magnetic field density dose delivered to the target tissues, the biological effects resulting from the application of the PEMFs to the target tissues can be categorized as (a) regenerative cellular effects or cytoprotective effects (e.g., myogenesis, osteogenesis, chondrogenesis, mitochondrial biogenesis, angiogenesis effects, cardioprotective effects, neuroprotective effects and anti-oxidative stress effects); or (b) degenerative cellular effects (e.g., anti-proliferative or apoptosis effects).

The aforementioned mechanosensitive tissues include various progenitor or stem cell classes (e.g., myoblasts, mesenchymal stem cells, chondrocytes, intervertebral disc stem cells, tenocytes, adipocytes, or osteoblasts), differentiated muscle tissue (e.g., skeletal muscle), vascular smooth muscle tissue, bladder smooth muscle tissue, cardiac tissue, bone, cartilage, tendons, ligaments, and/or collagen or other extracellular matrix components deposited from mechanosensitive cell types or secreted (by exocytosis or other cellular pathway) from the tissue in freely soluble form, associated with binding/transport protein(s), or in vesicular form as exosomes, microvesicles or multivesicular bodies. In various embodiments, the target tissues include or are mechanosensitive tissues, for instance, particular skeletal muscles, joints, tendons, ligaments, bones, portions of the spine, portions of the pelvis, portions of the thorax, the heart, bladders, and/or skin areas. The target tissues can additionally or alternatively include or be other tissues (e.g., fatty tissues/fat deposits, or portions of the central and peripheral nervous systems including head, spine, and central and peripheral neuronal populations contained therein). In general, the target tissues to which PEMFs are directed in accordance with embodiments of the present disclosure can depend upon embodiment details, the type of subject under consideration and their current biological condition or state (systemic inflammatory and metabolic status), and/or a PEMF exposure, treatment, therapy, or intervention objective under consideration.

Furthermore, the application of the PEMFs to the target tissues gives rise to biological effects without requiring that the target tissues to undergo mechanical strain (although the target tissues can be exposed to physical stress or mechanical strain before, during, and/or after the application of PEMFs thereto, depending upon embodiment details, target tissues under consideration, or a PEMF exposure objective under consideration). For instance, for regenerative purposes the PEMFs are typically applied to the target tissues without imparting a mechanical strain per se (although a subset of the cellular pathway activated by mechanical forces are recruited by PEMFs) or producing a detrimental amount of additional physical/chemical stress to the target tissues during the application of the PEMFs thereto (e.g., the PEMFs can be applied to the target tissues while the subject is relaxed (e.g., inactive), generally relaxed, immobilized because of injury, illness or advanced age, or in a state of little or minimal physical exertion with respect to the target tissues under consideration). The PEMFs will not impede the healing of tissues in cases of clinical immobilization when movement may be restricted, prohibited or ill advised, but will instead enhance tissue mending as a result of muscle stimulation releasing trophic and regenerative agents (including inflammatory and anti-inflammatory agents) in freely soluble form or associated with binding/transport protein(s) (that may also be released from muscle in response to PEMF stimulation), in vesicular form as exosomes, microvesicles or multivesicular bodies, or in combination. Moreover, fat, bone, connective tissues, hematopoietic cell component (stem cell, macrophage, neutrophil, lymphocytes, etc), liver or other tissues once stimulated by the previously outlined factors that are released by skeletal muscle in response to PEMF stimulation at the EMF efficacy window of skeletal muscle may release secondary trophic factors and/or associated binding proteins, cytokines, inflammatory or anti-inflammatory agents or vesicular (exosomes, microvesicles or multivesicular bodies) population that themselves have regenerative properties.

PEMFs themselves embody a form of oxidative stress, stimulating the production of reactive oxygen species (ROS; FIGS. 20A and 20B). Low levels of oxidative stress and accompanying release of inflammatory factors can serve as a positive signal for adaptive tissue/cells growth and/or metabolic stabilization through a process of mito-hormesis or hormesis. Conversely, high levels of ROS can be damaging is surpassing the threshold for benefit and push the cell into the realm of damage. PEMFs may hence be employed to promote health (FIGS. 30-32), lifespan (FIG. 67), function (FIG. 24) and oxidative resilience (FIGS. 37-41) or to inhibit cell proliferation and promote apoptosis (FIGS. 48-51), either extreme being associated with a particular EMF efficacy window.

With respect to actual, likely/expected, partial, and/or potential mechanisms or pathways by which biological effects can arise as a result of the application of PEMFs to target tissues in accordance with embodiments of the present disclosure, the PEMFs can at least affect, mediate, recruit, modulate, or activate TRPC1 or TRPV2 channels and the passage of calcium ions therethrough (FIG. 55), which in turn can stimulate or increase the expression of (a) Insulin-like Growth Factor 1 (IGF-1); (b) peroxisome proliferator-activated receptor gamma coactivator 1-alpha (PGC-1a); (c) nitrous oxide synthase (NO); (d) fibronectin-type III domain-containing 5 (FND-C5) and/or (e) vascular endothelial growth factor (VEGF) as a result of the role that TRPC1/TRPV2 channels play in the activation, expression, modulation, or upregulation of IGF-1, PGC-1α, NO, FND-C5 and VEGF.

Such mechanisms or pathways can involve a set of target tissues to which PEMFs are being or have been applied, as well as tissues in biochemical communication with the target tissues (e.g., identical tissue type or other tissue classes that are biologically communicated via agents (trophic and regenerative agents in freely soluble form or in association with binding/transport protein(s), in vesicular form as exosomes, microvesicles or multivesicular bodies, or in combination) delivered through the blood stream or interstitial fluid to neighboring tissues responsive to biochemical changes in the target tissues, such as by way of downstream or serially activated biological processes).

Various embodiments in accordance with the present disclosure are additionally directed to systems, apparatuses, devices, and processes/procedures by which PEMFs having particular set or types of PEMF signal parameters defined by amplitude (mT), frequencies (Hz), symmetry (asymmetric or symmetric signal relative to baseline), field gradients (T/s rise and falls), directionality and uniformity of the applied field and duration (minutes) of exposure are applied to specific target tissues in accordance with a predetermined PEMF exposure set preferentially stimulating that tissue in question (hereby known as the electromagnetic (EMF) efficacy window (EEW window)), treatment, or therapy paradigm or regimen (e.g., which can be standardized, customized, or subject-specific) that includes, establishes, or defines single or multiple PEMF exposure, treatment, or therapy sessions, such that for a given set of target tissues under consideration (a) a maximum or total target tissue PEMF exposure time or magnetic flux density/electromagnetic energy dose during any given PEMF exposure session is intentionally or preferentially limited in accordance with a session efficacy window (EMF window) (e.g., approximately 5-15 minutes, or about 10 minutes); and possibly (b) (i) a minimum time period is established between successive PEMF exposure sessions in accordance with a regimen EMF efficacy window, and/or (ii) a maximum or total number of PEMF exposure sessions across a predetermined time period, such as a predetermined number of days (e.g., 3 days, 5 days, one week, 10 days, or two weeks), is intentionally or preferentially limited in accordance with the empirically determined regimen EMF efficacy window.

Consequently, with respect to a given PEMF exposure session, exposure of the same or substantially the same target tissues to PEMFs outside the session efficacy window can be avoided or prevented, leading to the requirement for field uniformity for best biological outcome; and with respect to an overall exposure regimen, exposure of the same or substantially the same target tissues to the PEMFs more frequently than specified or recommended by the regimen EMF efficacy window can be avoided or prevented. A given session EMF efficacy window and/or a corresponding regimen efficacy window can depend upon embodiment details, a set of target tissues under consideration, a subject state or condition under consideration, and/or a PEMF exposure objective under consideration. Additional details relating to session efficacy windows and regimen efficacy windows are provided below.

Multiple embodiments in accordance with the present disclosure are also directed to systems, apparatuses, devices, and processes/procedures for managing the incorporation of particular environmental factors, events, activities, substances, interventions, treatments, and/or therapies as part of a PEMF exposure regimen, and/or the avoidance of other environmental factors, events, activities, substances, interventions, treatments, and/or therapies as part of the PEMF exposure regimen, for instance, based upon (a) the nature or composition of the target tissue(s) under consideration, (b) the subject's physiological profile and the nature and state/status of subject physical capabilities, disabilities, or injuries under consideration, and (c) a PEMF exposure objective or outcome (e.g., an intended regenerative/cytoprotective or degenerative cellular effect) under consideration.

More particularly, some embodiments in accordance with the present disclosure are directed to systems, apparatuses, devices, and processes/procedures for regulating, associating, or linking synergistic events, activities, substances, interventions, treatments, and/or therapies with a PEMF exposure objective as part of a PEMF exposure regimen; and avoiding the association or linkage of anti-synergistic activities, substances, interventions, treatments, and/or therapies with the PEMF exposure objective as part of the PEMF exposure regimen. Still more particularly, a PEMF exposure regimen directed to a given type of regenerative or degenerative cellular or system physiologic process can include, recommend, be associated or linked with, or require subject exposure to certain environmental conditions, and/or subject ingestion or subject avoidance of certain types of nutritional/neutraceutical or pharmaceutical substances. Depending on a PEMF exposure objective under consideration, specific nutritional or pharmaceutical substances can act directly on TRPC1/TRPV2 channel expression or function, while other nutritional or pharmaceutical substances can interfere with the expression or the ability of TRPC1/TRPV2 channels to function under a given modality (e.g., as channels that open in response to emptying of intracellular calcium reserves or mechanical stimulation).

For instance, a PEMF exposure regimen directed to a given set of regenerative cellular processes can include, recommend, be associated or linked with, or require subject exposure to hot or cold temperatures, and/or subject ingestion of one or a combination of nutritional or pharmaceutical adjuvants such as capsaicin, vitamin A, vitamin D, vitamin E or related compounds (e.g., tocopherols and/or tocotrienols), certain allyl isothiocyanates (AITCs; found in wasabi, mustard oil, etc), cinnamon, its extracts, or structurally-related biflavonoid (Cinnamtannin B-1, procyanidins A1, B2 or morelloflavone,), certain fatty acids (conjugated linoleic acids, omega-3 fatty acids, etc), foods providing dietary fibres that are converted by the host microbiome into short-chain fatty acids (butyric acid, acetic acid, propionic acid, etc) with biological activity, direct ingestion of such short-chain fatty acids, in the absence of, or combination with probiotics containing implicated microbiome constituents (for example, *Clostridium tyrobutyricum* for butyrate and *Bacteroides thetaiotaomicron* for acetate and propionate), caffeine, and/or other substances at particular concentrations and times relative to the initiation of a PEMF exposure session (e.g., a predetermined/recommended number of minutes or hours prior to initiation of the PEMF exposure session, or within a predetermined/recommended number of minutes or hours after termination of the PEMF exposure session), where such events/actions or substances can synergistically enhance the target tissues' regenerative response to PEMF signal exposure. A PEMF exposure regimen directed to regenerative cellular processes can additionally or alternatively recommend or require subject avoidance of certain types of nutritional substances at particular concentrations and times relative to the initiation or completion of a PEMF exposure session, where such avoided substances can interfere with the target tissues' regenerative response to PEMF signal exposure or change the position of the EMF efficacy window. PEMF stimulation may also predispose a tissue to respond more efficaciously to a nutritional agent with modulatory capacity. For instance, PEMFs may upregulate the expression of the vitamin D receptor, thereby predisposing a tissue more sensitive to vitamin D3, which, in turn, may modulate the response of that tissue to subsequent PEMF stimulation.

Thus, a number of embodiments in accordance with the present disclosure are directed to systems, apparatuses, devices, and/or processes/procedures for associating, linking, or regulating (a) subject intake of and/or target tissue exposure to particular nutritional and/or pharmacological substances that regulate, cross-regulate, modulate, activate, or enhance TRPC1, TRPV2 or other TRP channel recruitment/activation/function with (b) one or more PEMF exposure sessions directed to target tissues under consideration for the enhancement of a particular PEMF exposure objective (e.g., the enhancement of one or more regenerative/cytoprotective cellular effects, or the enhancement of one or more degenerative cellular effects). Additional aspects of such embodiments are described in greater detail below.

In a similar or analogous manner, at least some embodiments in accordance with the present disclosure are directed to systems, apparatuses, devices, and processes/procedures for managing the avoidance of events, activities, substances, interventions, treatments, and/or therapies that would be counterproductive or contra-indicated with respect to achieving intended biological effects as a result of exposing target tissues to PEMFs. For instance, a PEMF exposure regimen can indicate or specify that (a) a subject should avoid the ingestion of substances (topically applied or ingested) that act as TRP channel blockers/antagonists or downregulators that can adversely affect or block the effects of the PEMFs prior to any given PEMF exposure session, for instance, for at least k hours (e.g., 0-72 hours) prior to each PEMF exposure session; and (b) substances such as aminoglycoside antibiotics (e.g., streptomycin, dihydrostreptomycin, gentamicin and neomycin) that can interfere with, attenuate, or block PEMF signals should not be present in or on the subject's body during any PEMF exposure session.

In view of the foregoing, PEMFs generated in accordance with embodiments of the present disclosure can be applied to target tissues of a very wide variety of subject types, including:

physically impaired, injured, disabled, clinically immobilized, or unhealthy/ill subjects, for purpose of activating or synergistically augmenting/enhancing subject-internal biological processes that can alleviate, ameliorate, remedy, overcome, or eliminate one or more types of metabolic, structural, and/or functional biological deficits experienced by such subjects due to inactivity;

healthy, generally healthy, or apparently healthy subjects who have or may have an increased likelihood of developing particular types of structural, functional, and/or metabolic biological deficits based upon their age, family history, and/or genetic profile, for purpose of delaying the onset of or prophylactically preventing the occurrence of such biological deficits;

subjects (e.g., healthy subjects) who actively engage in athletic/sports activities (where PEMFs can be applied to particular target tissues before or after subject participation in an athletic/sports activity), in order to synergistically enhance the beneficial physiological effects (metabolic, anabolic, and/or hormonal effects) of such activities, reduce recovery time, and/or reduce potential adverse effects (e.g., inflammation) associated with over-exertion during such activities;

subjects seeking physiological effects that simulate or mimic various beneficial effects of athletic/sports activities, without actively engaging in or being able to actively engage in such activities;

overweight or underweight subjects, for corresponding body composition modification purposes by way of muscle enhancement or enhanced fatty acid oxidation, insulin stabilization and other metabolic benefits;

subjects seeking aesthetic, cosmetic, or appearance enhancement, for instance, in facial/neck tissues (e.g., skin), as a result of enhanced collagen, trophic agent, extracellular matrix component or exosome/microvesicle release and/or muscle tissue production in target tissues following the application of PEMFs thereto;

subjects seeking anti-aging effects or enhanced well-being/wellness;

individuals afflicted by, or predisposed to, osteoporosis and other types of subjects.

The application of PEMFs generated in accordance with embodiments of the present disclosure to target tissues of any of the above subject types can occur in association/combination with subject use or ingestion of one or more types of nutritional/pharmacological adjuvants, in a manner analogous to that set forth above and elsewhere herein.

In non-limiting representative example situations, PEMFs generated in accordance with embodiments of the present disclosure can be applied to target tissues for purpose of addressing, treating, reducing the likelihood of, reducing adverse effects of, slowing the progression of, or delaying or preventing the onset of one or more of the following: muscle loss; bone loss; tendon weakening or damage; tissue damage/injury; osteoarthritis; sarcopenia; osteopenia; metabolic syndrome; type II diabetes; hypertension; cardiovascular disease; cachexia; peripheral artery disease; chronic fatigue syndrome; depression; memory impairment in the elderly; maintenance of central and peripheral nervous tissue; central nervous communication with peripheral musculature; muscular dystrophy (e.g., x-linked muscular dystrophy); obesity; tissue ageing; muscular and/or neural senescence; physical immobilization; and other conditions.

PEMF APPLICATION SYSTEM

FIG. 1A is a schematic illustration showing portions of a PEMF application system 100a configured for applying low amplitude extremely low frequency (ELF) pulsed electromagnetic fields (PEMFs) to target tissues in accordance with an embodiment of the present disclosure, such as target tissues of one or more human beings or animals, or target tissues carried by an in vitro structure, vessel, or chamber. In an embodiment, the system 100a includes a control system, control unit, or controller 110; and at least one waveform or pulse generator 300 that is couplable or coupled to the controller 110 as well as at least one set of PEMF application coils 400. The pulse generator 300 is connected to an amplifier (not shown) that is specifically adapted to support the frequency range relevant to the PEMF signal used. Each set of PEMF coils 400 is arranged in accordance with a PEMF coil configuration 450 that facilitates or enables efficient and/or efficacious application of the PEMF signals or waveforms to particular target tissues under consideration, as detailed below. The system 100a also includes at least one power supply (not shown) by which the controller 110 and the pulse generator(s) 300 are powered, in a manner readily understood by individuals having ordinary skill in the relevant art.

Each pulse generator 300 is configured for generating or outputting electrical signals by which each set of PEMF application coils 400 outputs PEMF signals or waveforms in accordance with particular PEMF signal or waveform parameters, as further described below. The structure of a given set of PEMF application coils 400 and its corresponding PEMF coil configuration 450 can depend upon embodiment details; the target tissues or cells to which the PEMFs are applied; the type of subject under consideration (e.g., adult, juvenile, diseased or injured human or animal) and the subject's current state or condition; and/or a PEMF exposure objective under consideration, as also described below.

FIGS. 1B-1D illustrate a representative PEMF signal or waveform and corresponding representative PEMF signal or waveform characteristics or parameters in accordance with an embodiment of the present disclosure. For purpose of brevity, PEMF signals or waveforms are simply referred to herein as PEMF signals. In various embodiments, the PEMF application system 100a is configured for exposing target tissues to symmetric and/or asymmetric PEMF signals (e.g., on a selectable or programmably defined basis), where an average magnetic flux density of symmetric PEMF signals equals zero, and an average magnetic flux density of asymmetric PEMF signals is nonzero (e.g., greater than zero). In various embodiments, at least some of the PEMF signals generated during a PEMF exposure session (e.g., each of the PEMF signals generated during the PEMF exposure session) are asymmetric PEMF signals; however, symmetric PEMF signals can additionally or alternatively be generated.

Also, in multiple embodiments at least some of the PEMF signals generated during the PEMF exposure session (e.g., each of the PEMF signals generated during the PEMF exposure session) include a plurality of PEMF bursts, where each PEMF burst includes a plurality of individual PEMF pulses therein. In several embodiments, individual PEMF pulses can be generated in the form of square waves, or approximately/generally square waves (although PEMF pulses can exhibit other or additional shapes in alternate embodiments).

As indicated above, a given pulse generator 300 includes electrical circuitry configured for generating electrical signals by which the set(s) of PEMF application coils 400 coupled thereto produce or output each PEMF burst within a PEMF burst sequence or train, and the sequence or train of PEMF pulses within each PEMF burst.

The pulse generator 300 generates such electrical signals in accordance with at least one set of PEMF signal parameters (e.g., which can be predetermined, selectable, or programmably specified, and which can be associated or linked with a PEMF exposure regimen). More particularly, during a PEMF exposure session within which PEMFs are generated in accordance with at least one set of PEMF signal parameters, temporally separated or sequential PEMF bursts are generated in accordance with at least one inter-burst frequency, which typically ranges between approximately 5.0-50.0 Hz. Within a given PEMF burst, individual PEMF pulses are generated in accordance with an intra-burst frequency, which typically ranges between approximately 5.0-2500.0 Hz. Additionally, each PEMF pulse can rise from a minimum to a plateau or maximum pulse amplitude, and/or fall from the plateau or maximum pulse amplitude to the minimum pulse amplitude within approximately 5.0-100.0 Ps (e.g., the rise time and/or fall time of each PEMF pulse is between 5.0-100.0 Ps). Furthermore, as indicated in FIG. 1C, in several embodiments the frequency spectrum of each PEMF pulse exhibits a plurality of frequency components below approximately 20.0 Hz; least one or a single dominant frequency component below approximately 5.0 Hz; and/or a dominant frequency component below approximately 0.5-1.0 Hz.

In a number of embodiments, once the inter-burst and/or intra-burst frequencies for a given PEMF exposure session have been selected, defined, or specified, the inter-burst and/or intra-burst frequencies remain constant during the PEMF exposure session. However, in certain embodiments, the inter-burst and/or intra-burst frequencies can be varied, modulated, or generated in a pseudo-random manner during a PEMF exposure session. Similarly, in some embodiments, within a given PEMF treatment regimen the inter-burst and/or intra-burst frequencies remain constant across each PEMF exposure session. Alternatively, the inter-burst and/or intra-burst frequencies can vary in a selectable, programmable, predetermined or pseudo-random manner from one PEMF exposure session to another within the PEMF treatment regimen.

In some embodiments, the pulse generator 300 can additionally generate electrical signals that result in the generation of PEMF signals as PEMF burst clusters, where each individual PEMF burst cluster includes multiple PEMF bursts. The PEMF signal parameters can include a PEMF burst cluster duration, which can correspond to or represent a session efficacy window; and possibly a PEMF burst cluster frequency or interval, for instance, which corresponds to a predetermined, selectable, or programmably defined number of hours or days between PEMF burst clusters. The PEMF burst cluster interval can correspond to or represent a regimen efficacy window.

In multiple embodiments, the pulse generator 300 and a given set of PEMF application coils 400 coupled thereto are configured for exposing particular target cells or tissues (e.g., certain skeletal muscle tissues) to a peak magnetic flux density amplitude between approximately 0.1-5.0 mT, for instance, about 0.2-3 mT, or about 0.5-1.5 mT, or approximately 1.0 mT. As a result of the rise and/or fall time of each PEMF pulse, the rate of magnetic flux density change of each PEMF pulse, and hence the rate of magnetic flux density change to which the target tissues are exposed at the onset and/or termination of each PEMF pulse, is approximately 10-100 T/s. In a number of embodiments, in order to selectively or preferentially upregulate TRPC1 channels, the magnetic flux density gradient (and in particular, the rising magnetic flux density gradient) of the PEMF signals to which target tissues are exposed is greater than or equal to about 20 T/s, for instance, at least approximately 35 T/s-65 T/s (e.g., approximately 50 T/s).

Each coil 400a,b within the set of PEMF application coils 400 includes a predetermined number of conductor windings therein, and exhibits a particular shape by which the coil 400a,b can uniformly, substantially uniformly, or generally uniformly expose target tissues to an intended magnetic flux density associated with a PEMF exposure, treatment, or therapy regimen.

Figure 2A:
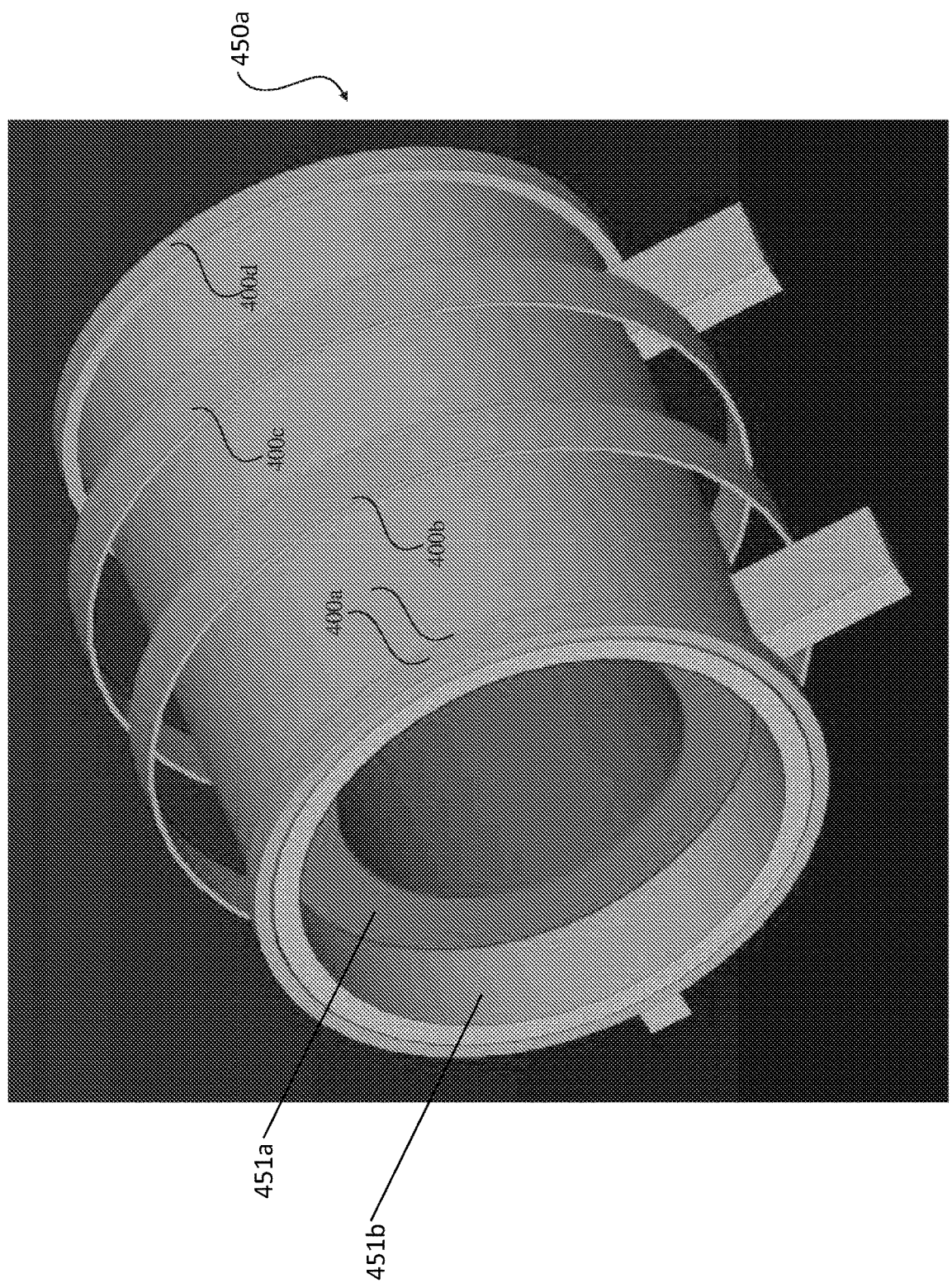

FIG. 2A illustrates aspects of a representative PEMF leg coil configuration 450a that accommodates portions of a subject's leg, including portions of their knee, in accordance with an embodiment of the present disclosure. As indicated in FIG. 2A, in an embodiment the PEMF leg coil configuration 450a includes four coils 400a-d, which uniformly direct PEMF signals longitudinally through the central region of the PEMF leg coil configuration 450a. The PEMF leg coil configuration 450a can include a case or housing 451b in which the coils 400a-d reside, as shown in FIG. 2A. The PEMF leg coil configuration 450a can include a cushion 451a. The PEMF leg coil configuration 450a can be placed horizontal to ground on a mobile table, so that the knee can be inserted easily with the foot first. The cushion 451a positions the leg within the volume of uniform magnetic field exposure. The case or housing 451b supports the weight of the coil configuration 450a and does not contain any metallic items or wood and can be made of PVC.

The four coils 400a-d have either 40 or 48 windings. Coil 400a and 400d, as well as coil 400b and 400c are identical in geometry and winding. All coils are winded in the same direction. Coil 400a and coil 400b are connected in series, likewise coil 400c and 400d. All coils are winded and glued on the case or housing 451b. The cushion 451a or similar structure is placed at the centre of the leg coil configuration 450a to support the leg and define the volume of uniform exposure. A temperature sensor (Pt 100) may be placed/glued inside the cushion 451a close to the leg.

By way of at least one PEMF leg coil configuration 450a such as that shown in FIG. 2A, PEMF signals generated in accordance with embodiments of the present disclosure can be applied to target leg tissues (e.g., muscle, cartilage, tendon, ligament, and/or bone tissue(s)) of one or each leg of a subject. For instance, PEMF signals can be generated as described herein, and applied to portions of a given leg or each leg prior (e.g., shortly or immediately prior) to one or more conventional leg-related events, exercises, activities, treatments, or therapy sessions involving the leg(s) under consideration (e.g., a physical therapy, ultrasound treatment, thermal treatment (e.g., heating or cooling), strength/weight training, muscular stretching, movement training, walking, running, and/or other type of session) to thereby synergistically enhance the physiological effects of such conventional events/treatment session(s) on one or more portions the subject's leg(s) (e.g., by way of PEMF-enhanced regeneration of cartilage, ligaments, tendons, muscles, and/or bones of an impaired or injured subject leg).

Furthermore, with respect to a subject leg on which a surgical procedure has been performed (e.g., anterior cruciate ligament (ACL) reconstruction surgery), during an initial surgery recovery period during which movement/motion of the subject leg under consideration is contra-indicated or to be avoided, PEMF signals can be generated as described herein and applied to this subject leg by way of a PEMF leg coil configuration 450a, such that post-surgical atrophy or muscle wasting in the subject leg under consideration is significantly or greatly reduced, minimized, or essentially avoided (e.g., because PEMF signals generated in accordance with embodiments of the present disclosure can simulate or mimic the effects of physical exercise, without imparting mechanical stress on the tissues of the subject leg that underwent surgery).

Analogously, PEMF signals generated in accordance with embodiments of the present disclosure can be post-surgically applied to other subject target tissues/another subject body part (e.g., hand, wrist, arm, foot, portions of the spine, etc.) during an initial surgery recovery period using an appropriate type of PEMF coil configuration 450. Following an initial surgery recovery period, PEMF signals generated in accordance with embodiments of the present disclosure can be applied to the subject target tissues/body part under consideration prior to or after a physical or movement therapy session.

Further analogously, PEMF signals generated in accordance with embodiments of the present disclosure can be applied to target tissues within a cast, splint, or brace worn by a subject in order to retard muscle and bone loss while the target tissues remain within the cast, splint, or brace. After removal of the cast, splint, or brace, PEMF signals can be applied to these and possibly other/related target tissues to enhance tissue development and recovery (e.g., PEMF signals can be applied before or after physical therapy or exercise involving these target tissues).

Figure 2B:
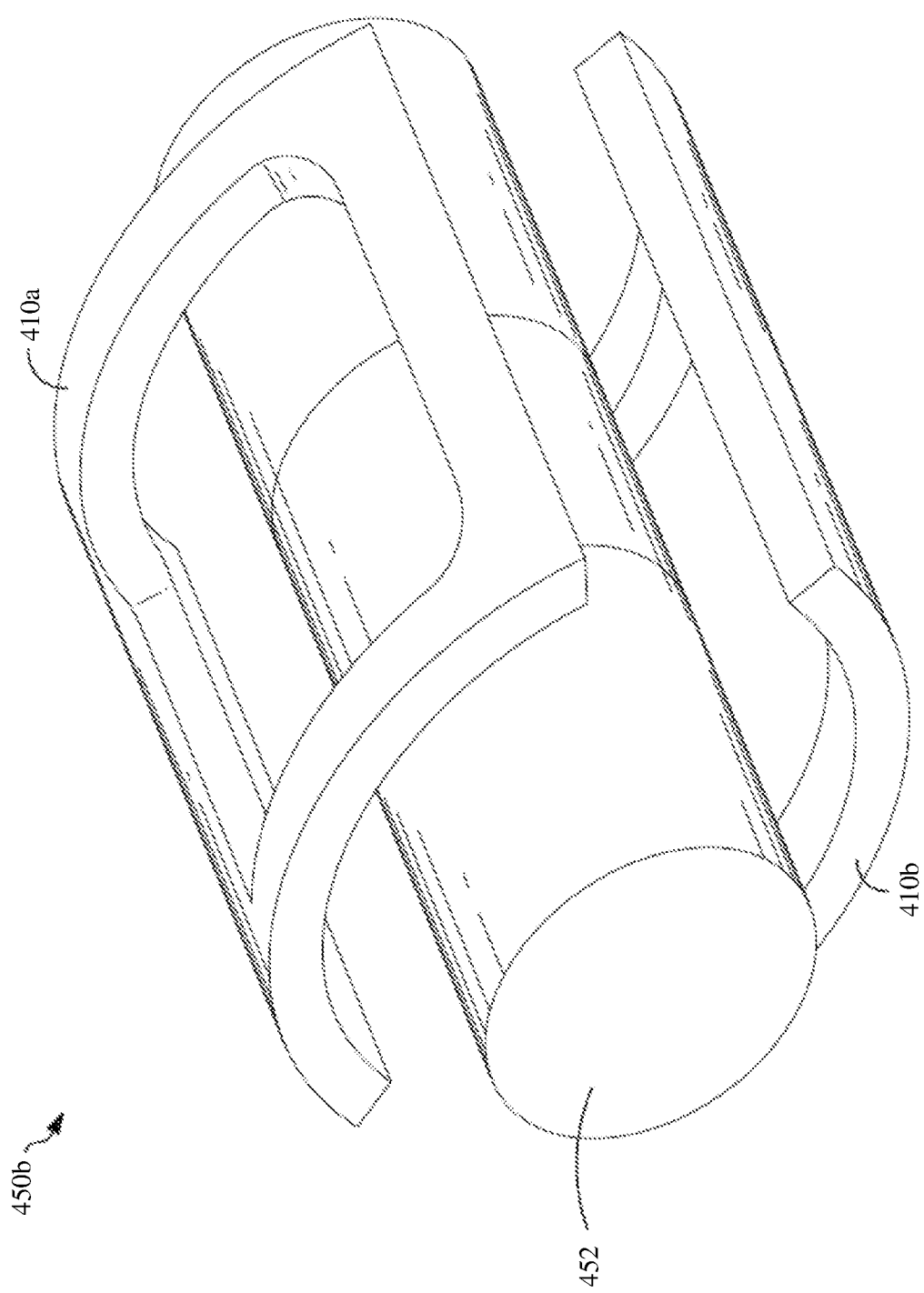

FIG. 2B illustrates aspects of a representative PEMF arm coil configuration 450*b* that accommodates portions of a subject's arm 452 in accordance with an embodiment of the present disclosure. In the embodiment shown, the PEMF arm coil configuration 450*b* includes two saddle coils 410*a, b*, between and within which portions of the subject's arm 452, such as their forearm or upper arm can be positioned. The PEMF arm coil configuration 450*b* of FIG. 2B can be utilized for applying PEMF signals to portions of one or each of a subject's arms, in a manner analogous or generally analogous to that described above for the PEMF leg coil configuration 450*a*. The PEMF arm coil configuration 450*b* can support intermittent exposure protocols with arbitrary signals (f<5 kHz) and a peak magnetic flux density of 2 mT. These protocols also include a pulsed signal, which comprises 15 bursts per second of 6 ms interval each with a maximum flux density of 2 mT. Each burst consists of twenty on-off cycles (150 μs on, 150 μs off) in the same field direction yielding an asymmetric exposure.

In one implementation, the coil includes 99 windings of a 1.8 mm thick copper wire, which is stacked to a 9×11 configuration. The wires are glued together and tightly fixed to a holding structure in order to reduce mechanical vibrations. The coil configuration applies a mean flux density of 0.68 mT per 1 A current. The inductance of one coil is estimated to 2 mH. A temperature probe (Pt 100) is placed between the coil solid and the fixing structure for the arm for subject safety.

FIGS. 2C-2E illustrate aspects of representative PEMF lower back, buttocks, and pelvic cavity coil configurations 450*c,d,e* that can respectively direct PEMF signals to portions of a subject's lower back region, buttocks region, and pelvic cavity in accordance with an embodiment of the present disclosure. FIGS. 2C-2E also indicate simulated magnetic flux density versus electrical current levels for such coil configurations. The PEMF lower back/buttocks coil configuration 450*c,d* can be incorporated into a seating device such as an office or desk chair or an automobile seat. For subjects that use wheelchairs, a PEMF lower back/buttocks coil configuration 450*c,d* can be carried by a docking station mounted to a structure such as a wall, whereby the back and/or seat of the wheelchair can move into position relative to the docking station such that the subject's lower back and/or buttocks are exposed to PEMF signals output by the PEMF lower back/buttocks coil configuration 450*c,d* for a pre-designated amount of time.

A PEMF lower back/buttocks coil configuration 450*c,d* can include two or more coil elements that are angularly adjustable relative to each other, such that the magnetic field produced by the coil configuration 450*c,d* can be directed into deeper or shallower target tissues as a result of adjustment of the angular separation between the coil elements (e.g., deeper magnetic field penetration of the correct EMF efficacy window characteristics for the tissue class targeted can result when the angular separation between two coil elements decreases from 180 degrees toward 0 degrees).

With reference to FIGS. 2C and 2D, which show a lower back and seated coil configuration, respectively, the volume of the homogeneous field (and correspondingly the amount/volume of tissue implicated) can be regulated by changing the angle between the coils (more acute angles create deeper fields), and whether the bending axis of the coils is aligned vertically (head to toe) or horizontally (left to right). The intensity of the field is a function of the current fed to the coils. For the gluteal muscle group (gluteus maximus, medius, minimus and tensor fasciae latae) and back musculature (posterior chain muscle group including gluteal muscle group, hamstrings, and lower back), a longer exposure to weaker fields (e.g. 20 minutes at 0.3 mT to 0.5 mT per week) is preferable. Different body regions can be also targeted using similar coil configuration strategies.

Such a coil configuration 450*c,d* can be referred to as an angularly adjustable saddle coil, and can carry a set of sensing elements for determining a current angle between its coil elements. This angle can be provided to the controller 110 as feedback, by which the controller 110 can automatically adjust or regulate the output of the pulse generator 300 to thereby adjust or regulate the magnetic field to which deeper or shallower target tissues are exposed in a predetermined or selectable/programmable manner.

Figure 2F:
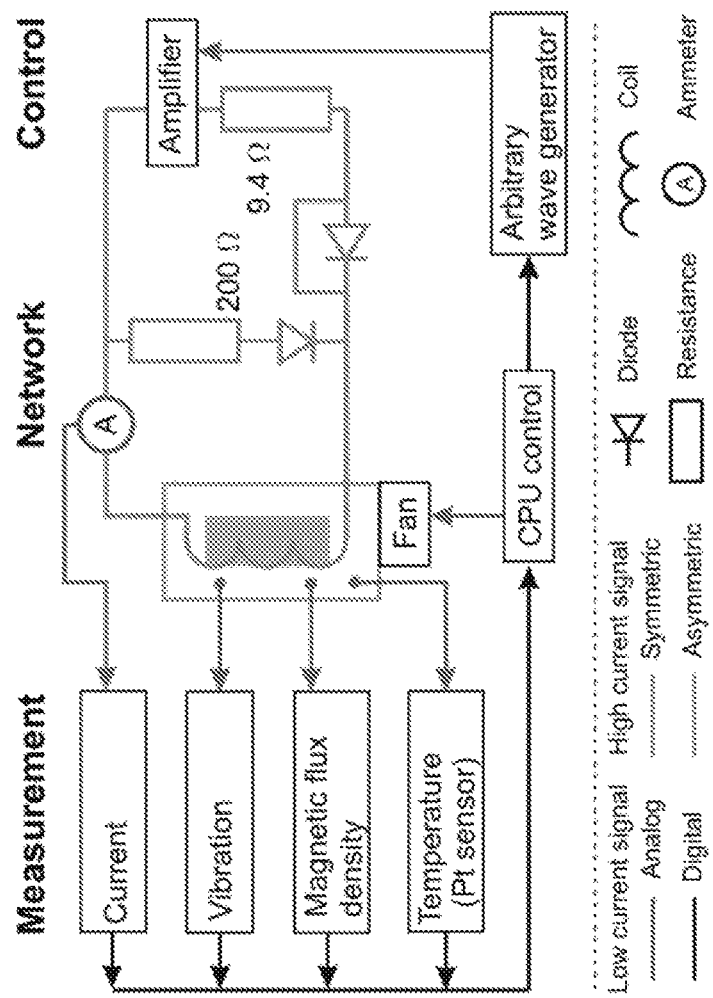
FIG. 2F shows a schematic of control unit for controlling the generation of electrical signals that result in the generation of PEMF signals by PEMF application coils in accordance with an embodiment of the present disclosure.

FIG. 2F shows a schematic of control unit for controlling the generation of electrical signals that result in the generation of PEMF signals by PEMF application coils in accordance with an embodiment of the present disclosure. The control unit monitors the electrical current and temperature of the coil configuration/applicator. The modulated current signal is provided by two 3 kW amplifiers. Furthermore, the control unit includes a resistive matching network allowing for application of symmetric and asymmetrical signals. The control unit supports arbitrary signals of frequencies up to 10 kHz and field density of 2 mT peak. A maximal flux gradient of 66 T/s is achieved. Each signal of various duration can be applied either symmetrically around zero or asymmetrically. The control unit supports protocols with selectable or definable (e.g., user defined) intermittent exposure cycles. The control unit monitors the temperature and the applied current. It will be appreciated by a person skilled in the art that the control unit may be implemented using other suitable components/configurations.

In an embodiment, a facial coil configuration (not shown) can be an angularly adjustable saddle coil configuration having a first coil element that exhibits or generally exhibits a contour or profile that follows the outline of portions of a subject's jaw line, and a second coil element that is positionable in front of or beside portions of the subjects face for purpose of applying PEMF signals to target facial skin tissues (e.g., for cosmetic/aesthetic enhancement purposes). Such a facial coil configuration can include a set of sensing elements for determining a current angle between its coil elements, which the controller 110 can as feedback for automatically adjusting/regulating the output of the pulse generator 300, in a manner analogous to that described above.

In an implementation, there is provided a PEMF animal or livestock coil configuration that can direct PEMF signals into the lateral sides of an animal subject such as a cow or horse. Such a coil configuration includes coils disposed on each of the animal's lateral sides, which can be carried by and maintained in position by two barriers, walls, panels, partitions, fences, gates, or similar structures between which the animal remains during a PEMF exposure session.

Other animal/livestock coil configurations can be positioned relative to or carried by one or more structures in which an animal can be enclosed. For instance, in the case of livestock, a set of PEMF coils can be positioned relative to or carried by portions of an animal stall for applying PEMF signals to target tissues while the animal is laying down/sleeping; and for the case of a pet such as a dog or cat, a set of PEMF coils can be positioned relative to or carried by a pet enclosure or bedding structure.

In an implementation, there is provided a PEMF—magnetic resonance (MR) coil configuration, in which an MR coil, such as a conventional MR coil that forms a portion of a conventional magnetic resonance imaging (MRI) system, is selectively configurable/configured by way of program instructions/software to generate PEMF signals in accordance with an embodiment of the present disclosure. In an embodiment, a display device that forms a portion of a PEMF-MRI system can provide a user interface 460 as shown in FIG. 2G by which a medical professional can selectively identify a given subject or patient, and view or indicate whether the PEMF-MR coil configuration is to generate PEMF signals or MRI signals for the subject under consideration. For a subject that is to be exposed to PEMF signals, the user interface 460 can receive input from the medical professional that indicates or defines corresponding PEMF exposure regimen details and/or corresponding PEMF exposure session details. The user interface 460 can additionally receive input from the medical professional to initiate a PEMF exposure session, during which target tissues of the subject (human or animal) are exposed to PEMF signals generated in accordance with an embodiment of the present disclosure by way of the PEMF-MR coil configuration.

As described above, a PEMF exposure regimen establishes or defines a set of PEMF exposure sessions. In various embodiments, within each PEMF exposure session particular target tissues can be exposed to PEMFs in accordance with specific PEMF signal parameters across an intentionally limited period of time that establishes or defines a session EMF efficacy window. In general, the efficacy window can be defined by PEMF signal amplitude, total time of target tissue exposure, and PEMF signal frequency (e.g., inter-burst frequency and/or intra-burst frequency). The session efficacy window is a consequence or expected consequence of developmental regulation or endogenous expression of TRP channels and hence, inherent mechanosensitivity of a cell or tissue and/or concomitant enzymatic/genetic or mechanical functional modulation. The existence of ambient magnetic fields present in the environment (for instance, tissue culture incubator for cells, or power line fields for human) and exposing cells, tissues or organisms can also influence nature of the EMF efficacy window.

In various embodiments, the session EMF efficacy window defines a minimum amount of time or lower time limit for exposing particular target tissues to the PEMF signals, and a maximum amount of time or upper time limit for exposing the target tissues to the PEMF signals. In other words, the target tissues under consideration should or are intended to be exposed to the PEMF signals for at least or approximately at least an amount of time defined by a lower bound of the session exposure window (e.g., within 10-20% of the session exposure window's lower temporal bound), but should not or are not intended to be exposed to the PEMF signals beyond or significantly beyond an upper bound of the session exposure window (e.g., within 10-20% of the session exposure window's upper temporal bound).

In multiple embodiments, the session EMF efficacy window is defined as a predetermined or approximate time window or interval within which target tissues of a given type should be or are exposable/exposed to PEMF signals during a PEMF exposure session, relative to a predetermined peak or total magnetic flux density to which the target tissues under consideration will be subjected by way of a given set of PEMF application coils during the PEMF exposure session.

The inventors have discovered that target tissue responsiveness to PEMF signals with respect to time using PEMF signal parameters and a given PEMF coil configuration intended to apply a given peak magnetic flux density amplitude to the target tissues (a) initially increases away from a baseline level upon initiation of target tissue exposure to the PEMF signals; (b) reaches a peak or plateau level within a time interval measured in minutes (e.g., several minutes to a few tens of minutes, depending upon PEMF signal parameters and PEMF coil configuration) following the initiation of target tissue exposure to the PEMF signals; and (c) subsequently decreases or returns back to the baseline level after the time at which the responsiveness of the target tissues to the PEMF signals peaked.

The decrease in responsiveness of the target tissues to the PEMF signals from the peak level back to the baseline level can exhibit a non-gradual, moderately steep, or steep negative slope versus time, and can occur within a time interval measured in minutes (e.g., several minutes to approximately 10 minutes, depending upon PEMF signal parameters and PEMF coil configuration). Consequently, continued target tissue exposure to the PEMF signals significantly beyond the time at which their responsiveness to the PEMF signals has peaked or plateaued is counterproductive, and hence such continued exposure should be avoided or prevented. Exposure of a cell/tissue/organism beyond the peak of the EMF efficacy window thus inhibits cell/tissue/organismal responses to PEMFs or stimuli impinging on commonly recruited cellular biochemical and genetic pathways that will subsequently negate effects of the fields; sufficient recovery time is required to overcome such a refractory period as outlined previously.

In several embodiments, for a given PEMF exposure session directed or primarily directed to target tissues of a particular type, the session exposure window's lower temporal bound corresponds or is expected to correspond to an elapsed time from the onset of PEMF signal application to the target tissues across which the responsiveness of the target tissues to the PEMF signals has increased from a baseline level to reach approximately 60-90% (e.g., about 70-80%) of a peak target tissue responsiveness level to the PEMF signals; and the session exposure window's upper temporal bound corresponds or is expected to correspond to an elapsed time from the onset of PEMF signal application to the target tissues at which the responsiveness of the target tissues to the applied PEMF signals has decreased approximately 10-40% (e.g., about 20-30%) from the peak target tissue responsiveness level. Thus, within the session exposure window, the responsiveness of the target tissues to the PEMF signals is substantially or very substantially greater than its baseline level, and remains near or generally near its peak level.

In multiple embodiments, when a set of target tissues under consideration includes significant amounts of muscle tissue (e.g., more than about 20% muscle tissue) or is substantially or primarily muscle tissue (e.g., more than about 50% muscle tissue) and the PEMF exposure session uses PEMF signal parameters and a set of PEMF application coils 400 that expose the target tissues to a peak magnetic flux density of approximately 1-2 mT using PEMF signals generated in a manner set forth herein, the session efficacy window is approximately 5-15 minutes (e.g., about 10 minutes). For instance, the session efficacy window can be at least approximately 5 minutes, up to approximately 15 minutes, but not longer than about 15 minutes. In a representative implementation, a standard or default session exposure window equals approximately 10 minutes. In several embodiments, beyond or past the upper time limit defined by the session efficacy window, exposure of the target tissues under consideration to the PEMF signals can be or is avoided or prevented.

In accordance with some embodiments of the present disclosure, session efficacy windows can be temporally (duration of exposure) constant or generally constant across different target tissue types, but the peak magnetic flux density or magnetic field amplitude for different target tissue types can be adjusted in order to preferentially or selectively produce PEMF signal exposure effects in certain target tissues under consideration, while producing fewer, few, significantly limited, or minimal PEMF signal exposure effects in other tissues that reside within the magnetic field distribution of the PEMF coil configuration 450 in use. For instance, in order to preferentially or selectively produce PEMF signal exposure effects in cartilage tissues rather than muscle tissues that extend along or surround the cartilage tissues, the session efficacy window can remain at approximately 5-15 minutes (e.g., approximately 10 minutes), but the peak magnetic flux density can be approximately doubled to approximately 2-3 mT, such that the peak magnetic flux density is in a range where the cartilage tissues under consideration have been found to respond to the PEMF signals, but the muscle tissues along/around those cartilage tissues are less responsive, non-responsive, or no longer responsive to the applied PEMF signals. Similarly, for preferentially or selectively producing PEMF signal exposure effects in bone tissues without giving rise to significant PEMF exposure effects in muscle tissues and possibly cartilage tissues, a peak magnetic flux density can be between approximately 2-3 mT during a total PEMF signal exposure time of 5-15 minutes (e.g., about 10 minutes); and for preferentially or selectively producing PEMF signal exposure effects in adipose tissues without giving rise to significant PEMF signal exposure effects in muscle, cartilage, or bone tissues, a peak magnetic flux density can be approximately 0.2-0.5 mT during a total PEMF signal exposure time of 5-15 minutes (e.g., about 10 minutes).

An additional manner to selectively stimulate one tissue over another is to direct the EMF fields relative to the tissue being targeted. The amplitude of the EMF efficacy window is lowest when the direction of the PEMF field lines is orthogonal to the long axis of a cell or tissue. In in vitro studies of myoblasts conducted by the inventors for instance, the field lines of the PEMF apparatus is in the direction of gravity and the long axis of cells in a tissue culture flask is perpendicular to this, giving an EMF efficacy window of 1-2 mT. Aligning myoblasts and PEMF lines in parallel pushes the EMF efficacy window to higher values. It is preferable to keep the EMF efficacy window as low as possible.

In view of the foregoing, a number of embodiments in accordance with the present disclosure enable tissue type specific PEMF exposure sessions by which PEMF signals are preferentially, selectively, or specifically applied to different types of target tissues (e.g., cellularly distinguishable target tissue types) within a common tissue volume during different PEMF exposure sessions. In some embodiments, for any given PEMF exposure session, the peak magnetic flux density or magnetic field intensity can be established such that one or more target tissue types within the tissue volume are responsive or highly responsive to the PEMF signals applied during a particular PEMF exposure session, and one or more other target tissue types within the tissue volume are significantly less responsive or essentially non-responsive to the PEMF signals applied during that PEMF exposure session, in a manner analogous to that indicated above.

For instance, with respect to a given tissue volume in which multiple distinct types of target tissues reside (e.g., the same tissue volume, or overlapping tissue volumes), on a selected day a PEMF exposure session can specifically stimulate certain muscle tissues within the tissue volume to thereby elicit direct and indirect biological effects as a result of stimulating these muscle tissues. On the same day or one, two, or a few days later (e.g., depending upon a regimen efficacy window), a subsequent PEMF exposure session (e.g., using the same or a different PEMF coil configuration 450) can specifically stimulate particular associated cartilage tissues within this tissue volume (possibly in addition to stimulating some of the same or related muscle tissues) to elicit direct effects in the cartilage tissues. Such a PEMF signal application paradigm or protocol can yield greater overall tissue development consequences in the cartilage tissues compared to cartilage tissue development consequences that would arise only from indirect effects following PEMF signal stimulation of the original muscle tissues.

Thus, with respect to different or cellularly distinguishable target tissue types within a common tissue volume, some embodiments in accordance with the present disclosure enable the preferential/selective/specific generation of direct PEMF signal exposure effects in certain types of target tissues during a PEMF exposure session, while intentionally reducing, minimizing, or essentially avoiding direct PEMF signal exposure effects in other types of target tissues within the tissue volume during the PEMF exposure session. This type of PEMF signal application paradigm by which different target tissue types within a given tissue volume can be preferentially, selectively, or specifically stimulated relative to each other by way of separate tissue type specific PEMF exposure sessions on different days, even though the multiple distinct target tissue types each reside within a common tissue volume, can be extended to additional or other target tissue types. In an analogous manner a PEMF exposure session can be designed to exclude or prevent the response of a tissue in an overlapping region of the body by selecting a EMF efficacy window that sufficiently stimulates the target tissue, while largely unaffected or inhibiting the undesired tissue.

The inventors have found that proper orientation of cells relative to an EMF field is essential for a meaningful biological outcome. In particular, the ideal induced currents are best achieved if the direction of the magnetic fields is perpendicular to the long axis of the cell or tissue in question. Accordingly, in an implementation, the direction of the EMF field emanating from a given coil design can be exploited to target tissues. Aligning the long axis of the cells/tissues parallel to the EMF field lines will change the EMF efficacy window to greater amplitude PEMFs. In other words, the organization of tissues to be targeted is preferably taken into consideration when formulating exposure paradigms.

Figure 2H:
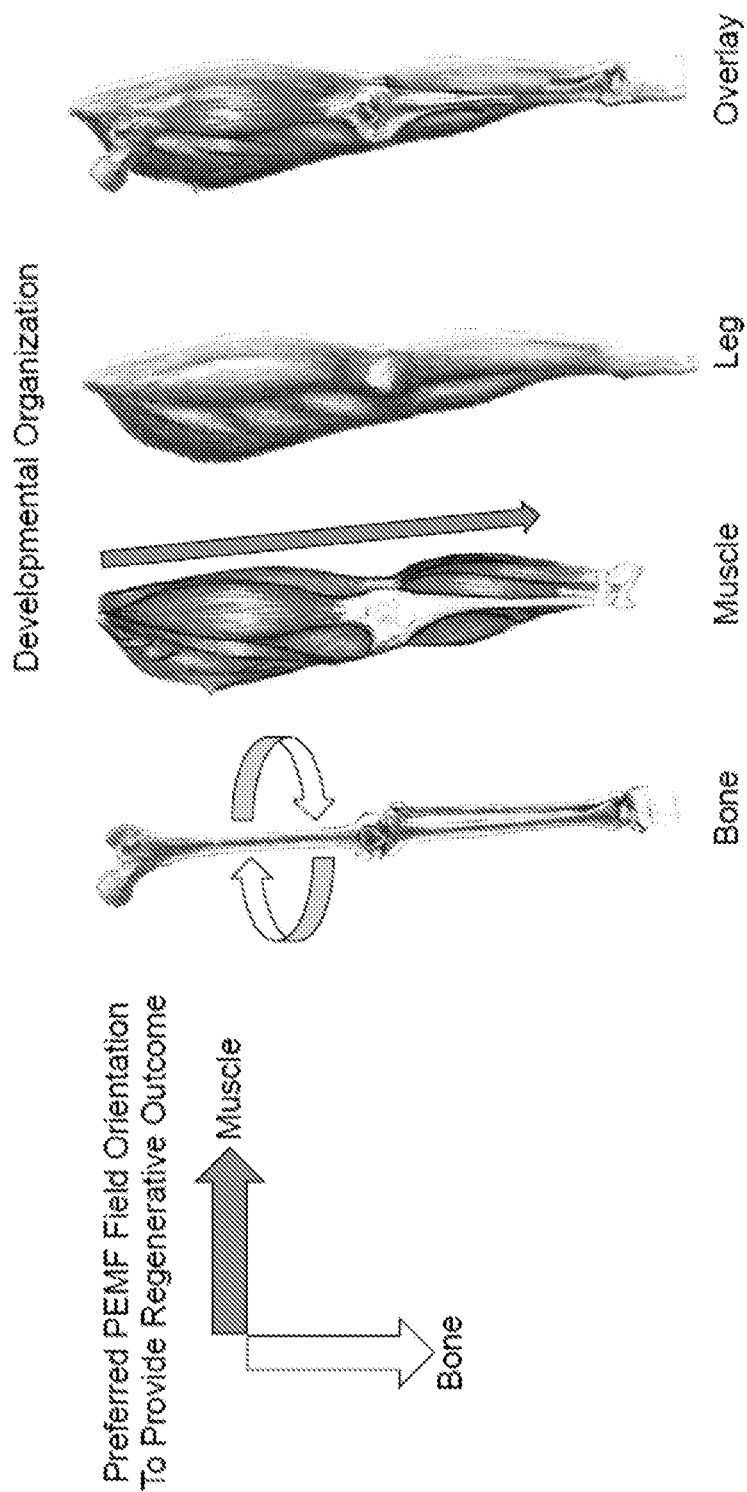
FIG. 2H shows a schematic of skeletal muscle and bones having different cell orientations and a direction of an EMF field to be applied in accordance with an embodiment of the present disclosure.

Given that tissues have different inherent organizational orientations in the body and the EMF efficacy window of a cell/tissue changes with direction of the EMF fields, a tissue can be targeted by changing the direction of the EMF field. For example, with reference to FIG. 2H, skeletal muscle and bones have different cell orientations—bone is organized circumferentially whereas muscle is organized vertically in a standing individual. These are developmentally defined alignments of the tissue that are orthogonal to each other. The direction of an EMF field can be changed depending on the desired biological outcome.

A cylindrical coil configuration (as shown and described above in relation to FIG. 2A) creates a field that is best aligned for the activation of bone, whereas a clam/saddle coil configuration (as shown and described above in relation to FIG. 2B) creates a field that is best aligned for the stimulation of muscle. Cartilage are responsive to both field directions, although its EMF efficacy window is about 2 mT, closer to that of bone.

A session exposure window can additionally or alternatively be defined in terms of a magnetic flux density dose limit or electromagnetic energy dose limit applied to target tissues of a given type, relative to which the PEMF signal responsiveness of the target tissues remains or is expected to remain well above a baseline responsiveness level (e.g., more than 50% above the baseline level). For a PEMF exposure session directed to one or more specific types of target tissues, an intended magnetic flux density to which the target tissues are exposed as well as an intended or optimal session exposure window can be estimated, determined, or defined by way of determining TRP channel expression levels for such target tissue types in response to PEMF signals generated in accordance with embodiments of the present disclosure, possibly in association/combination with adjunctive or synergistic interventions (e.g., a set of nutritional interventions) that can module TRP channel expression).

As mentioned above, a PEMF exposure regimen includes a number of PEMF sessions across which target tissues are exposable/exposed to PEMF signals. In a number of embodiments, in addition to limiting the exposure of a given set target tissues to PEMF signals by way of the session exposure window, the exposure of the same target tissues to PEMF signals is limited by a regimen EMF efficacy window. The regimen EMF efficacy window can establish (a) a minimum time period between successive PEMF exposure sessions that should transpire before the same target tissues of a given subject can be exposed to PEMF signals; and/or (b) a maximum number of PEMF sessions directed to the same target tissues of the subject within the span of a certain number of days or weeks (e.g., 3 days, 5 days, 1 week, or two weeks). The regimen EMF efficacy window can thus indicate, establish, or define a recommended PEMF exposure session schedule for the subject's target tissues under consideration. The regimen EMF efficacy window can enhance the likelihood that the biological effects arising from exposure of the target tissues to the PEMF signals have sufficient time to progress toward a plateau level or completion. The regimen EMF efficacy window is advantageously at its lowest value when the field lines of the PEMF signals are perpendicular to the long axis or axes of the cell or developmentally determined orientation of tissue to be targeted.

For instance, as a result of an exercise session involving particular muscle tissues, restructuring/growth of the muscle tissues occurs in response to mechanical stresses imparted to the muscle tissues during the exercise session. However, the overwhelming majority of such muscle tissue restructuring/growth occurs after the exercise session has ended (e.g., across the next 1-2 days, including during rest or sleep periods, following the exercise session). Because the application of PEMF signals to muscle tissues in accordance with embodiments of the present disclosure mimics or simulates the biological effects of exercise on the muscle tissues, without requiring the muscle tissues to actually experience mechanical stress, the regimen efficacy window can be employed to augment the response and subsequent physical adaptations of muscle to an exercise stimulus or to provide a rest period during which biological effects that mimic physical exercise can progress toward a plateau level or completion. When a set of target tissues under consideration includes significant amounts of muscle or cartilage tissue, a standard or default regimen efficacy window in accordance with an embodiment of the present disclosure can indicate that at least 4-72 hours (e.g., at least about 24 hours, or approximately 48 hours) should preferably elapse between successive PEMF exposure sessions directed to this same set of target tissues using the same PEMF signal parameters, and/or a total number of PEMF exposure sessions for this set of target tissues should preferably be limited to 3-5 sessions per week (e.g., 3 sessions per week).

A PEMF exposure regimen or PEMF exposure regimen definition can include, link to, or specify a subject identifier (ID) that uniquely identifies a particular subject, a subject name, and possibly subject contact information (e.g., a set of subject telephone numbers such as a mobile phone number, and/or a set of subject e-mail addresses).

For a given subject ID, the PEMF exposure regimen can include one or more target tissue IDs, each of which uniquely corresponds to a set of subject target tissues to which PEMF signals are to be applied; possibly a PEMF coil configuration ID corresponding to each target tissue ID, which specifies a type of PEMF coil configuration 450 suitable for applying PEMF signals to the associated set of target tissues; PEMF signal parameters corresponding to each target tissue ID; a PEMF exposure session schedule, such as a weekly, monthly, and/or quarterly PEMF exposure session schedule corresponding to each target tissue ID; regimen efficacy window information corresponding to each target tissue ID; and session efficacy window information corresponding to each target tissue ID. In some embodiments, for a subject ID under consideration the PEMF exposure regimen can also include information identifying a set of synergistic or adjunctive treatments corresponding to the subject ID, and a synergistic or adjunctive treatment schedule relative to the regimen efficacy window or the PEMF exposure session schedule. For instance, the PEMF exposure regimen can indicate that a particular subject should ingest a specific set of nutritional adjuvants approximately n hours prior to each PEMF exposure session. A given PEMF exposure regimen can be stored in a database, as further described below.

Figure 3:
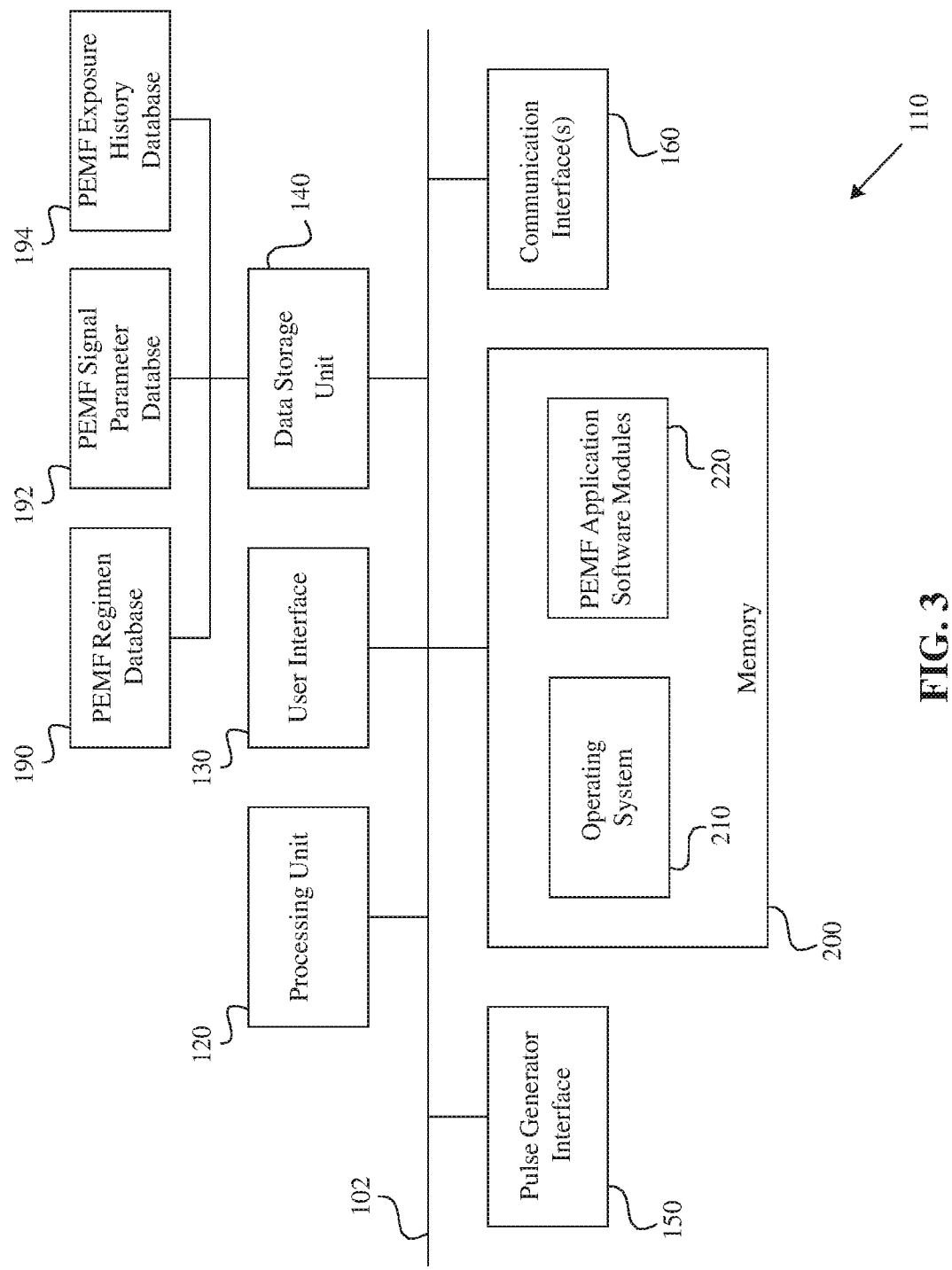
FIG. 3 is a block diagram showing portions of a representative controller in accordance with an embodiment of the present disclosure.

FIG. 3 is a block diagram of a controller 110 for a PEMF application system 100a in accordance with an embodiment of the present disclosure. In an embodiment, the controller 110 includes at least one processing unit 120; a user interface 130; and a memory 200. The processing unit 120 can include or be a microprocessor configured for executing stored program instructions, or another type of device such as a state machine. In several embodiments, the user interface 130 can include or be a keyboard, a pointing device such as a mouse, and a display device (e.g., a flat panel display). The memory 200 can include an operating system 210 as well as PEMF application program instruction sets/software modules 220 which, when executed by the processing unit 120, manage or direct aspects of particular PEMF exposure, treatment, or therapy processes in accordance with embodiments of the present disclosure, as further described below. The controller 110 can also include a data storage device 140 such as a hard disk drive or solid state disk drive; a pulse generator interface unit 150; and possibly a communication interface 160 such as a network interface unit by which the controller 110 can transfer information (e.g., signals and/or data) to and/or receive information from external systems, apparatuses, or devices, as also described below. The PEMF application system 100a can further include one or more PEMF regimen databases 190, PEMF signal parameter databases 192, and/or PEMF exposure history databases 194 that are accessible to the controller 110, where portions of such databases 190, 192, 194 can reside locally on or remote from the controller 110. Each of the foregoing elements of the controller 110 can be coupled to a common set of signal/data transfer pathways 102 such as buses. The pulse generator is connected to an amplifier that is specifically adapted to support the frequency range relevant to the PEMF signal used. In a number of embodiments, the controller 110 can include or be a computing system or device (e.g., a desktop, laptop, tablet, or other type of computer system). In certain embodiments, the controller 110 can include or be an embedded system, for instance, which utilizes a microcontroller or other type of device (e.g., a (re)programmable logic device such as a Field Programmable Gate Array (FPGA)) as its processing unit 120.

In general, the specific structure, characteristics, and capabilities of the controller 110 and the PEMF application system 110a can depend upon the intended type(s) of subjects to which the PEMF application system 100a is directed; the type(s) of PEMF application coils 400 that can or will be utilized; the type(s) of target tissues to which the PEMF application coils 400 can uniformly apply PEMF signals; and a supported set of system capabilities. For instance, a system configured for applying PEMF signals to human subjects can include each element of the PEMF application system 100a described above, as well as particular additional hardware and/or software elements that are relevant or useful for managing the application of PEMF signals, either alone or in combination with certain synergistic or adjunctive interventions, treatments or therapies, to human subjects. Analogously, a system configured for applying PEMF signals to animal subjects can include each element of the PEMF application system 100a described above, as well as particular additional hardware and/or software elements that are relevant or useful for managing the application of PEMF signals, either alone or in combination with specific synergistic or adjunctive treatments or therapies, to one or multiple animal subjects of a given animal type. Particular representative non-limiting examples of additional or other types of systems are elaborated upon hereafter with respect to FIGS. 4-5, which correspond to, include, are based upon, or are extensions of the PEMF application system 100a described above.

Figure 4A:
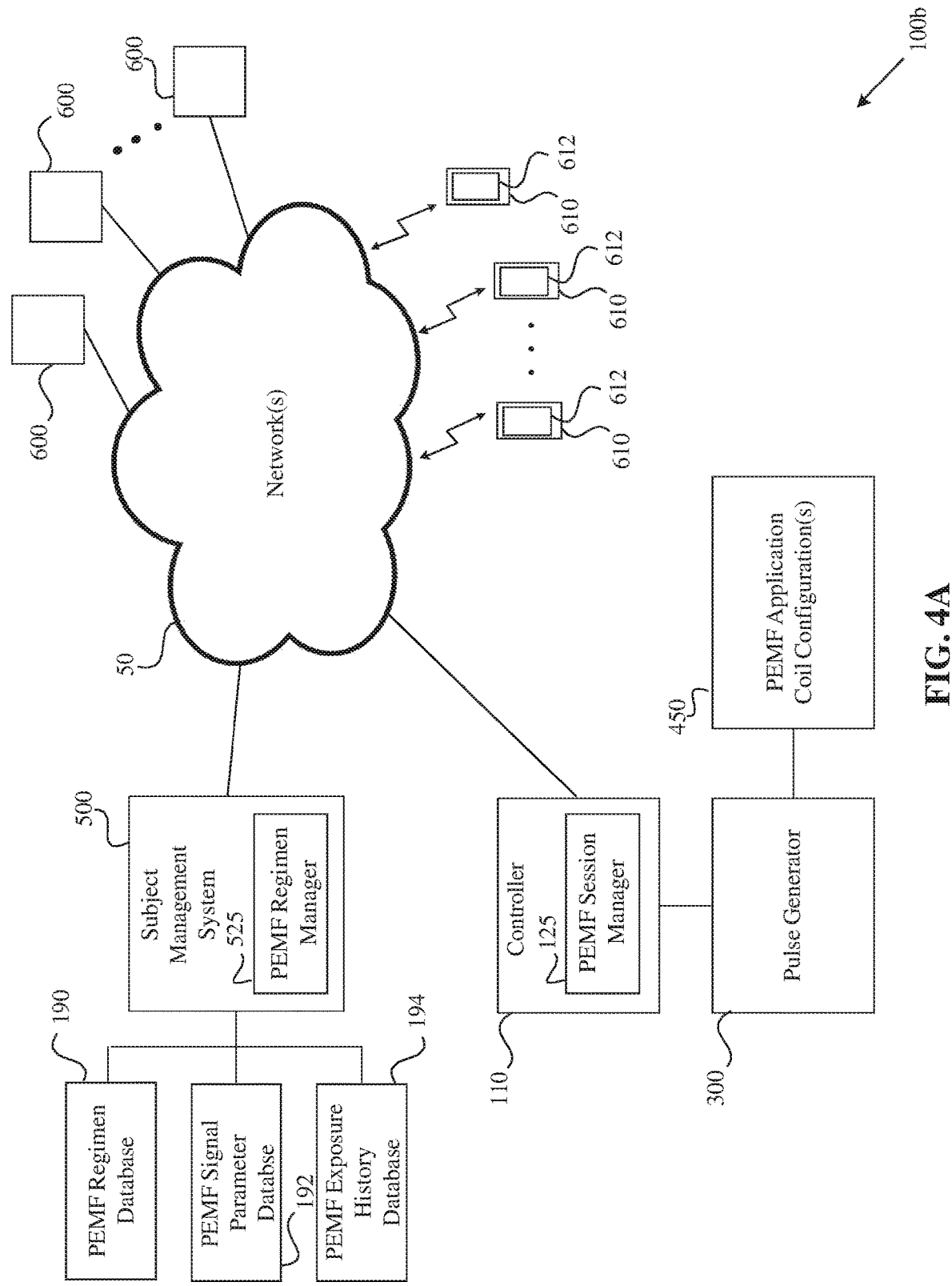
FIG. 4A is a schematic illustration showing portions of a system for managing the application of PEMFs as well as the application of synergistic or adjunctive events, activities, treatments, interventions, or therapies to human subjects in accordance with an embodiment of the present disclosure.

FIG. 4A is a schematic illustration of a representative system 100b for applying PEMF signals to target tissues of human subjects in accordance with an embodiment of the present disclosure. More particularly, the system 100b of FIG. 4A is configured for managing the application of PEMF signals as well as one or more types of synergistic or adjunctive treatments or therapies to human subjects. The system 100b of FIG. 4A may include each element of the system 100a described above with respect to FIGS. 1A to 2A-M, and further includes a subject management system 500, which can be local (e.g., on-site) or remote (e.g., off-site) with respect to the controller 110 depending upon embodiment details. The subject management system 500 can include a PEMF regimen manager 525 that includes program instruction sets/software modules by which PEMF exposure regimens can be defined and managed, and communication between the subject management system 500 and (a) the controller 110, and possibly (b) subject electronic and/or computing devices can occur.

In the embodiment shown, the controller 110 and the subject management system 500 are configured for communication with each other by way of a set of communication networks 50 such as one or more of a local area network (LAN), a wide area network (WAN), and the Internet. The subject management system 500 can further be configured for communication with subject electronic and/or computing devices by way of the set of communication networks 50, where the subject electronic and/or computing devices can include personal computers 600 and/or mobile telephones 610 used by or accessible to subjects.

In some embodiments, based upon information in the PEMF regimen database 190, the subject management system 500 can issue notifications/messages to one or more types of subject communication destinations or devices, such as subject computers/computing devices 600, subject mobile telephones 610, and/or other types of subject communication devices. Such notifications/messages can include one or more reminders directed to a given subject prior to their next scheduled PEMF exposure session, indicating that the subject is to ingest a particular set of nutritional or pharmacological adjuvants within a specified timeframe before the start of this PEMF exposure session. Additionally or alternatively, the subject management system 500 can support, provide, or link to a downloadable PEMF management mobile application 612 that is executable by subject mobile telephones 610, and which provides a subject user interface configured for (a) communicating such notifications/messages to subjects in accordance with each subject's PEMF treatment regimen details, and possibly (b) providing a calendar by which subjects can track/manage their scheduled PEMF exposure sessions. The subject management system 500 can additionally be configured for communicating surveys or questionnaires to subject communication devices 600, 610 at particular times (e.g., on a monthly basis with respect to the date of a subject's initial PEMF exposure session) by which subjects can indicate levels of perceived change in their biological/physiological state or condition over time, and/or provide other types of feedback relating to PEMF signal exposure.

In an embodiment such as that shown in FIG. 4A, the controller 110 can include a PEMF session manager 225, which includes program instruction sets/software modules that reside within the controller's memory 200 and which are executable by the controller's processing unit 120 such that the controller 110 can direct the exposure of PEMF signals to an appropriate set of target tissues of given subject (e.g., using an appropriate PEMF application coil configuration 450) during a PEMF exposure session in accordance with an appropriate set of PEMF signal parameters and an appropriate exposure session window. The PEMF session manager 225 can be configured for communication with the subject management system's PEMF regimen manager 525. Depending upon embodiment details, one or more sets of PEMF signal parameters can reside in the PEMF signal parameter database 192 and/or locally on the controller 110, for instance, in a look-up table stored in a nonvolatile memory. The table of FIG. 4B shows an exemplary look-up table. In certain embodiments, one or more exposure windows can be locally stored on the controller 110 in a look-up table.

Figure 5:
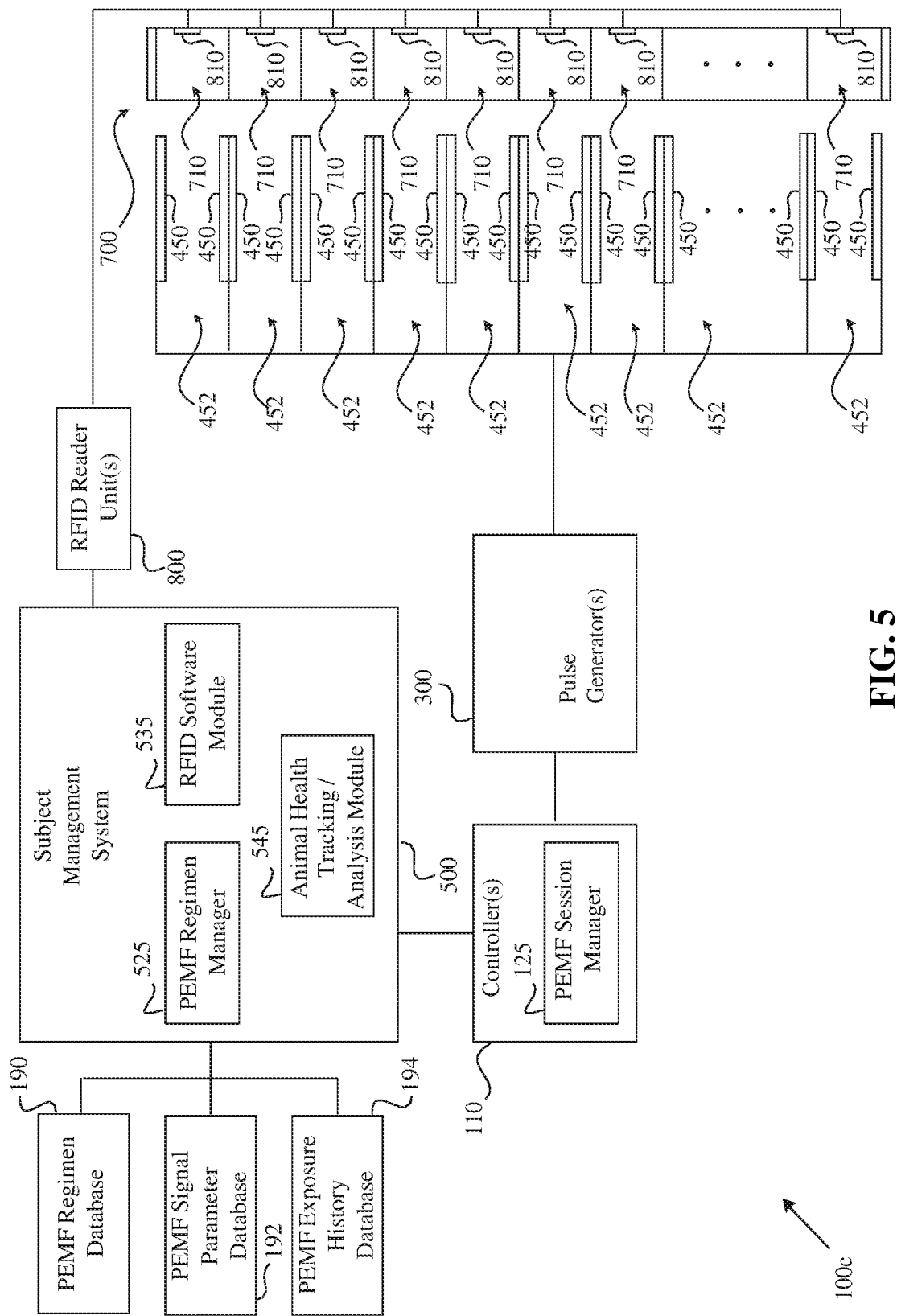
FIG. 5 is a schematic illustration showing portions of a system for managing the application of PEMFs to particular types of animal subjects such as livestock in accordance with an embodiment of the present disclosure.

FIG. 5 is a schematic illustration of a representative system 100c for simultaneously applying PEMF signals to target tissues of multiple animal subjects such as livestock (e.g., cattle, horses, swine, sheep, or poultry) in accordance with an embodiment of the present disclosure. The system 100c includes a subject management system 500; at least one controller 110, each of which is coupled to the subject management system 500; at least one pulse generator 300 coupled to the controller; and a plurality of PEMF coil configurations 450 couplable/coupled to the pulse generator(s) 300.

Depending upon embodiment details, each PEMF coil configuration 450 can expose particular target tissues of one side of a single animal to PEMF signals; or each PEMF coil configuration 450 can expose particular target tissues of one side of up to two animals (e.g., adjacent animals) to PEMF signals. For instance, in some embodiments directed to applying PEMF signals to the animals while they are collectively eating side-by-side at a feeding station 700 that includes a set of feed containers such as a trough structure and which provides multiple feed access points 710 at which the animals can reach and ingest their feed or feed mix, a given PEMF coil configuration 450 can expose target tissues on the lateral side of a single animal to PEMF signals, such that a given PEMF coil configuration pair 450 can apply PEMF signals to the two lateral sides of one animal. In such an embodiment, each PEMF coil configuration 450 can be arranged along or as a portion of a barrier, wall, panel, partition, fence, gate, or similar structure that separates or segregates one feed access point 710 from another, and which thus separates or segregates the animals from each other while they eat.

In several embodiments, the system 100c further includes at least one RFID reader unit 800 coupled to the controller 110 or the subject management system 500, where each RFID reader unit 800 is configured for reading animal IDs present in RFID tags worn by the animals while the animals are at the feeding station by way of a set of RFID antennas 810 coupled the RFID reader unit 800, in a manner readily understood by individuals having ordinary skill in the relevant art. Depending upon embodiment details, the RFID antennas 810 can be disposed relative to feed access point in various manners. For instance, the RFID antennas 810 can be carried by the set of feed containers 710 near or across from the animals' heads at each feed access point; carried by the barrier structures that support the PEMF coil configurations 450; or positioned above the animals' heads and bodies. The controller 110 or the subject management system 500 can include an RFID software module 535 within its memory 200, which when executed reads and records the animal ID of each animal at the feeding station 700 (e.g., on a recurring basis, such as every q seconds).

In accordance with a PEMF exposure regimen for the animals, at particular times of day on certain days and in response to the detection of animal presence at the feeding station (e.g., when animals are located at each of the feeding station's feed access points 710 or the majority of feed access points 710), the controller 110 can direct the pulse generator(s) 300 to be active while the animals are eating to thereby provide a feeding time PEMF exposure session during which the PEMF signals are applied in a manner that satisfies an exposure window (e.g., for a period of 5-15 minutes, or about 10 minutes during feeding), after which the pulse generator 300 can be automatically inactivated, disabled, or turned off. In several embodiments, the pulse generator(s) 300 can be selectively activated and inactivated in accordance with a regimen efficacy window, for instance, such that they drive the PEMF coil configurations 450 only on alternating days, or every $r^{th}$ day.

The subject management system 500 can include an animal health tracking/analysis module 545 that when executed associates animal IDs with PEMF exposure session data for the animals. Depending upon the structure of the feeding station 700, the feeding station 700 can include a number of sensing devices configured for detecting, monitoring, or measuring certain information or signals relevant to the animals' current state of health and/or their feed consumption during any given feeding session. For instance, the feeding station 700 can include sensors configured for detecting an amount of feed consumed by each animal during the feeding session; the weight of each animal at each feed access point at one or more times during the feeding session; the body temperature of each such animal during the feeding session; and/or other information. The feeding station 700 can be coupled to the subject management system 500 such that at least some of such information can be communicated to and analyzed by the animal health tracking/analysis module 545, in association with PEMF exposure session data for each animal.

In various embodiments, one or more nutritional or pharmacological adjuvants (e.g., capsaicin, which can be coated or encapsulated with a starch and/or other biocompatible substance such as hydroxypropyl methylcellulose to manage animals' flavor intensity tolerance, as needed) can be included in the animal feed. For a feeding station 700 having automated feed mixing and/or dispensing capabilities, the animals' feed composition, or individual animals' feed composition, for any given feeding session can also be communicated to the animal health tracking/analysis module 545.

The animal health tracking/analysis module 545 and/or the feeding station 700 can include or be based upon portions of commercially available systems, for instance, a GrowSafe feed intake and monitoring system (GrowSafe Systems Ltd., Airdrie, Alberta Canada, www.growsafe.com) or other type of system.

By way of exposing animals to PEMF signals in a manner that satisfies or follows a PEMF exposure regimen in accordance with an embodiment of the present disclosure (e.g., which can include a regimen efficacy window and/or an exposure efficacy window in a manner identical, essentially identical, or analogous to that described above), animal tissues that have been exposed to such PEMF signals on a regular basis over a sufficiently long period of time spanning the animals' juvenile phase into their adulthood can exhibit an enhanced or significantly enhanced growth rate and overall growth. In particular, exposure of animal muscle tissues to PEMF signals in accordance with embodiments of the present disclosure, from the animals' juvenile phase into their adulthood, can give rise to increased or significantly increased muscle mass in the animals exposed to such PEMF signals compared to animals that have not been exposed to the PEMF signals. Furthermore, exposure of animal muscle tissues to PEMF signals in accordance with embodiments of the present disclosure can increase the fat content of such muscle tissues, thereby enhancing the palatability of such tissues for consumers. In such cases body regions possessing the greatest relative proportions of muscle mass can be targeted for optimal hormonal, metabolic and anabolic effect(s).

In view of the foregoing, it will be readily understood by individuals having ordinary skill in the relevant art that alternate embodiments of the present disclosure can be configured for applying PEMF signals in one or more manners set forth herein to in vitro meat tissues to thereby enhance the growth rate, mass, and palatability of such tissues.

Figure 6:
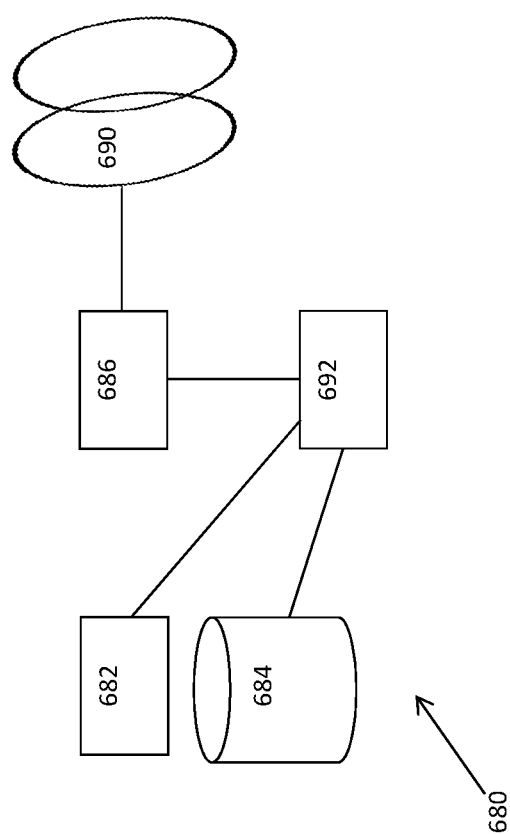
FIG. 6 is a schematic illustration showing a system for applying a pulsed electromagnetic field (PEMF) to a cell in accordance with an embodiment of the present disclosure.

FIG. 6 is a schematic illustration of a representative system 680 for applying a pulsed electromagnetic field (PEMF) to a cell in accordance with an embodiment of the present disclosure. The 680 includes a sensor 682, memory module 684, pulse generator 686 and controller 692. The sensor 682 is configured to obtain a characteristic of the cell. A plurality of characteristics and EMF efficacy window data is stored in the memory module 684. Each characteristic has its corresponding EMF efficacy window data. The pulse generator 686 is coupled to a set of PEMF coils 690 and is configured to generate an output of electrical pulses to drive the set of PEMF coils 690. The controller 692 is in communication with the sensor 682, the memory module 684 and the pulse generator 686, and is configured to: retrieve, from the memory module 684, the EMF efficacy window data that corresponds to the characteristic of the cell obtained by the sensor 682; and control the output of the pulse generator 686 based on the retrieved EMF efficacy window data such that the set of PEMF coils 690 apply a PEMF in accordance with the EMF efficacy window data. The system 680 may further include an amplifier (not shown) that is in communication with the pulse generator 686. The amplifier is configured to support the frequency range of the PEMF signal.

In an implementation, the EMF efficacy window data described above may comprise PEMF signal parameters. The PEMF signal parameters may comprise one of more of: amplitude, frequency, symmetry, field gradient, uniformity, direction and duration of the PEMF that is emitted by the set of PEMF coils 690.

As described above, the direction of the EMF field emanating from a given coil design can be exploited to target tissues. Aligning the long axis of the cells/tissues parallel to the EMF lines changes the EMF efficacy window, requiring smaller/greater amplitude PEMFs. The direction of the EMF field can be changed depending on the characteristic of the cell in question/the type of tissue to be targeted. In an implementation, the direction of the EMF field can be varied by using different coil configurations. With reference back to FIG. 2H, a cylindrical coil configuration (as shown and described above in relation to FIG. 2A) creates a field that is best aligned for the activation of bone, whereas a clam/saddle coil configuration (as shown and described above in relation to FIG. 2B) creates a field that is best aligned for the stimulation of muscle in a leg. The set of PEMF coils 690 can comprise multiple coil configurations (e.g. a cylindrical coil configuration and a clam/saddle coil configuration), and the controller 692 can be configured to selectively operate one or more of the multiple coil configurations at particular periods of time. For example, if the sensor 682 detects that the muscle cell in question is part of muscle tissue, the controller 692 can be configured to selectively operate the clam/saddle coil configuration of the set of PEMF coils 690 in order to target the cell in question. On the other hand, if the sensor 682 detects that the cell in question is part of a bone, the controller 692 can be configured to selectively operate the cylindrical coil configuration of the set of PEMF coils 690 in order to target the bone cell. Similarly, if an entire leg is to be treated, during a first PEMF application period, only the clam/saddle coil configuration is activated by the controller 692 to target the muscles in the leg, and during a second subsequent PEMF application period, only the cylindrical coil configuration is activated by the controller 692 to target the bones in the leg.

In another implementation, the set of PEMF coils 690 can comprise an array of individual PEMF coils that are disposed in a variety of fixed positions in a three-dimensional space. One or more of the individual PEMF coils in the array can be selectively activated (by the controller 692 and pulse generator 686) to generate EMF fields with different directions relative to a cell/tissue in question. For example, to generate an EMF field that is orthogonal to a first cell's long axis, only the PEMF coils that are able to generate such a field are activated. To generate an EMF field that is orthogonal to a second cell's long axis, the second cell having a long axis in different orientation with respect to the first cell, only the PEMF coils that are able to generate such a field are activated.

In yet another implementation, the set of PEMF coils 690 can comprise an array of individual movable PEMF coils that can be selectively moved (via suitable coil actuating mechanisms controlled by controller 692) relative to a cell/tissue in question. For example, the coil actuating mechanisms can move each individual coil from one position to another position such that the array of individual coils can be positioned in a manner to form different coil configurations (e.g. cylindrical, clam, saddle, cavity, etc.).

In an implementation, the plurality of characteristics described above may comprise a type of the cell. The cell may be part of a tissue, in which case the sensor 682 is a tissue sensor that is capable of detecting a type of the tissue.

As an example, the tissue sensor 682 detects that a tissue under analysis comprises a cell that is part of skeletal muscle tissue. In other words, the characteristic of the cell (i.e. cell type) is "skeletal muscle". With reference back to Table 1, a plurality of characteristics (cell types) and EMF efficacy window data is stored in the memory module 684. Each characteristic has its corresponding EMF efficacy window data. For example, the EMF efficacy window data corresponding to skeletal muscle is 1 mT in amplitude, 10 minutes in duration, frequency of 15 Hz, and orthogonal directionality. The controller 692 is configured to retrieve, from the memory module 684, the EMF efficacy window data that corresponds to the characteristic of the cell obtained by the sensor 682 and control the output of the pulse generator 686 based on the retrieved EMF efficacy window data such that the set of PEMF coils 690 apply a PEMF in accordance with the EMF efficacy window data (i.e. 1 mT in amplitude, 10 minutes in duration, frequency of 15 Hz, and orthogonal directionality) to the skeletal muscle tissue.

Alternatively or in addition to the sensor 682, the system 680 may include a user input module (not shown in FIG. 6) for receiving characteristic(s) of the cell that is inputted by a user. For example, the user input module may include a keypad for a user to input the characteristic(s) of the cell. In such an implementation, the controller 692 is configured to retrieve, from the memory module 684, the PEMF efficacy window data that corresponds to the characteristic of the cell received by the user input module.

The sensor 682 may be capable of detecting the volume of the tissue within the PEMF coils 690, and the controller can be configured to focus the optimised PEMF onto the affected area. For example, when targeting treatment of ACL, the patient puts his knee through the PEMF coils, and the field's focus point may be affected by a knee of a fat person versus a thin one. For example, an ultrasonic sensor may be used to detect how close the boundary of that person's knee is to the coils and the controller can correct the focus of the field.

In an implementation, data relating to a plurality of PEMF regimens may be stored in the memory module 684. Each characteristic described above may have its corresponding PEMF regimen. The data relating to the plurality of PEMF regimens may comprise a minimum time period between successive PEMF application sessions and/or a maximum number of PEMF application sessions within a certain amount of time. With reference back to Table 1, the field "exposures/week" indicates that maximum number of PEMF application sessions within a week for cells having different characteristics. For example, "skeletal muscle" is preferably exposed to the PEMF once a week, at the maximum.

The system 680 may further include an identification module (not shown) for obtaining an identity of the cell. A PEMF application history of an identified cell relating to at least one previous application of PEMF to the identified cell may be stored in the memory module 684. The controller 692 is further configured to control the output of the pulse generator 686 based on the PEMF exposure history of the identified cell for a subsequent application of PEMF to the identified cell. The identification module may also be capable of obtaining an identity of a tissue or a subject (human, animal, etc.) and the memory module may further store a PEMF application history of an identified tissue/subject relating to at least one previous application of PEMF to the identified tissue/subject. The controller may be further configured to control the output of the pulse generator based on the PEMF exposure history of the identified tissue/subject for a subsequent application of PEMF to the identified cell. In other words, the system 680 may be capable of personalize human or animal treatment based on age, metabolic status or body composition.

The system 680 may further include a detector (not shown) for detecting the response from the cell after a first application of PEMF. The controller 692 is further configured to control the output of the pulse generator 686 based on the detected response from the cell for a second subsequent application of PEMF to the cell.

While features, aspects, and/or advantages associated with certain embodiments have been described in this disclosure, other embodiments can also exhibit such features, aspects, and/or advantages, and not all embodiments need necessarily exhibit such features, aspects, and/or advantages to fall within the scope of the disclosure. It will be appreciated by a person of ordinary skill in the art that aspects of several of the above-disclosed embodiments can be desirably combined into other different systems, apparatuses, devices, processes, procedures, and/or applications/health indications. In addition, various modifications, alterations, and/or improvements within the scope and spirit of the present disclosure may be made to one or more embodiments disclosed herein by a person having ordinary skill in the art.

EXPERIMENTAL SECTION

Acceleration of Myogenesis Using PEMF
Materials and Methods
Cell Culture

C2C12 mouse skeletal myoblasts were obtained from American Type Culture Collection (ATCC; LGC Standards, Molsheim Cedex, France) and cultured in growth medium (GM) consisting of Dulbecco's modified Eagle medium (DMEM; Life Technologies, Lucerne, Switzerland) supplemented with 10-20% fetal bovine serum (FBS; PAA, Basel, Switzerland) and 2 mM L-glutamine (Life Technologies) in a humidified atmosphere at 37° C. in 7% $CO_2$ (4,6,8). Cells were passaged every 48 hours to maintain them below 40% confluency. Myoblasts were seeded at 2000 cells/cm$^2$ in 25-cm$^2$ flasks (Semadeni, Ostermundigen, Switzerland). Special care was taken to only examine cells before 5-6 passages after thawing and to not allow the cells to grow beyond 60% confluence at any point prior to their exposure to PEMFs. When these criteria were followed, cells responded characteristically to PEMFs.

The differentiation of myoblasts was induced with a change in serum composition of the medium from 10% FBS to 2% horse serum at 48 hours after plating or as specified. For the determination of fusion index, cells were fixed with 1% methanol-free formaldehyde and F-actin was stained with rhodamine phalloidin (Sigma-Aldrich, cat. P1951). DAPI (Sigma-Aldrich, cat. D9542) was used for visualizing nuclei. Series of 4 images with 20× magnification were taken for each sample and myotube area was calculated by manually delimiting the myotube periphery using ImageJ (Cell Counter plugin). 2-Aminoethyl diphenylborinate (2-APB; Sigma, Switzerland) was administered to cells 15-30 minutes before exposure to PEMFs at a working concentration of 100 µM in GM and was replaced summarily afterwards with age-matched media from sister cultures.

Calcium Imaging

In preparation for measurement of changes in intracellular calcium in response to PEMF treatment with flow cytometry myoblasts (50,000 cells) were spun down (1000 RCF; 5 minutes), resuspended in 2 ml of PBS and next loaded with 20 µl Calcium Green-1, AM (50 µg in 100 µl DMSO; Molecular Probes) for 30 minutes at 37 C in the dark. Following incubation, cells were washed once, resuspended into 500 µl PBS and placed on ice before registry in a BD FACSAria Flow Cytometer (FL1 channel). For plate reading assessment of intracellular calcium, myoblasts were plated into 96 black well plates (Brand 96 Flat Bottom Black) at 10,000 cells/wells. Cultures were washed once with PBS and supplied with 250 µl growth media to which Calcium Green-1 AM (50 µg in 100 µl DMSO; Molecular Probes) had been added at a dilution of 1:1000. Myoblasts cultures were then incubated in a standard tissue culture incubator for 5 minutes, followed by PEMF exposure for 10 minutes and then replaced in the incubator for an additional 15 minutes at 37° C. before washing with 37° C. PBS. Calcium measurement was conducted using a Tecan Infinite 200Pro plate reader with excitation wavelength and emission wavelengths set to 500 nm and 535 nm, respectively, and bandwidth excitation and emission wavelengths set to 9 and 20 nm, respectively.

Western Blots and PCR

Total protein extraction was carried out using Radioimmunoprecipitation assay (RIPA) lysis buffer containing 50 mM NaCl (Numi), 1 mM EDTA, 50 mM Tris-HCl, 1% Triton X-100, 0.05% SDS, 1× Protease inhibitor and 0.1% Sodium deoxycholate. Lysates were collected using cell a scraper and incubated at 4° C. for 30 minutes before being spun at 12000 rpm for 15 minutes at 4° C. Protein samples with 1× loading dye were next boiled it at 90° C., run on SDS PAGE, transferred to nitrocellulose membrane, blocked with 5% skimmed milk powder and probed with anti-P/CAF (Santa Cruz Biotechnology), anti-E2F1 (Abcam), anti-MyoD (Santa Cruz Biotechnology), anti-p21 (Santa Cruz Biotechnology), anti-β-actin (Sigma).

For histone protein extract, 1× Laemmli buffer containing 62.5 mM Tris, pH 6.8, 10% glycerol 2% SDS, 1× protease inhibitor was added to the cells and lysates collected. Samples were heated for 10 minutes at 90° C. then allowed to cool down to room temperature. Samples were next briefly mixed with sonication, heated for 5 minutes at 90° C. in 5× loading buffer, before being run on SDS PAGE. Transfer of proteins was to nitrocellulose membranes, which were blocked and immunoblotted with H3K9ac (abcam) and anti-H3 (abcam) antibodies. PCR was conducted as previously described (6,8).

Pulsed Electromagnetic Field (PEMF) Exposure

The PEMF exposure device used in this study produces a spatially homogeneous, time-varying field, consisting of barrages of pulses, each lasting 6 ms, repeated at a frequency of 15 Hz. Each pulse train consists of 20×150 μsec asymmetric pulses separated by 150 μsec interpulse intervals to the 0 flux level. The magnetic flux density rose to maximal level within 20-50 μsec and dropped equally as rapidly (50 T/s). Flux magnitude and time of duration were applied as indicated in the results and ranged between 0.5 and 2 mT for exposure durations of 5-60 minutes. All PEMF-treated samples were compared to time-matched control samples (0 mT) that were manipulated in exactly the same as experimental samples, including placement into the PEMF-generating apparatus for the designated time, except that the apparatus was set to generate a magnetic field signal.

Live Cell Imaging

Live cell imaging was conducted using a Cell-IQ® Live Cell Imaging System (CM Technologies Oy). Examples of cytokinetic profiles and recently divided cells were input into the Cell-IQ Analyser™ software which enabled morphological classification and quantification of the cell populations to be made over the 48 hour imaging period. Two six-well dishes were simultaneously monitored for cell division; both plates were placed into our PEMF device for 10 minutes, but only one was exposed to 1 mT magnetic fields. Three wells from each dish were monitored per condition and three wells from each dish received 100 mM 2-APB.

Simulation of Microgravity

Gravitational mechanical unloading was achieved with a Random Positioning Machine (RPM). The RPM was kept in a temperature-controlled room at 37° C. The calculated gravity exerted upon cells on the RPM was below 0.02 g. Cells were seeded 15 hours prior to the start of the RPM experiment at 8000/cm$^2$. At 15 hours some samples were incubated with 5 mM CaCl$_2$ for 10 min, washed twice with PBS, given aged matched GM and placed onto the RPM. Other samples were exposed to PEMF at 37° C. (0.5 or 1.5 mT) for 10 min before being placed onto the RPM. Samples were fixed after 2 hours for subsequent cell cycle analysis as described below.

Cell Cycle Analysis

Following RPM treatment (above) cells were fixed and stored at −20° C. in 70% ice-cold ethanol for 12 to 18 hours prior to staining. Cell cycle was analyzed based on DNA content using a propidium iodide (PI)/RNase staining kit (BD Biosciences, cat#550825) by FACS.

Mechanical Vibration of C2C12 Myoblasts

This inherent vibration of the PEMF coil system was measured with a vibration transducer BU-21771-000 (Knowles Electronics, Itasca, USA) in the frequency range of 50-6000 Hz. Cultures dishes of C2C12 myoblasts were then stimulated with a mechanical signal mimicking the vibration caused by PEMF exposure system with a TV50018 shaker system (Tira GmbH, Schaulkau, Germany).

Results

TRPC1 expression is elevated in C2C12 myoblasts during the first 24 hours in culture, agreeing with its reputed role in satisfying the calcium requirement for proliferation. Changes in TRPM7 expression, by contrast, more closely follows the time course of cell cycle withdrawal. The expression patterns of TRPC1 and TRPM7 thus correspond with pre- and post-differentiated states in myoblasts, respectively. Given previous reports that PEMFs stimulate the proliferation of diverse stem cell classes and moreover, induce calcium increments in C2C12 myoblasts, whether PEMFs could provoke calcium entry via TRP channels was tested and if so, whether sensitivity to PEMFs parallels the expression pattern of either channel.

Figure 12:
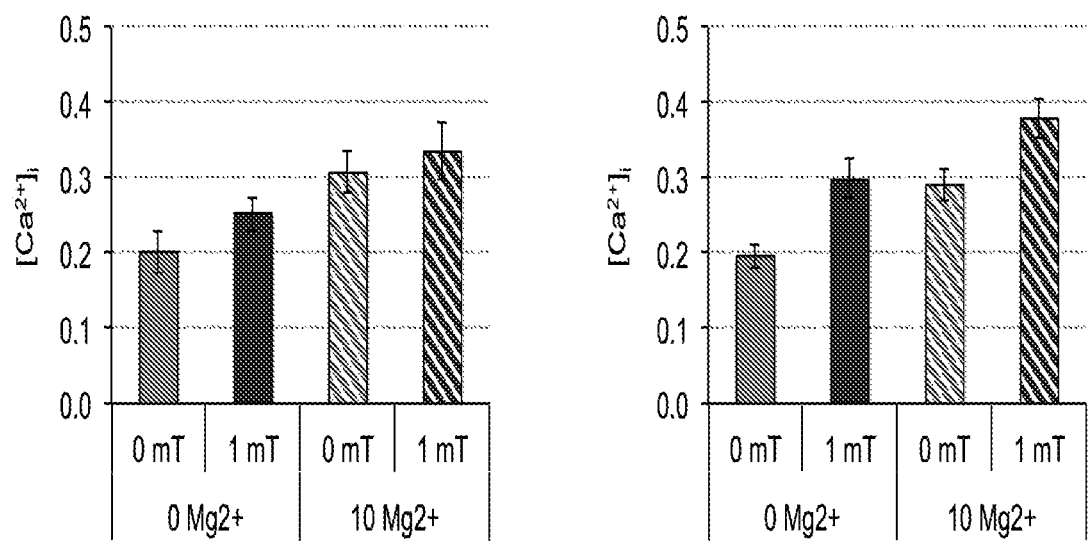
FIG. 12 shows that TRPM7 channels are not responsible for the entry of calcium in response to PEMF exposure. Raising extracellular magnesium to 10 mM does not prevent PEMFs from raising intracellular calcium, but rather augmented both basal and PEMF-induced calcium levels. This result indicates that TRPM7 channels are not responsible for the entry of calcium in response to PEMF exposure (cf 20). Duplicate experiments; 12 wells assayed per condition by plate reading.

Brief (10 minutes) exposure to PEMFs (1 mT) applied within the first 24 hours of plating augmented cytosolic calcium levels (blue) to a similar degree as 1 μM ionomycin (light green; FIG. 7A). Next the calcium responses of paired myoblast cultures to PEMFs applied at either 18 or 48 hours after seeding were compared. Although, resting calcium levels were lower after 48 hours in culture (FIG. 7B, left), PEMFs were still able to augment cytosolic calcium levels by a similar relative percentage over baseline at either time point (FIG. 7B, right), indicating that the implicated calcium entry pathway was still operational yet, down-regulated at 48 hours. Pharmacologically antagonizing TRPM7/C1 channels with 2-APB precluded the ability of PEMFs to provoke calcium increments, indicating that PEMFs open either one or both of these channels (FIG. 7C). Selectively antagonizing TRPM7 by raising extracellular magnesium to 10 mM did not prevent PEMFs from raising intracellular calcium, suggesting that PEMFs are largely targeting TRPC1 (FIG. 12).

Figure 7:
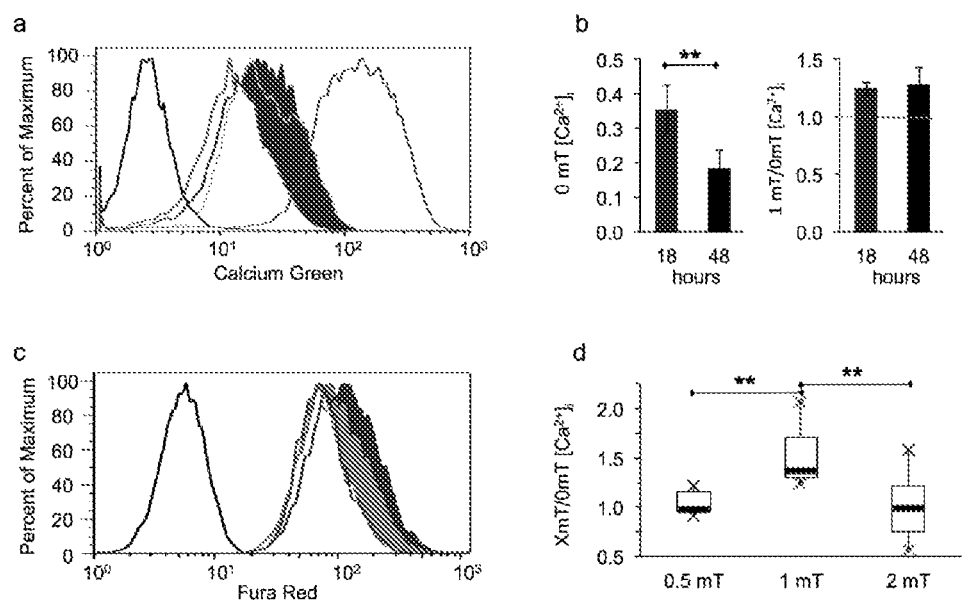
FIG. 7 shows the stimulation of TRP-mediated calcium entry into C2C12 myoblasts by PEMFs. A) Exposing myoblasts to 1 mT PEMFs (10 min; blue) increased $[Ca^{2+}]_i$ to a comparable magnitude as 1 µM Ionomycin (30 min; light green) relative to unexposed cells (10 min; red). The blue-shaded region depicts the increase in $[Ca^{2+}]_i$ produced by PEMFs. Five-hour application of ionomycin (1 µM; dark green) produced lethal $[Ca^{2+}]_i$. Distribution of unstained cells is shown in black. B, left) Resting $[Ca^{2+}]_i$ was attenuated after 48 hours in culture. Nonetheless, exposure to 1 mT PEMFs (10 min) produced similar relative increases in $[Ca^{2+}]_i$ at both 18 hours and 48 hours (right). C) 2-APB (10 µM) reduced $[Ca^{2+}]_i$ to a common baseline in both unstimulated (0 mT; grey-blue) and stimulated (1 mT; grey) myoblasts. Unexposed (0 mT; red) and exposed (1 mT; blue) cells in the absence of 2-APB. The red region depicts the $[Ca^{2+}]_i$ attributed to the activity of TRP channels under resting conditions. D) Exposure of myoblasts to 0.5 mT, 1 mT, or 2 mT PEMFs (10 min) produced increases of $[Ca^{2+}]_i$ of 6%±14% (n=4), 53%±30% (n=11) and 7%±39% (n=5), respectively. ** reflects highly significant differences (>99% confidence).
Figure 13:
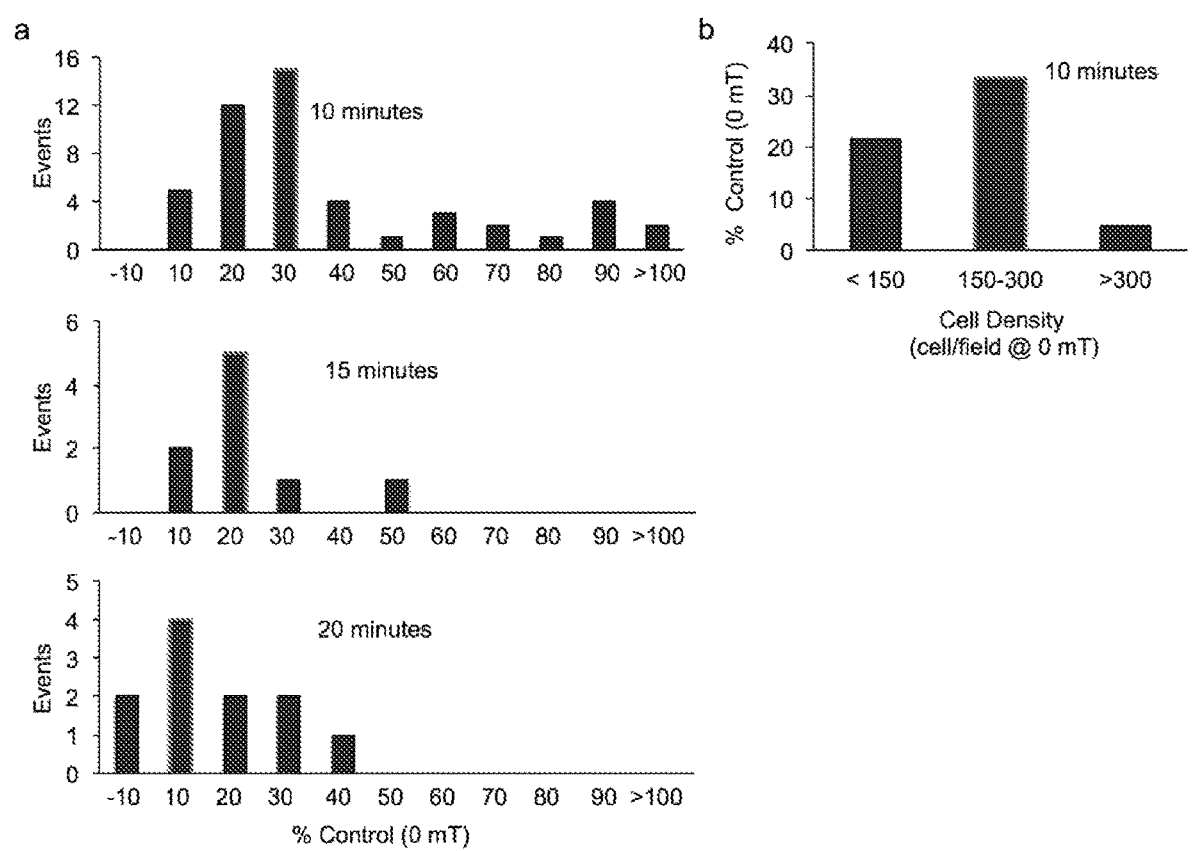
FIG. 13 shows the frequency distributions of 1 mT PEMF responses at 10, 15 and 20 minute exposures. A) Peak in response amplitude shifts to lower values with increasing time of exposure. B) Cell density determines responsiveness to PEMFs. Cell density was obtained by calculating the mean number of cells per 16-20 microscopic fields of view (20×) under control conditions (0 mT). Cultures not exhibiting the optimal cell density at time of PEMF application because they were dividing too slowly (lower confluence) or too rapidly (higher confluence) were less response to the fields, helping account for the high variability in responses.

2-APB reduced the cytosolic calcium levels to a common baseline in both untreated (gray) and PEMF-treated (teal) myoblasts (FIG. 7C), exposing TRP channels open at "rest" (red region). Next, testing was performed to determine if the PEMF signals could stimulate the proliferation of myoblasts by augmenting resting TRP channel activity and if so, the minimum time required to do so. A single 5-minute exposure to 1 mT PEMFs applied within the first 24 hours of culturing was sufficient to enhance proliferation (FIG. 8A). Nonetheless, the greatest increase in proliferation was observed in response to a 10-minute exposure. By contrast, exposure durations greater than 15 minutes had no effect over proliferation (also see FIG. 13A). 2-APB abolished the ability of PEMFs to enhance proliferation (FIG. 8A, light blue), substantiating that TRPC1-mediated calcium entry leads to proliferation (FIG. 7C). Likewise, cyclosporin A also prevented PEMFs from enhancing proliferation (FIG. 8A; inset), indicating that PEMF-induced calcium entry activates calcineurin/NFAT calcium-dependent signaling. If, on the other hand, PEMFs were applied at 48 hours after plating, proliferation enhancement was diminished (FIG. 8C). In summary, PEMFs promote proliferation by increasing calcium entry via TRPC1 (FIG. 7); an effect that is diminished after 48 hours in culture due to TRPC1 down-regulation (FIG. 7B (left)), not reduced sensitivity of TRPC1 to PEMFs (FIG. 7B, right). Given that basal expression of TRPM7 is overall higher than that of TRPC1 and increases further at 48 hours, when sensitivity to PEMFs wanes (FIG. 8C), corroborates that PEMFs are not targeting TRPM7, but TRPC1.

Exposure to PEMFs of 1 mT amplitudes was most consistent at increasing proliferation (FIG. 8D). Although stronger fields often gave greater proliferative responses they also occasionally inhibited proliferation. One interpretation of this result may be that stronger fields stimulate differentiation (cell cycle withdrawal) as well as proliferation (cell cycle entry), as both processes require calcium. Next, tests were performed to determine whether PEMFs could likewise promote myogenic differentiation. Exposing proliferating myoblasts to PEMFs (1 mT) increased mean myotube area (FIG. 9A), which was prevented with neomycin (100 μM), agreeing with data that the aminoglycoside antibiotics antagonize TRPC1. PEMF exposure produced the greatest differentiation when applied only once within 18 hours of plating. Adhering to this protocol PEMF-treatment (1.5 mT, 10 min) increased the number of larger myotubes and decreased the proportion of smaller myotubes (FIG. 9B). If, by contrast, PEMFs (1.5 mT, 10 min) were administered to myoblasts after 48 hours of plating, a tendency towards smaller myotubes was observed (FIG. 9C). The enhancement in myotube development observed with early PEMF delivery is depicted in FIGS. 9D and 9E. In both images nascent myotubes are colored in green, whereas larger, more mature myotubes are shown in red (0 mT; FIG. 9D) or blue (1.5 mT; FIG. 9E). The incidence of nascent myotubes (green) is greater in unstimulated (FIG. 9D) than in PEMF-treated cultures (FIG. 9E). Conversely, PEMF-treatment produced a greater number of larger anastrosomal-like myotubes (blue; FIG. 9E) relative to control (red; FIG. 9D). Also noticeable are the relatively fewer unfused reserve myoblasts in the PEMF-treated cultures, suggesting that commitment to fusion (cell cycle withdrawal) is more encompassing following early exposure to the fields (next section). Whether PEMF-induced calcium entry merely primes myogenesis or exerts a determinant influence over myogenic status was next tested. Daily PEMF stimulation (hatched) mitigated myotube formation, particularly with reference to singly PEMF-treated cells (blue; FIG. 9E), but also relative to untreated cultures (red), indicating that repeated stimulation is counterproductive.

Figure 10:
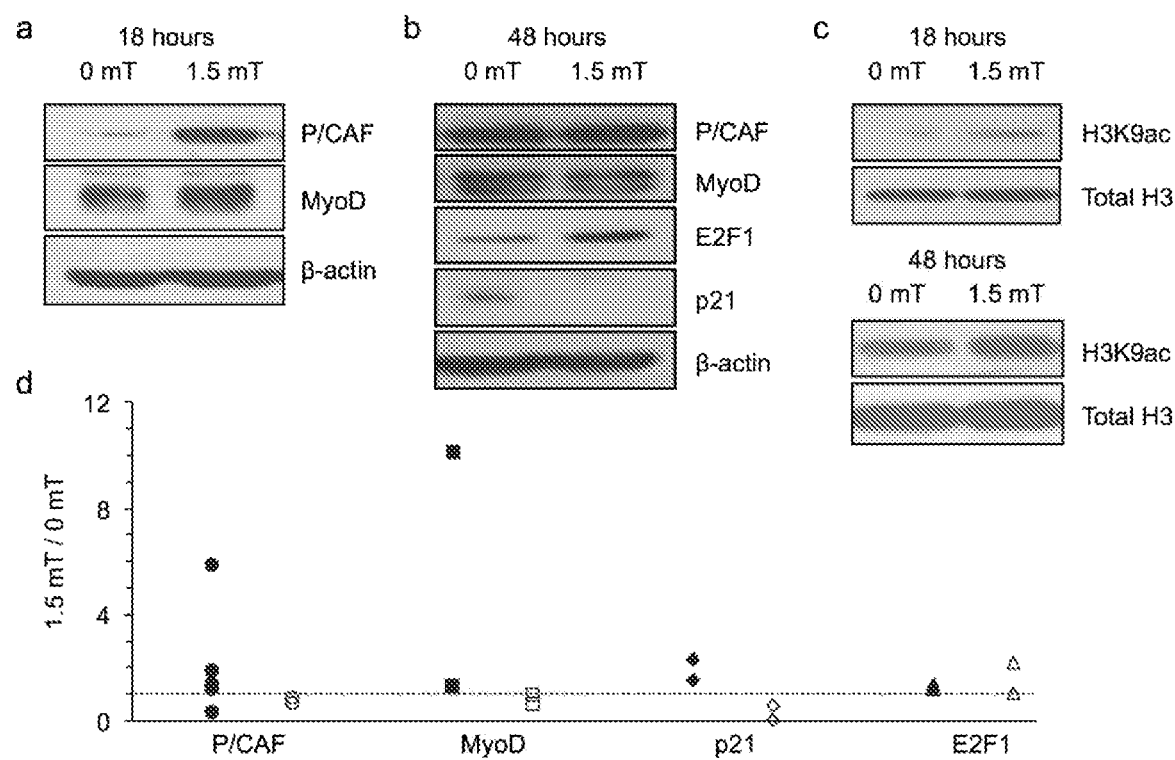
FIG. 10 shows that PEMFs promote and defer differentiation when applied to cells at 18 hours and 48 hours respectively. A) Exposure of myoblasts to 1.5 mT PEMFs at 18 hours of plating increased the expression of both P/CAF (histone acetyltransferase) and E2F1 (myogenic regulatory factor). B). Changes in the expression of P/CAF, a cell cycle regulator (p21) and myogenic regulatory factors (MyoD, E2F1) in response to exposure to 1.5 mT after 48 hours of plating. Changes in protein expression were relatively modest in comparison to those measured at 18 hours. C) Changes in histone acetylation (via P/CAF) in response to 1.5 mT PEMF exposure for 10 minutes after 18 hours (top) and 48 hours (bottom) after plating. Histone modifications in response to PEMFs are stronger after 18 hours in culture. D) Magnitude of change in the expression of P/CAF, MyoD, p21 and E2F1 after 18 hours (solid symbols) or 48 hours (open symbols) in response to 1.5 mT PEMF exposure for 10 minutes. Six replicates are shown for P/CAF at 18 hours; all others are duplicates. The greatest increases in expression were observed at 18 hours for all proteins, except E2F1. The dashed red line indicates level of no change. All values are normalized to beta-actin.

Chromatin modifying enzymes regulate myogenic progression by modulating the activity of myogenic regulatory factors as well as altering accessibility of the transcription machinery to chromatin via histone post-translational modification. The expression of P/CAF (histone acetyltransferase; 22), a pro-differentiation epigenetic enzyme, was followed, following stimulation with 1.5 mT PEMFs at 18 and 48 hours. At 18 hours the expression of P/CAF rose with PEMF stimulation (FIG. 10A); changes in P/CAF expression at 48 hours were less noticeable (FIG. 10B). Global levels of H3K9ac (histone target of P/CAF) also rose more after exposure at 18 hours (FIG. 10C, upper panels), than at 48 hours (FIG. 10C, lower panels). MyoD was upregulated in response to early PEMF application, coinciding with its activation through acetylation by P/CAF and reflecting accelerated differentiation, particularly at early time points. By contrast, the expression of E2F1 and p21 were upregulated and down-regulated, respectively, at later time points (FIG. 10B), indicating that differentiation was being deferred at the expense of proliferation with later PEMF stimulation. FIG. 10D shows a composite of responses from a subset of markers after exposure to 1.5 mT PEMFs at 18 hours (solid symbols) and 48 hours (open symbols) after plating. The developmental status of myoblasts hence determines their response to PEMFs, generally exhibiting dichotomous responses at earlier and later time points and serving to defer differentiation when applied at later time points.

Figure 8:
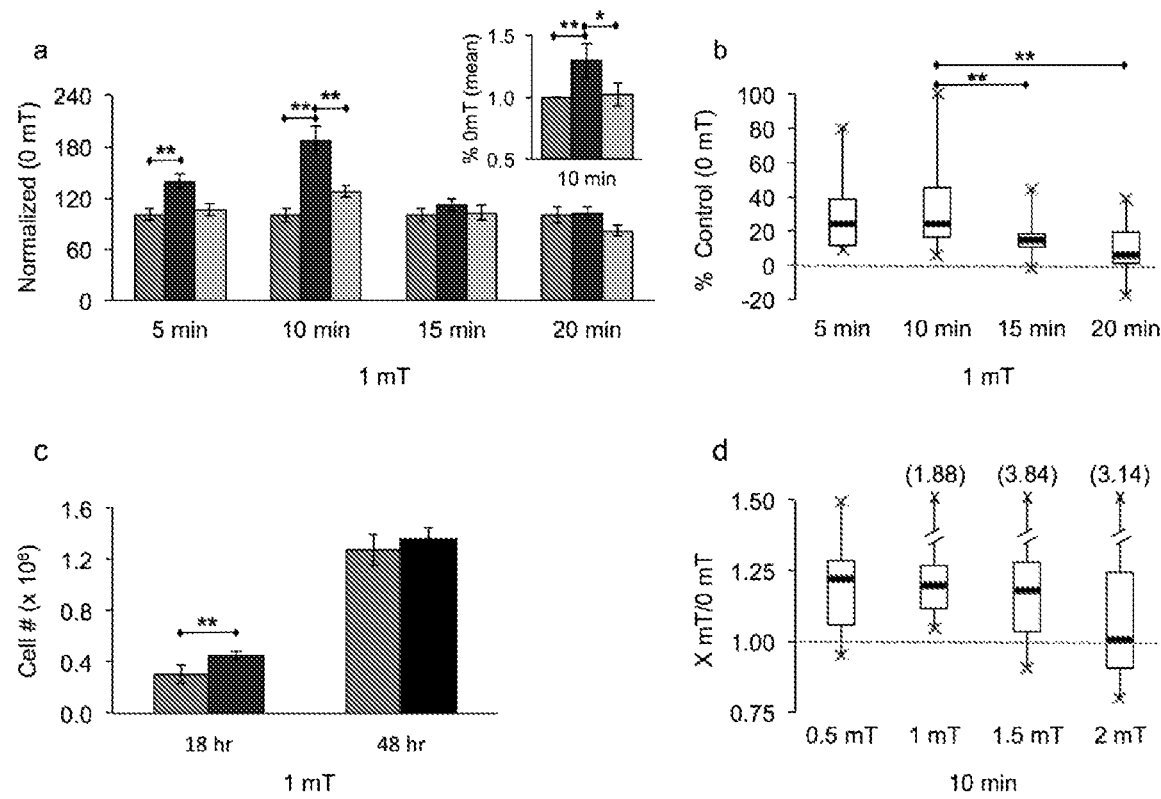
FIG. 8 shows the effect of brief exposure of C2C12 myoblast to PEMFs on proliferation when applied within 18 hours after plating. A) Myoblasts were exposed to 1 mT PEMFs for the indicated times in the presence (light blue) or absence (dark blue) of 100 µM 2-APB. All values are normalized to control cultures (red; 0 mT). Inset) Cyclosporin A (2 μM, light blue) abolished PEMF-induced proliferation (blue) relative to unexposed cells (red). B) Range of proliferation changes after 5 min (n=7), 10 min (n=49), 15 min (n=9) or 20 min (n=11) of exposure to 1 mT PEMFs. Mean changes in proliferation for 5 min, 10 min, 15 min or 20 min of exposure were 31%+25%, 34%+26%, 16%+13% and 9%+17% (sd), respectively (also see Supplementary FIG. 2). C) 1 mT PEMFs applied to myoblasts after 18 (n=12) or 48 (n=8) hours in culture. ** and * indicate >99% and >95% confidence levels, respectively. D) Box plots of response values (stimulated/nonstimulated means; n=20); 18%+14%, 24%+20%, 30%+63% and 18%+53% for exposures to 0.5 mT, 1 mT, 1.5 mT and 2 mT, respectively.
Figure 9:
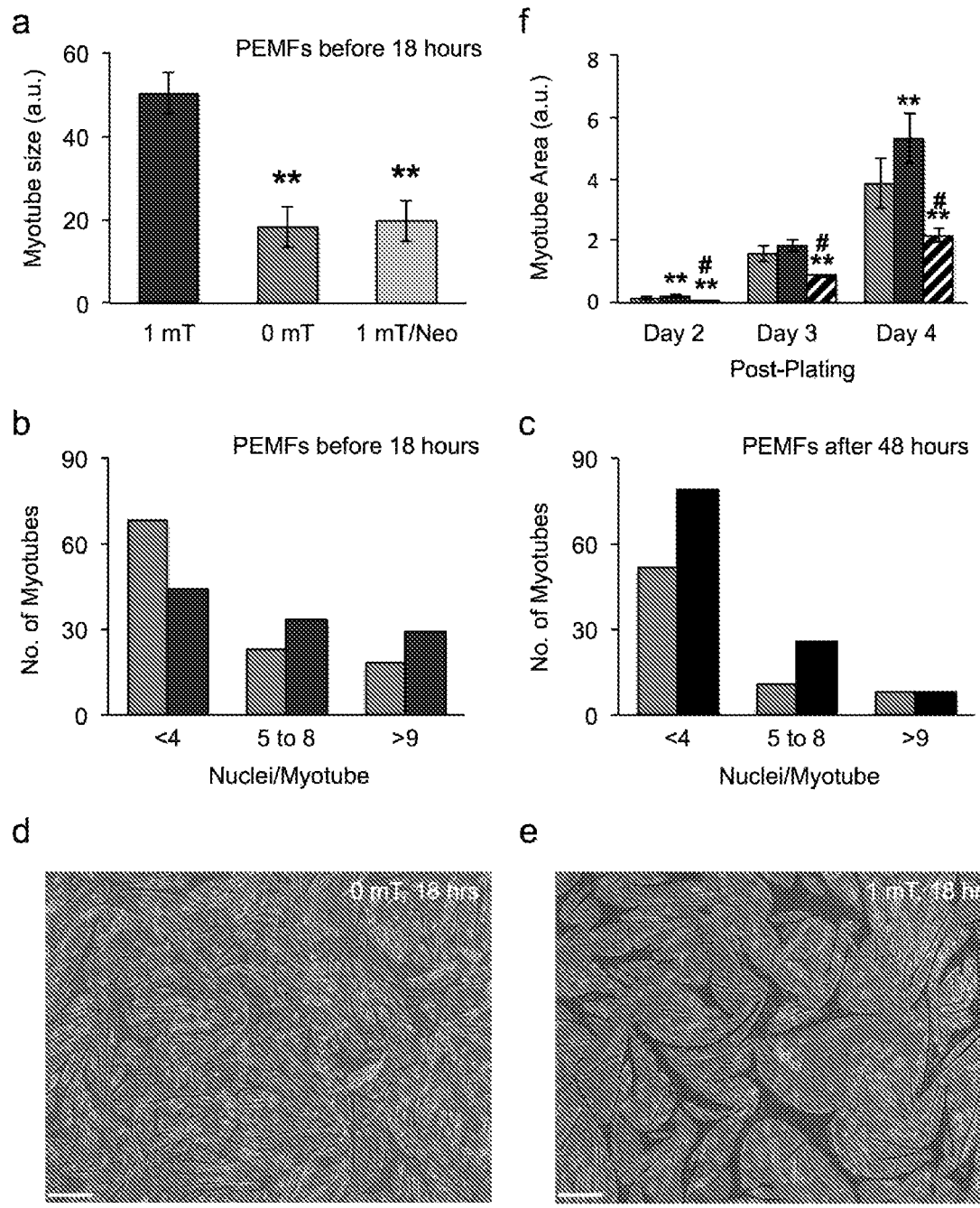
FIG. 9 shows the effect of PEMFs on differentiation of myoblasts if applied once within first 18 hours of plating. A) Early application of PEMFs (1 mT) enhances myotube size and is prevented by the co-administration of neomycin (100 μM). B) Early PEMF exposure (1.5 mT) increased the number of larger myotubes and decreased the number of smaller myotubes relative to unexposed (0 mT) myoblast cultures. C) Myoblasts exposed to PEMFs (1.5 mT) after 48 hours exhibited an increase in number of smaller myotubes when compared to non-exposured cultures. D) Control culture showing nascent (0 mT, green) and more mature myotubes (red) 3 days following switching to differentiation media (see Materials and methods). E) C2C12 culture exposed to 1 mT PEMFs at 18 hours and then differentiated with serum withdrawal for 3 days showing nascent (green) and more mature myotubes (blue). Scale bar equals 100 μm. F) Four consecutive days of PEMF (1.5 mT) exposure (commencing on the second day of plating and continuing 3 days post-differentiation) results in attenuated myotube area (hatched) relative to non-exposed (red) singly-exposed cultures (24 hours, blue). Myoblasts were switched to differentiation media 8 hours after first PEMF exposure at 18 hours post plating.
Figure 11:
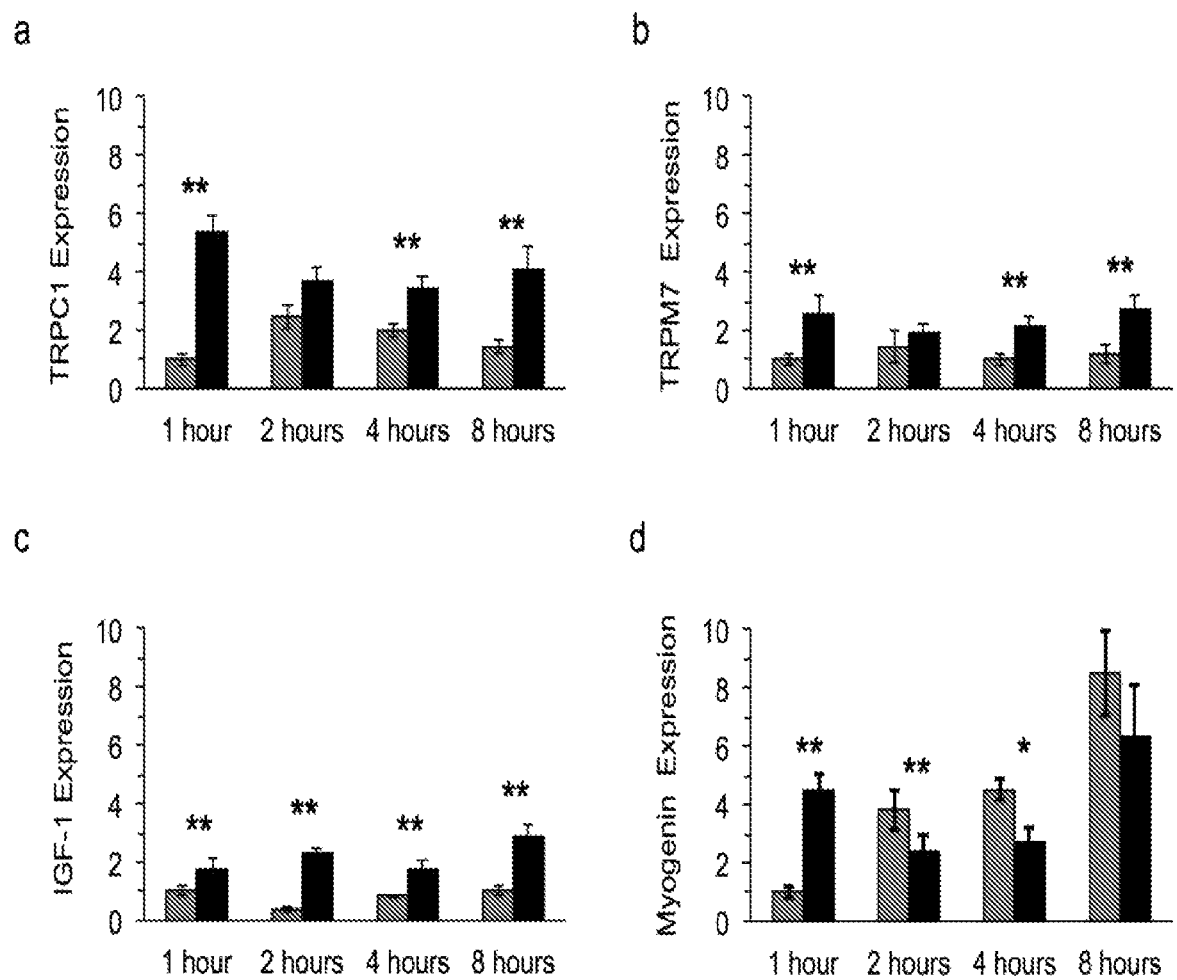
FIG. 11 shows that application of PEMFs after 48 hours reinstitutes the expression of TRPC1. PEMFs (2 mT for 10 minutes; black) applied to myoblasts at 48 hours of plating prolongs the expression of TRPC1 (A) to a greater degree than that of TRPM7 (B) relative to their respective control scenarios (0 mT; red). C) IGF-1 expression also increased with identical PEMF exposure. D) Myogenin expression level initially increased and then declined after a few hours following PEMF exposure at 48 hours. ** indicates highly significant differences (>99% confidence).

One mechanism whereby PEMFs may hinder differentiation when applied after 48 hours (FIG. 9C) is by enhancing calcium entry via remaining TRPC1 channels at a time when their expression normally wanes (FIGS. 7B, 8C). PEMFs applied at 48 hours post-plating increased TRPC1 expression (FIG. 11A) more than TRPM7 (FIG. 11B), consistent with the finding that PEMF-mediated calcium entry activates calcineurin (FIG. 8A) that, in turn, up-regulates TRPC1 expression, but not TRPM7. The insulin-like growth factor type 1 (IGF-1) gene is also under calcineurin control and likewise increased following PEMF-treatment (FIG. 11C). Myogenin promotes myoblast differentiation in a manner that is dependent on both calcineurin and MyoD. Myogenin expression first increased and then decreased following PEMF exposure at 48 hours (FIG. 11D), likely reflecting calcineurin stimulation (FIG. 8A) and reduction in myoD expression at later time points (FIG. 11D). This result also agrees with previous findings that stretch curtails myogenin expression upon reinitiating proliferation. Thus, beyond 48 hours in culture myoblasts respond to PEMFs with augmented calcium entry (FIG. 7C) that, in turn, up-regulates TRPC1 expression (FIG. 11A), acting to defer differentiation (FIGS. 9C, 9E, 10B). On the other hand, early PEMF stimulation exerts a pro-myogenic effect by first activating TRPC1, thereby stimulating proliferation (FIG. 8) and subsequently accelerating entry into differentiation (FIG. 9).

Biological Response Windows Characterize Both Mechanical and PEMF Stimulation

A finite window of PEMF parameters was found to be most myogenic; 1 mT amplitude PEMFs applied to cells for 10 minutes were most effective at stimulating proliferation; shorter (<5 minutes) or longer (>15 minutes) exposure times were less effective (FIGS. 8A,B) as were lower (<0.5 mT) or higher (>1.5 mT) field amplitudes (FIG. 8D), resulting from the optimal balance of stimulated proliferation and differentiation. The PEMF signals of this study thus exhibit a classical calcium-dependent biological window of responsiveness as previously described for electromagnetic stimulation of cells or tissues. One study examining adipose-derived stem cells found that PEMFs applied at a frequency of 30 Hz were more osteogenic than either lower (7.5, 10, 15 Hz) or higher (45, 60, 75 Hz) frequencies as were PEMFs of 1 mT more osteogenic than either lower (0.1 mT) or higher (2, 3 mT) amplitudes (cf FIGS. 7 & 8). Also using 1 mT amplitude PEMFs, a similar frequency window was observed for bone marrow MSCs directed into the osteogenic lineage, whereby lower frequencies (10, 30 Hz) were more beneficial at promoting differentiation than were higher frequencies (50, 70 Hz). This report distinguishes itself from these previous studies in the brevity of PEMF stimulation necessary to obtain a biological outcome, 10 minutes versus 8 or 2 hours, respectively.

Biological response windows similarly define cellular mechanosensitivity. Cyclic stretching of MSCs (10% strain, 15 min) at a frequency of 1 Hz was more effective at enhancing proliferation than either lower (0.1 Hz or 0.5 Hz) or higher (1.5 Hz) frequencies. Stretching MSCs for 15 minutes (10% strain, 1 Hz) stimulated proliferation more than shorter (5 minutes) or longer (30-60 minutes) stretching intervals, or smaller (5%) or greater (15%) strain values, closely recapitulating our PEMF time—(FIG. 8A,B) and amplitude-dependencies (FIG. 8D). Another study showed that 5% strain was more effective at stimulating the proliferation of MSCs than were greater strains of 8%-15% (0.03 Hz, 240 min/day). Stretching osteoblasts (0.5 Hz, 20% stretch) for 5 or 10 minutes caused greater activation of the PI3K survival pathway than did 30 minutes (cf FIG. 8). Another study controlling for changes in substrate rigidity showed enhanced proliferation and spreading of embryonic fibroblasts in response to cyclic stretch (5%) applied at a frequency of 0.1 Hz, but not at lower (0.01, 0.03 Hz) or higher (0.3, 1, 10 Hz) stretching frequencies. The existence of mechanical response windows of similar temporal and magnitude characteristics to those observed with PEMF stimulation supports the conclusion that PEMFs are impinging upon a fundamental mechanotransduction process.

Figure 14:
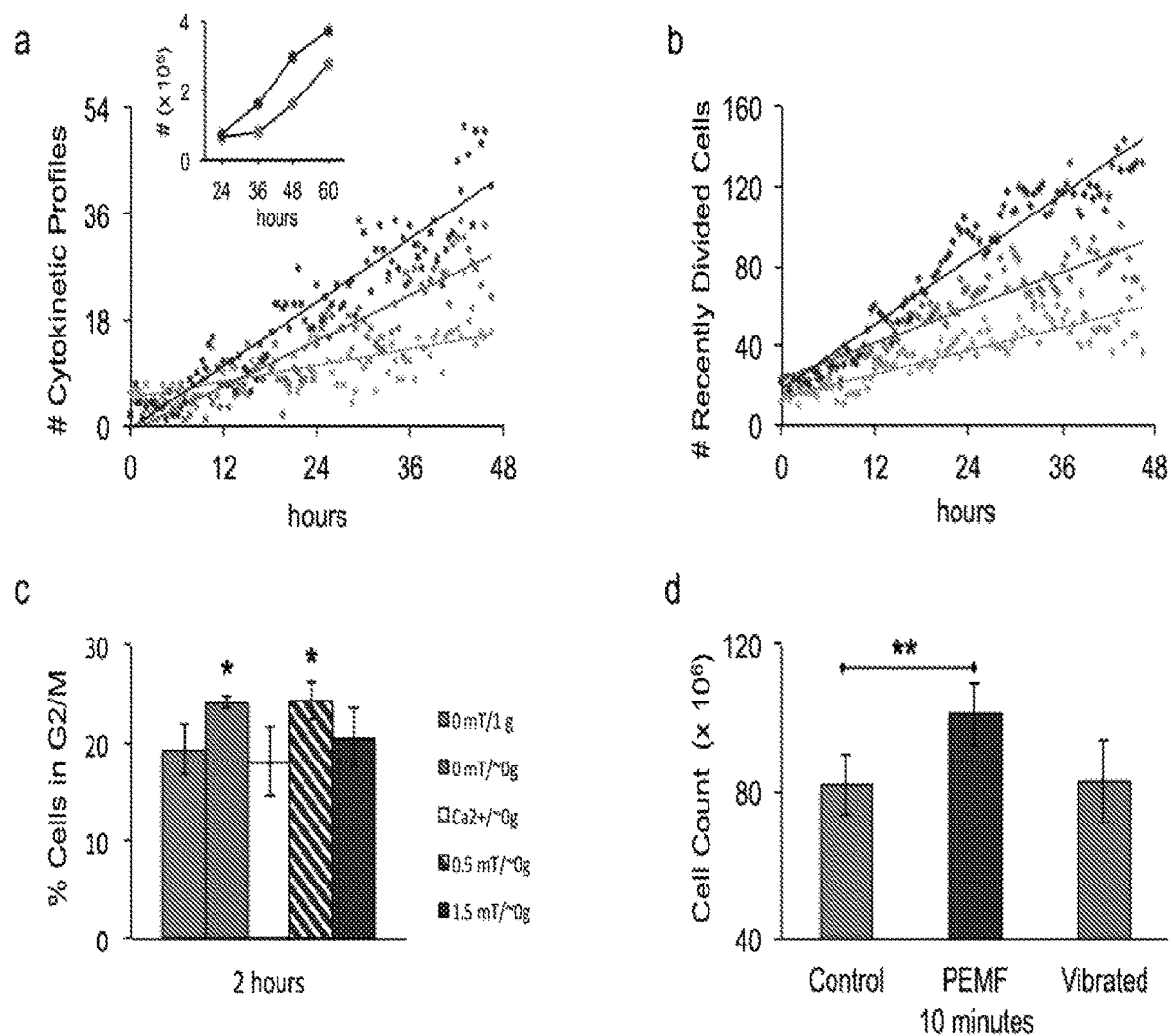
FIG. 14 shows that PEMFs accelerate the rate of myoblast proliferation and can counteract the effects of simulated microgravity without imparting a mechanical stress. A) Incidence of appearance of cytokinetic profiles during the first 48 hours of plating in the presence (blue, light blue) and absence of PEMF (red) exposure. Light blue symbol represents cell growth in the combined presence of 1 mT PEMFs and 2-APB (1 μM). Inset) Proliferation kinetics of myoblast with (blue) and without (red) exposure to 1 mT PEMFs for 10 minutes 12 hours after plating. B) Incidence of appearance of recently divided cells during the first 48 hours of plating PEMF exposure. Light blue symbol represents cell growth in the presence of 2-APB (1 μM) under unstimulated conditions (0 mT). Proliferation kinetics was assayed by monitoring the time-dependent increase of cytokinetic cell profiles, represented by adjoined spherical cell bodies and recently divided cells, depicted by a pair of bipolar somas joined by a bridge of cytoplasm as previously described (32). C) PEMFs (10 minutes, 1.5 mT; dark blue) reverse the accumulation of cells within the G2/M phase of the cell cycle as a result of mechanical unloading (simulated microgravity; green) relative to the normally loaded (1 gravity) and unexposed scenario (red) at 2 hours. The transient addition of 5 mM CaCl2 to the bathing media 10 minutes before introduction into simulated microgravity was able to mimic the effects of 1.5 mT PEMFs at 2 hours, whereas 0.5 mT PEMFs was ineffective at reversing G2/M accumulation, demonstrating dose-responsiveness. D) Mechanically vibrating myoblasts at the same frequency and amplitude as they might experience during PEMF exposure (light blue) does not recapitulate the effects of 1 mT field exposure (blue), showing no statistical difference from nonvibrated cells not exposed to fields (red). ** and * indicate highly significant and significant differences (>99% and >95% confidence levels), respectively, from control and loaded cells (red).

Finally, the PEMF paradigms of this study elicit opposite changes in TRPC1 and IGF-1 expression (increase) than those reported by simulated gravity (decrease) (FIG. 11) as well as counteract the cell cycle retardation brought on by simulated microgravity (FIG. 14), consistent with the interpretation that PEMFs are biochemically emulating mechanical input.

Novelties of PEMF Stimulation Paradigms of the Present Invention

The PEMF paradigms of the present invention differ from those of most other studies in the timing of exposure, both in terms of how long and when they are applied. First, the best results on murine myoblasts were obtained with much shorter exposure times (5-10 minutes) than those commonly reported in the EMF scientific literature. Most published PEMF studies have focused on osteogenic outcome and typically employ much longer stimulation regimens of hours per day for up to weeks at a time. Secondly, PEMF exposure was limited to the first 24 hours after plating, a stipulation not widely adhered to in the field.

The brief stimulation protocol of the present study is exceptional, even when compared with the typically longer durations of mechanical stimulation required to promote myogenesis.

Field Directionality

Field directionality of the PEMF is an important parameter in the EMF efficacy window. Application of the PEMF in the correct field direction confers enhanced cell proliferation, cell differentiation and the production of factors, such as reactive oxygen species.

Application of PEMF in *C. elegans* downwards, upwards and horizontally shows that the field directionality correlates with the generation of reactive oxygen species (ROS), wherein the PEMF applied downward results in an increase in ROS generation whilst application of the PEMF horizontally results in a decrease in ROS generation (FIG. 67). Generation of ROS is in turn related to lifespan extension in *C. elegans*. Consequently, the directionality of the PEMF applied exerts and effect on lifespan extension of *C. elegans*.

Figure 68:
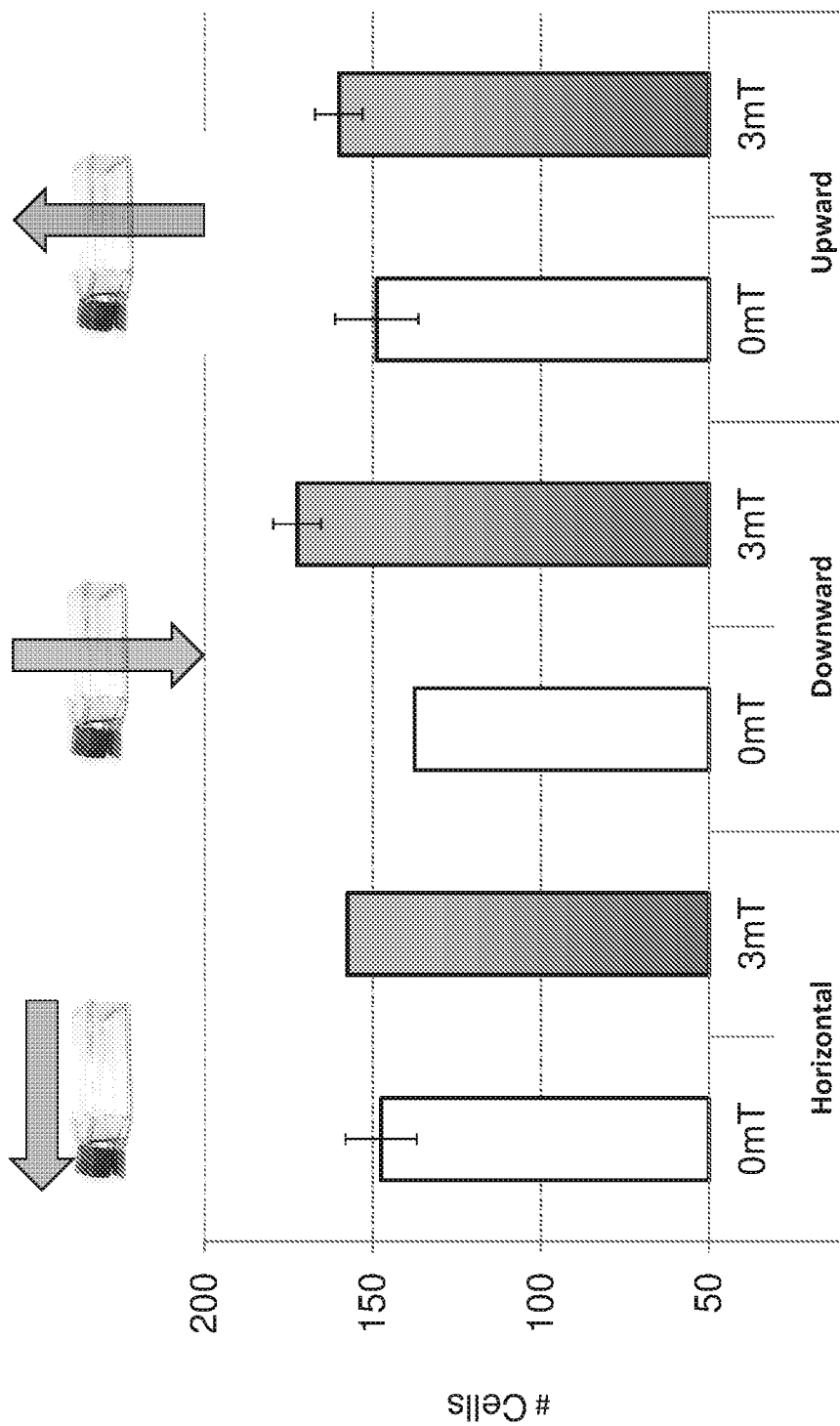
FIG. 68 shows that proliferation is more greatly enhanced by stimulation of cells with PEMFs in the correct orientation.

Field directionality also enhances cell proliferation when applied in the correct direction. As shown in FIG. 68, the application of a PEMF in a downward direction vertical with gravity enhances cell proliferation to a greater extent than application of the PEMF in a horizontal direction, or in an upward direction vertical against gravity.

Figure 70:
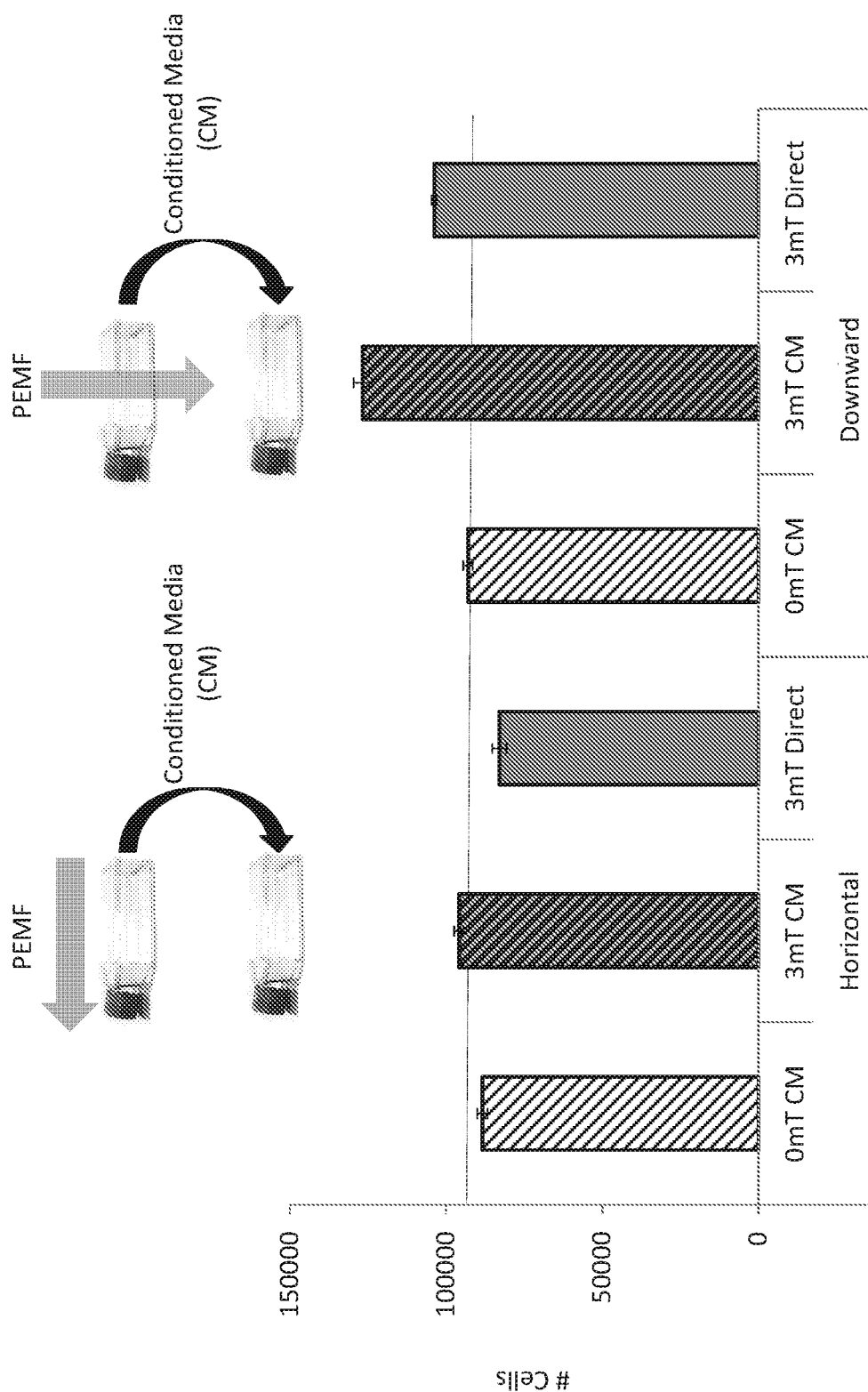
FIG. 70 shows that conditioned media collected from cells stimulated with PEMFs of the correct orientation is more effective at promoting cell responses than conditioned media collected from cell stimulated in the non-preferred orientation.

Field directionality also results in the efficacy of conditioned media produced from cells stimulated by the PEMF. In particular, cells stimulated with PEMF in a vertical direction results in conditioned media that is more effective at promoting cellular responses than conditioned media collected from cells stimulated with PEMF with a horizontal field directionality (FIG. 70).

In general, PEMFs applied in a direction that is perpendicular or orthogonal to the long axis of the cell or tissue in question gives rise to optimal biological effects.

FIGS. 15 to 56 relate to appropriate PEMF parameters and effects.

Figure 15:
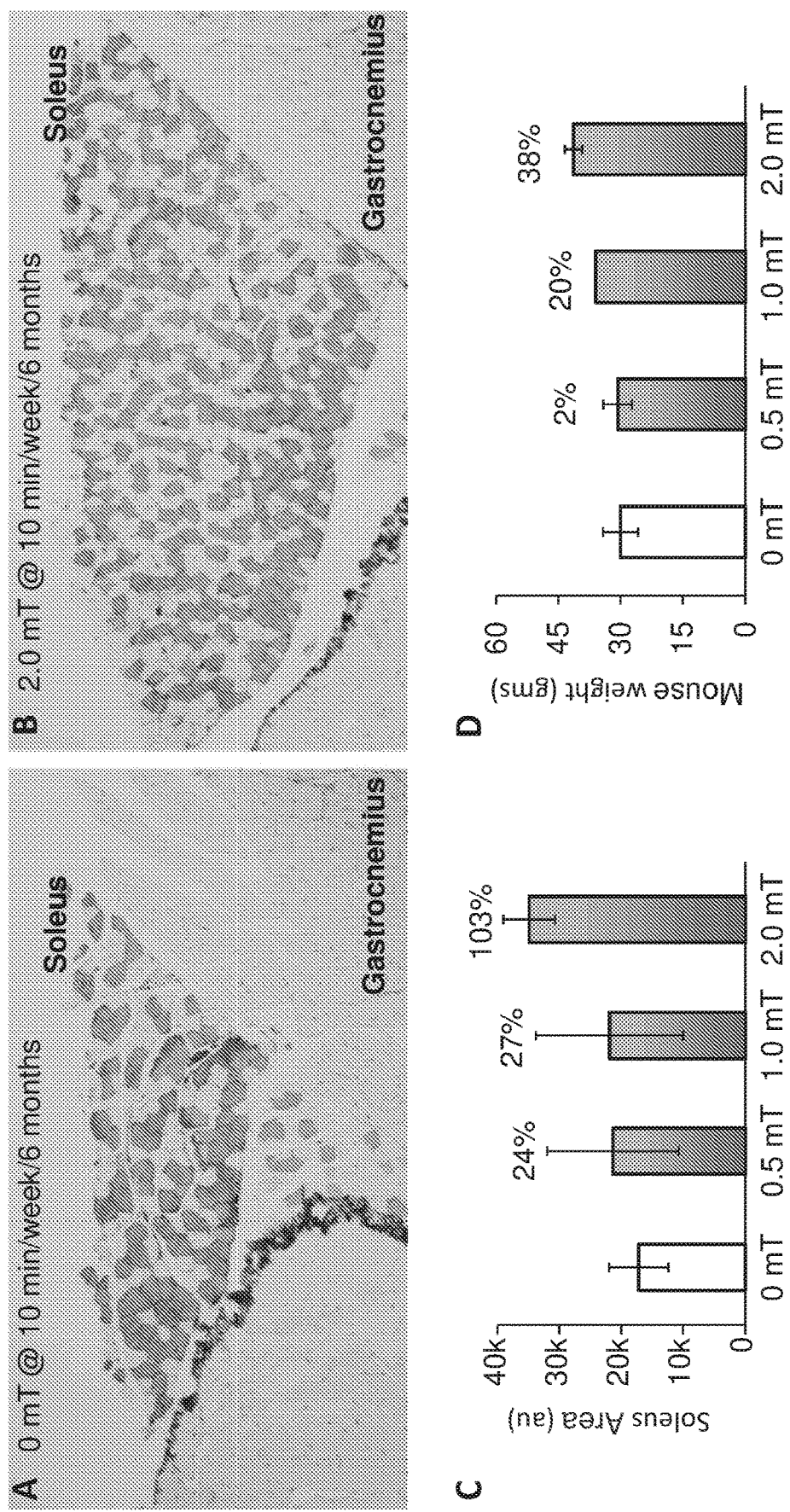
FIG. 15 shows that PEMFs cause a disproportionate increase in the size of oxidative muscles (soleus) relative to mouse size.

FIG. 15 shows that PEMFs cause a disproportionate increase in the size of oxidative muscles (soleus) relative to mouse size. A) Solei muscle from a mouse placed into the PEMF apparatus weekly for 6 months, but not exposed to active fields (0 mT). B) Solei muscle from a mouse exposed to 2 mT PEMFs weekly for 6 months. Oxidative muscle fibres are stained dark. C) Mean size of Solei from mice exposed to varying PEMF amplitudes weekly for 6 months. D) Weight of mice exposed to varying PEMF amplitudes weekly for 6 months. All PEMF exposures (0 mT. 0.5 mT, 1 mT and 2 mT) were for 10 minutes.

Figure 16:
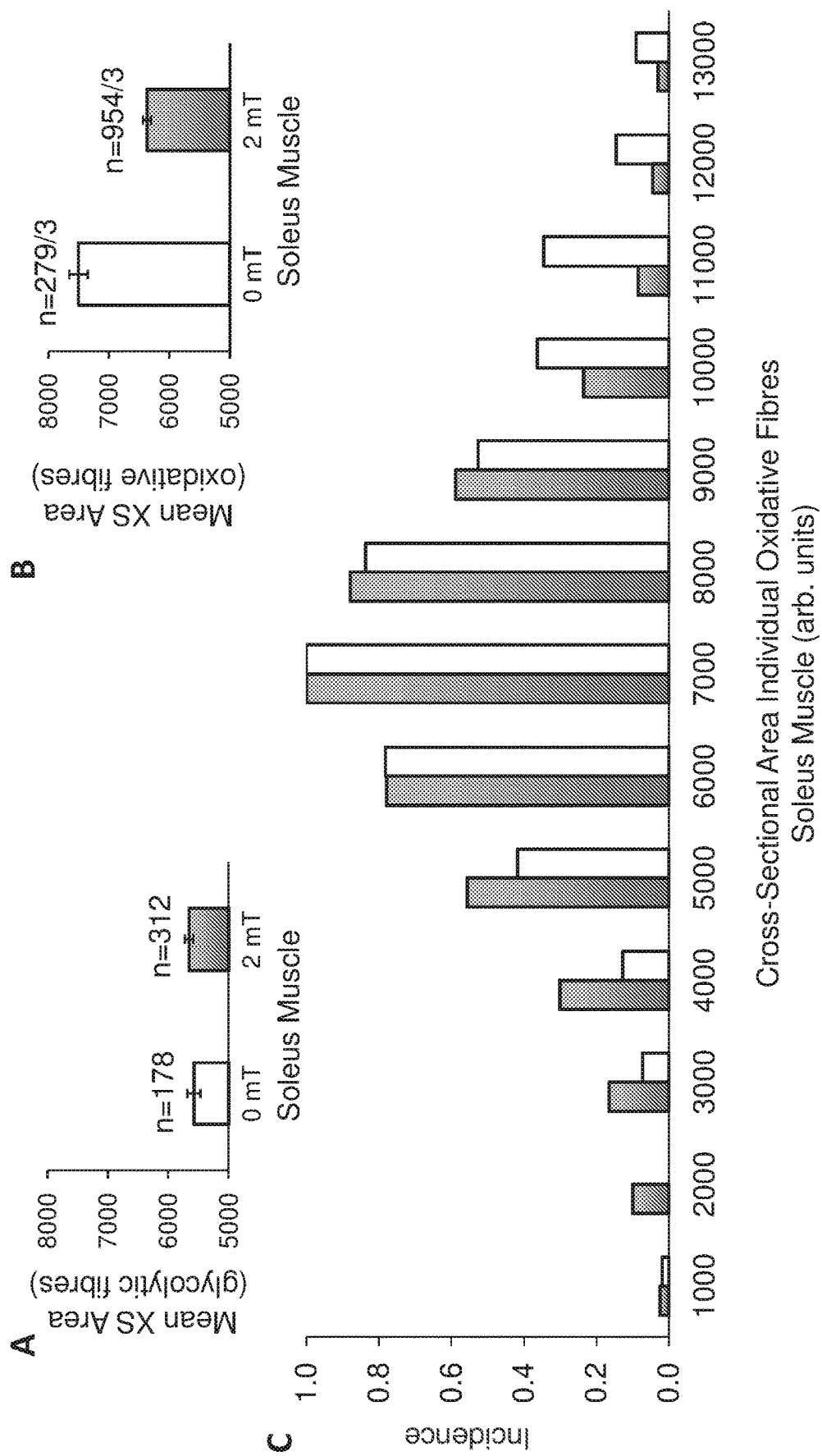
FIG. 16 shows that cross-sectional area of oxidative fibres decreases to accommodate increased oxygen demand.

FIG. 16 shows that cross-sectional area of oxidative fibres decreases to accommodate increased oxygen demand. Weekly exposure of mice to 2 mT PEMFs (10 minutes) for 24 weeks preferentially decreased the cross-sectional area of individual oxidative muscle fibers in the soleus muscle over control (0 mT) values; the cross-sectional area of glycolytic fibers is unchanged (inset, left). This effect is reminiscent of studies showing that exercising animals or overexpressing myogenin produces a similar effect and assists in the oxygen expensive process of fatty acid oxidation.

Figure 17:
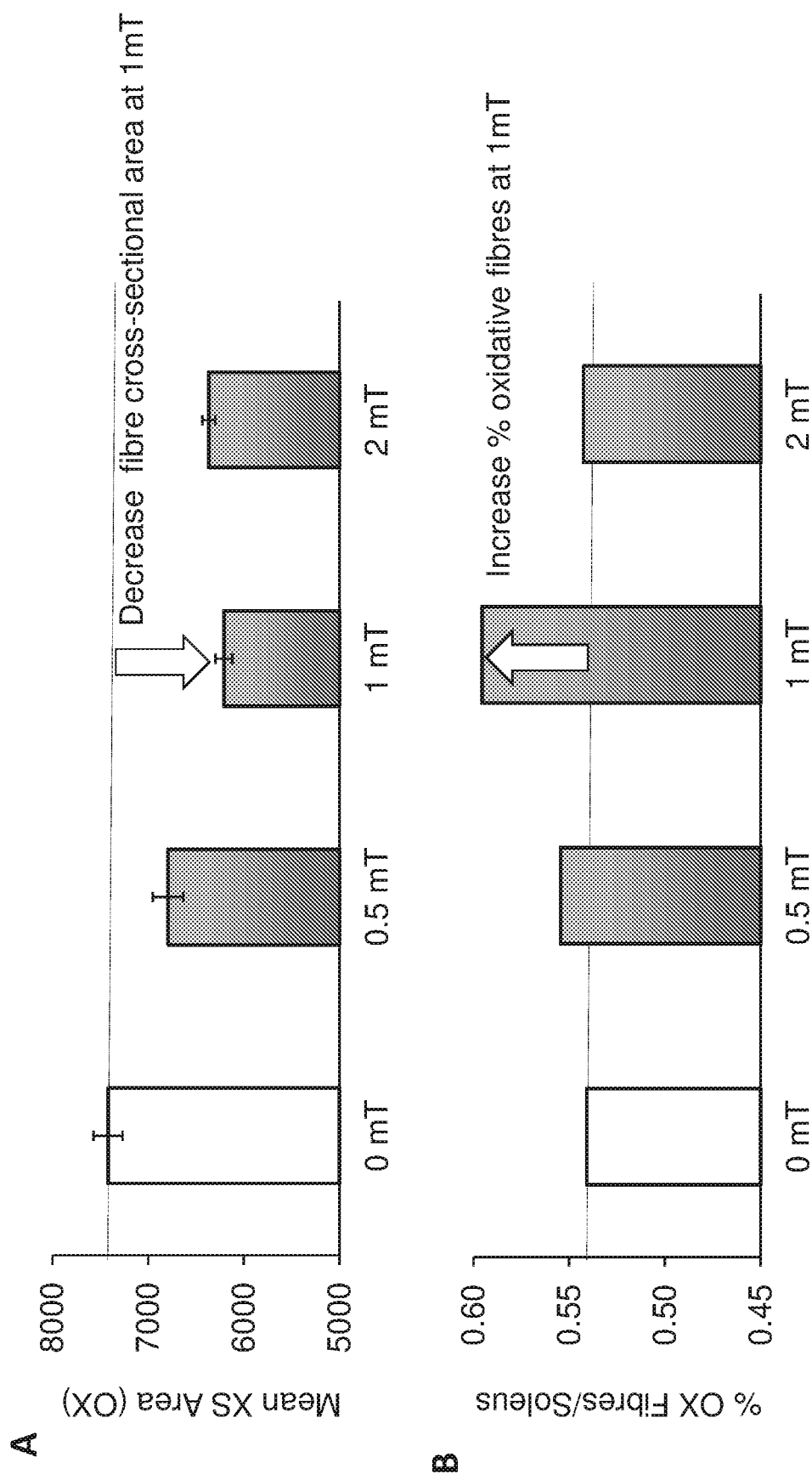
FIG. 17 shows that the number of oxidative fibres increase with PEMF stimulation near the EMF efficacy window of skeletal muscle.

FIG. 17 shows that the number of oxidative fibres increase with PEMF stimulation near the EMF efficacy window of skeletal muscle. The effect of PEMF treatment over oxidative muscle is greatest at 1 mT both in terms reduced cross-sectional area (top) and overall percentage of oxidative fibres. Mice were exposed to PEMFs for 6 months with the indicated fields.

Figure 18:
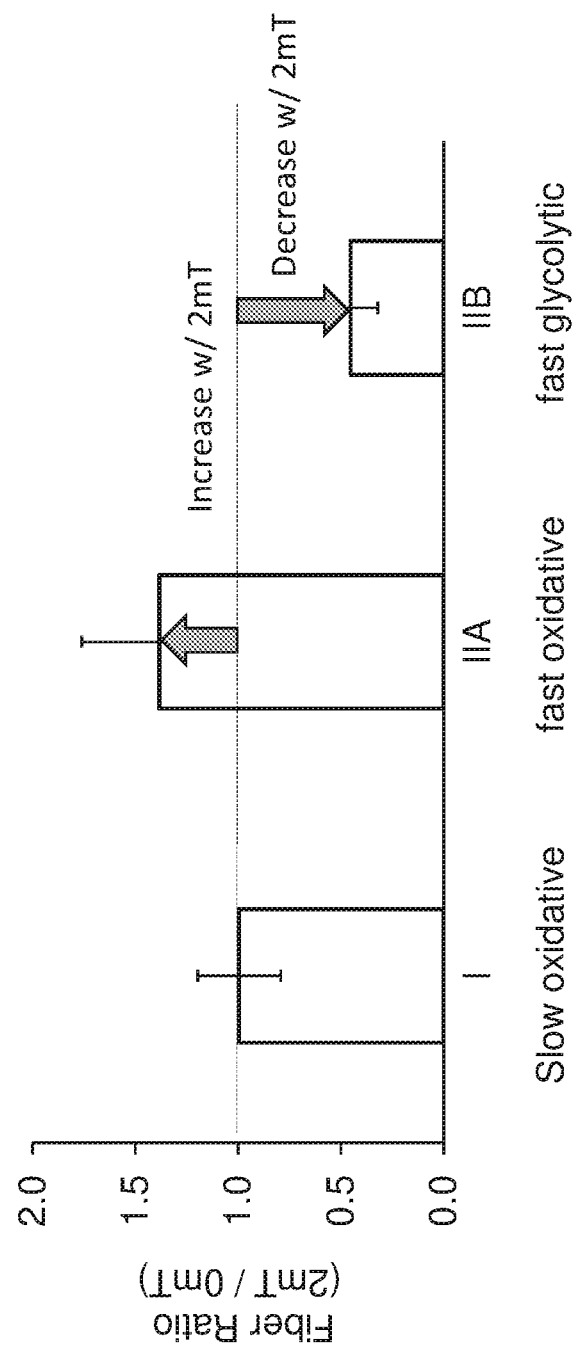
FIG. 18 shows that PEMF exposure recapitulates the fast-to-slow muscle fibre switch characteristic of exercise.

FIG. 18 shows that PEMF exposure recapitulates the fast-to-slow muscle fibre switch characteristic of exercise. (6 months treatment @ 2 mT for 10 min/week)

Figure 19:
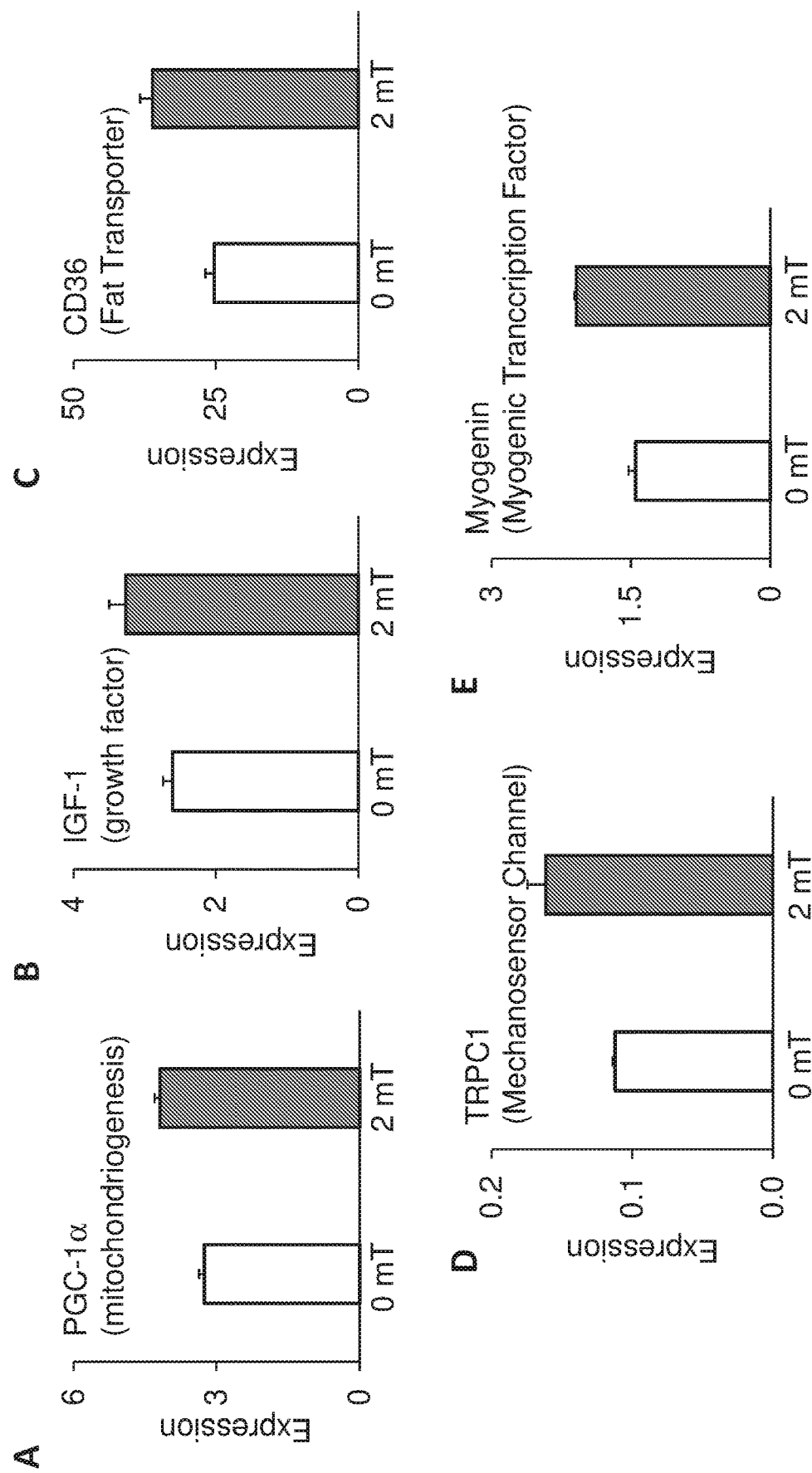
FIG. 19 shows that PEMFs upregulate expression of genes involved in mitochondriogenesis, fatty acid oxidation and general myogenesis.

FIG. 19 shows that PEMFs upregulate expression of genes involved in mitochondriogenesis, fatty acid oxidation and general myogenesis. Muscle gene expression enhanced by PEMF treatment as indicated. With the exception of C (CD36) all demonstrated genes are transcriptionally regulated by calcineurin/NFAT. Accordingly, response to the fields can be precluded by cyclosporin administration (not shown). The principal functions of these genes are shown in the parentheses. (6 months treatment @ 2 mT for 10 min/week) FIG. 20A shows that PEMF-induced TRPC1-mediated calcium entry in myoblasts increases oxygen consumption rate (OCR) and reactive oxygen species (ROS) production. A) Human myoblast measurement showing increased OCR six hours following exposure to 1.5 mT PEMFs for 10 minutes. B) The production of reactive oxygen species (ROS) also increases 15 minutes after PEMF (1.5 mT) exposure.

FIG. 20B shows that PEMF-induced TRPC1-mediated calcium entry in myoblasts increases oxygen consumption rate (OCR) and reactive oxygen species (ROS) production. C) Oxygen consumption rate (OCR) in response to PEMF stimulation obeys the same EMF efficacy window as proliferation. D) TRPC1 channel antagonist (SKF-96365) blocks OCR in response to PEMF exposure. Cells were exposed to PEMFs and oxygen consumption measured 6 hours later. These cellular responses obey a mitohormeitic EMF efficacy window particular for skeletal muscle. ROS production is a function of PEMF-stimulated calcium entry and hence also follows the EMF efficacy window for a cell type (not shown).

Figure 21:
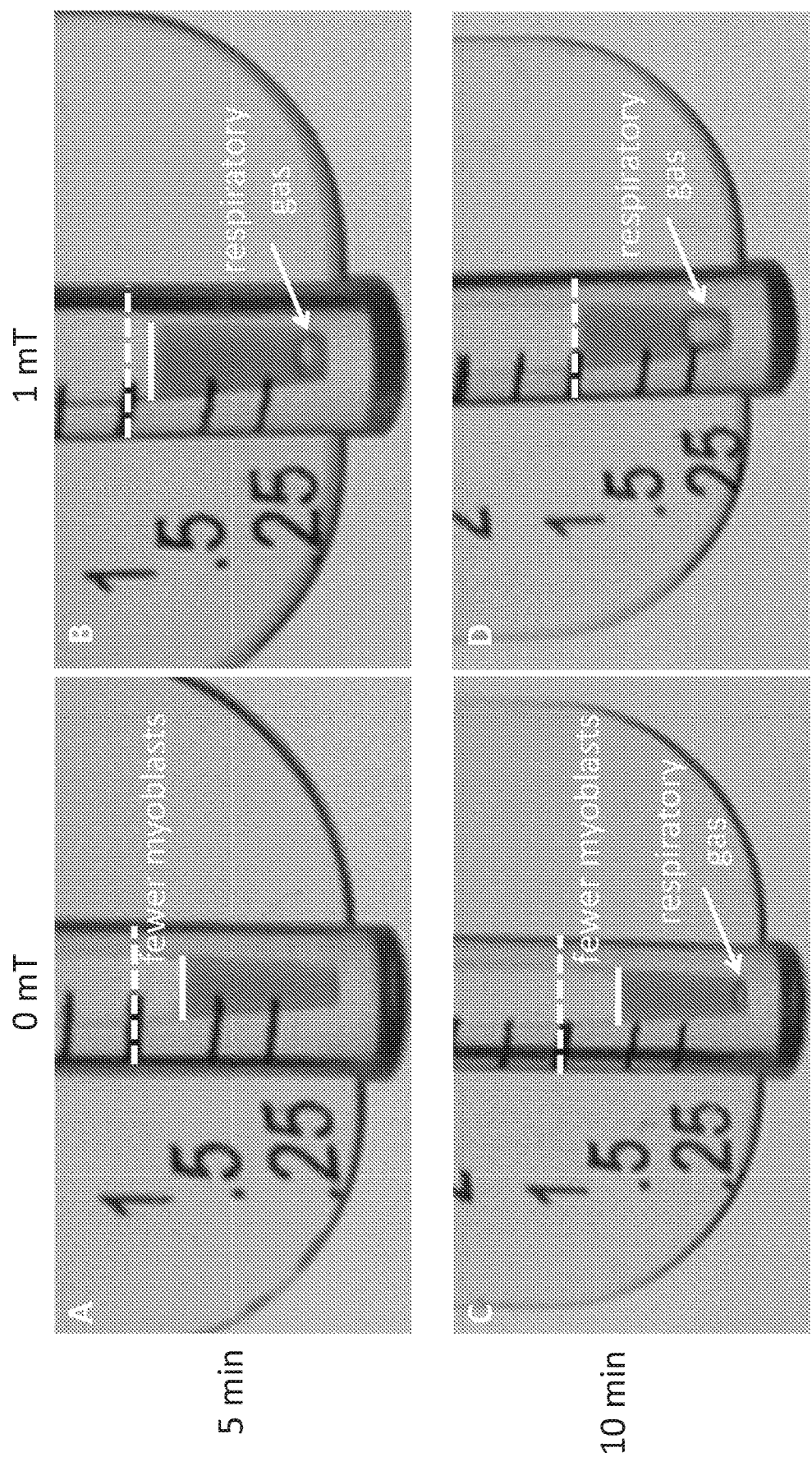
FIG. 21 shows that PEMF stimulation produces respiratory gases.

FIG. 21 shows that PEMF stimulation produces respiratory gases. A&C) Flasks containing cells were placed within the PEMF apparatus, but did not receive active fields (0 mT). B & D) Cell flasks received 1 mT PEMFs for 5 minutes (B) or 10 minutes (D) before being detached from the flask 12 hours later and spun down in Volupac tubes (Sartorius) for volumetric analysis. The arrows show gas bubbles produced by cellular respiration increases in response to PEMF exposure.

Figure 22:
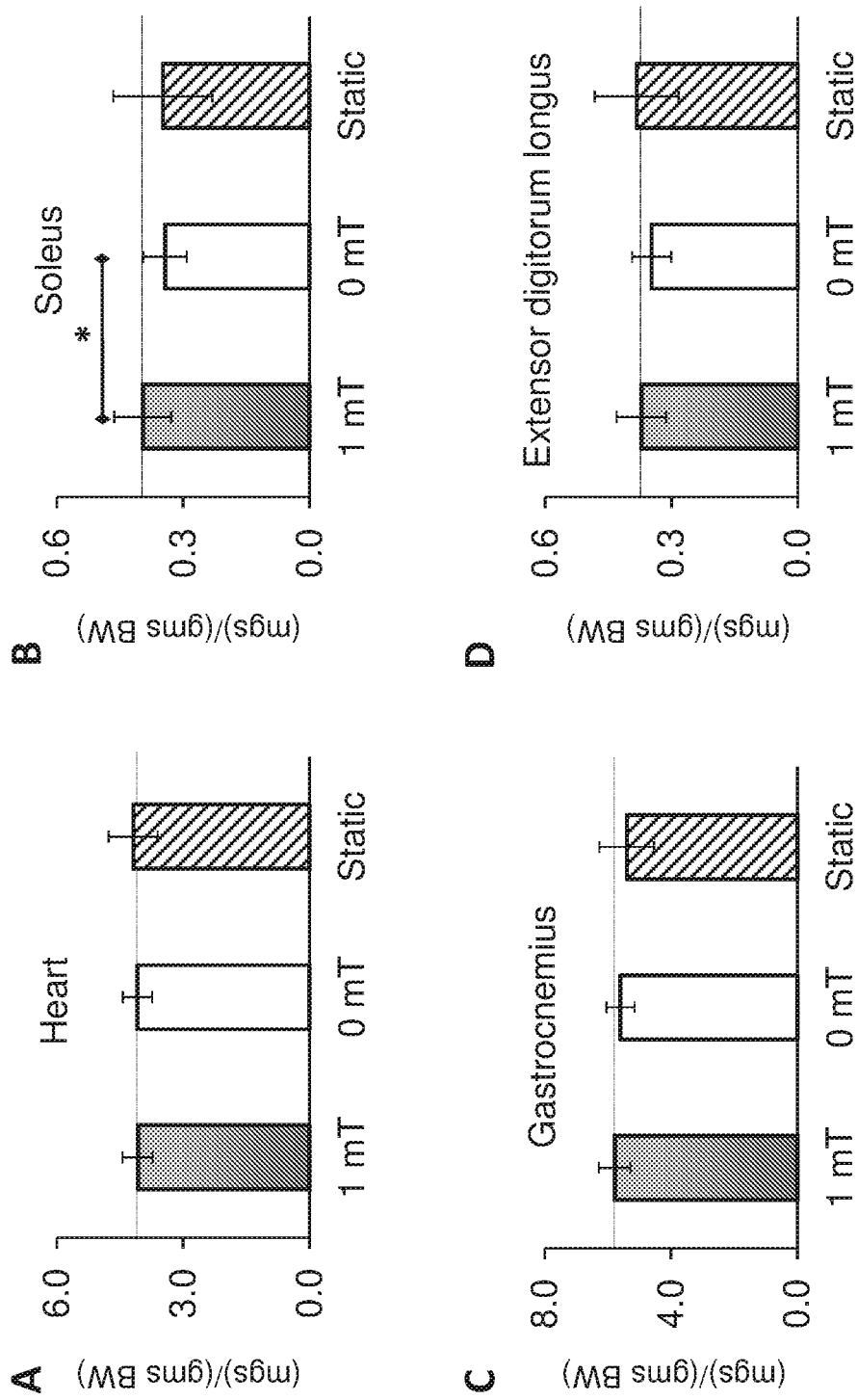
FIG. 22 shows that PEMF exposure targets oxidative muscles when applied at the EMF efficacy window of skeletal muscle.

FIG. 22 shows that PEMF exposure targets oxidative muscles when applied at the EMF efficacy window of skeletal muscle. PEMFs preferentially increase the relative weight (muscle weight/total body weight) of an oxidative muscle (soleus) over that of a mixed muscle (gastrocnemius) or predominantly fast muscle (extensor digitorum longus) in mice (4 months treatment @ 1 mT for 10 minutes/week). * indicates significant difference (>95% confidence level). A) Heart, B) Soleus, C) Gastrocnemius, and D) Extensor digitorum longus. All values are normalized to bodyweight of the mouse donating the tissue.

FIG. 23 shows that PEMF exposure induces angiogenesis principally in oxidative muscle when applied near the EMF efficacy window of skeletal muscle. PEMFs preferentially increase angiogenesis in oxidative muscle (soleus) compared to a mixed muscle (gastrocnemius) in mice (4 months treatment @ 1 mT for 10 minutes/week). By contrast, an observed upregulation in the number of myonuclei is greater in the gastrocnemius versus soleus. Soleus (A & C) and gastrocnemius (B & D) analysis of blood vessel (A & B) and nuclei (C & D) density (/mm$^2$). PEMF treatment apparently counteracts the effect of stress induced by the MRI mode of delivery. ** and * indicate >99% and >95% confidence levels, respectively.

Figure 24:
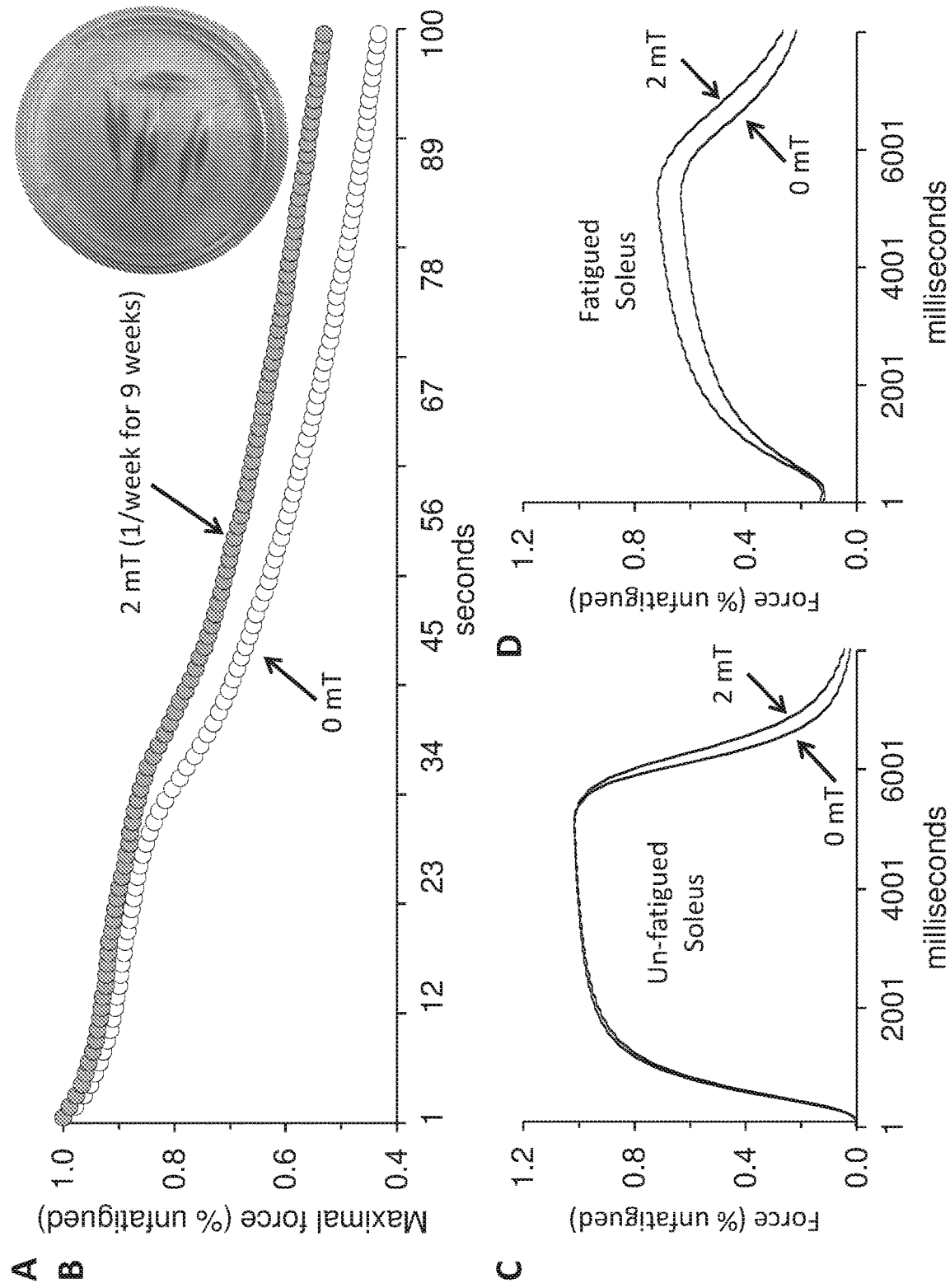
FIG. 24 shows that PEMFs enhance fatigue resistance after just a few months of weekly exposure.

FIG. 24 shows that PEMFs enhance fatigue resistance after just a few months of weekly exposure. A) Solei muscle were surgically removed from mice exposed to 2 mT PEMFs on a weekly basis or mice that had been placed in our PEMF apparatus, but not exposed to active fields. Solei were contracted exogenously with voltage and rate of fatigue analyzed. B) Images of isolated solei muscle from control (0 mT) and PEMF-treated (2 mT) mice. C) The effect of PEMF-treatment on unfatigued soleus is small. D) The effect of PEMF-treatment on fatigued soleus is much more pronounced.

Figure 25:
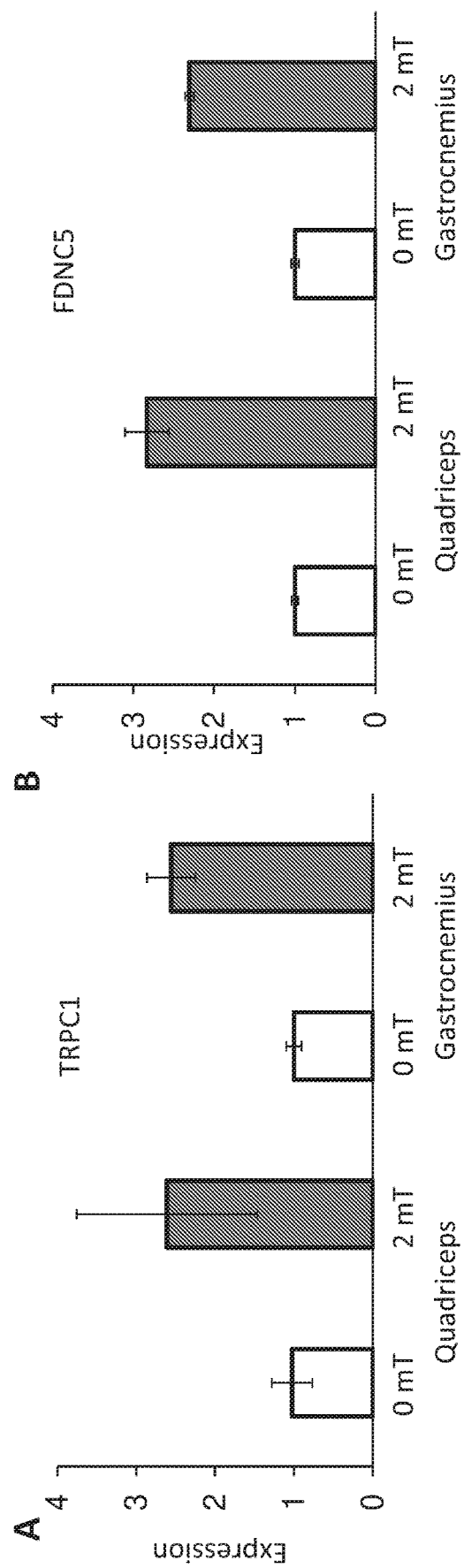
FIG. 25 shows that PEMFs upregulate expression of muscle genes in vivo involved in the systemic "Browning" of adipose tissue (B; FNDC5) and correlates with TRPC1 expression (A).

FIG. 25 shows that PEMFs upregulate expression of muscle genes in vivo involved in the systemic "Browning" of adipose tissue (B; FNDC5) and correlates with TRPC1 expression (A). (6 months treatment @ 2 mT for 10 min/week).

Figure 26:
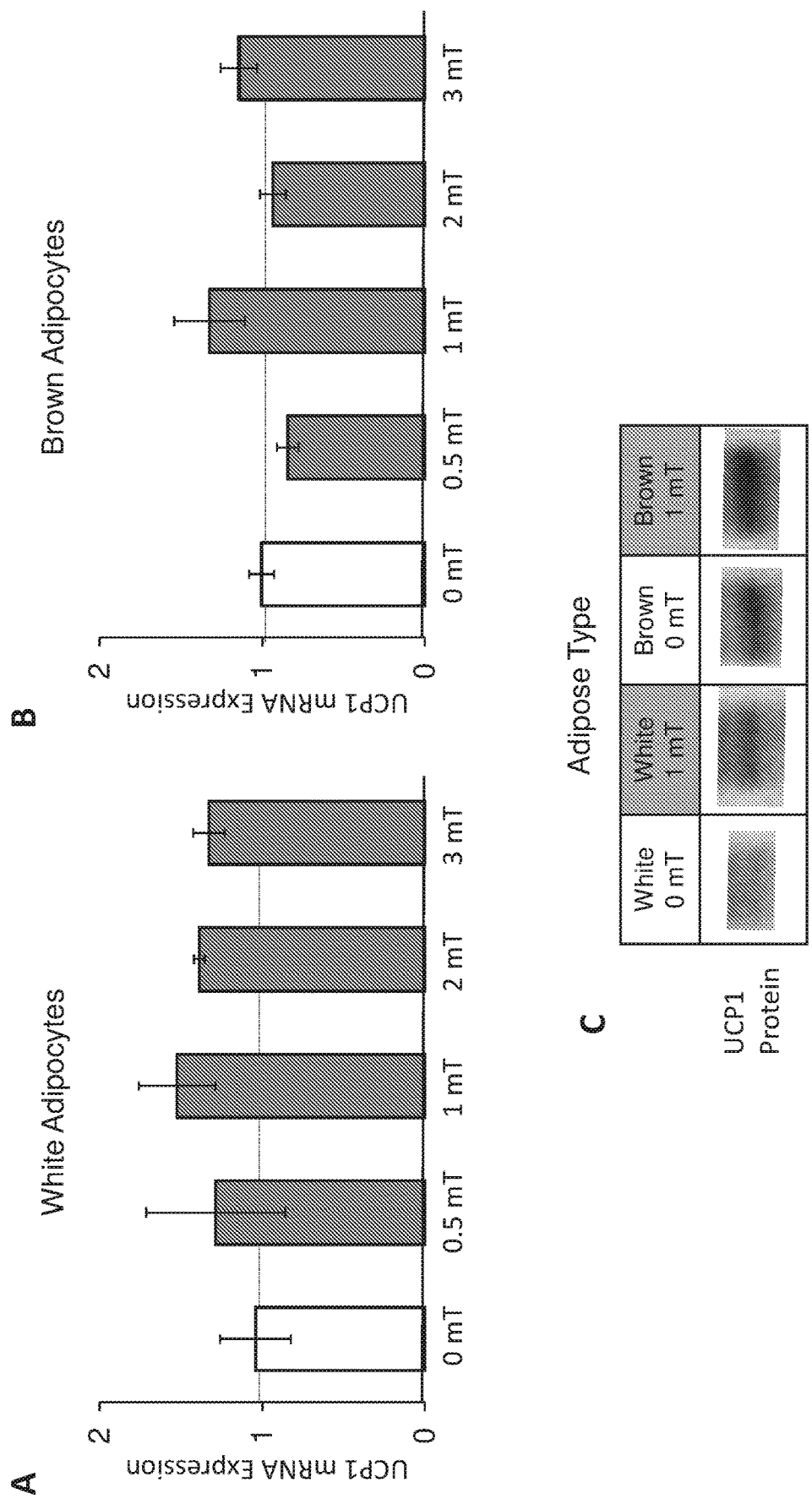
FIG. 26 shows EMF Efficacy Window of MSCs differentiated into White or Brown adipocytes in vitro.

FIG. 26 shows EMF Efficacy Window of MSCs differentiated into White or Brown adipocytes in vitro. UCP1 expression is taken as an indication of "Browning".

Figure 27:
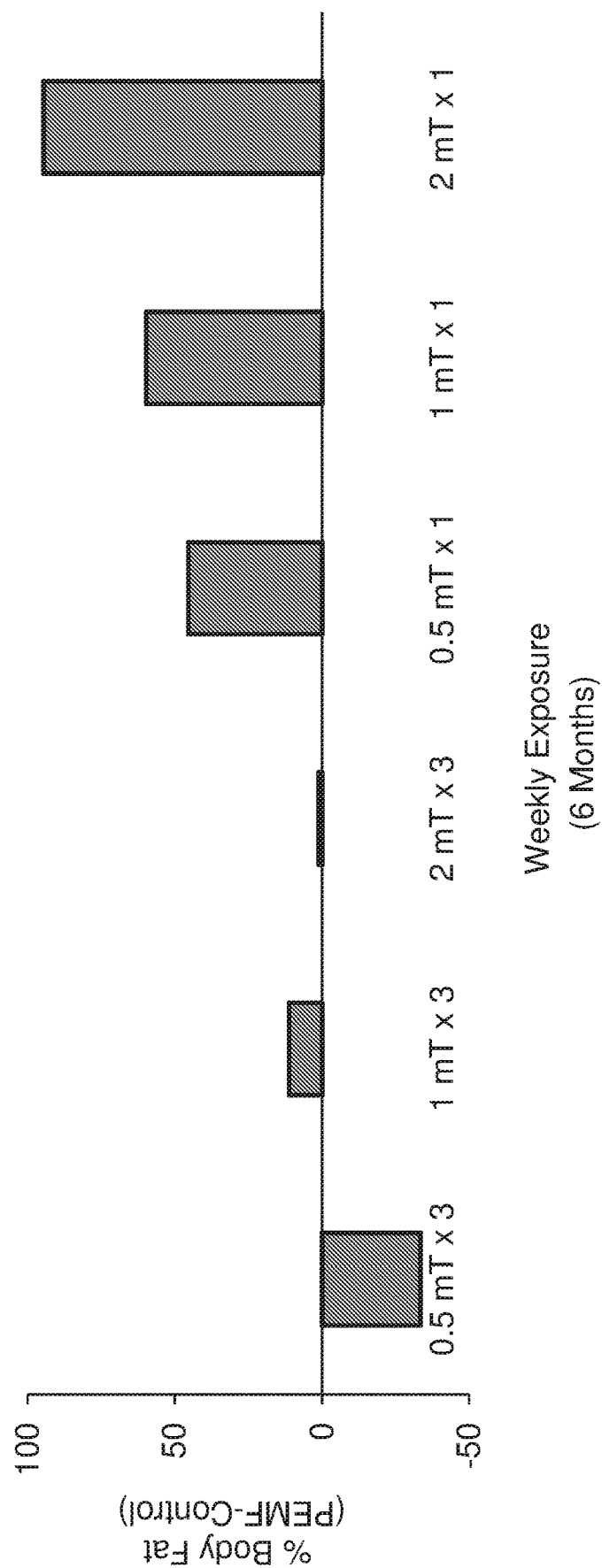
FIG. 27 shows that multiple PEMF session/week at low intensity minimizes adipose accumulation.

FIG. 27 shows that multiple PEMF session/week at low intensity minimizes adipose accumulation. Percentage body fat decreases in mice in response to exposure to low field strengths applied multiply per week.

Figure 28:
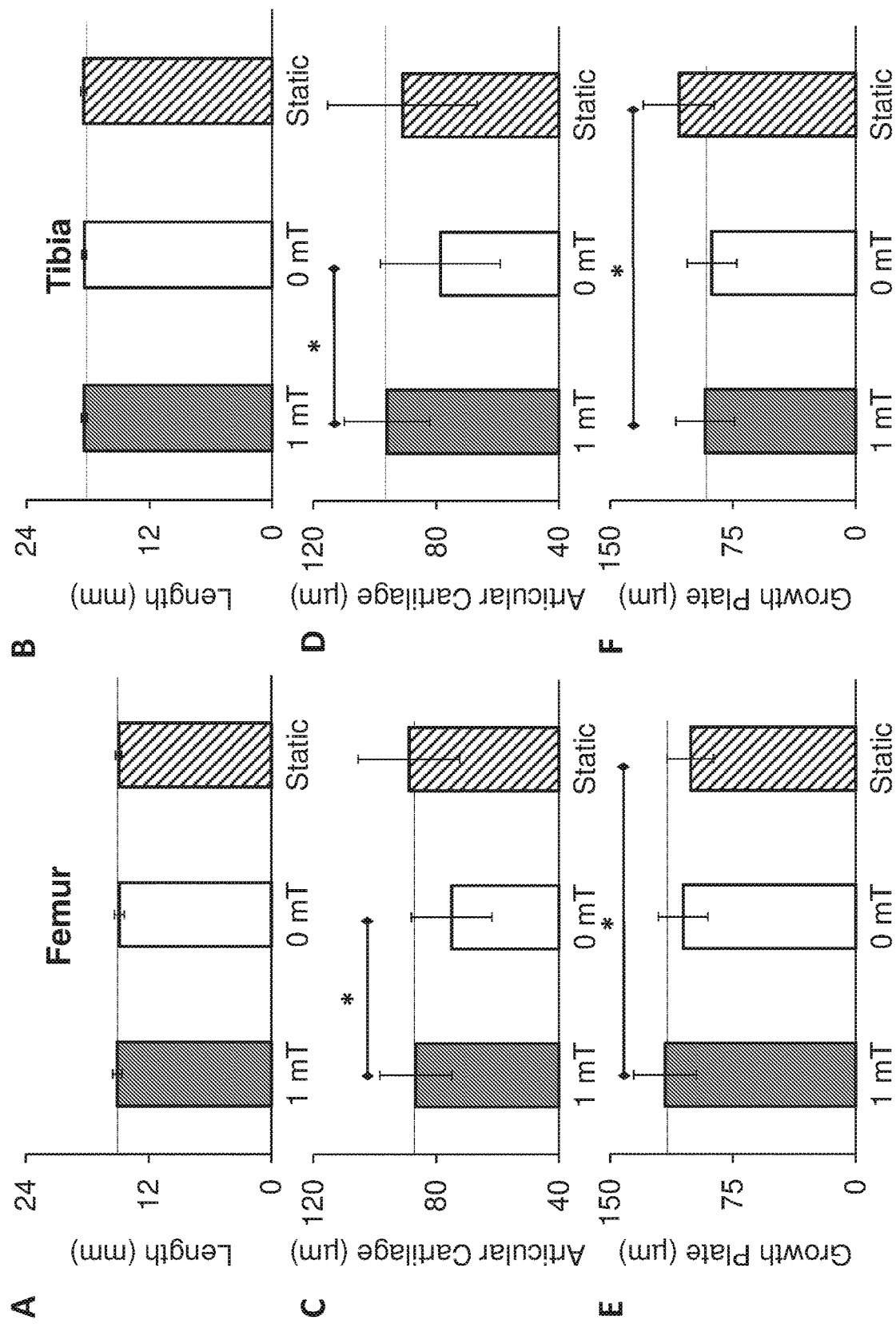
FIG. 28 shows that exposing mice to PEMFs of the EMF efficacy window of skeletal muscle enhances in vivo chondrogenesis downstream of myokine release.

FIG. 28 shows that exposing mice to PEMFs of the EMF efficacy window of skeletal muscle enhances in vivo chondrogenesis downstream of myokine release. Measurements from the femur (A, C, D) and tibia (B, D, F). A, B) Bone length. C, D) Articular cartilage. E, F) Growth plate. There is generally a difference between the indices of mice exposed to either 0 mT or 1 mT PEMFs originating from the MRI machine. The data indicates that the noise produced by the MRI gave rise to catabolic stress that exposure to 1 mT PEMFs was able to counteract.

Figure 29:
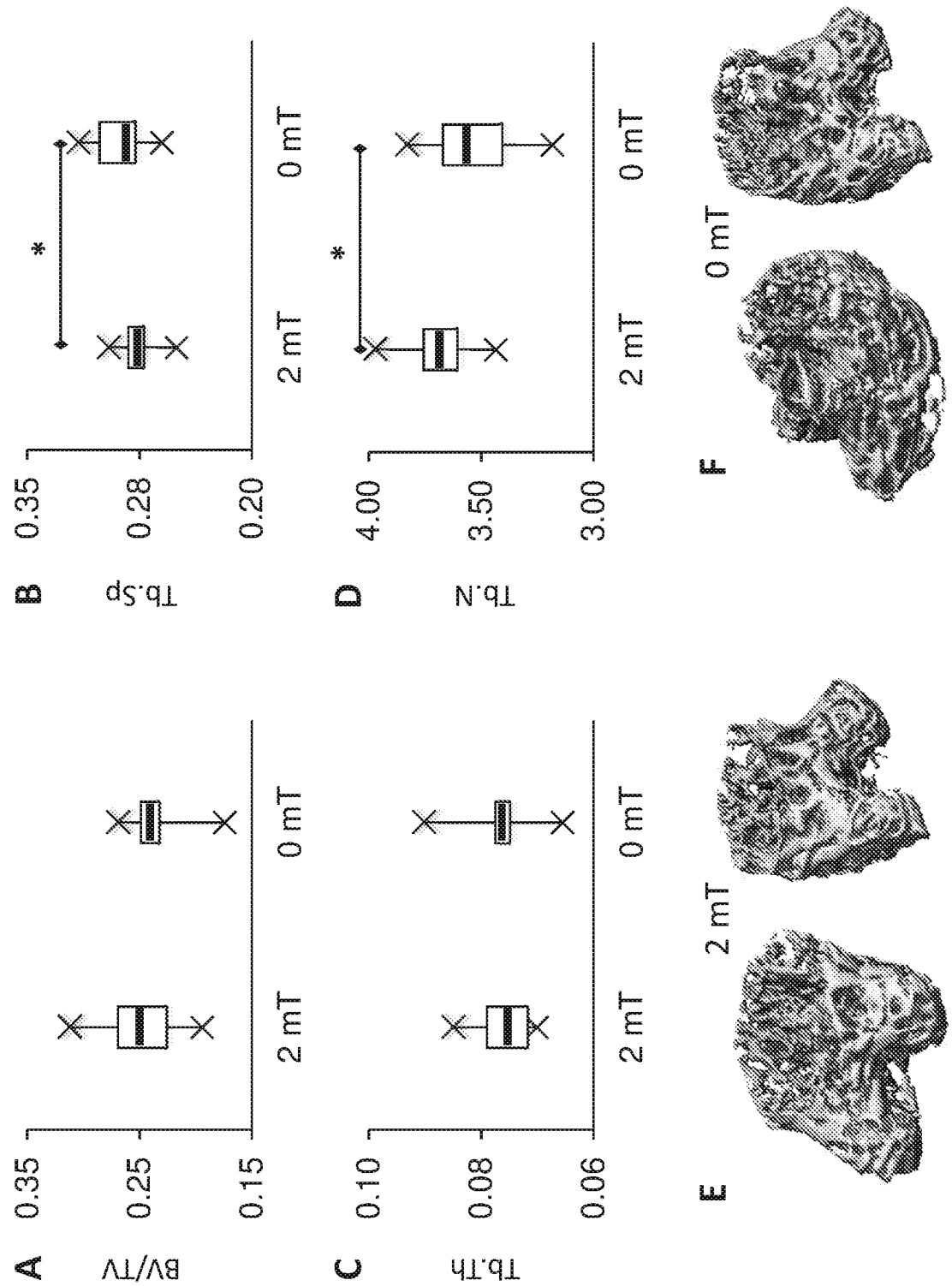
FIG. 29 shows that bone mineral density increases in response to PEMF treatment of mice at the EMF efficacy window of skeletal muscle.

FIG. 29 shows that bone mineral density increases in response to PEMF treatment of mice at the EMF efficacy window of skeletal muscle. A) Trabecular bone volume (BV/TV) shows a tendency to increase that does not reach significance. B) Trabecular Thickness (Tb.Th) does not change. C) Trabecular Spacing (Tb.Sp) increases significantly. D) Trabecular Number (Tb.N) increases significantly. Mice were treated for 6 months with 2 mT PEMFs for a single session of 10 min/week.

Figure 30:
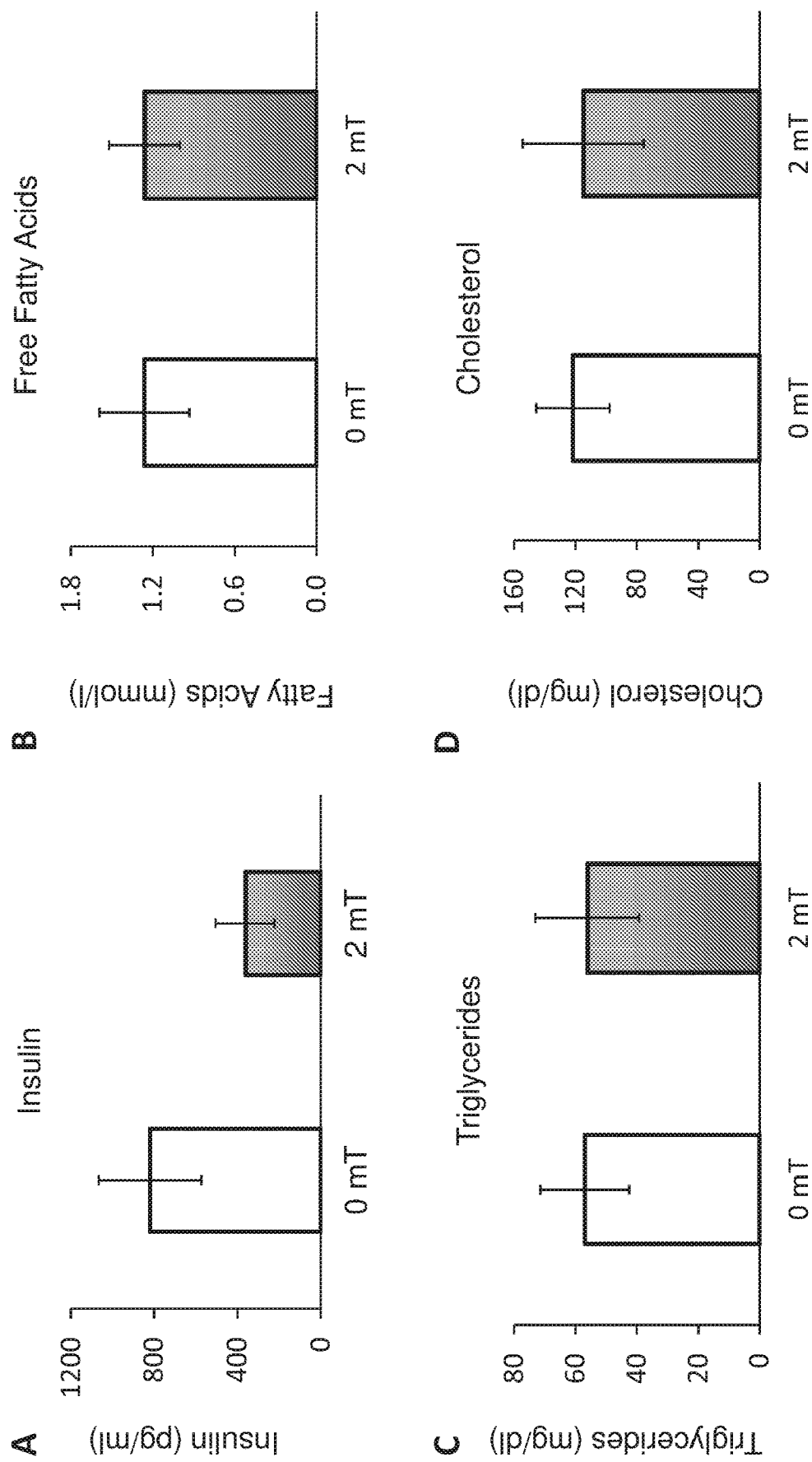
FIG. 30 shows that weekly PEMF exposure stabilizes insulin levels in mice when delivered at the EMF efficacy window of skeletal muscle.

FIG. 30 shows that weekly PEMF exposure stabilizes insulin levels in mice when delivered at the EMF efficacy window of skeletal muscle. Insulin-Sensitivity improves following PEMF treatment. (6 months @ 2 mT for 10 min/week)

Figure 31:
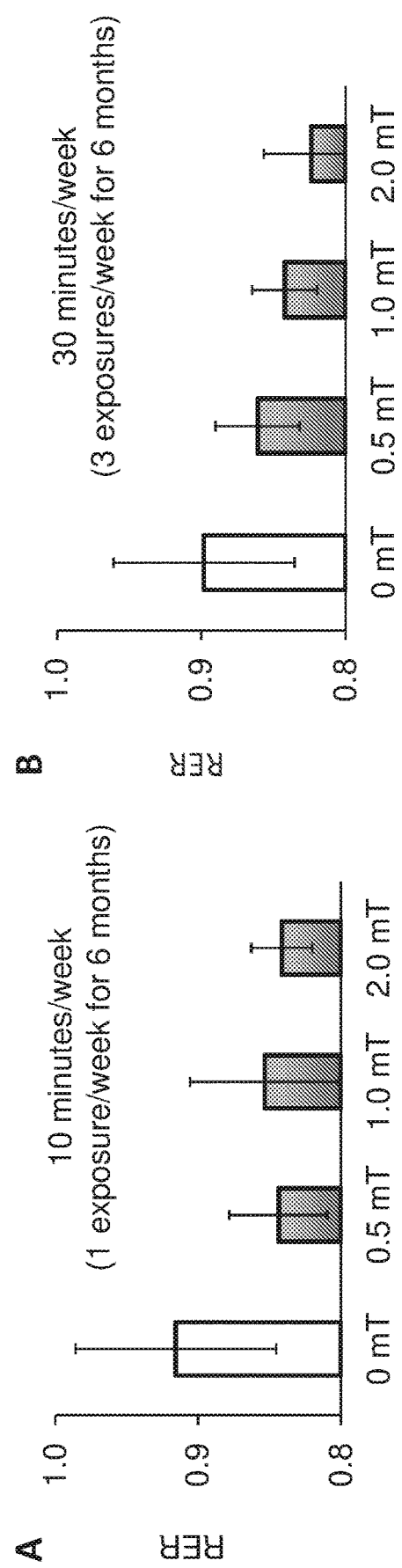
FIG. 31 shows that PEMF exposure reduces Respiratory Exchange Ration (RER), indicating greater fatty acid oxidation.

FIG. 31 shows that PEMF exposure reduces Respiratory Exchange Ration (RER), indicating greater fatty acid oxidation. RER drops in trained individuals.

Figure 32:
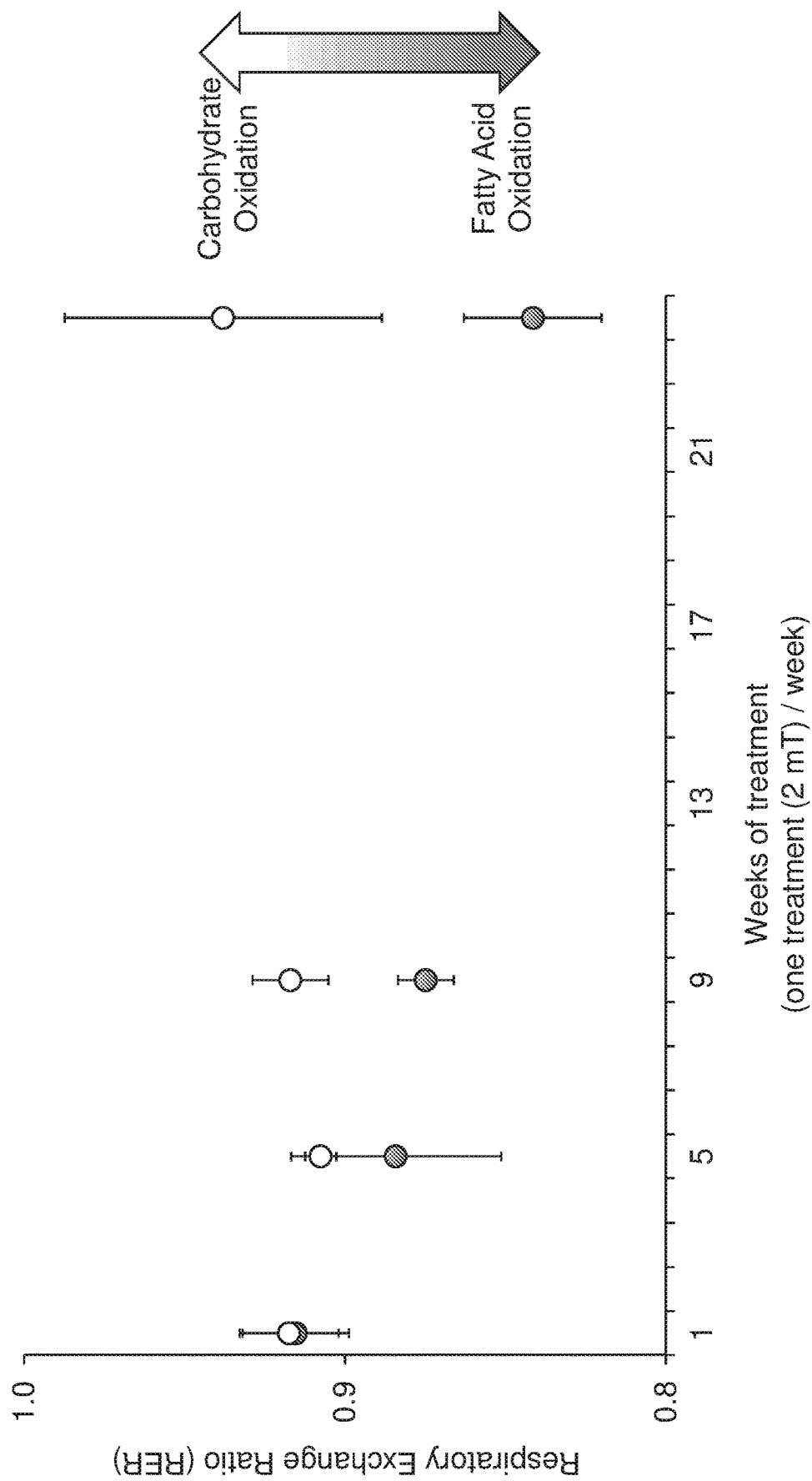
FIG. 32 shows that a drop in RER is evident as soon as 5 weeks after commencement of PEMF treatment as indicated.

FIG. 32 shows that a drop in RER is evident as soon as 5 weeks after commencement of PEMF treatment as indicated.

FIG. 33 shows that PEMFs protect against systemic inflammation. Sampling of inflammatory markers (as indicated) stabilized by weekly PEMF exposure at the EMF efficacy window of skeletal muscle. 10 mice per group, treated once weekly with 1 mT PEMFs for 4 months.

Figure 34:
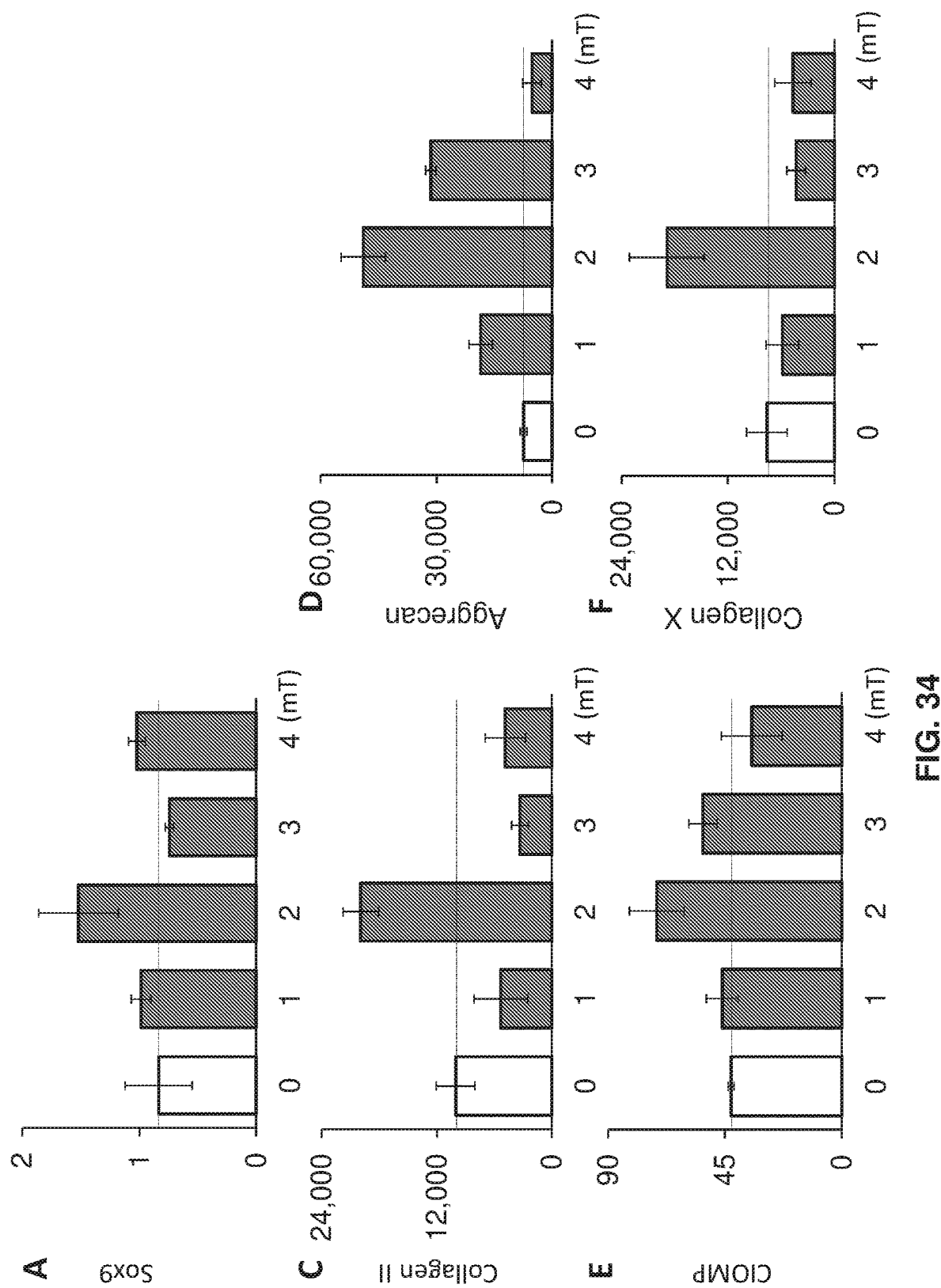
FIG. 34 shows that the EMF efficacy window of in vitro chondrogenesis from MSCs is conserved across several chondrogenic genes as indicated.

FIG. 34 shows that the EMF efficacy window of in vitro chondrogenesis from MSCs is conserved across several chondrogenic genes as indicated; 2 mT PEMFs applied once for 10 minutes gave the best chondrogenic outcome. PEMFs off peak (2 mT) from the EMF efficacy window for chondrogenesis were often inhibitory relative to control (0 mT).

Figure 35:
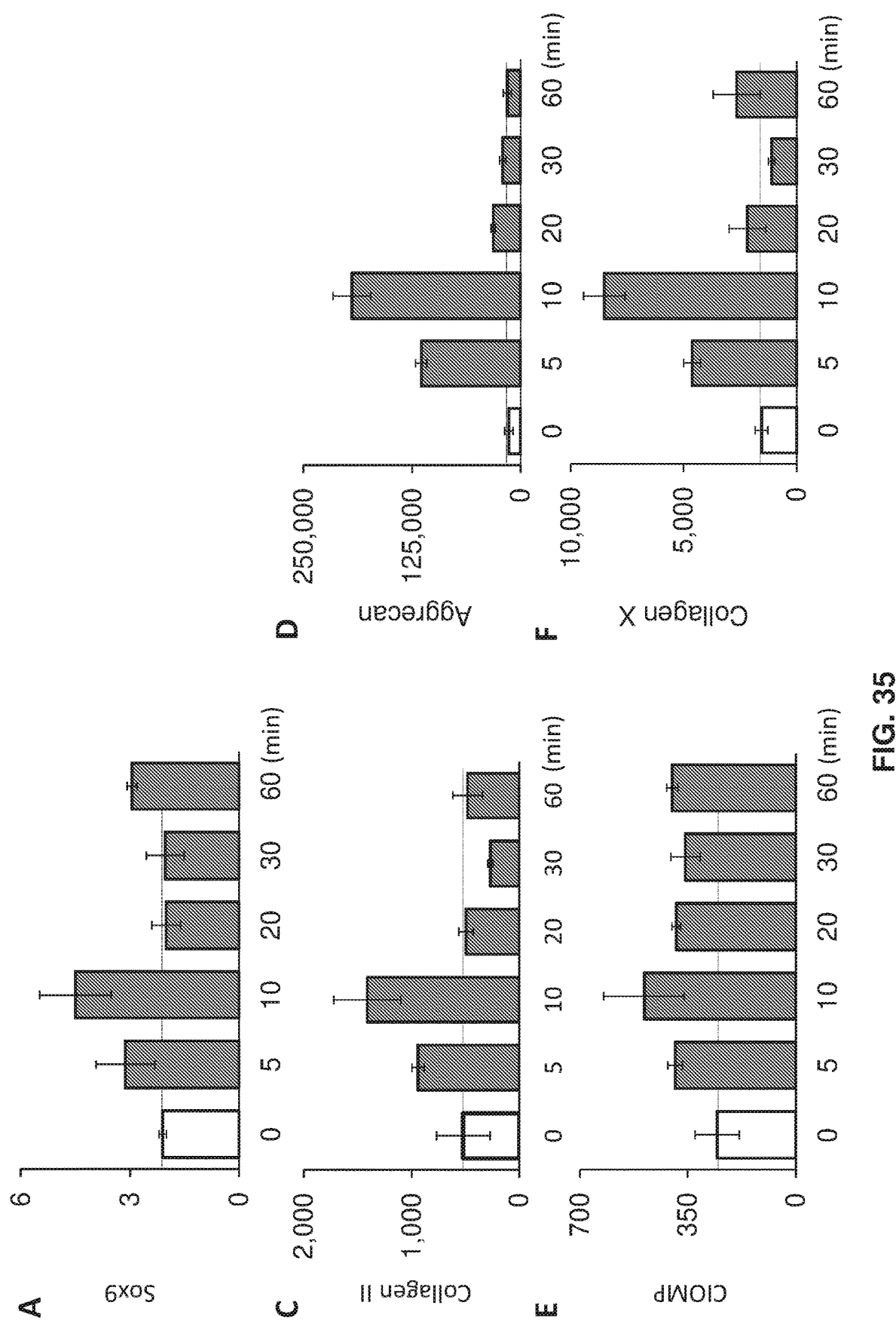
FIG. 35 shows that the EMF efficacy window is conserved across several chondrogenic genes (as indicated) during in vitro chondrogenesis of MSCs.

FIG. 35 shows that the EMF efficacy window is conserved across several chondrogenic genes (as indicated) during in vitro chondrogenesis of MSCs; 2 mT PEMFs applied once for 10 minutes gave the best chondrogenic outcome. PEMFs off peak (2 mT) from the EMF efficacy window for chondrogenesis were often inhibitory relative to control (0 mT).

Figure 36:
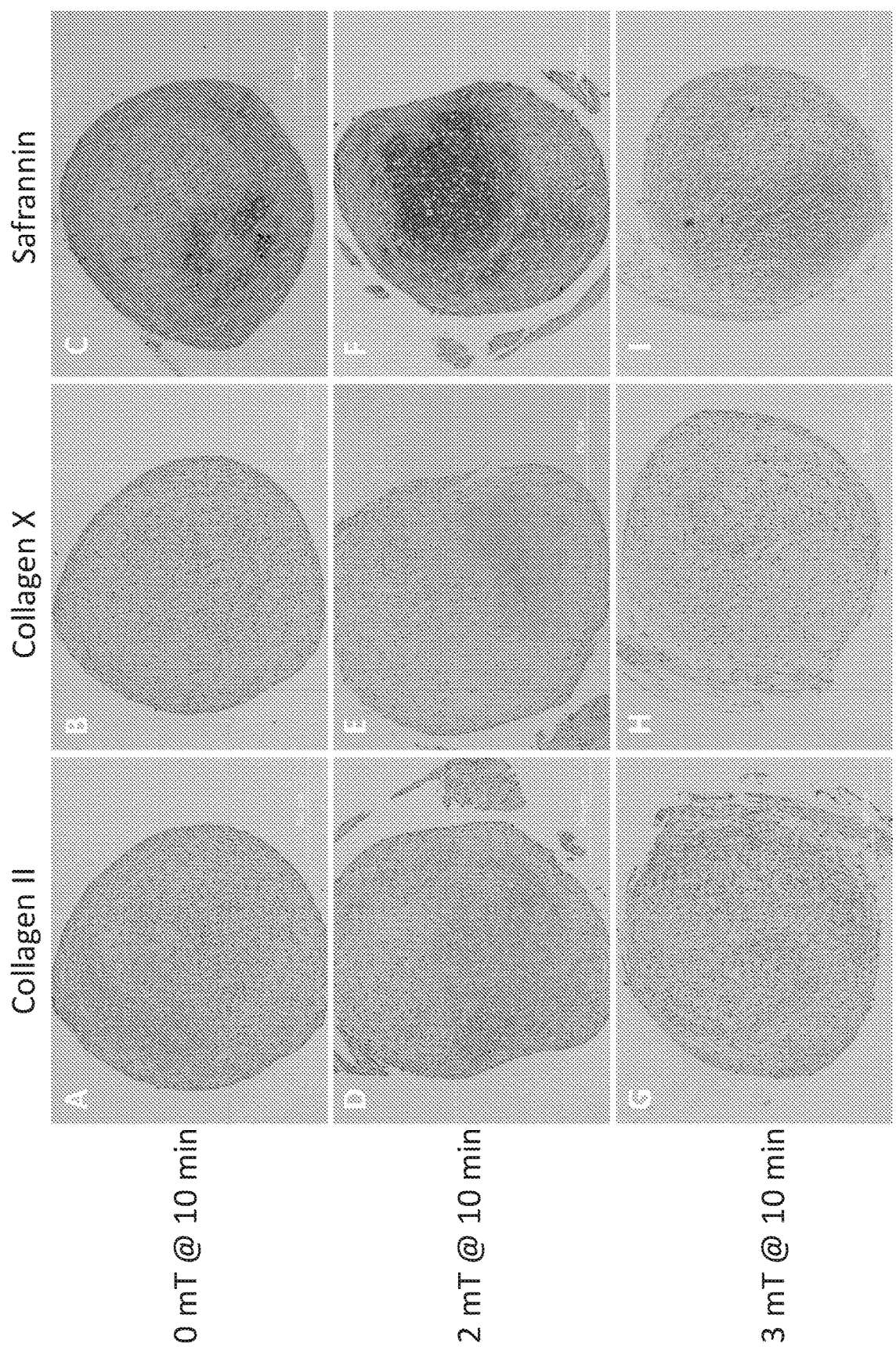
FIG. 36 shows that The MSC EMF efficacy window is conserved during in vitro chondrogenesis.

FIG. 36 shows that The MSC EMF efficacy window is conserved during in vitro chondrogenesis. Histological determination of chondrogenic induction using collagen II (A,D,G), collagen X (B,E,H) and Safrannin (C,F,I) staining as indicators of chondrogenic induction. 2 mT PEMFs applied once for 10 minutes gave the best chondrogenic result. PEMFs off peak (10 minutes) from the EMF efficacy window for chondrogenesis were inhibitory relative to control (0 mT).

FIG. 37 shows that PEMF exposure does not increase resting apoptosis (top) and is able to protect against apoptosis in response to apoptotic stimuli (below). Top) PEMF exposure at the indicated amplitudes for 30 minutes does not induce significant levels of apoptosis. Bottom) Low amplitude (0.5 mT) PEMFs applied one hour after an apoptotic stimulus (1 mM $H_2O_2$) protected C2C12 myoblasts against the induction of apoptosis.

FIG. 38 shows that pre-Exposure of cardiac myocytes to their EMF Efficacy Window (3 mT for 10 minutes) protects against oxidative damage. Rat cardiacmyocyte cell line (H9C2) cells were exposed to 3 mT for 10 minutes before addition of 50 μM $H_2O_2$. Cell viability was determined by Flow Cytometry 5 hours after addition of $H_2O_2$.

Figure 39:
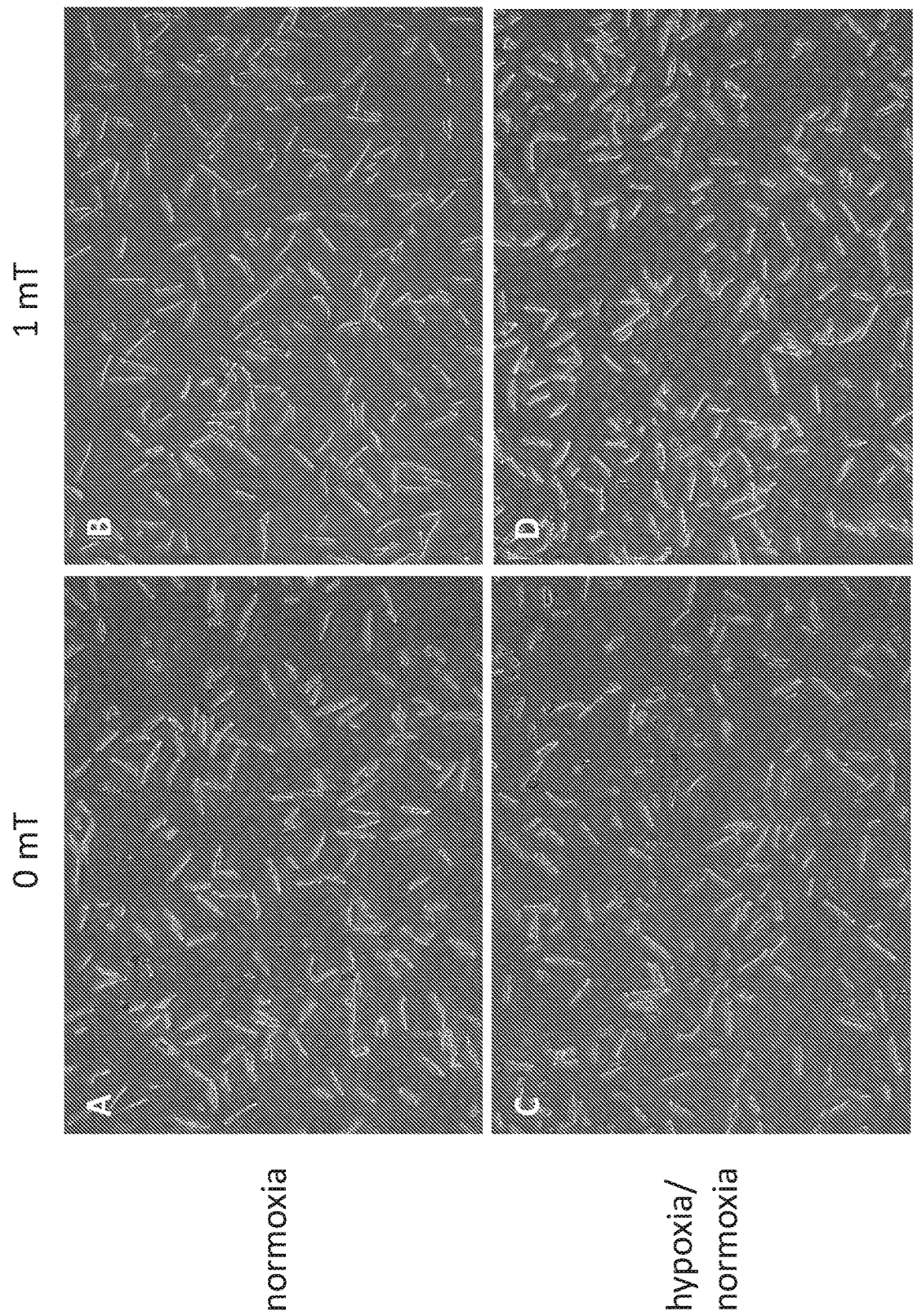
FIG. 39 shows that PEMFs protect primary cardiac myocytes from hypoxia-induced damage.

FIG. 39 shows that PEMFs protect primary cardiac myocytes from hypoxia-induced damage. Brief PEMF exposure (10 minutes at 1 mT) protects primary cardiac myocytes from oxidative damage resulting from the transition from hypoxia to normoxia.

Figure 40:
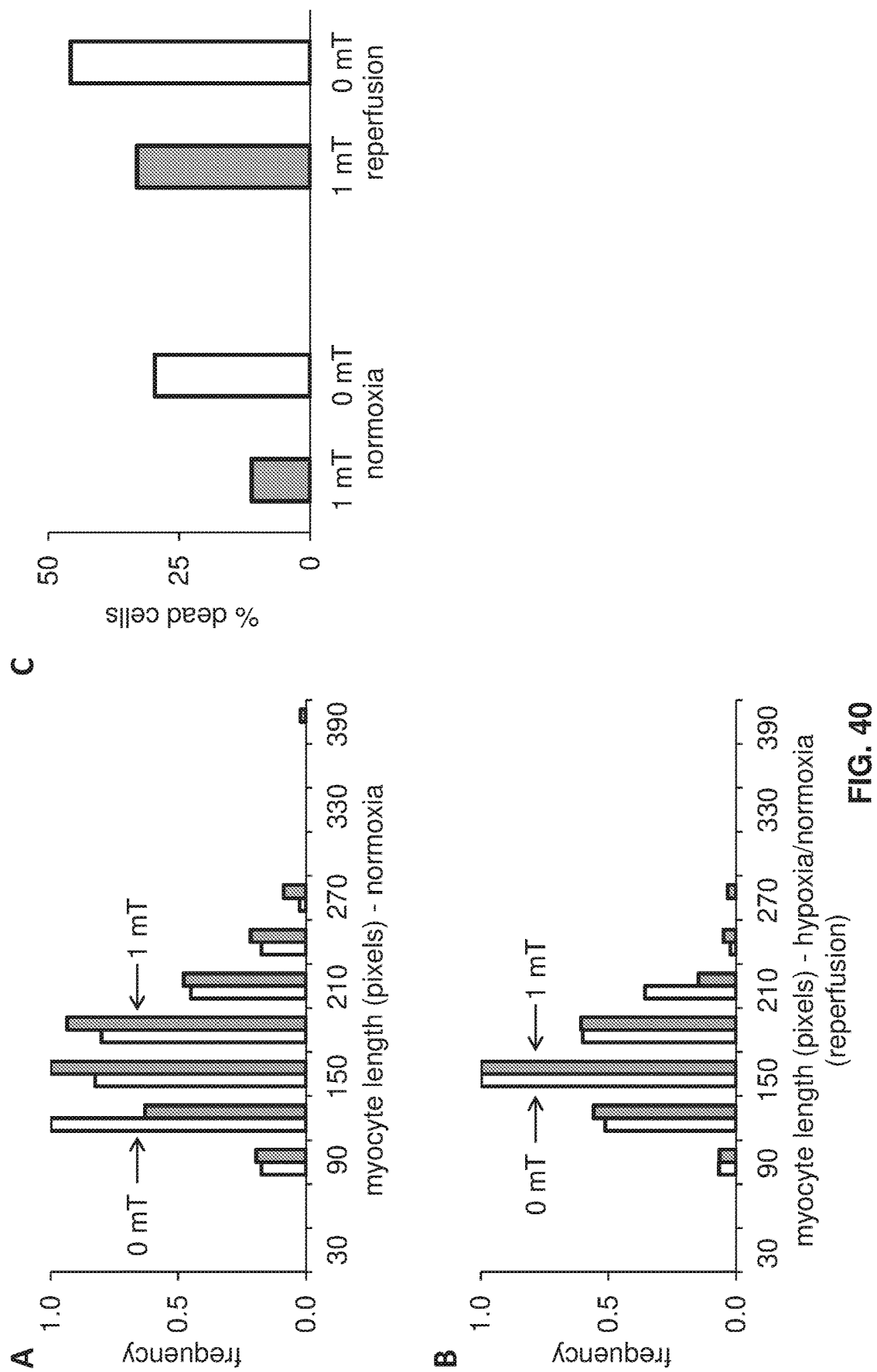
FIG. 40 shows that PEMFs protect primary cardiac myocytes from hypoxia damage.

FIG. 40 shows that PEMFs protect primary cardiac myocytes from hypoxia damage. Morphological data transformation of images shown in FIG. 39.

Figure 41:
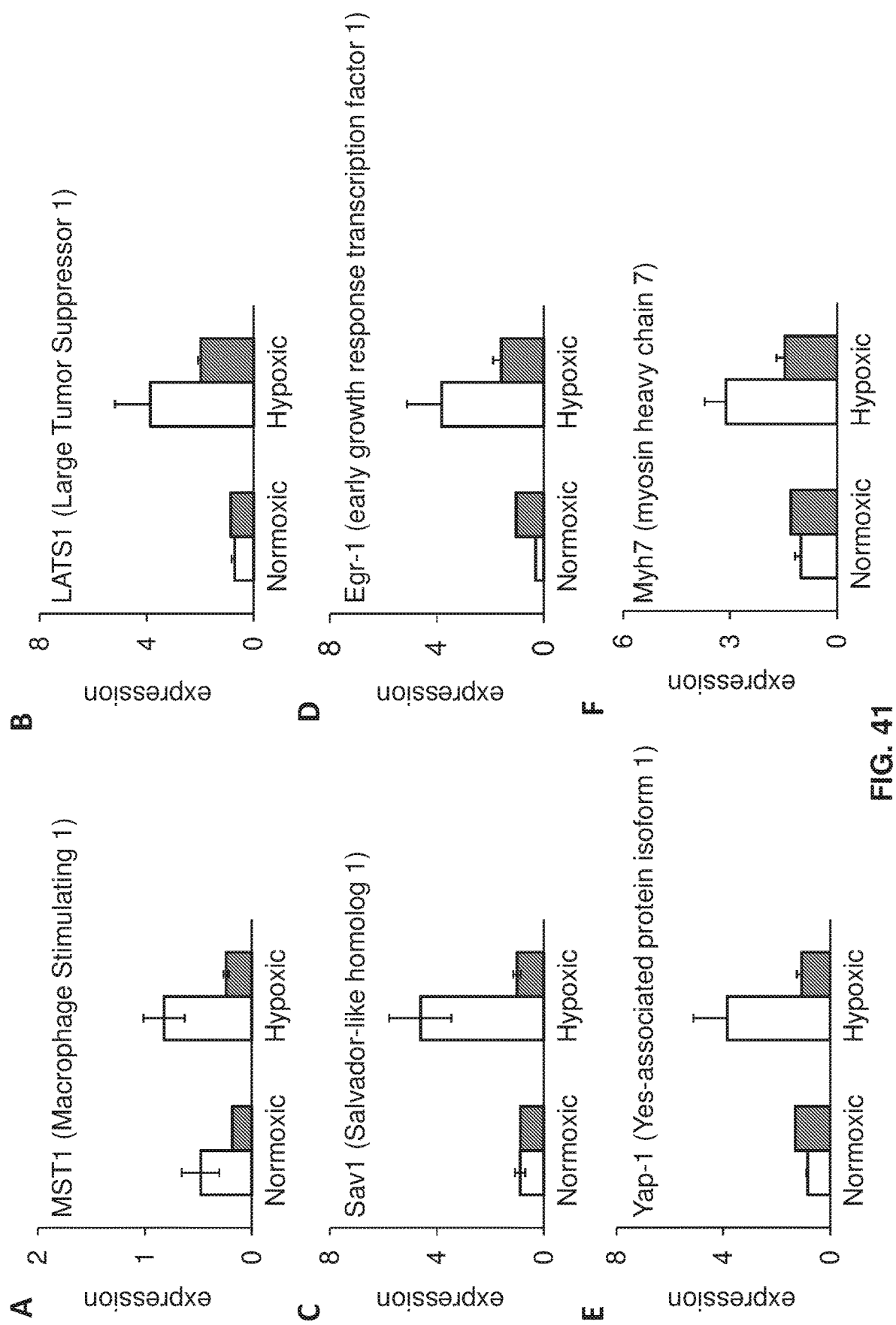
FIG. 41 shows that PEMFs protect primary cardiac myocytes from hypoxia damage.

FIG. 41 shows that PEMFs protect primary cardiac myocytes from hypoxia damage. Genetic data transformation of images shown in FIG. 39.

FIG. 42 shows that PEMFs at the EMF Efficacy window of muscle has a cardioprotective effect as indicated by the upregulation of the indicated genes.

Figure 43:
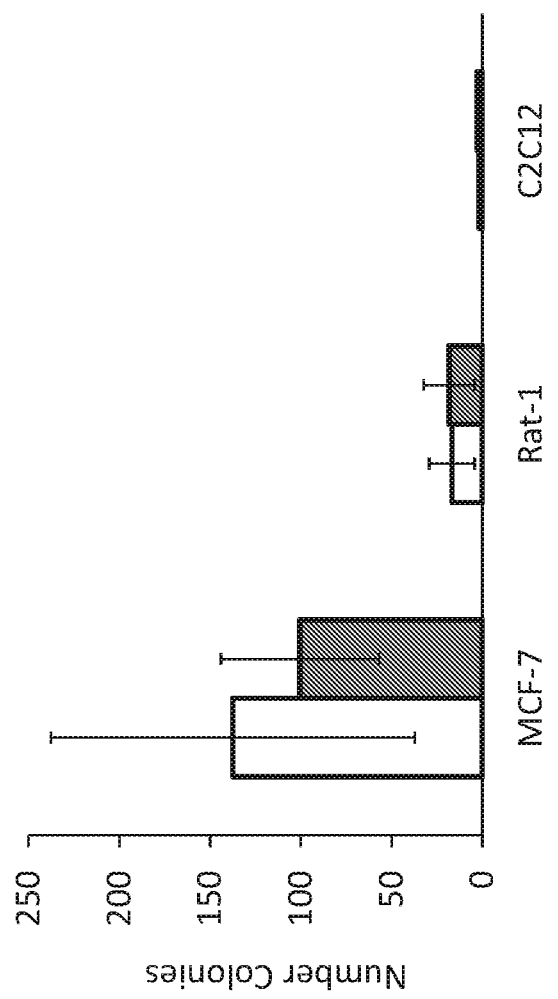
FIG. 43 shows that PEMF exposure does not induce malignant transformation of cells.

FIG. 43 shows that PEMF exposure does not induce malignant transformation of cells; an induced ability to grow in soft agar. 1 mT PEMFs were applied for 20 minutes and did not induce transformation of cells as indicated by the ability to grow in colonies in soft agar.

Figure 44:
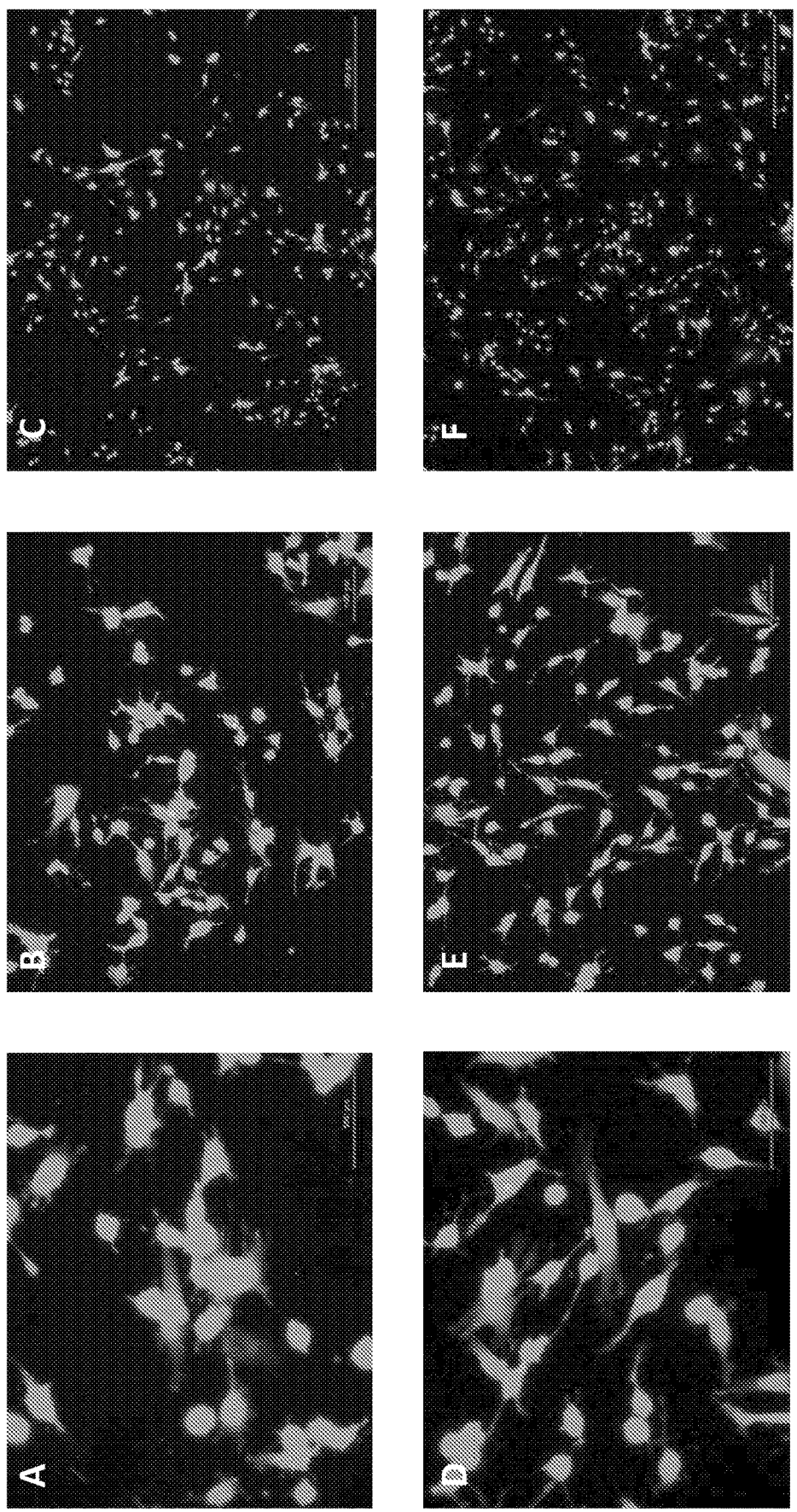
FIG. 44 shows that exposing H9C2 cardiacmyocytes to PEMFs outside of their EMF efficacy window of 3 mT does not increase cell death.

FIG. 44 shows that exposing H9C2 cardiacmyocytes to PEMFs outside of their EMF efficacy window of 3 mT does not increase cell death. Live/dead staining showing that exposure of H9C2 cardiacmyocytes to 4 mT PEMFs for 10 minutes does not compromise cell viability. H9C2 cardiacmyocytes are responsive to 3 mT PEMFs (10 minutes) with proliferation, whereas they do not respond to 4 mT PEMFs with proliferation (see FIG. 45 for example). Live cells are shown in green, whereas dead cells are shown in red.

Figure 45:
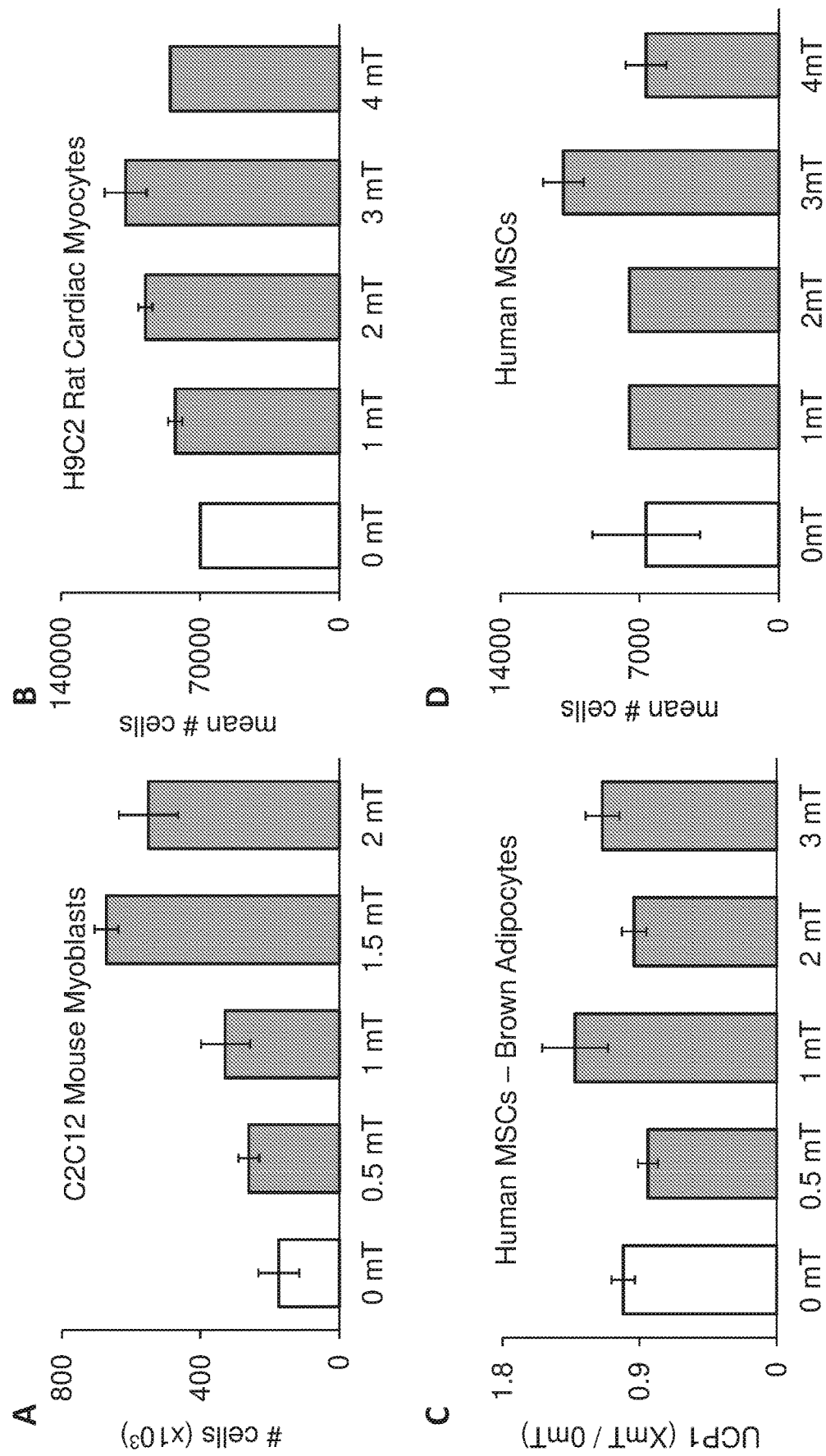
FIG. 45 shows examples of EMF efficacy windows for distinct cell classes.
Figure 46:
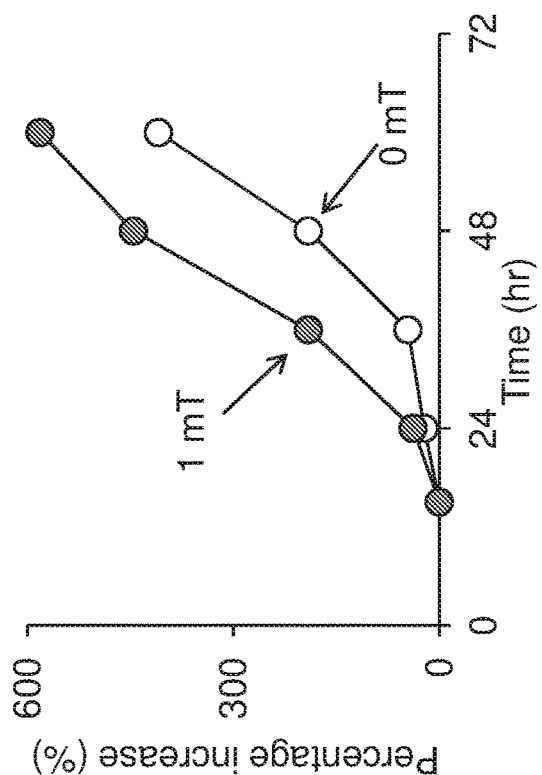
FIG. 46 shows that growth Curves reflect EMF Efficacy (3 mT) window of the cell types in question.
Figure 46:
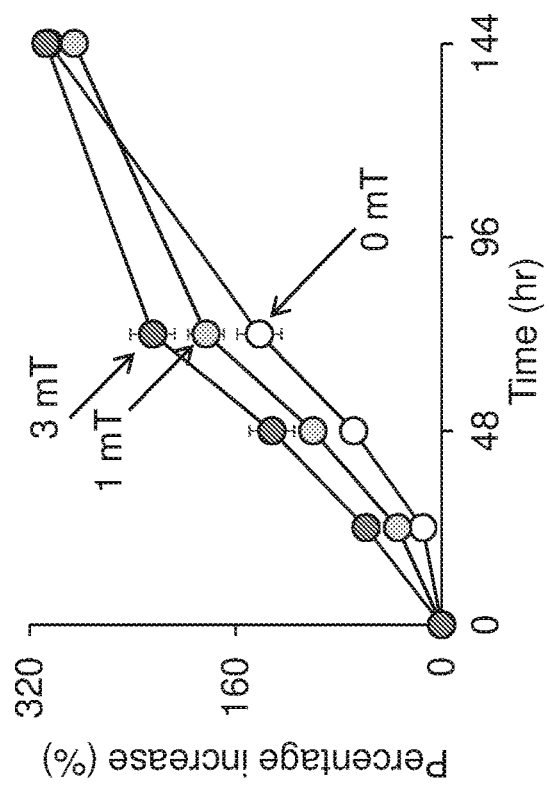
Figure 46:
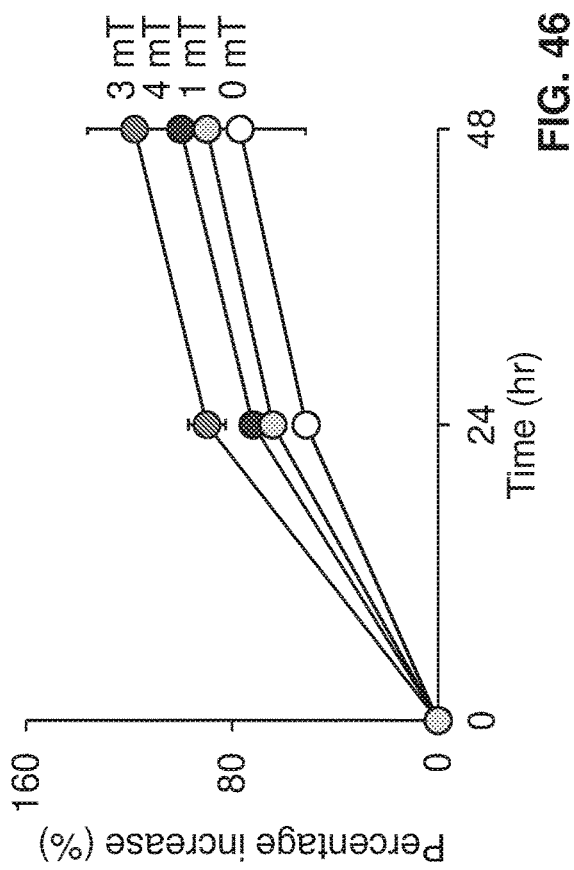

FIG. 45 shows examples of EMF efficacy windows for 2 distinct cell classes. H9C2 rat cardiac myocytes and human PT-2501 MSCs exhibit an enhancement in proliferation in response to exposure to 3 mT PEMFs applied for 10 minutes. Also see EMF efficacy window of MSCs directed into chondrogenesis (FIG. 34, FIG. 35) FIG. 46 shows that growth Curves reflect EMF Efficacy (3 mT) window of the cell types in question: A). B). C). D). Also see EMF efficacy window of rat H9C2 cardiac myocytes (also see FIG. 45 panel B).

Figure 47:
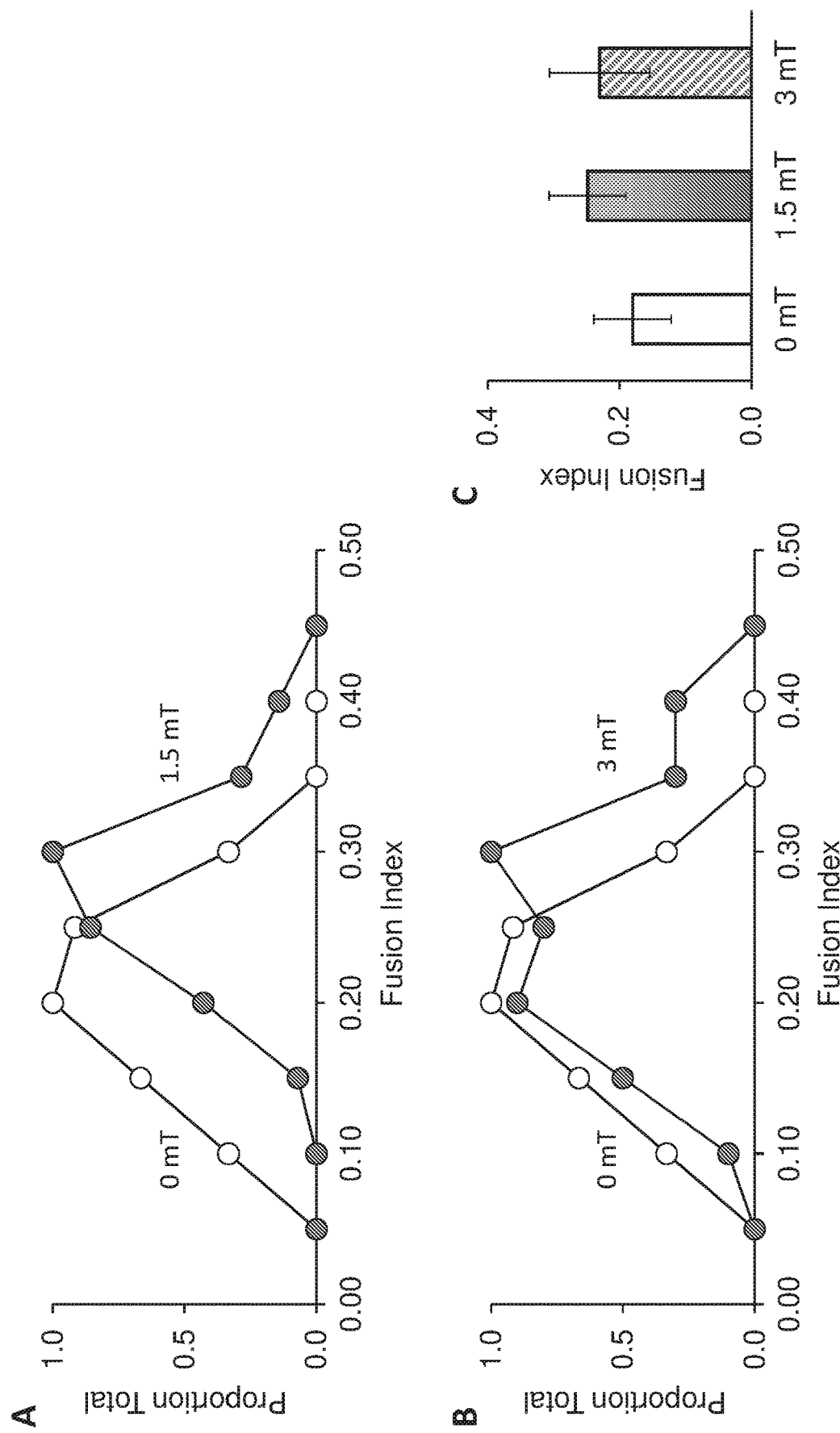
FIG. 47 shows that tissue differentiation obeys the EMF efficacy window of progenitor cell proliferation.

FIG. 47 shows that tissue differentiation obeys the EMF efficacy window of progenitor cell proliferation. PEMFs were applied to myoblasts (18 hours postplating) at the amplitudes indicated and differentiation (myotube size) was examined 10 days later (also see FIG. 45 panel A).

Figure 48:
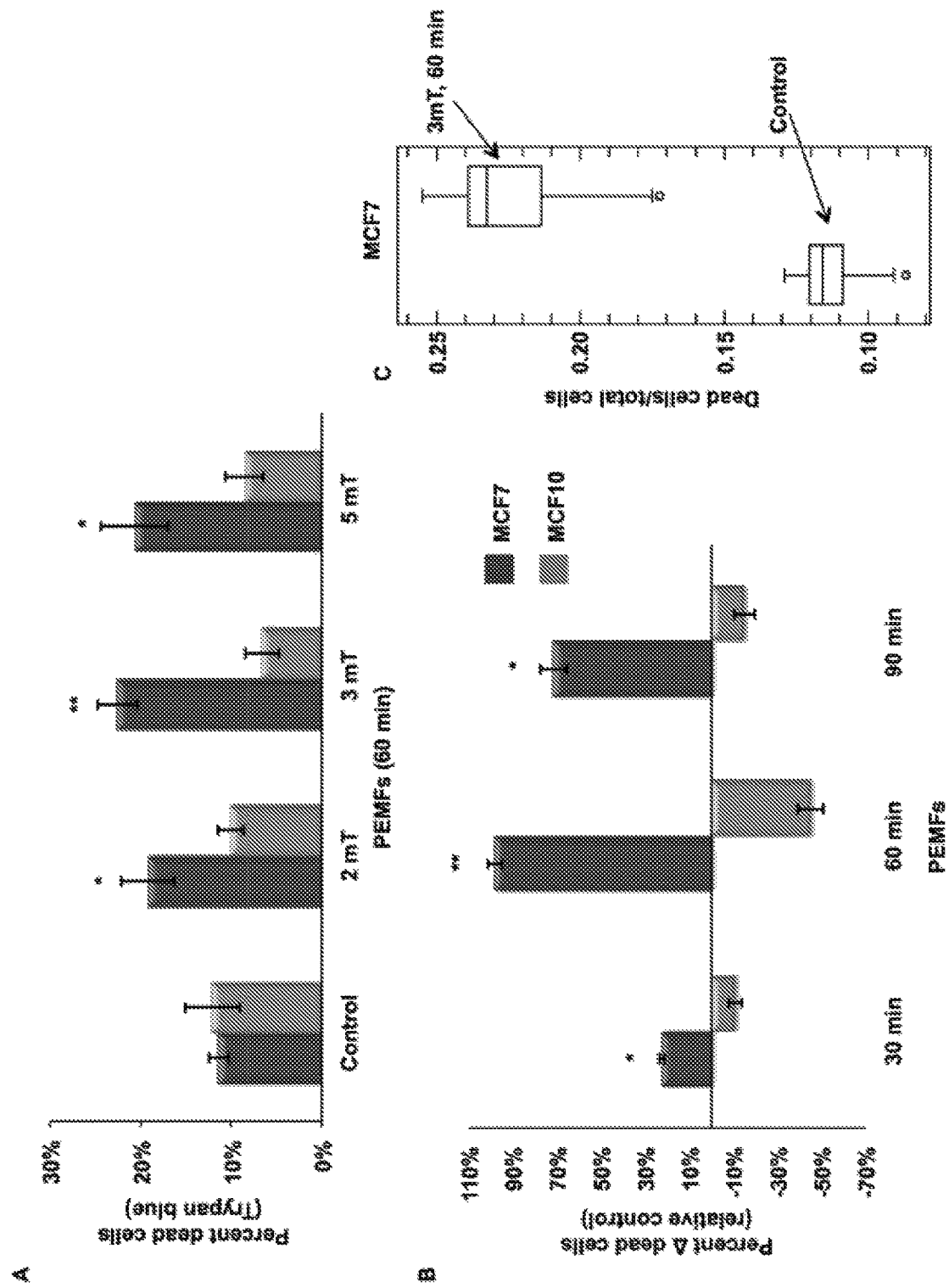
FIG. 48 shows the EMF Efficacy Window for cancer cell killing.

FIG. 48 shows the EMF Efficacy Window for cancer cell killing. 3 mT PEMFs applied for 60 minutes for 3 consecutive days selectively kills MCF-7 breast cancer cells relative to controls, whereas cell viability was improved in MCF-10 normal breast cells subjected to the same exposure paradigm. Adapted from Crocetti et al. (2013) *Low Intensity and Frequency Pulsed Electromagnetic Fields Selectively Impair Breast Cancer Cell Viability.*

Figure 49:
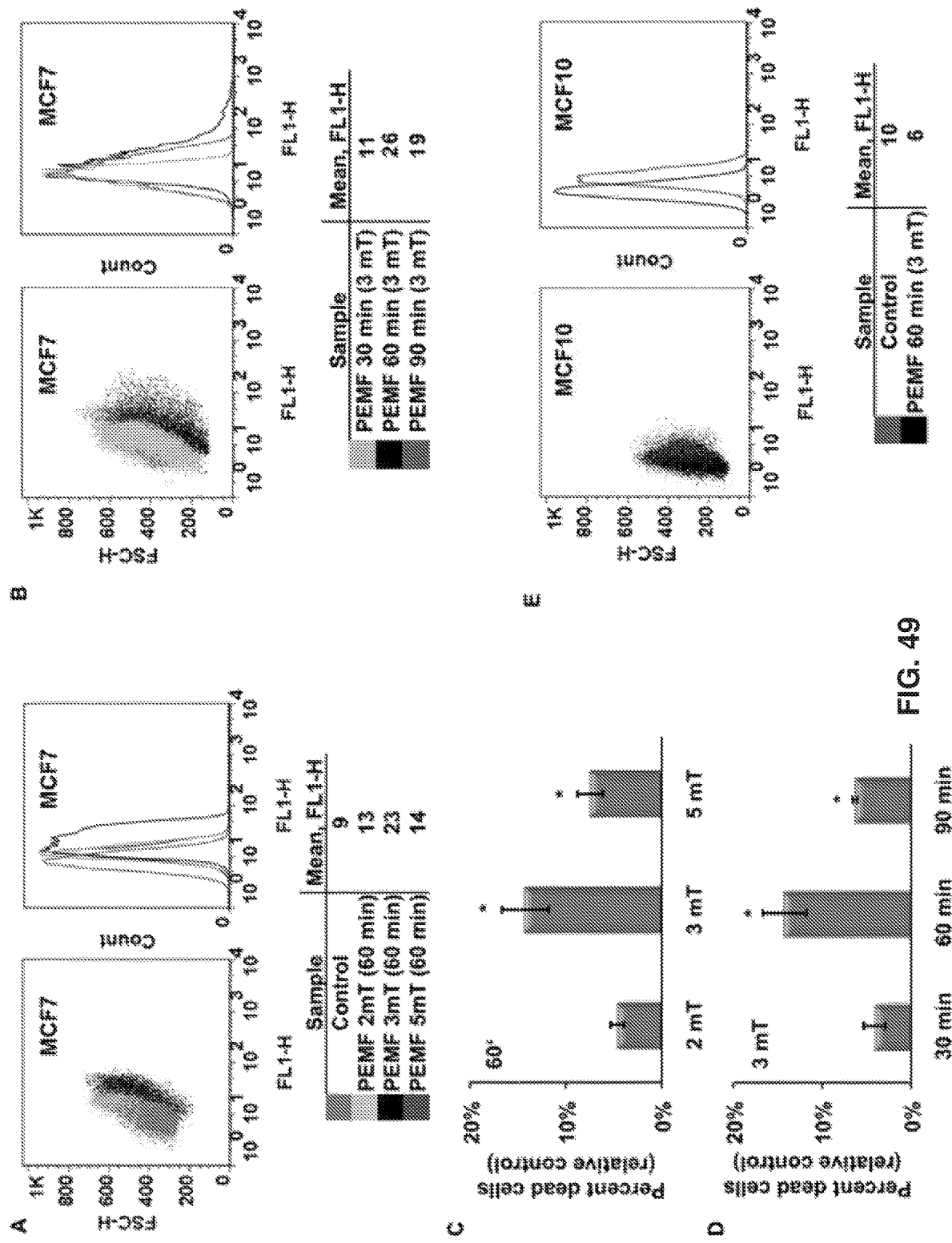
FIG. 49 shows the EMF Efficacy Window for cancer cell killing.

FIG. 49 shows the EMF Efficacy Window for cancer cell killing. 3 mT PEMFs applied for 60 minutes for 3 consecutive days selectively kills MCF-7 breast cancer cells relative to controls (right shift), whereas cell viability was improved in MCF-10 normal breast cells subjected to the same exposure paradigm (left shift). Adapted from Crocetti et al. (2013) *Low Intensity and Frequency Pulsed Electromagnetic Fields Selectively Impair Breast Cancer Cell Viability.*

Figure 50:
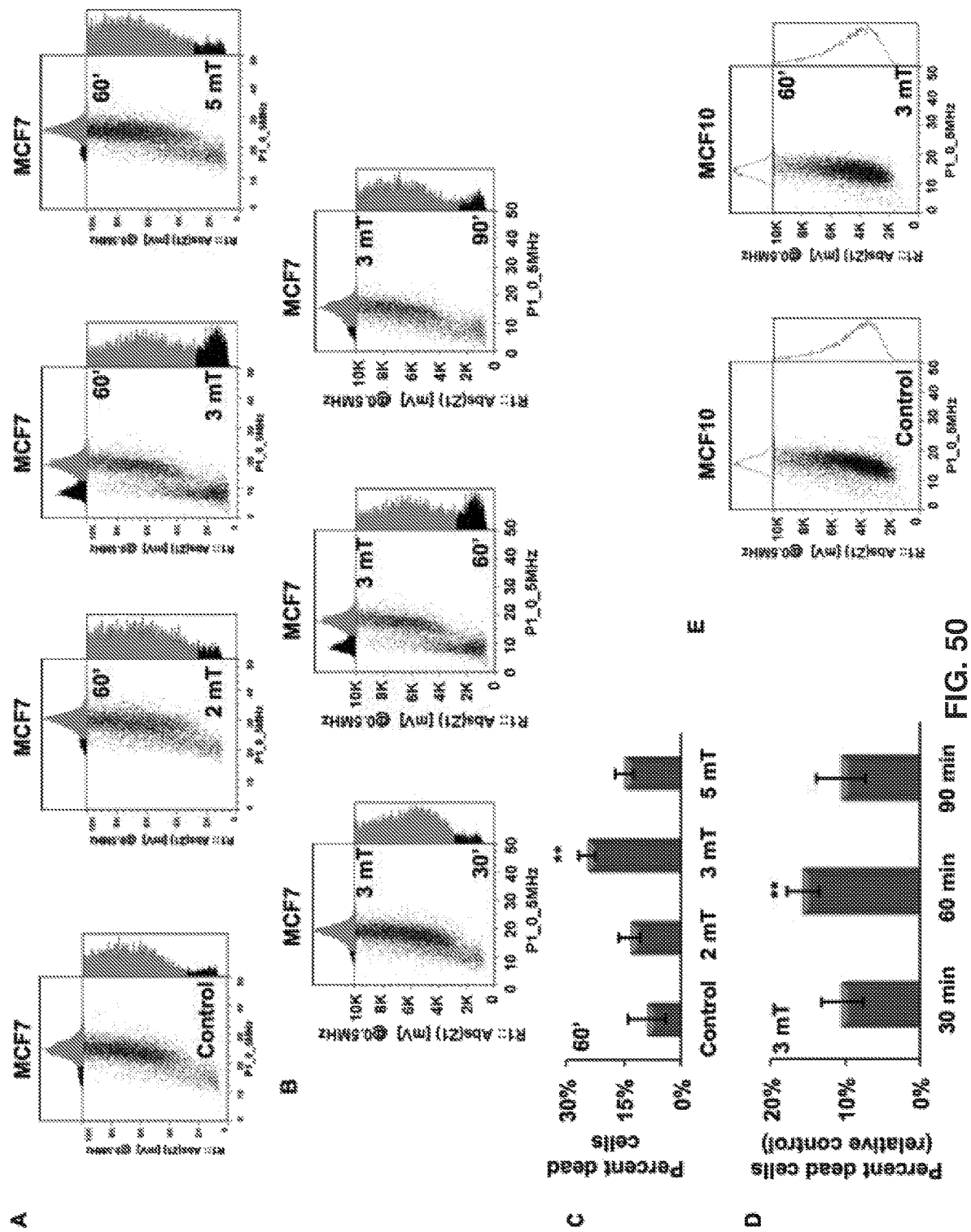
FIG. 50 shows the EMF Efficacy Window for cancer cell killing.

FIG. 50 shows the EMF Efficacy Window for cancer cell killing. 3 mT PEMFs applied for 60 minutes for 3 consecutive days selectively kills MCF-7 breast cancer cells relative to controls, whereas MCF-10 normal breast cells subjected to the same exposure are unharmed. Adapted from Crocetti et al. (2013) *Low Intensity and Frequency Pulsed Electromagnetic Fields Selectively Impair Breast Cancer Cell Viability.*

Figure 51:
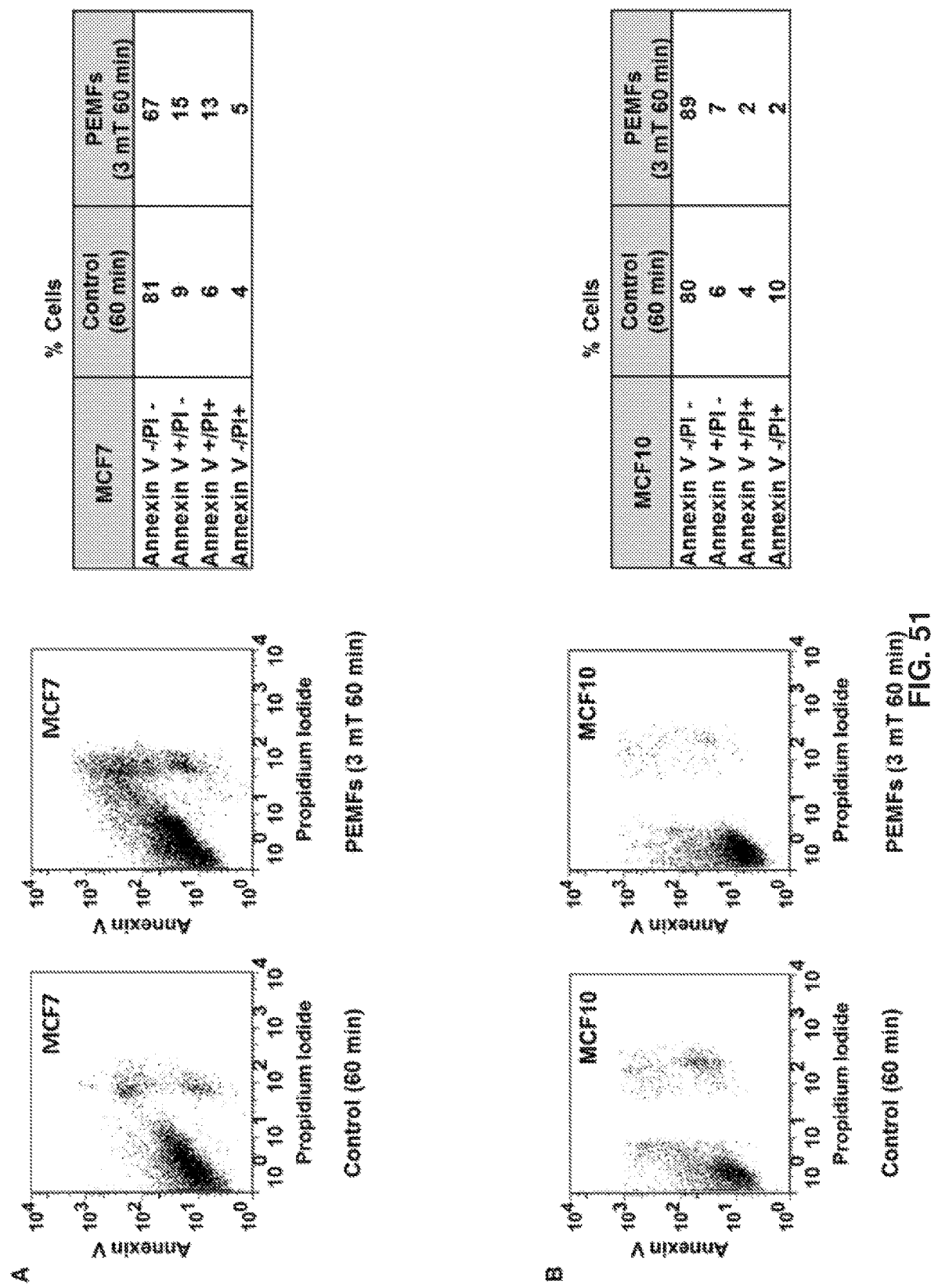
FIG. 51 shows the EMF Efficacy Window for cancer cell killing.

FIG. 51 shows the EMF Efficacy Window for cancer cell killing. 3 mT PEMFs applied for 60 minutes for 3 consecutive days selectively kills MCF-7 breast cancer cells relative to controls (67% versus 81% viability, respectively), whereas cell viability was instead enhanced in MCF-10 normal breast cells subjected to the same exposure paradigm (89% versus 80% viability, respectively). Adapted from Crocetti et al. (2013) *Low Intensity and Frequency Pulsed Electromagnetic Fields Selectively Impair Breast Cancer Cell Viability.*

Figure 52:
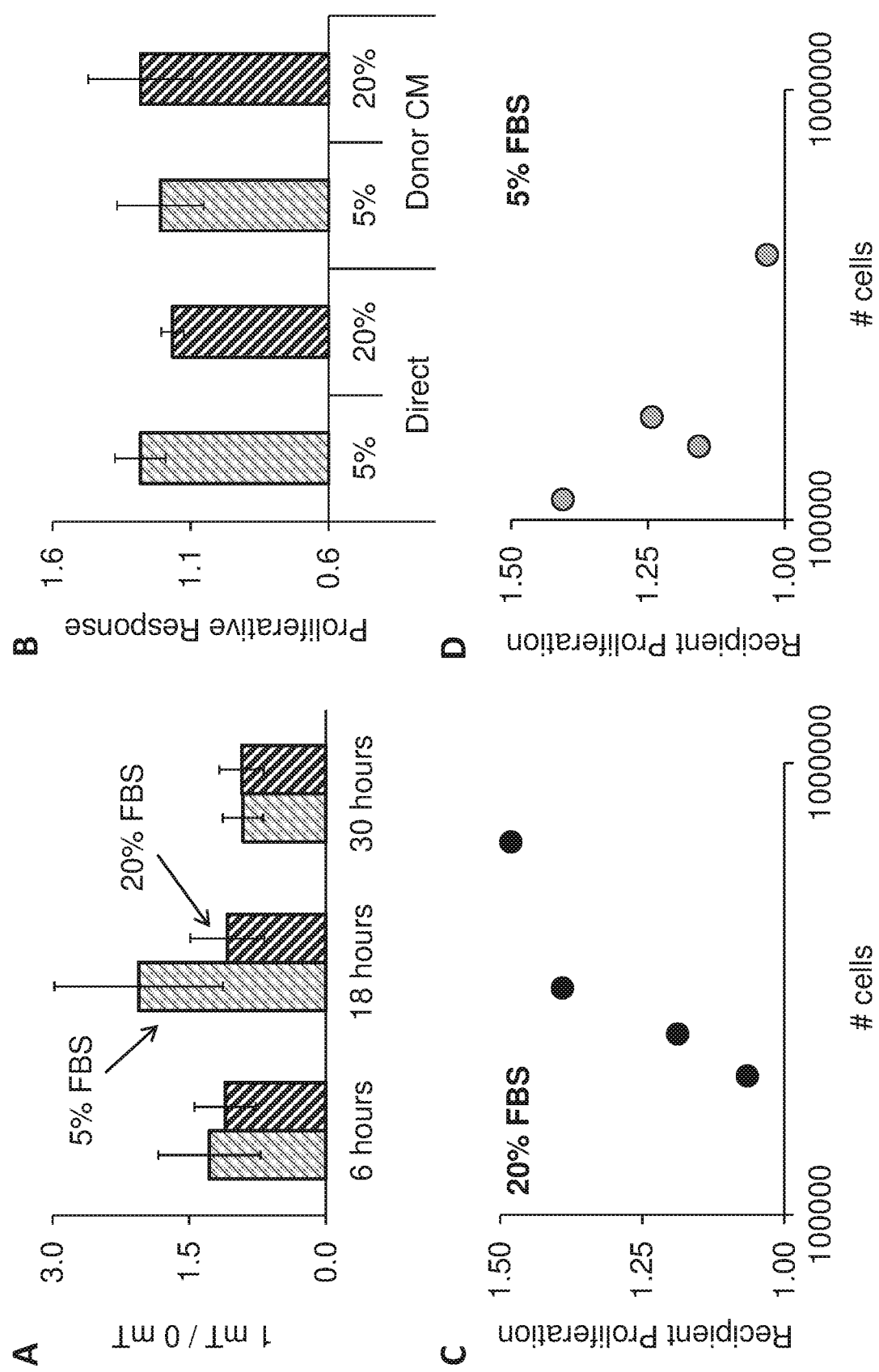
FIG. 52 shows that extracellular serum factors regulate sensitivity to PEMFs in myoblasts and conditioning of media.

FIG. 52 shows that extracellular serum factors regulate sensitivity to PEMFs in myoblasts and conditioning of media. A) Growing myoblasts in 5% Fetal Bovine Serum (FBS) enhanced response to PEMF when stimulated 18 hours after plating. B). Growing myoblasts in 20% FBS produced conditioned media of greater potency (also see FIGS. 57 to 72). Proliferative response of recipient cells provided conditioned media from donor cells grown in 20% FBS (C) or 5% FBS (D) at the indicate cell densities.

Figure 53:
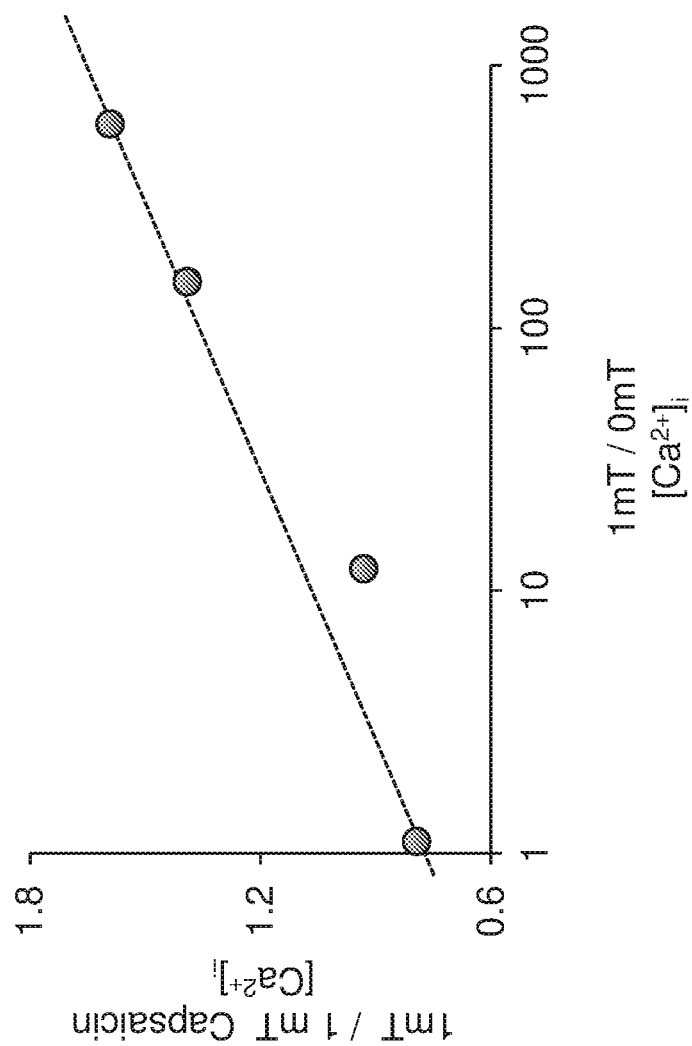
FIG. 53 shows that capsaicin calcium response is inversely related to response to 1 mT PEMFs in C2C12 myoblasts.

FIG. 53 shows that capsaicin calcium response is inversely related to response to 1 mT PEMFs in C2C12 myoblasts.

FIG. 54 shows that PEMFs stimulate calcium entry in Jurkat T Cells and follows their EMF efficacy window of 2 mT for 10 minutes.

Figure 55:
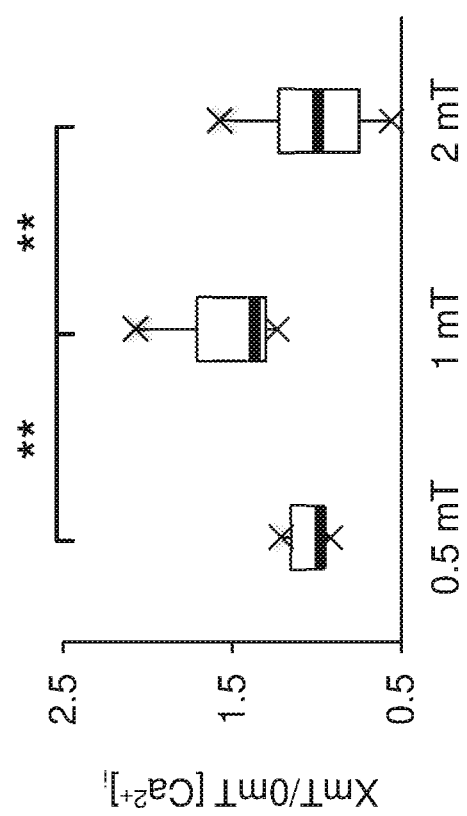
FIG. 55 shows that PEMFs stimulate calcium entry in skeletal myoblasts and follows their EMF efficacy window.

FIG. 55 shows that PEMFs stimulate calcium entry in skeletal myoblasts and follows their EMF efficacy window.

FIG. 56 shows that PEMF exposure at the EMF efficacy window of skeletal muscle progenitor cells produces epigenetic changes that reflect overall acceleration of myogenesis.

FIGS. 57 to 72 relate to conditioned media and effects.

Figure 57:
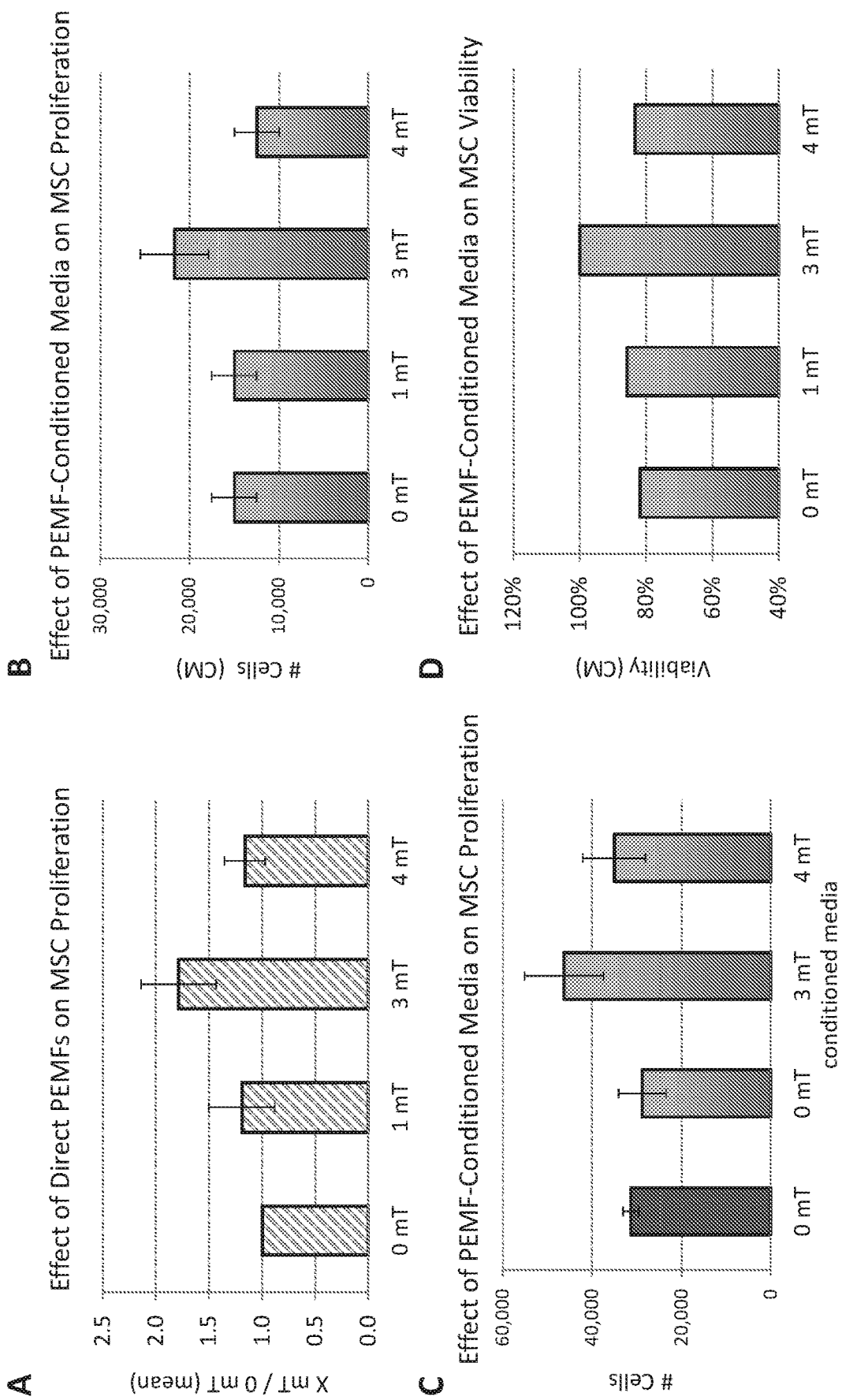
FIG. 57 shows that PEMFs induce mesenchymal stem cells (MSCs) to proliferate and to condition of their extracellular environments (conditioned media).

FIG. 57 shows that PEMFs induce mesenchymal stem cells (MSCs) to proliferate and to condition of their extracellular environments (conditioned media). Direct (A) and indirect effects (B-D) of PEMF stimulation of human MSCs at their appropriate electromagnetic (EMF) windows. A) Directly exposing MSCs to specific PEMFs stimulates proliferation. B) Conditioned media harvested from hMSCs appropriately simulated with PEMFs stimulates the proliferation of naïve (unstimulated) hMSCs. Naive cells were given conditioned media harvested from hMSCs exposed to all the indicated fields. C) Same experimental conditions as panel B except that untreated (no media change) cells are shown in dark blue for reference. D) Improvement in hMSC viability with conditioned media from hMSCs mirrors their specific EM window.

Figure 58:
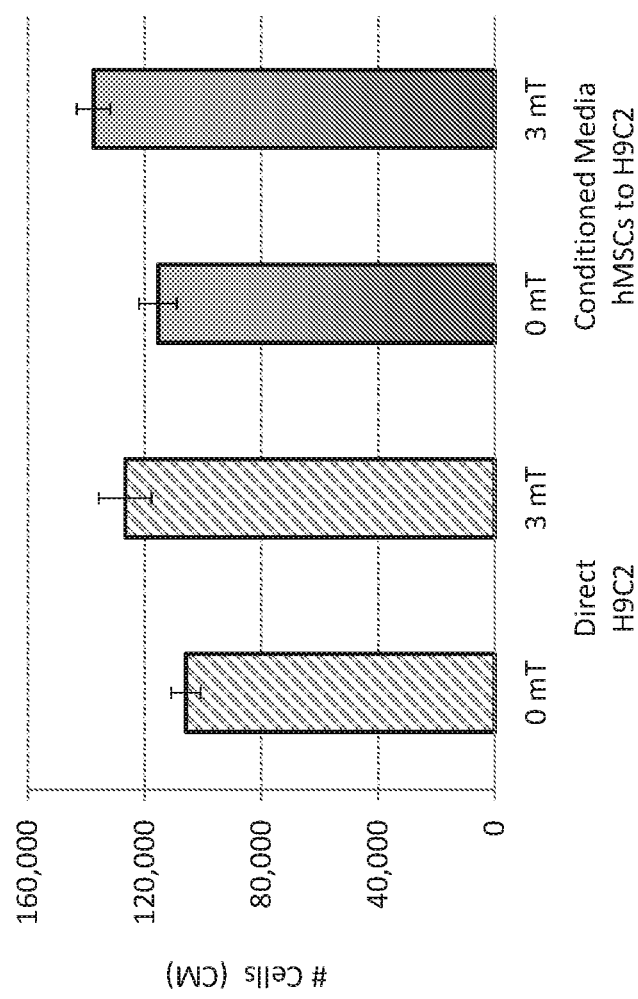
FIG. 58 shows that conditioned media harvested from human mesenchymal stem cells is beneficial to other cell classes.

FIG. 58 shows that conditioned media harvested from human mesenchymal stem cells is beneficial to other cell classes. Rat cardiac myocytes (H9C2 cell line) administered conditioned media harvested from human MSCs respond with elevated proliferation to a similar degree as if directly stimulated with identical PEMFs.

Figure 59A:
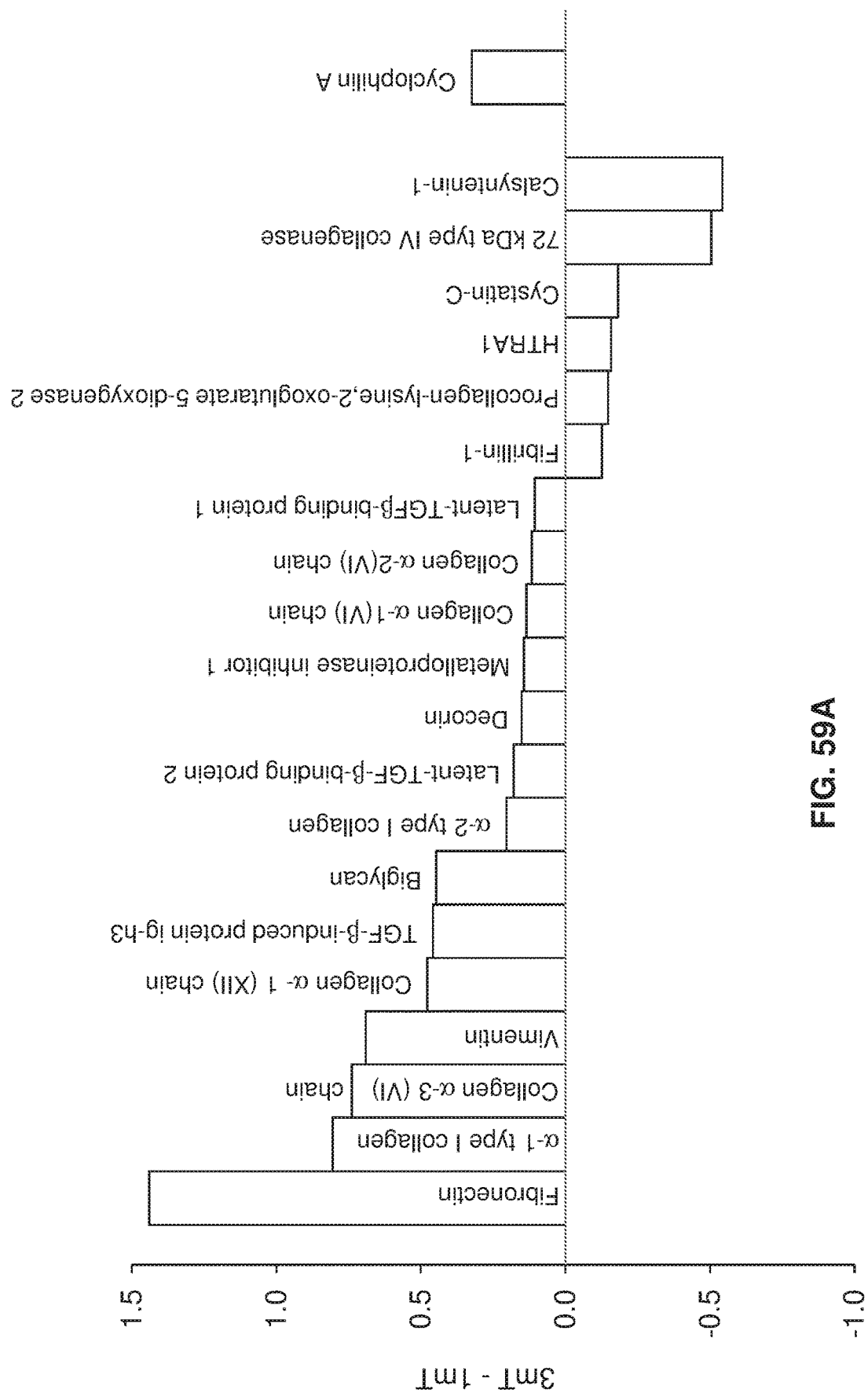
FIG. 59A shows that PEMF-conditioned media contains elevated levels of ECM components and down-regulated levels of ECM-degradation enzymes.

FIG. 59A shows that PEMF-conditioned media contains elevated levels of ECM components and down-regulated levels of ECM-degradation enzymes. Molecular markers for exosomes also increase.

FIG. 59B shows regenerative trophic factors released by MSCs in response to PEMF stimulation. Bioactive agents released into the extracellular media following PEMF stimulation of MSCs at their EMF efficacy window. Shown is the proportion change (3 mT/0 mT) in concentration of an indicated agent 18 hours after PEMF exposure.

Figure 60:
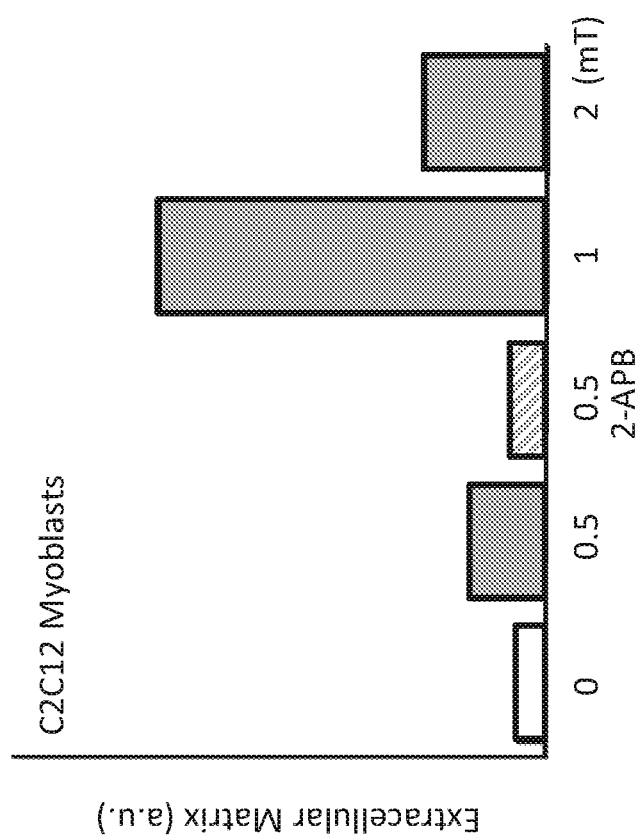
FIG. 60 shows that PEMF exposure causes the production of extracellular matrix at its specific EMF efficacy window.

FIG. 60 shows that PEMF exposure causes the production of extracellular matrix at its specific EMF efficacy window. Sum frequency generated microscopy reveals that C2C12 myoblasts exposed to PEMFs for 10 minutes increase their deposition of extracellular matrix, an effect that is negated by blocking TRPC channels and is most pronounced at the field strength, 1 mT, the peak of EMF efficacy window of skeletal myoblasts.

Figure 61:
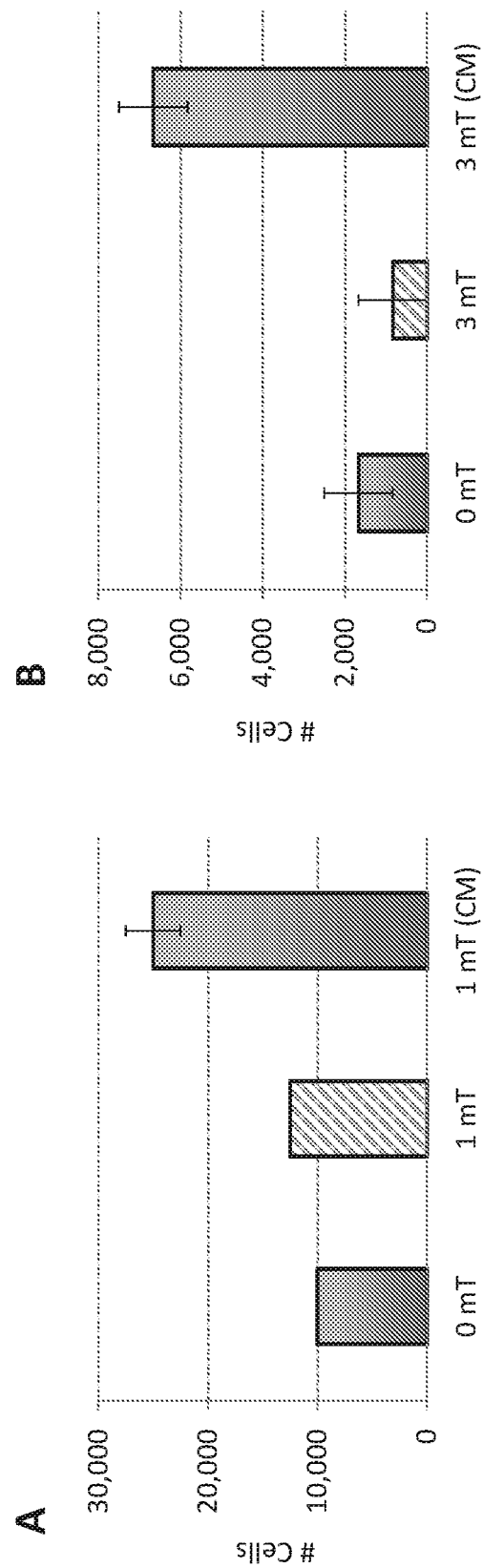
FIG. 61 shows that conditioned media can elicit responses from cells under conditions where PEMFs are incapable of eliciting responses directly.

FIG. 61 shows that conditioned media can elicit responses from cells under conditions where PEMFs are incapable of eliciting responses directly. A) Conditioned media (1 mT (CM)) produces response from cells stimulated below their optimal field strength (3 mT). B) PEMF-conditioned media (3 mT (CM)) from hMSCs can stimulate proliferation in cells over-passaged into quiescence, whereas direct stimulation with PEMFs had no effect.

Figure 62A:
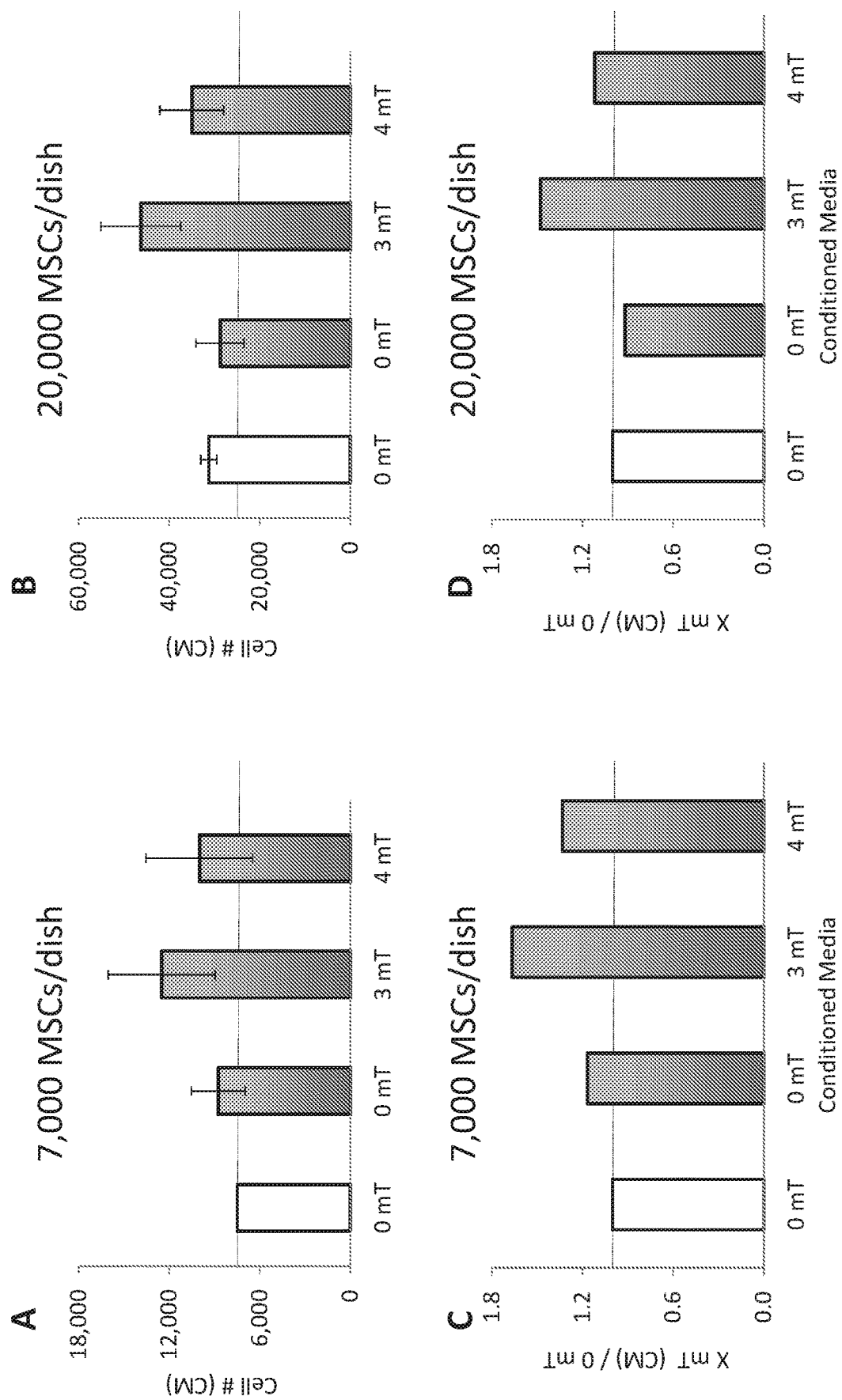
FIG. 62A shows that potency of conditioned media is inversely graded with density of donating MSCs.

FIG. 62A shows that potency of conditioned media is inversely graded with density of donating MSCs. The electromagnetic window of human MSCs is identical for cells plated at either low (A; 7,000 cells/dish) or high (B; 20,000 cells/dish) density. By contrast, the relative strength of the response is greatest for low (A; ~48% @ 3 mT (CM)) versus high (B; ~67% @ 3 mT (CM)) density cultures. Overconfluent concultures are less responsive to PEMF stimulation.

Figure 62B:
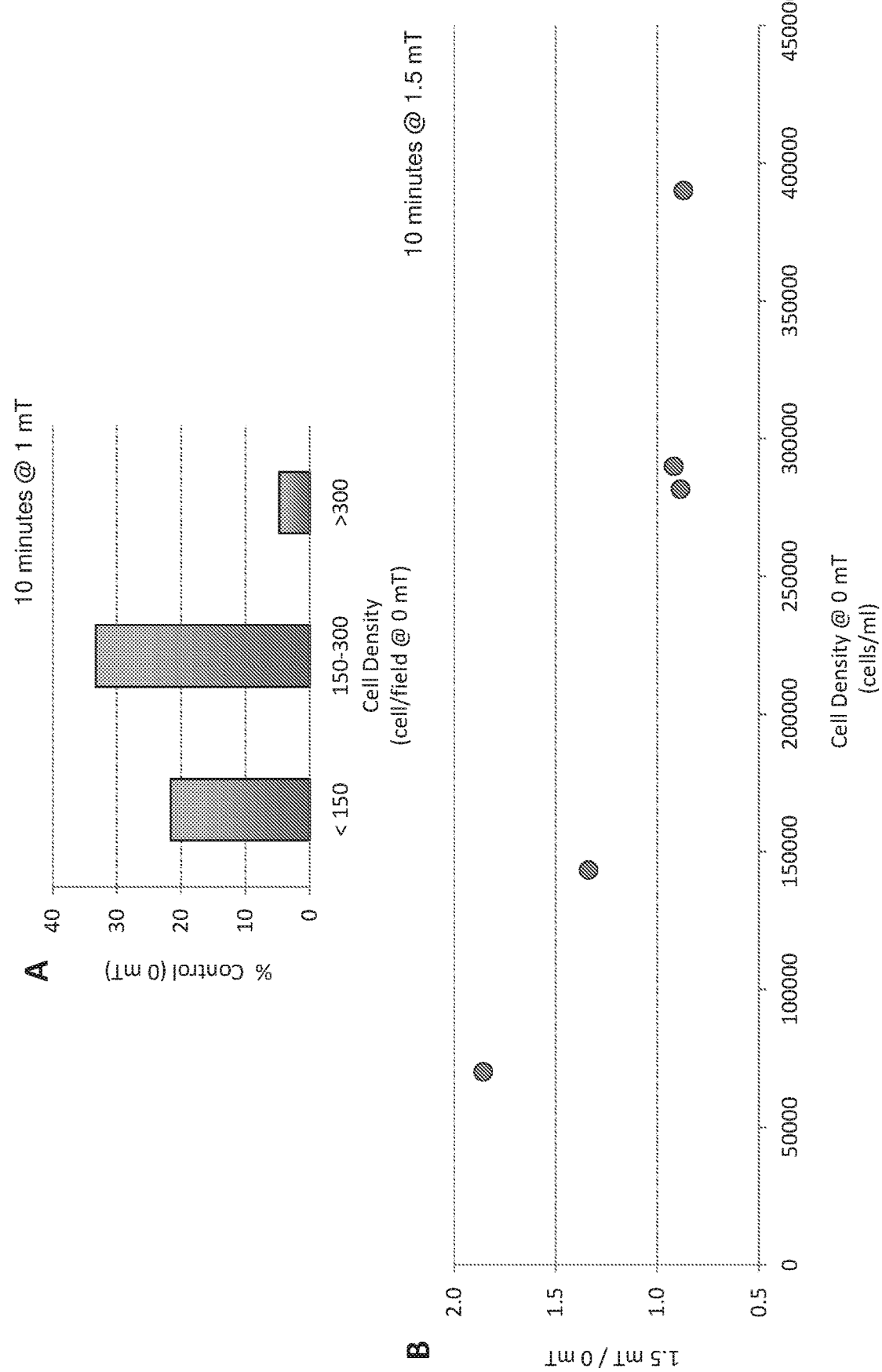
FIG. 62B shows that cell density regulates proliferative response to directly applied PEMFs.

FIG. 62B shows that cell density regulates proliferative response to directly applied PEMFs. A) High C2C12 cell density precludes the effects of PEMFs. Cell density in controls was determined at the time of counting; 15 hours post PEMF. B) C2C12 cellw respond to PEMFs more robustly at low density (cell/ml).

Figure 62C:
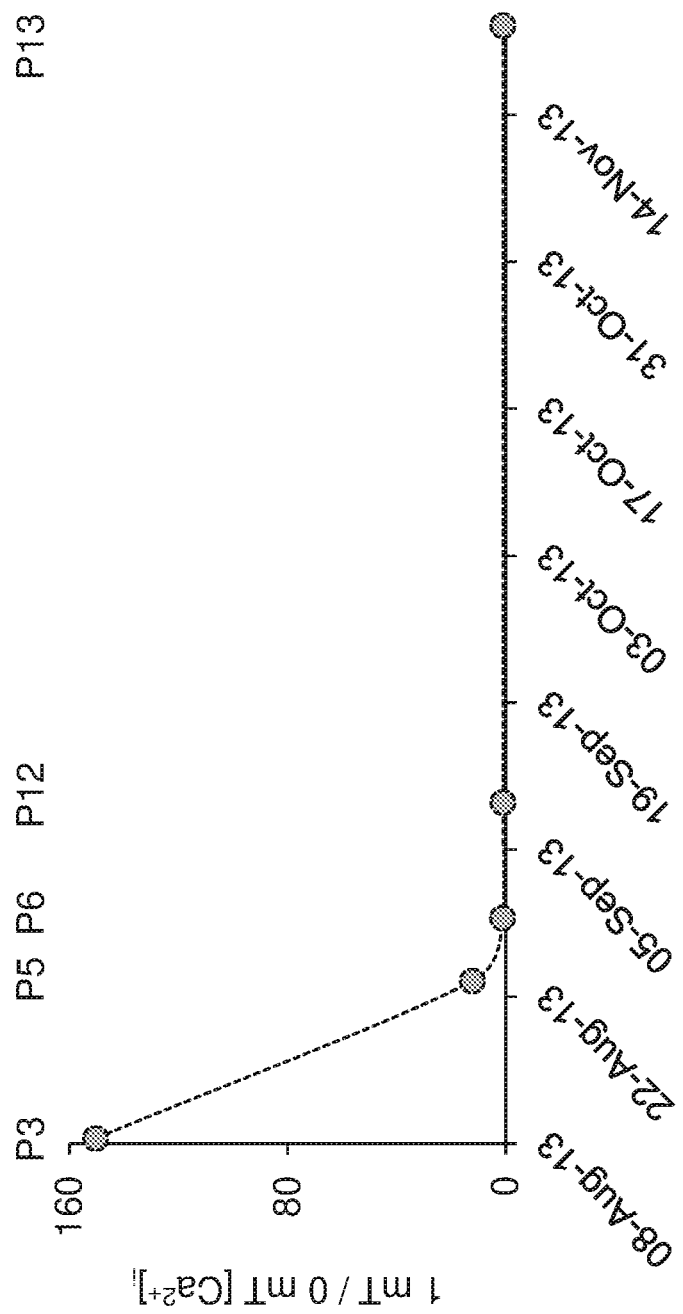
FIG. 62C shows that cell quiescence regulates calcium response to directly applied PEMFs.

FIG. 62C shows that cell quiescence regulates calcium response to directly applied PEMFs. Plate reading calcium measurements demonstrate that PEMF induced calcium responses decrement with serial passaging.

C2C12 Myoblasts

Figure 62D:
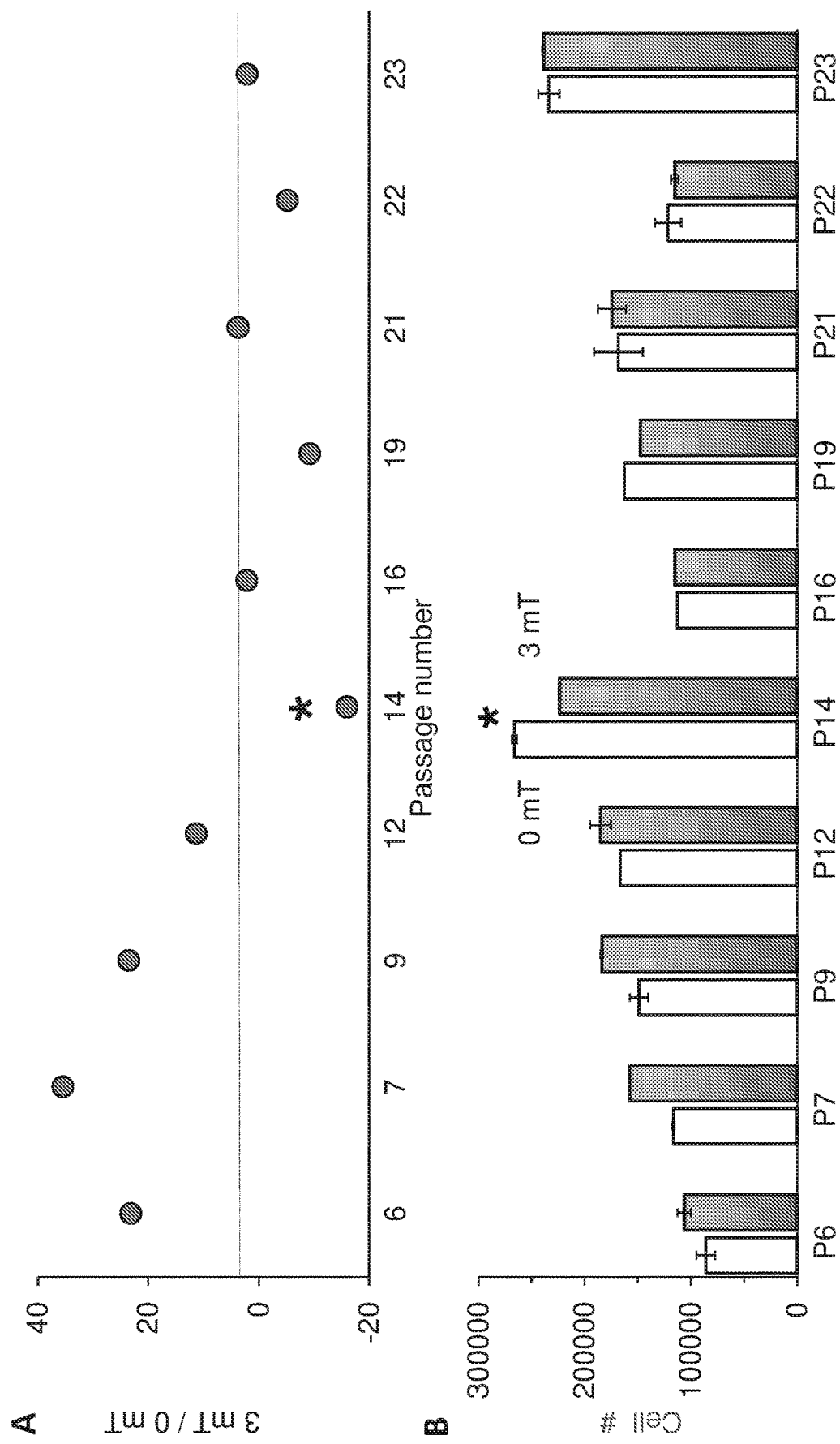
FIG. 62D shows that cell quiescence regulates sensitivity to directly applied PEMFs.

FIG. 62D shows that cell quiescence regulates sensitivity to directly applied PEMFs. A) Change in proliferation with PEMF stimulation (3 mT/0 mT) applied at the EMF efficacy window of H9C2 cardiac myocytes. B). Raw data from panel A. Passage 14 cells (*) were allowed to achieve higher than normal confluency and consequently were inhibited by PEMFs. The first passage after thawing consistently responds moderately to PEMFs as cells are frozen at high density. All data present the means of triplicates.

Figure 63:
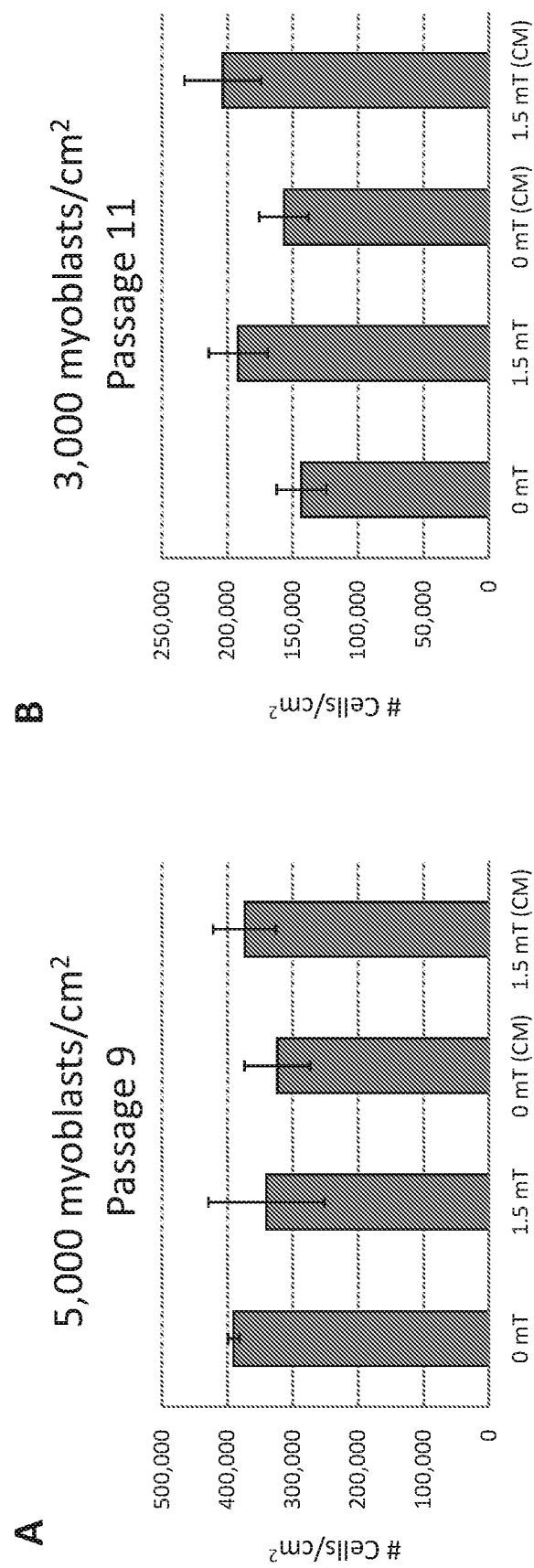
FIG. 63 shows that conditioned media from PEMF-stimulated C2C12 myoblasts confers proliferation to naïve C2C12 myoblasts and is inversely graded with density of donating cells.

FIG. 63 shows that conditioned media from PEMF-stimulated C2C12 myoblasts confers proliferation to naïve C2C12 myoblasts and is inversely graded with density of donating cells. Conditioned media harvested from C2C12 myoblasts that were exposed to 1.5 mT PEMFs (myoblast EMF window) transfers proliferative capacity to naïve (un-exposed) and age-matched myoblasts. A) Cells plated at higher density and hence, withdrawing from the cell cycle are less responsive to the fields as well as produce media with less proliferative potency than cells plated at lower density (B), despite being from a higher passage.

Overconfluent Concultures are Less Responsive to PEMF Stimulation.

Figure 64:
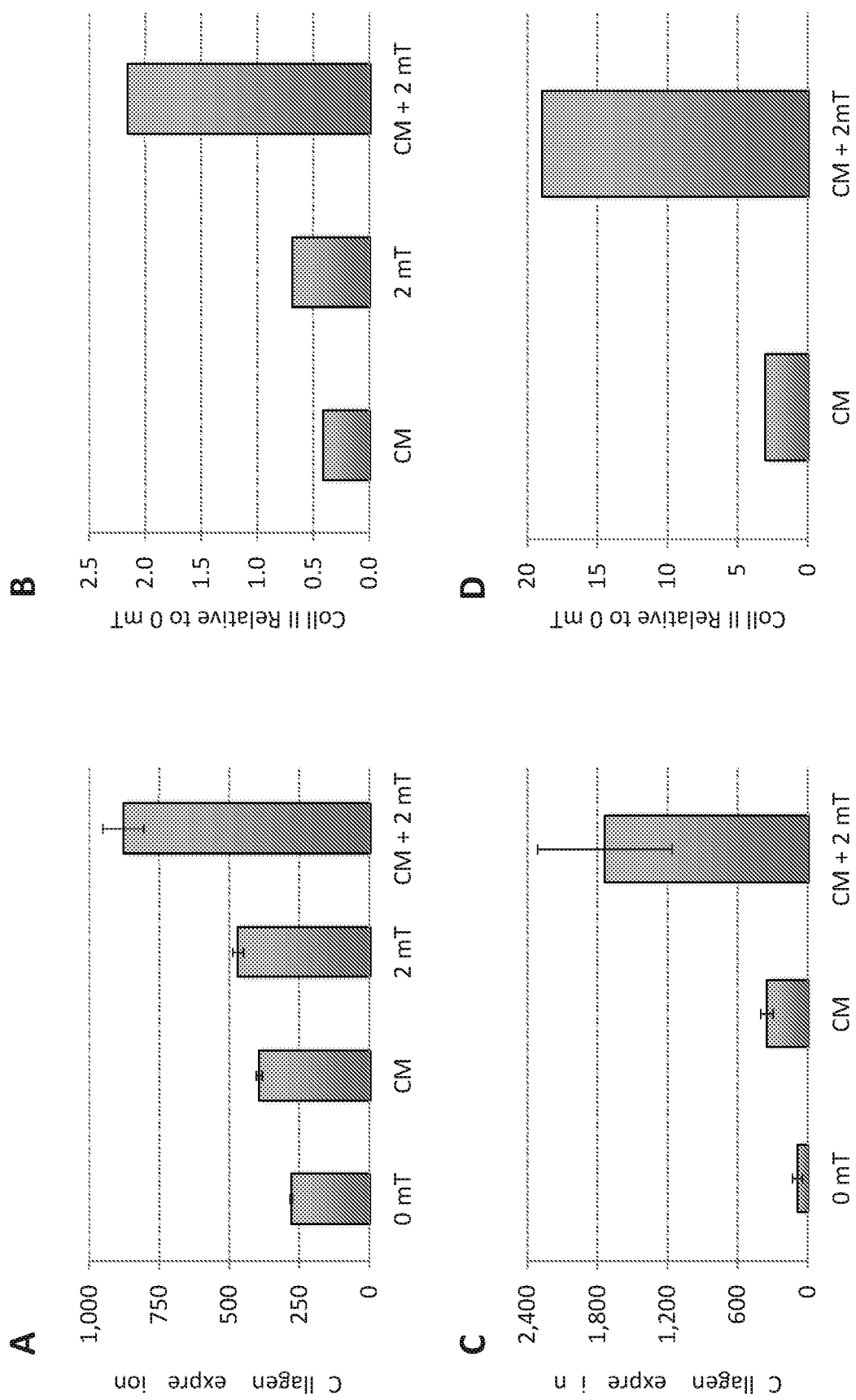
FIG. 64 shows the supraadditive effect of conditioned media plus direct PEMFing over over chondrogenic induction of human MSCs.

FIG. 64 shows the supraadditive effect of conditioned media plus direct PEMFing over over chondrogenic induction of human MSCs. A) The combined effect of conditioned media and direct PEMF (CM+2 mT) exposure is greater than the sum of the two individual effects, (CM) or (2 mT). B) Relative changes (to 0 mT) of the effects observed in panel A. C) Combined effect of conditioned media and direct PEMF (CM+2 mT) exposure is 18-fold greater than the individual effect of conditioned media (CM). D) Relative changes (to 0 mT) of the effects observed in panel C.

Figure 65:
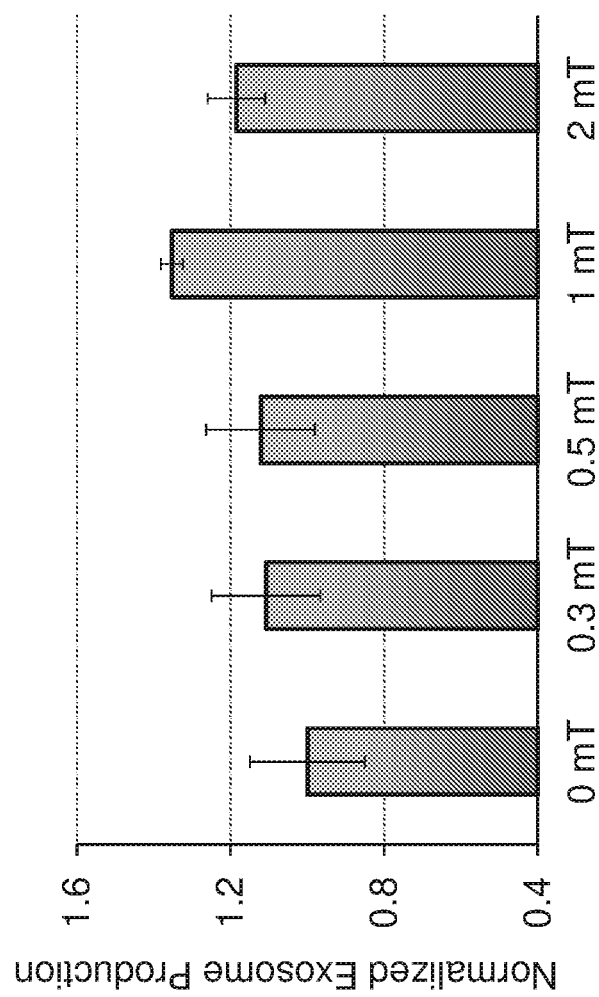
FIG. 65 shows exosome production in response to PEMFs; apparent EMF efficacy window of muscle.

FIG. 65 shows exosome production in response to PEMFs; apparent EMF efficacy window of muscle. PEMFs stimulate the secretion of exosome from stem cells at their specific electromagnetic window. Cells were directly stimulated with the PEMFs of the indicated amplitude.

Figure 66:
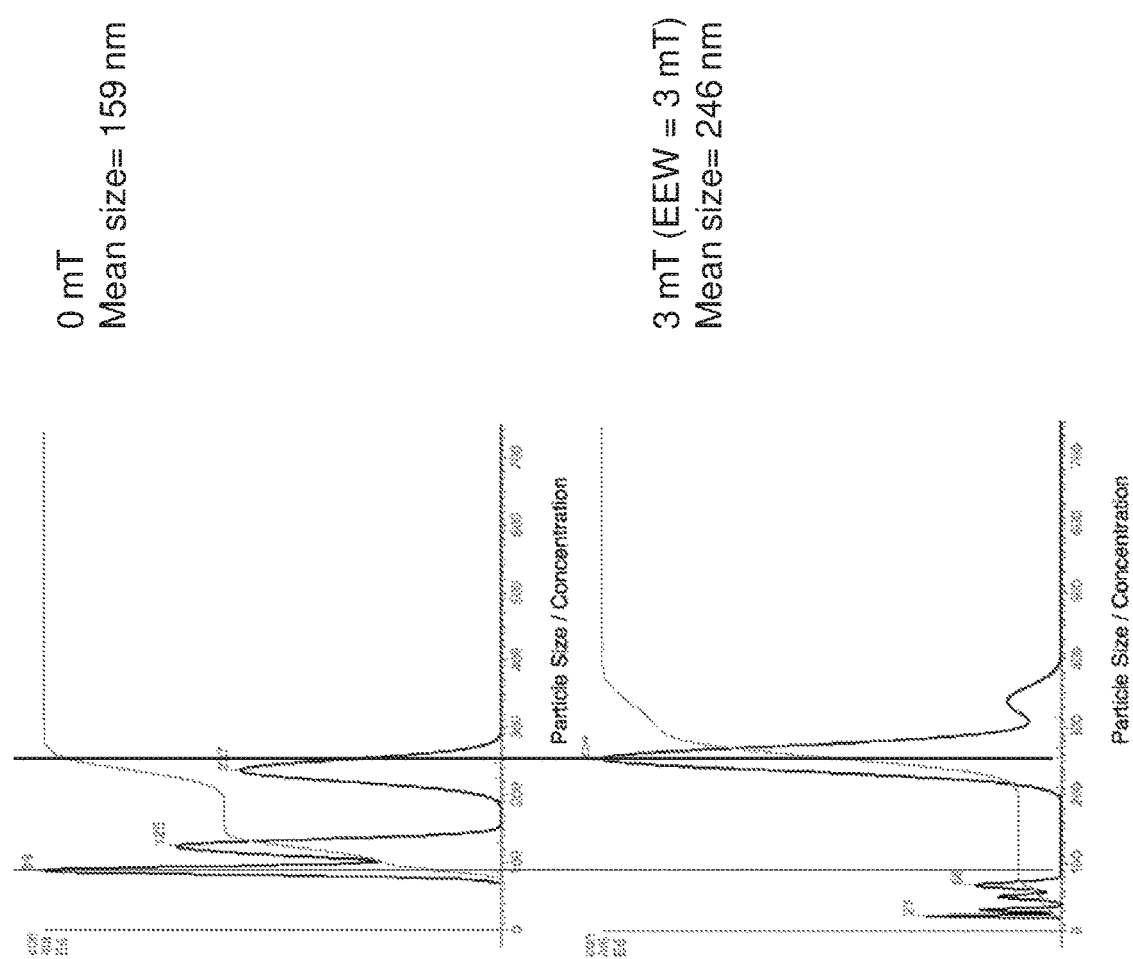
FIG. 66 shows that exosome size is shifted to larger values in response to PEMF stimulation of the correct electromagnetic window (EEW) for MSCs.

FIG. 66 shows that exosome size is shifted to larger values in response to PEMF stimulation of the correct electromagnetic window (EEW) for MSCs. Microvesicle/exosome profile changes after exposure to PEMFs of appropriate EMF window. The concentration of exosomes produced also increases with PEMF stimulation.

FIG. 67 shows lifespan extension in *C. elegans* correlated field orientation and ROS production. Lifespan extension is correlated with the generation of reactive oxygen species (ROS) in response to the correct field orientation. The result also demonstrates a life-span related EMF efficacy window that is modulated by field direction.

FIG. 68 shows that proliferation is more greatly enhanced by stimulation of cells with PEMFs in the correct orientation. Exposure of cells to PEMFs of the correct orientation (downward) confers greatest cell growth.

Figure 69:
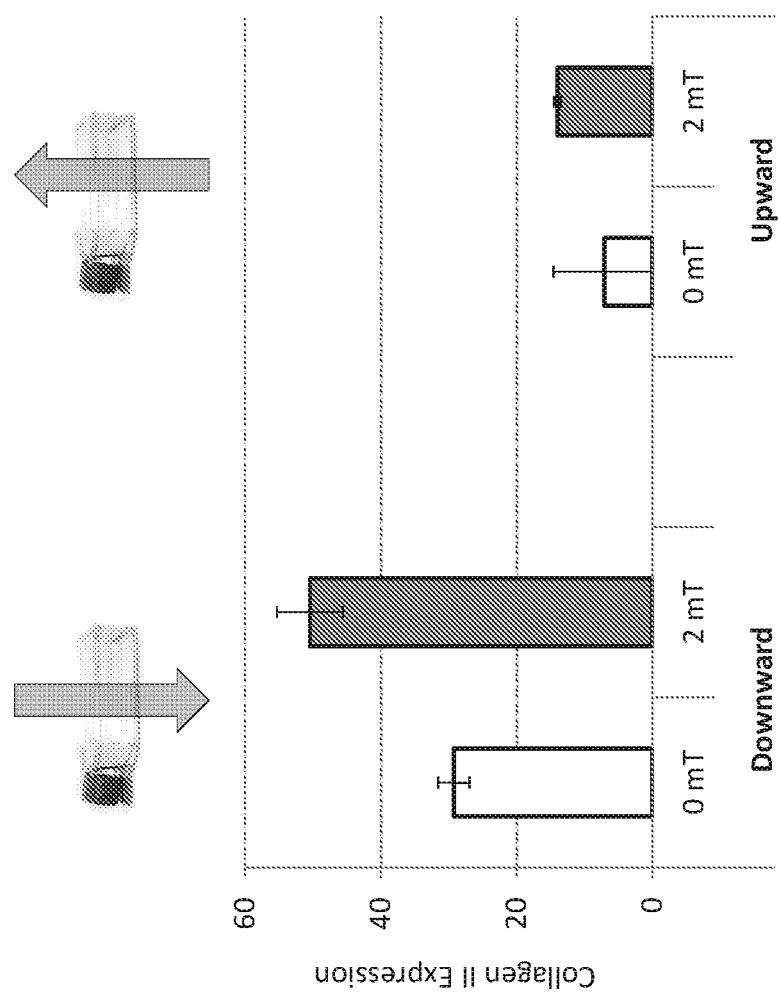
FIG. 69 shows that fields in the correct orientation more effectively promote chondrogenesis.

FIG. 69 shows that fields in the correct orientation more effectively promote chondrogenesis. MSCs directed into chondrogenesis produced relatively greater levels of collagen II when stimulated to PEMFs of the appropriate orientation.

FIG. 70 shows that conditioned media collected from cells stimulated with PEMFs of the correct orientation is more effective at promoting cell responses than conditioned media collected from cell stimulated in the non-preferred orientation. Conditioned media (CM) was obtained from MSCs cultures exposed to PEMFs (0 mT & 3 mT) in the preferred (vertical) and non-preferred (horizontal) orientations and supplied to naïve cultures (not exposed to PEMFs). Only CM originating from cultures exposed to PEMFs of the correct EMF efficacy amplitude and in the preferred orientation conferred cell growth. Solid blue bars represent cells directly stimulated with PEMFs of said orientation. Cell growth conferred with CM from preferred orientation and EMF efficacy window cultures produced greater proliferation than direct PEMF stimulation. Dotted line depicts non-exposed level of proliferation.

Figure 71:
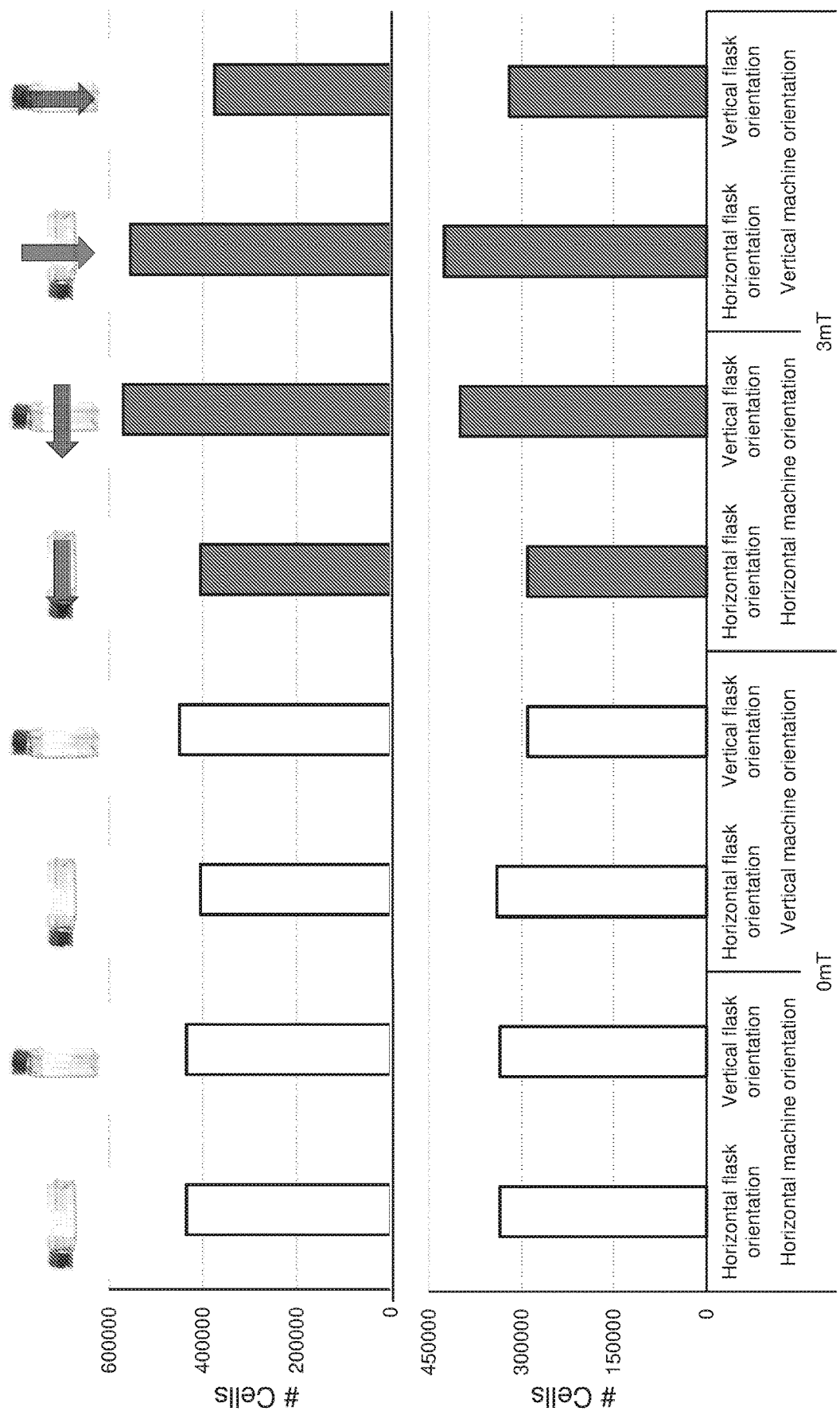
FIG. 71 shows that field and cell orientation combine for optimal effect.

FIG. 71 shows that field and cell orientation combine for optimal effect. Proper orientation of the cells relative to the fields is essential for biological outcome. The ideal induced currents will be best achieved if the direction of the magnetic fields is perpendicular to the long axis of the cell or tissue in question. Aligning the long axis of the cells/tissues parallel to the magnetic field lines will change the EMF efficacy window, requiring greater amplitude PEMFs. The alignment and organization of tissues to be targeted must be taken into consideration with exposure paradigms are to be designed.

Figure 72:
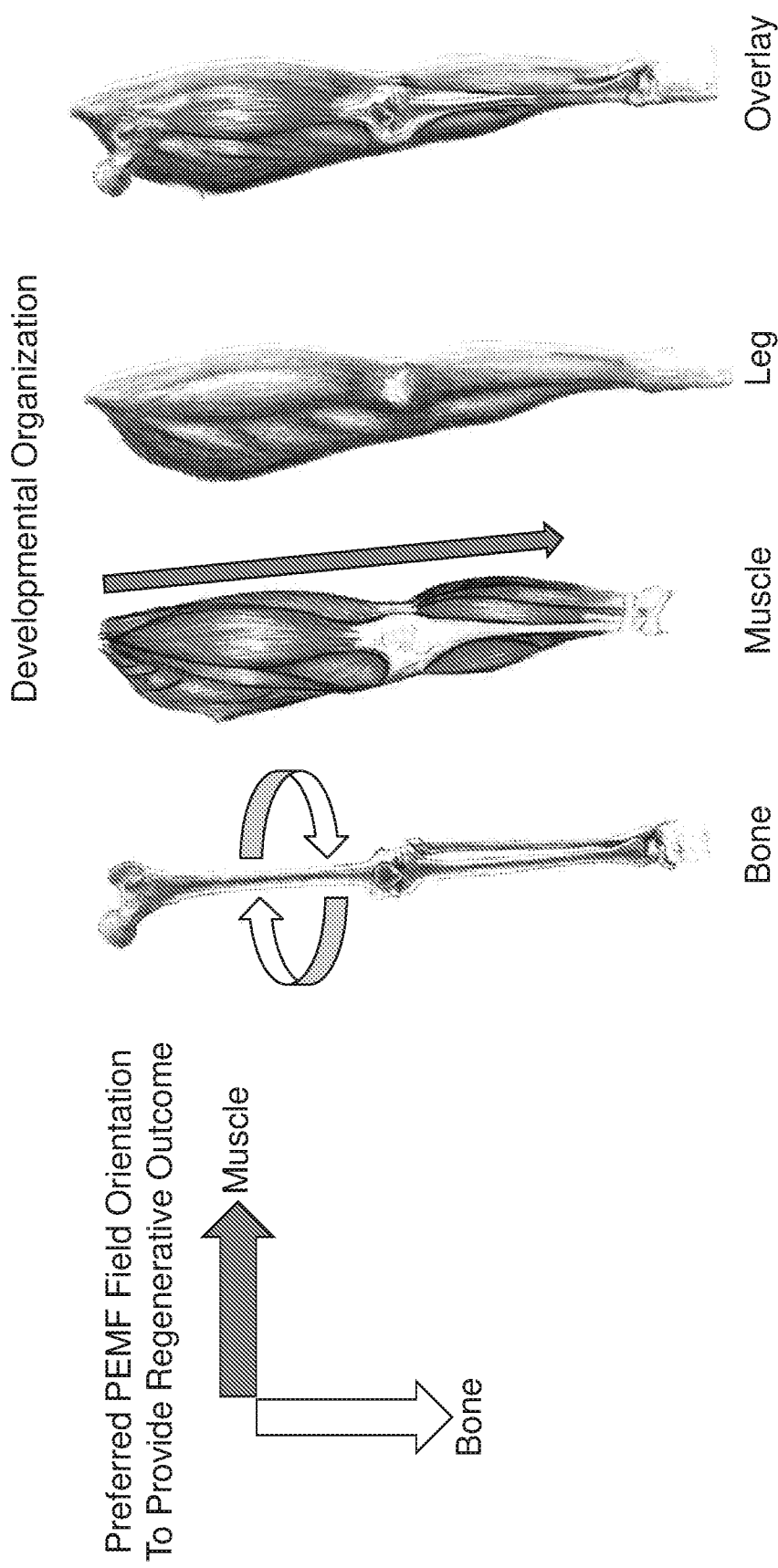
FIG. 72 shows that field orientation can be used to target different tissues.

FIG. 72 shows that field orientation can be used to target different tissues. Given that: 1) tissues have different inherent organizational orientations in the body and; 2) the EMF window of a tissue will change with orientation of the pulsing magnetic fields; then 3) a tissue can be targeted just by changing the orientation of the field. In this example bone is organized circumferentially, whereas muscle is organized vertically in a standing individual. The orientation of the field will depend on the biological outcome anticipated.

The invention claimed is:

1. A system for generating pulsed electromagnetic fields (PEMFs) for application to target tissues or target cells during a plurality of successive PEMF sessions, comprising:
a set of PEMF coils;
a memory module;
a pulse generator coupled to the set of PEMF coils and configured to generate an output of electrical pulses to drive the set of PEMF coils; and
a controller in communication with the memory module and the pulse generator, wherein the controller is configured to control the pulse generator such that during each PEMF session:

each PEMF pulse has a peak magnetic flux density between 0.1-5.0 mT and a rate of magnetic flux density change between 35-65 T/s; and the set of PEMF coils generates a plurality of PEMF pulses across a PEMF exposure time of at least five minutes but not more than fifteen minutes, and wherein the memory module and/or a database store PEMF session signal parameters corresponding to multiple distinct target tissue types or target cell types and store PEMF regimen parameters for each distinct target tissue type or target cell type, wherein the PEMF session signal parameters for each distinct target tissue type or target cell type comprise one of more of: amplitude, frequency, symmetry, field gradient, uniformity, and direction and duration of the PEMF pulses emitted by the set of PEMF coils during PEMF sessions corresponding to the target tissue type or target cell type, as well as a maximum PEMF exposure time or magnetic flux density dose for PEMF sessions corresponding to the target tissue type or target cell type, and wherein the PEMF regimen parameters indicate for each distinct target tissue type or target cell type a minimum time period between successive PEMF sessions for the target tissue type or target cell type and/or a maximum number of PEMF sessions to which the target tissue type or target cell type is to be exposed within a certain amount of time. and wherein the controller is further configured to retrieve PEMF session signal parameters from the memory module for controlling the output of the pulse generator.

2. The system as claimed in claim 1, wherein the PEMF session signal parameters corresponding to distinct target tissue types or target cell types comprise at least two of:

myoblast parameters specifying for each PEMF session a PEMF exposure time of 10 minutes and/or a peak PEMF pulse magnetic flux density of 1.5 mT;

skeletal muscle parameters specifying for each PEMF session a PEMF exposure time of 10 minutes and/or a peak PEMF magnetic flux density between 1.5-3.0 mT;

cardiac muscle parameters specifying a PEMF exposure time of 10 minutes and/or a peak PEMF pulse magnetic flux density of 3.0 mT;

lymphocyte parameters specifying a PEMF exposure time of 10 minutes and/or a peak PEMF pulse magnetic flux density of 2.0 mT;

mesenchymal stem cell parameters specifying a PEMF exposure time of 10 minutes and/or a peak PEMF pulse magnetic flux density of 3.0 mT;

chondrocyte parameters specifying a PEMF exposure time of 10 minutes and/or a peak PEMF pulse magnetic flux density of 2.0 mT;

adipocyte parameters specifying a PEMF exposure time of 10 minutes and/or a peak PEMF magnetic flux density of 1.0 mT; and smooth muscle parameters specifying a PEMF exposure time of 10 minutes and/or a peak PEMF pulse magnetic flux density of 3.0 mT.

3. The system as claimed in claim 1, wherein for each target tissue type or target cell type, the PEMF regimen parameters specify a maximum number of PEMF sessions per week less than or equal to three.

4. The system as claimed in claim 1, further comprising a detector for detecting the response from the cell after a first application of PEMF, wherein the controller is further configured to control the output of the pulse generator based on the detected response from the cell for a second subsequent application of PEMF to the cell.

5. The system as claimed in claim 1, wherein the set of PEMF coils comprises a pair of opposing saddle coils.

6. The system as claimed in claim 1, further comprising a seating device for supporting a subject in a seated position, and wherein the set of PEMF coils is configured to apply PEMF pulses through portions of the seating device.

7. The system as claimed in claim 6, wherein the set of PEMF coils is built into the seating device.

8. The system as claimed in claim 1, further comprising an animal feeding station at which the set of PEMF coils is deployed.

9. The system as claimed in claim 1, wherein the set of PEMF coils comprises a magnetic resonance imaging (MRI) coil.

10. The system as claimed in claim 1, wherein the set of PEMF coils is adapted to apply the PEMF pulses to a cell culture medium containing the target cells during each PEMF session.

11. The system as claimed in claim 1, wherein the target tissues or target cells include a long axis, and wherein the set of PEMF coils is configured to apply each PEMF pulse orthogonal to the long axis of the target tissues or target cells.

12. A system for generating pulsed electromagnetic fields (PEMFs) for application to target tissues or target cells during a plurality of successive PEMF sessions, comprising:

a set of PEMF coils, wherein the set of PEMF coils is configured to generate magnetic field lines in a downward direction vertical with gravity;

a memory module;

a pulse generator coupled to the set of PEMF coils and configured to generate an output of electrical pulses to drive the set of PEMF coils; and a controller in communication with the memory module and the pulse generator, wherein the controller is configured to control the pulse generator such that during each PEMF session:

each PEMF pulse has a peak magnetic flux density between 0.1-5.0 mT and a rate of magnetic flux density change between 10-100 T/s; and the set of PEMF coils generates a plurality of PEMF pulses across a PEMF exposure time of at least five minutes but not longer than fifteen minutes.

13. The system as claimed in claim 12, wherein the target tissues or target cells include a long axis, and wherein the set of PEMF coils is further configured to apply each PEMF pulse orthogonal to the long axis of the target tissues or target cells.

* * * * *